United States Patent [19]
Srivastava et al.

[11] Patent Number: 5,874,411
[45] Date of Patent: *Feb. 23, 1999

[54] OLIGOSACCHARIDE GLYCOSIDES HAVING MAMMALIAN IMMUNOSUPPRESIVE AND TOLEROGENIC PROPERTIES

[75] Inventors: Om P. Srivastava; Geeta Srivastava; Roman Szweda; David R. Bundle; Ole Hindsgaul; H. Rizk Hanna, all of Edmonton, Canada; Kevin Holme, Alameda, Calif.; Frank W. Barresi; Minghui Du, both of Edmonton, Canada

[73] Assignee: Glycomed Incorporated, Alameda, Calif.

Related U.S. Application Data

[60] Provisional application No. 60/006,593 Nov. 13, 1995.

[21] Appl. No.: 754,097
[22] Filed: Nov. 13, 1996
[51] Int. Cl.$^6$ .............................. A61K 31/70; C07H 15/00
[52] U.S. Cl. .......................... 514/25; 536/4.1; 536/17.2; 536/17.9; 536/18.4
[58] Field of Search .............................. 514/25; 536/4.1, 536/17.2, 17.9, 18.4

[56] References Cited

U.S. PATENT DOCUMENTS

| | | | |
|---|---|---|---|
| 5,079,353 | 1/1992 | Ratcliffe et al. | 536/53 |
| 5,143,712 | 9/1992 | Brandley et al. | 424/1.1 |
| 5,591,835 | 1/1997 | Abbas et al. | 536/4.1 |

FOREIGN PATENT DOCUMENTS

| | | |
|---|---|---|
| WO 91/19502 | 12/1991 | WIPO . |
| WO 92/22564 | 12/1992 | WIPO . |
| WO92 22564 | 12/1992 | WIPO . |
| WO93 24506 | 12/1992 | WIPO . |

OTHER PUBLICATIONS

Abbas et al., "Tumor–Associated Oligosaccharides II: Synthesis of Sialyl–X–Antigenic Determinant," *Proc. Japanese– German Symp. Berlin*, pp. 20–21 (May 1988).

Amvam–Zollo et al., "Streptococcus pneumoniae Type XIV Polysaccharide: Synthesis of a Repeating Branched Tetrasaccharide With Dioxa–Type Spacer–Arms," *Carbohydr. Res.*, 150:199–212 (1986).

Banoub, et al., "1,2–Orthoacetate Intermediates in Silver Trifluoromethanesulphonate Promoted Koenigs–Knorr Synthesis of Disaccharide Glycosides," *Can J. Chem.*, 57:2091 (1979).

Carlson, et al., "A Greatly Improved Procedure for Ruthenium Tetraoxide Catalyzed Oxidations of Organic Compounds," *J. Org. Chem.*, 46:3936 (1981).

Chernyak et al., "A New Type of Carbohydrate–Containing Synthetic Antigen: Synthesis of Carbohydrate–Containing Polyacrylamide Copolymers Having The Specificity of 0:3 And 0:4 Factors Of Salmonella," *Carbohydr. Res.*, 128:269–282 (1984).

Dahmen et al., "2–Bromoethyl Glycosides: Applications in the Synthesis of Spacer–Arm Glycosides," *Carbohydr. Res.*, 118:292–301 (1983).

Deter–Jusynski, et al., "Studies on the Koenigs–Knorr Reaction Part IV: the Effect of Participating Groups on the Stereochemistry of Disaccharide Formation," *Carbohydr. Res.*, 28:61–74 (1973).

Ekborg et al., "Synthesis of Three Disaccharides of the Preparation of Immunogens Bearing Immunodeterminants Known to Occur on Glycoproteins," *Carbohydr. Res.*, 110:55–67 (1982).

Fernandez–Santana et al., "Glycosides of Monoallyl Diethylene Glycol. A New Type of Spacer Group For Synthetic Oligosaccharides," *J. Carbohydr. Chem.*, 8:531–537 (1989).

Finan, et al., "2,4, 6–Tri–O–Acetyl–3–O–Benzyl–x–D–Glucopyranosyl Bromide: A New Intermediate for the Koenigs–Knorr Synthesis of Glycosides," *J. Chem. Soc.*, 3089 (1962).

Fügedi et al., "Thioglycosides as Glycosylating Agents in Oligosaccharide Synthesis," *Glycoconj. J.*, 4:97–108 (1987).

Kameyama et al., "Total Synthesis of Sialyl Lewis X," *Carbohydr. Res.*, 209:$C_1$–$C_4$ (1991).

Larsen, et al., "PADGEM–Dependent Adhesion of Platelets to Monocytes and Neutrophils is Mediated by a Lineage–Specific Carbohydrate, LNF III (CD15)," *Cell*, 63:467–474 (1990).

Lee, et al., "Synthesis of 3–(2–Aminoethylthio)Propyl Glycosides," *Carbohydr. Res.*, 37:193–201 (1974).

Lemieux, et al., "The Azidonitration of Tri–O–Acetyl–D–Galactal," *Can. J. Chem.*, 57:1244–1251 (1979).

Lemieux, et al., "Synthesis of Derivatives of N–Acetyl–D–Lactosamine from D–Lactal Hexaacetate. Hexa–O–Acetyl–2–Deoxy–2–Phthalimido–β–D–Lactosyl Chloride," *Can. J. Chem.*, 60:63–67 (1982).

Lowe, et al., "ELAM–1–Dependent Cell Adhesion to Vascular Endothelium Determined by a Transfected Human Fucosyltransferase cDNA," *Cell*, 63:475–484 (Nov. 1990).

Luengo, et al., "Synthesis of C–Fucopyranosyl Analogs of GDP–L–Fucose as Inhibitors of Fucosytransferases," *Tetrahedron Lett.*, 33(46):6911–6914 (1992).

Okamoto, et al., "Glycosidation of Sialic Acid," *Tetrahedron*, 46(17):5835–5857 (1990).

Paulsen, "Advances in Selective Chemical Synthesis of Complex Oligosaccharides," *Angew. Chem. Int. Ed. Eng.*, 21(3):155–173 (Mar. 1982).

Paulson, et al., "Synthese Von Oligosaccharid–Determinanten Mit Amid–Spacer Vom Typ Des T–Antigens*." *Carbohydr. Res.*, 104:195–219 (1982). (English Abstract Only).

(List continued on next page.)

Primary Examiner—Kathleen K. Fonda
Attorney, Agent, or Firm—Burns, Doanes, Swecker & Mathis LLP

[57] ABSTRACT

Disclosed are novel oligosaccharide glycosides having mammalian immunosuppressive and tolerogenic properties, pharmaceutical compositions containing such oligosaccharide glycosides and to methods of using such oligosaccharide glycosides to modulate cell-mediated immune responses in a mammal.

11 Claims, 53 Drawing Sheets

OTHER PUBLICATIONS

Phillips, et al., "ELAM–1 Mediates Cell Adhesion by Recognition of a Carbohydrate Ligand, Sialyl–Le$^x$," *Science*, 250:1130–1132 (1990).

Rana, et al., "Synthesis of Phenyl 2–Acetamido–2–Deoxy–3–O–α–L–Fucopyranosyl–β–D–Glucopyranoside and Related Compounds*," *Carbohydr. Res.*, 91:149–157 (1981).

Schmidt, "New Methods for the Synthesis of Glycosides and Oligosaccharides–Are There Alternatives to the Koenigs–Knorr Method" *Angew. Chem. Int. Ed. Eng.*, 25:212–235 (1986).

Walz, et al., "Recognition by ELAM–1 of the Sialyl–Le$^x$ Determinant on Myeloid and Tumor Cells," *Science*, 250:1132–1135 et seq. (Nov. 1990).

BeMiller, et al., *J. Carbohydr. Chem.*, 9:39 (Nov. 1990).

Bundle, et al., Can. J. Chem., 57(6):662–668 (Mar. 1979).

Sugawara, et al., Chem. Abstracts, 118(15):148071z(1993).

Dicioccio, et al., J. Biol. Chem., 257(2):714–718 (Jan. 1982).

Du, et al., Carbohydr. Res., 286:87–105 (Jun. 1996).

Field, et al., Carbohydr. Res., 276(2):347–363 (Oct. 1995).

Baisch, et al., Bioorg. Med. Chem. Lett., 6(7):749–754 (Apr. 1996).

Baisch, et al., Bioorg. Med. Chem. Lett., 6(7):755–758 (Apr. 1996).

Uchiyama, et al., Syn. Lett., 6:499–501 (1996).

Scheme for the Synthesis of 2-Substituted 3'-Sulfo-Le$^x$-OR

Scheme for the Synthesis of 4'-Sulfo-Lactose-OR and 4'-Phospho-Lactose-OR:

Scheme for the Synthesis of 3',6'-Disulfo-Le$^C$-OR and 3',6'-Diphospho-Le$^C$-OR:

Scheme for the Synthesis of 3',4',6'-Tri-O-Sulfo-Le$^x$-OR:

Scheme for the Synthesis of 3'-Sulfo-Y-Tetrasaccharide-OR

Scheme for the Synthesis of 4'-Chloro,6'-Chloro and 4',6'-Dichloro Derivatives of 3'-Sulfo-Le$^X$-OR:

5,874,411

OLIGOSACCHARIDE GLYCOSIDES HAVING MAMMALIAN IMMUNOSUPPRESIVE AND TOLEROGENIC PROPERTIES

REFERENCE TO PROVISIONAL APPLICATION

This application claims the benefit of U.S. Provisional Application Ser. No. 60/006,593 filed Nov. 13, 1995.

BACKGROUND OF THE INVENTION

1. Field of the Invention

This invention relates to novel oligosaccharide glycosides having mammalian immunosuppressive and/or tolerogenic properties. This invention also relates to pharmaceutical compositions comprising such oligosaccharide glycosides and to methods of using such oligosaccharide glycosides to modulate cell-mediated immune responses in a mammal.

References

The following references are cited in this application as superscript numbers at the relevant portion of the application:

1. Brandley, et al., U.S. Pat. No. 5,143,712, issued Sep. 1, 1992, for "Method of Determining a Cite of Inflammation Utilizing ELAM-1 Ligands"
2. Paulson, et al., International Patent Application Publication No. WO 91/19502, published 26 Dec., 1991, for "Intercellular Adhesion Mediators"
3. Lowe, et al., Cell, 63:475–485 (1990).
4. Phillips, et al., Science, 250:1130–1132 (1990).
5. Walz, et al., Science, 250:1132 et seq. (1990).
6. Larsen, et al., Cell, 63:467–474 (1990).
7. Ippolito, et al., U.S. patent application Ser. No. 07/714, 161, filed Jun. 10, 1991 for "Immunosuppressive and Tolerogenic Oligosaccharide Glycosides".
8. Ippolito, et al., U.S. patent application Ser. No. 07/889, 017, filed May 26, 1992 for "Immunosuppressive and Tolerogenic Oligosaccharide Glycosides".
9. Ippolito et al., U.S. patent application Ser. No. 08/081, 214, filed Jun. 23, 1993 for "Time Dependent Administration of Oligosaccharide Glycosides Related to Blood Group Determinants Having a Type I or Type II Core Structure in Reducing Inflammation in a Sensitized Mammal Arising From Exposure to an Antigen".
10. Ekborg, et al., Carbohydr. Res., 110:55–67 (1982).
11. Dahmen, et al., Carbohydr. Res., 118:292–301 (1983).
12. Rana, et al., Carbohydr. Res., 91:149–157 (1981).
13. Amvam-Zollo, et al., Carbohydr. Res., 150:199–212 (1986).
14. Paulsen, et al., Carbohydr. Res., 104:195–219 (1982).
15. Chemyak, et al., Carbohydr. Res., 128:269–282 (1984).
16. Fernandez-Santana, et al., J. Carbohydr. Chem., 8:531–537 (1989).
17. Lee, et al., Carbohydr. Res., 37:193 et seq. (1974).
18. Finan, et al., J. Chem. Soc., 3089 (1962).
19. Paulsen, et al., Carbohydr. Res., 133:C1 (1984).
20. BeMiller, et al., J. Carbohydr. Chem., 9:39 (1990).
21. Lemieux, et al., Can. J. Chem., 57:1244 (1979).
22. Lemieux, et al., Can. J. Chem., 60:63 (1982).
23. Srivastava, et al., U.S. patent application Ser. No. 08/343,020, filed Nov. 21, 1994 for "Process for the Synthesis of 3'-Substituted Lewis$^x$ Compounds".
24. Banoub, et al., Can. J. Chem., 57:2091 (1979).
25. Okamoto, et al., Tetrahedron, 46(17):5835–5837 (1990).
26. Abbas, et al., Proc. Japanese-German Symp. Berlin, pp. 20–21 (1988).
27. Paulsen, Agnew. Chem. Int. Ed. Eng., 21:155–173 (1982).
28. Schmidt, Agnew. Chem. Int. Ed. Eng., 25:212–235 (1986).
29. Fügedi, et al., Glycoconj. J., 4:97–108 (1987).
30. Kameyama, et al., Carbohydr. Res., 209:$C_1$–$C_4$ (1991).
31. Ratcliffe, et al., U.S. Pat. No. 5,079,353, issued Jan. 7, 1992 for "Sialic Acid Glycosides, Antigens, Immunoadsorbents, and Methods for Their Preparation"
32. Ippolito, et al., U.S. patent application Ser. No. 08/081, 212, filed Jun. 25, 1993 for "Immunosuppressive and Tolerogenic Modified Lewis$^C$ and LacNAc Compounds"
33. Luengo, et al., Tetrahedron Lett., 33:6911 (1992)
34. Carlsen, et al., J. Org. Chem., 46:3936 (1981)
35. Unverzagt, et al., J. prakt. Chem., 334:570–578 (1992)
36. Deter-Jusynski, et al., Carbohydr. Res., 28:61–74 (1973)

The disclosures of each of the above-referenced publications, patents and patent applications are herein incorporated by reference in their entirety to the same extent as if each individual publication, patent or patent application was specifically and individually indicated to be incorporated by reference in its entirety.

2. State of the Art

A number of sialylated and sialylated/fucosylated oligosaccharide glycosides have been proposed as mediators of cell adhesion in that they are ligands for selectins (or LEC-CAM's)[3,4,5,6]. Such selectins, including E-selectin, L-selectin and P-selectin, have been implicated as playing a seminal role in cell mediated inflammatory conditions and, heretofore, it has been postulated in the art that ligands for such selectins would possess anti-inflammatory properties[1,2]. In this regard, sialylated, fucosylated, and sialylated and fucosylated oligosaccharide structures relating to blood group determinants having a type I or a type II core structure, including Lewis$^x$, Lewis$^A$, sialyl Lewis$^x$ and sialyl Lewis$^A$, have been shown by Ippolito et al.[7,8] to possess in vivo immunomodulating and tolerogenic properties in mammals including anti-inflammatory immunomodulating properties. Additionally, modified Lewis$^x$-OR, Lewis$^C$-OR and LacNAc-OR compounds having a sulfate group, a phosphate group or a carboxylate containing group at the 2, 3 and/or 6-positions of the galactose unit have also been disclosed to possess immunosuppressive and tolerogenic properties.[9,23] In addition, synthetic procedures for the preparation of such modified compounds have been reported.[23]

Notwithstanding these disclosures in the art, additional carbohydrate structures having immunomodulating and tolerogenic properties in mammals would provide valuable structure activity relationships and, in their own right, would be useful in providing anti-inflammatory immunomodulating properties.

SUMMARY OF THE INVENTION

This invention provides novel oligosaccharide glycosides which are useful for modulating cell mediated immune responses in a mammal, including cell mediated and immune directed inflammatory responses to an antigen in a sensitized mammal.

The oligosaccharide glycosides of this invention are represented by Formula I and II below:

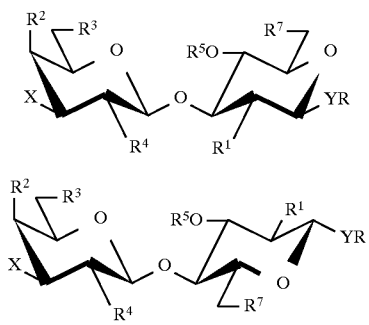

wherein:

Y is oxygen, sulfur or —NH—;

R is an aglycon of at least 1 carbon atom;

$R^1$ is selected from the group consisting of —OH, $NH_2$, —$N_3$, —NHC(O)$R^6$, and -fuc(C)amido, wherein $R^6$ is selected from the group consisting of
   alkyl of from 1 to 6 carbon atoms,
   cycloalkyl of from 3 to 8 carbon atoms,
   aryl of from 6 to 14 carbon atoms,
   alkaryl of from 7 to 20 carbon atoms,
   heteroaryl of from 2 to 5 carbon atoms and from 1 to 3 hetero atoms selected from the group consisting of nitrogen, sulfur and oxygen,
   substituted alkl of from 1 to 6 carbon atoms having one to three substituents independently selected from the group consisting of halo, nitro, cyano, carboxyl, amino, alkylamine of from 1 to 6 carbon atoms, alkoxy of from 1 to 6 carbon atoms, thiol, hydroxyl, thioalkoxy of from 1 to 6 carbon atoms and —C(O)$R^7$ where $R^7$ is selected from the group consisting of hydrogen and alkyl of from 1 to 6 carbon atoms,
   substituted aryl of from 6 to 14 carbon atoms having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)$R^6$ where $R^6$ is selected from the group consisting of hydrogen and alkyl of from 1 to 6 carbon atoms, and
   substituted alkyl having from 7 to 20 carbon atoms and having one to three substituents on the aryl moiety independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)$R^7$ where $R^7$ is selected from the group consisting of hydrogen and alkyl of from 1 to 6 carbon atoms,
   substituted heteroaryl of from 2 to 5 carbon atoms and from 1 to 3 hetero atoms selected from the group consisting of nitrogen, sulfur and oxygen having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)$R^7$ where $R^7$ is selected from the group consisting of hydrogen and alkyl of from 1 to 6 carbon atoms;

$R^2$ is selected from the group consisting of hydrogen, hydroxyl, halo, —$OSO_3H$ and —OP(O)(OH)$_2$;

$R^3$ is selected from the group consisting of hydrogen, hydroxyl, halo, —$OSO_3H$ and —OP(O)(OH)$_2$;

$R^4$ is selected from the group consisting of hydroxyl, halo and —O-L-fucosyl;

$R^5$ is selected from the group consisting of hydrogen, L-fucose and L-fucose substituted at the 2, 3, and/or 4-positions with a substituent selected from the group consisting of halo, hydrogen, alkoxy, —$OSO_3H$ and —OP(O)(OH)$_2$;

$R^7$ is selected from the group consisting of hydrogen, hydroxy, —OS(O)$_3$H, —OP(O)(OH)$_2$, halo, azido, —$NH_2$, —NHC(O)$R^6$, and -fuc(C)amido, wherein $R^6$ is selected from the group consisting of
   alkly of from 1 to 6 carbon atoms,
   cyclokyl of from 3 to 6 carbon atoms,
   aryl of from 6 to 14 carbon atoms,
   alkaryl of from 7 to 20 carbon atoms,
   heteroaryl of from 1 to 8 carbon atoms and from 1 to 4 hetero atoms selected from the group consisting of nitrogen, sulfur and oxygen,
   heterocyclic of from 1 to 8 carbon atoms and from 1 to 4 hetero atoms selected from nitrogen, sulfur or oxygen within the ring
   substituted alkyl of from 1 to 6 carbon atoms having one to three substituents independently selected from the group consisting of halo, nitro, cyano, carboxyl, amino, alkylamine of from 1 to 6 carbon atoms, alkoxy of from 1 to 6 carbon atoms, thiol, hydroxyl, thioalkoxy of from 1 to 6 carbon atoms and —C(O)$R^7$ where $R^7$ is selected from the group consisting of hydrogen and alkyl of from 1 to 6 carbon atoms,
   substituted aryl of from 6 to 14 carbon atoms having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)$R^7$ where $R^7$ is selected from the group consisting of hydrogen and alkyl of from 1 to 6 carbon atoms, and
   substituted alkaryl having from 7 to 20 carbon atoms and having one to three substituents on the aryl moiety independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)$R^7$ where $R^7$ is selected from the group consisting of hydrogen and alkyl of from 1 to 6 carbon atoms,
   substituted heteroaryl of from 2 to 5 carbon atoms and from 1 to 3 hetero atoms selected from the group consisting of nitrogen, sulfur and oxygen having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)$R^7$ where $R^7$ is selected from the group consisting of hydrogen and alkyl of from 1 to 6 carbon atoms;

and X is selected from the group consisting of hydroxyl, chloro, —$OSO_3H$ or —OP(O)(OH)$_2$, and pharmaceutically acceptable salts thereof with the proviso that when $R^2$ is hydroxyl, $R^1$ is —OH, $NH_2$, —$N_3$ or —NHC(O)$R^6$ where $R^6$ is alkyl of from 1 to 4 carbon atoms, $R^5$ is hydrogen, L-fucosyl, 4-sulfo-L-fucosyl or 4-phospho-L-fucosyl, $R^7$ is hydrogen, hydroxy, —OS(O)$_3$H, azido, —$NH_2$, —NHC(O)$R^6$ where $R^6$ is alkyl of from 1 to 4 carbon atoms, and X is hydroxy, —OSO$_3$H or —OP(O)OH$_2$ and pharmaceutical salts thereof, then $R^3$ is not hydroxyl, —OSO$_3$H or —OP(O)(OH)$_2$ and pharmaceutical salts thereof.

In particular, the compounds disclosed in either International Patent Application Nos. WO 92/22564 and WO 93/24506 are specifically excluded from the compounds of formula I and II of this application.

Preferably, R is an aglycon of from 1 to 20 carbon atoms, more preferably R is an aglycon of from 1 to 10 carbon atoms and still more preferably is selected from the group consisting of —(CH$_2$)$_8$COOCH$_3$, —(CH$_2$)$_5$OCH$_2$CH═CH$_2$ and —(CH$_2$)$_8$CH$_2$OH.

Preferably, $R^1$ is fuc(C)amido or —NHC(O)R$^6$ where $R^6$ is alkyl containing 1 to 4 carbon atoms, cycloalkyl containing 5 or 6 carbon atoms, phenyl, substituted phenyl having one or two substituents independently selected from acetyl, nitro, or amino. More preferably, $R^1$ is —NHC(O)R$^6$ where $R^6$ is phenyl, o-nitrophenyl and p-nitrophenyl.

$R^2$ is preferably selected from the group consisting of hydroxyl, chloro and hydrogen. More preferably, $R^2$ is hydroxyl or hydrogen.

Preferably, $R^3$ is selected from the group consisting of hydroxy, chloro and deoxy. More preferably, $R^3$ is chloro or deoxy.

$R^5$ is preferably L-fucose.

X is preferably —OSO$_3$H, —OP(O)OH$_2$ or a pharmaceutically acceptable salt thereof. More preferably, X is —OSO$_3$H or a pharmaceutically acceptable salt thereof.

Preferred compounds for use in this invention include, by way of example, 8-methoxycarbonyloctyl-2-benzamido-3-O-(α-L-fucopyranosyl)-4-O-[3-O-sulfo-β-D-galactopyranosyl]-2-deoxy-β-D-glucopyranoside 8-methoxycarbonyloctyl-2-p-nitrobenzamido-3-O-(α-L-fucopyranosyl)-4-O-[3-O-sulfo-β-D-galactopyranosyl]-2-deoxy-β-D-glucopyranoside 8-methoxycarbonyloctyl-2-o-acetylbenzamido-3-O-(α-L-fucopyranosyl)-4-O-[3-O-sulfo-β-D-galactopyranosyl]-2-deoxy-β-D-glucopyranoside 8-methoxycarbonyloctyl-2-cyclohexamido-3-O-(α-L-fucopyranosyl)-4-O-[3-O-sulfo-β-D-galactopyranosyl]-2-deoxy-β-D-glucopyranoside 8-methoxycarbonyloctyl-2-fuc(C)amido-3-O-(α-L-fucopyranosyl)-4-O-[3-O-sulfo-β-D-galactopyranosyl]-2-deoxy-β-D-glucopyranoside 8-methoxycarbonyloctyl-2-p-nitrobenzamido-4-O-(β-D-galactopyranosyl)-2-deoxy-β-D-glucopyranoside 8-methoxycarbonyloctyl-4-O-(4-O-sulfo-β-D-galactopyranosyl)-β-D-glucopyranoside 8-methoxycarbonyloctyl-4-O-(4-O-phospho-β-D-galactopyranosyl)-β-D-glucopyranoside 8-methoxycarbonyloctyl-2-acetamido-3-O-(α-L-fucopyranosyl)-4-O-[3,4,6-tri-O-sulfo-β-D-galactopyranosyl]-2-deoxy-β-D-glucopyranoside 8-methoxycarbonyloctyl-2-acetamido-3-O-(α-L-fucopyranosyl)-4-O-[3-O-sulfo-2-O-(α-L-fucopyranosyl)-β-D-galactopyranosyl]-2-deoxy-β-D-glucopyranoside 8-methoxycarbonyloctyl-2-acetamido-3-O-(α-L-fucopyranosyl)-4-O-[6-chloro-6-deoxy-3-O-sulfo-β-D-galactopyranosyl)]-2-deoxy-β-D-glucopyranoside 8-methoxycarbonyloctyl-2-acetamido-3-O-(α-L-fucopyranosyl)-4-O-[6-deoxy-3-O-sulfo-β-D-galactopyranosyl]-2-deoxy-β-D-glucopyranoside 8-methoxycarbonyloctyl-2-acetamido-3-O-(α-L-fucopyranosyl)-4-O-[4-chloro-4-deoxy-3-O-sulfo-β-D-galactopyranosyl]-2-deoxy-β-D-glucopyranoside 8-methoxycarbonyloctyl-2-acetamido-3-O-α-L-fucopyranosyl)-4-O-[4,6-dichloro-4,6-dideoxy-3-O-sulfo-β-D-galactopyranosyl]-2-deoxy-β-D-glucopyranoside 8-methoxycarbonyloctyl-2-acetamido-3-O-(α-L-fucopyranosyl)-4-O-[4,6-dideoxy-3-O-sulfo-β-D-galactopyranosyl]-2-deoxy-β-D-glucopyranoside 2-acetamido-2-deoxy-3-O-(α-L-fucopyranosyl)-4-O-[3-O-sulfo-β-D-galactopyranosyl]-β-D-glucopyranosyl azide 2-acetamido-2-deoxy-3-O-(α-L-fucopyranosyl)-4-O-[3-O-sulfo-β-D-galactopyranosyl]-β-D-glucopyranosyl amine 2-acetamido-2-deoxy-3-O-(α-L-fucopyranosyl)-4-O-[3-O-sulfo-β-D-galactopyranosyl]-β-D-glucopyranosyl benzamide 2-acetamido-2-deoxy-3-O-(α-L-fucopyranosyl)-4-O-[3-O-sulfo-β-D-galactopyranosyl]-β-D-glucopyranosyl p-nitrobenzamide 2-acetamido-2-deoxy-3-O-(α-L-fucopyranosyl)-4-O-[3-O-sulfo-β-D-galactopyranosyl]-β-D-glucopyranosyl butyramide 2-acetamido-2-deoxy-3-O-(α-L-fucopyranosyl)-4-O-[3-O-sulfo-β-D-galactopyranosyl]-β-D-glucopyranosyl acetamide 2-acetamido-2-deoxy-3-O-(α-L-fucopyranosyl)-4-O-[3-O-sulfo-β-D-galactopyranosyl]-β-D-glucopyranosyl stearamide 2-acetamido-2-deoxy-3-O-(α-L-fucopyranosyl)-4-O-[3-O-sulfo-β-D-galactopyranosyl]-β-D-glucopyranosyl L-serine 2-acetamnido-2-deoxy-3-O-(4-deoxy-α-L-fucopyranosyl)-4-O-(3-O-sulfo-β-D-galactopyranosyl)-β-D-glucopyranoside 8-methoxycarbonyloctyl 2-acetamido-2-deoxy-3-O-(4-O-sulfo-α-L-fucopyranosyl)-4-O-(3-O-sulfo-β-D-galactopyranosyl)-β-D-glucopyranoside 8-methoxycarbonyloctyl 2-acetamido-2-deoxy-3-O-(3-O-sulfo-α-L-fucopyranosyl)-4-O-(3-O-sulfo-β-D-galactopyranosyl)-β-D-glucopyranoside 8-methoxycarbonyloctyl 2-acetamido-2-deoxy-3-O-(3-O-methyl-α-L-fucopyranosyl)-4-O-(3-O-sulfo-β-D-galactopyranosyl)-β-D-glucopyranoside phenylalanine amido-2-(fuc(C)-amido)-4-O-[3-O-sulfo-β-D-galactopyranosyl]-β-D-glucopyranoside 2-benzamido-2-deoxy-3-O-(4-deoxy-α-L-fucopyranosyl)-4-O-(3-O-sulfo-β-D-galactopyranosyl)-β-D-glucopyranosyl benzamide cyclohexylalanine amido-2-(fuc(C)-amido)-4-O-[3-O-sulfo-β-D-galactopyranosyl]-β-D-glucopyranoside tryptophanamido-2-fuc(C)-amido-4-O-(3-O-sulfo-β-D-galactopyranosyl)-β-D-glucopyranoside acetamido-2-(fuc(C)-amido-4-O-[3-O-sulfo-β-D-galactopyranosyl)-2-deoxy-β-D-glucopyranoside benzamido 2-(fuc(C)-amido)-4-O-[3-O-sulfo-β-D-galactopyranosyl])-2-deoxy-β-D-glucopyranoside 8-methoxycarbonyloctyl-2-acetamido-3-O-(α-L-fucopyranosyl)-4-O-[3-O-sulfo-β-D-galactopyranosyl]-6-O-sulfo-β-D-glucopyranoside 8-methoxycarbonyloctyl 2-acetamido-3-O-(α-L-fucopyranosyl)-4-O-[4,6-dichloro-dideoxy-3-O-sulfo- β-D-galactopyranosyl]-6-benzamido-2,6-dideoxy-β-D-glucopyranoside 8-methoxycarbonyloctyl-2-acetamido-3-O-(α-L-fucopyranosyl)-4-O-[4,6-dideoxy-3-O-sulfo-β-D-galactopyranosyl]-6-benzamido-2,6-dideoxy-β-D-glucopyranoside 8-methoxycarbonyloctyl-2-acetamido-3-O-(α-L-fucopyranosyl)-4-O-[3-O-sulfo-β-D-galactopyranosyl]-6-amino-2,6-dideoxy-β-D-glucopyranoside 8-methoxycarbonyloctyl-2-acetamido-3-O-(α-L-fucopyranosyl)-4-O-[3-O-sulfo-β-D-galactopyranosyl]-6-benzamido-2,6-dideoxy-β-D-glucopyranoside 8-methoxycarbonyloctyl-2-acetamido-3-O-(α-L-fucopyranosyl)-4-O-[3-O-sulfo-β-D-galactopyranosyl]-6-chloro-2,6-dideoxy-β-D-glucopyranoside 2-acetamido-3-O-(α-L-fucopyranosyl)-4-O-[4,6-dichloro-dideoxy-3-O-sulfo-β-D-galactopyranosyl]-2-deoxy-β-D-glucopyranosyl azide 2-acetamido-3-O-(α-L-fucopyranosyl)-4-O-[4,6-dideoxy-3-O-sulfo-β-D-galactopyranosyl]-2-deoxy-β-D-glucopyranosyl azide 2-benzamido-2-deoxy-3-O-(α-L-fucopyranosyl)-4-O-[3-O-sulfo-β-D-galactopyranosyl]-β-D-glucopyranoside benzamide 8-methoxycarbonyloctyl-2-amino-3-O-(α-L-fucopyranosyl)-4-O-[4,6-dichloro-dideoxy-3-O-sulfo-β-D-galactopyranosyl]-2-deoxy-β-D-glucopyranoside 8-methoxycarbonyloctyl-2-benzamido-3-O-(α-L-fucopyranosyl)-4-O-[4,6-dichloro-dideoxy-3-O-sulfo-β-D-galactopyranosyl]-2-deoxy-β-D-glucopyranoside 8-methoxycarbonyloctyl-2-benzamido-3-O-(α-L-fucopyranosyl)-4-O-[4,6-dideoxy-3-O-sulfo-β-D-galactopyranosyl]-2-deoxy-β-D-glucopyranoside 8-methoxycarbonyloctyl-2-amino-4-O-(α-L-fucopyranosyl)-3-O-[3-O-sulfo-β-D-galactopyranosyl]-2-deoxy-β-D-glucopyranoside 8-methoxycarbonyloctyl-2-benzamido-4-O-(α-L-fucopyranosyl)-3-O-[3-O-sulfo-β-D-galactopyranosyl]-2-deoxy-β-D-glucopyranoside 8-methoxycarbonyloctyl-2-p-nitrobenzamido-4-O-(α-L-fucopyranosyl)-3-O-[3-O-sulfo-β-D-galactopyranosyl]-2-deoxy-β-D-glucopyranoside 8-methoxycarbonyloctyl-2-(fuc(c)-amido)-4-O-[3-O-sulfo-β-D-galactopyranosyl]-2-deoxy-β-D-glucopyranoside as well as pharmaceutically acceptable salts thereof and further including the above compounds wherein the aglycon is replaced by an aglycon of from 1 to 20 carbon atoms.

This invention further provides a pharmaceutical composition suitable for administration to a mammal which composition comprises a pharmaceutically inert carrier and an effective inflammation-reducing amount of an oligosaccharide glycoside of Formula I or II.

This invention additionally provides a method of reducing antigen-induced inflammation in a mammal which method comprises administering to said mammal an effective inflammation-reducing amount of a oligosaccharide glycoside of Formula I or II.

BRIEF DESCRIPTION OF THE DRAWINGS

FIGS. 15A and 15B (collectively FIG. 15) illustrate a reaction scheme for the synthesis of 8-methoxycarbonyloctyl 2-N-acetamido-2-deoxy-3-O-(3-O-methyl-α-L-fucopyranosyl)-4-O-(3-O-sulfo-β-D-galactopyranosyl)-β-D-glucopyranoside.

DETAILED DESCRIPTION OF THE PREFERRED EMBODIMENTS

Figure 1A:
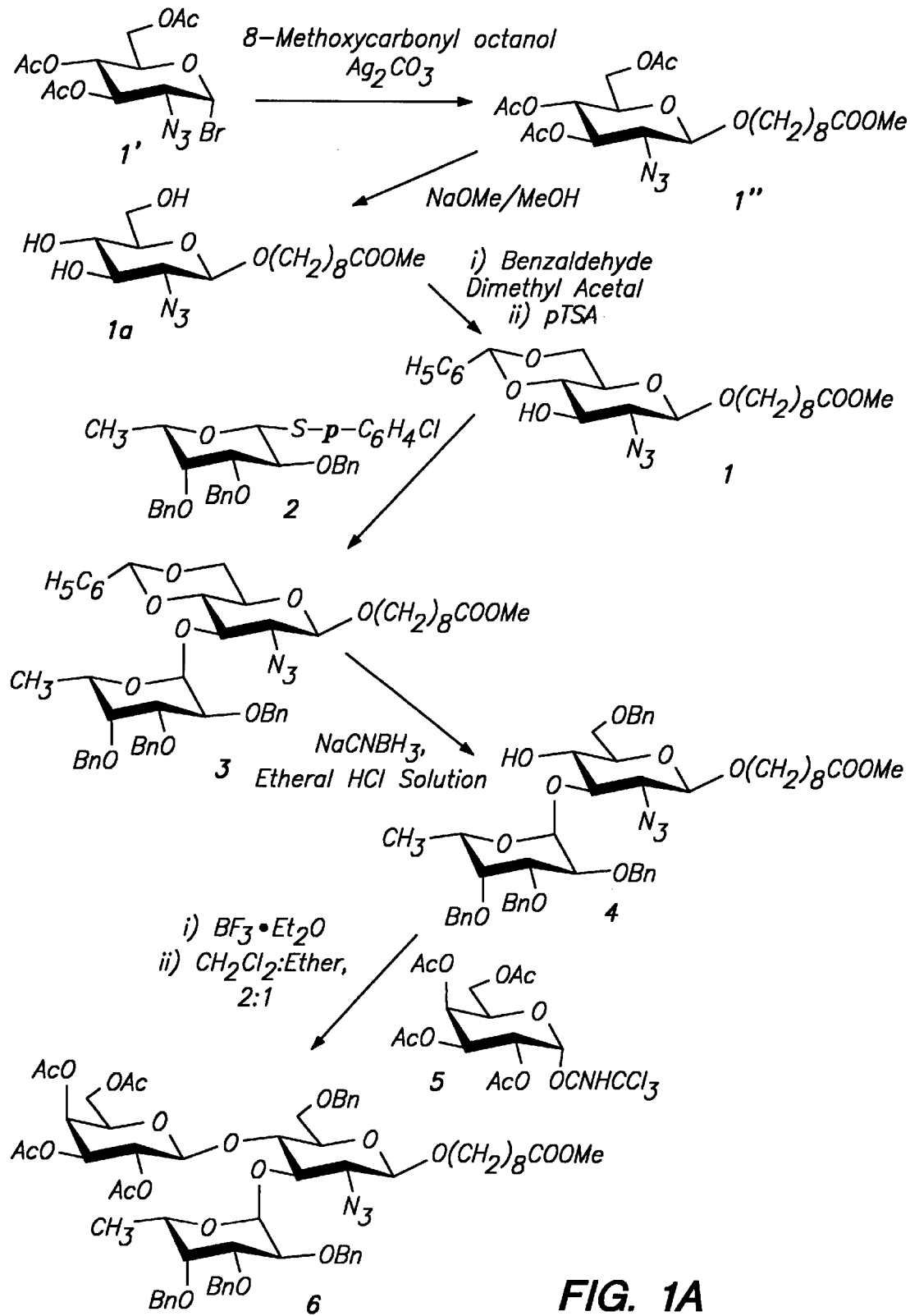
FIGS. 1A, 1B, 1C and 1D (collectively FIG. 1) illustrate a reaction scheme for the synthesis of 2-substituted 3'-sulfo Lewis$^x$-OR compounds [R=—$(CH_2)_8CO_2CH_3$].
Figure 1B:
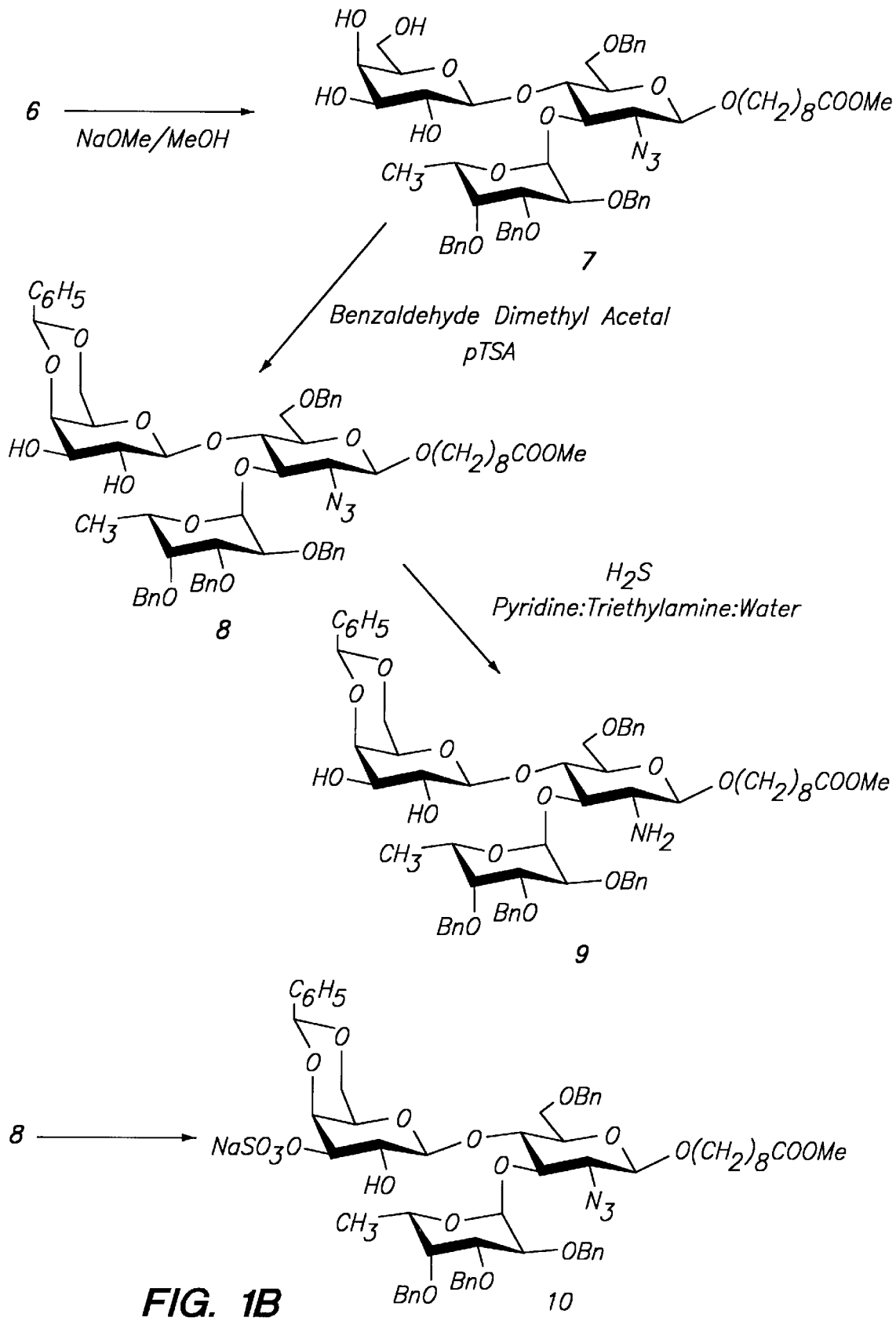
Figure 1C:
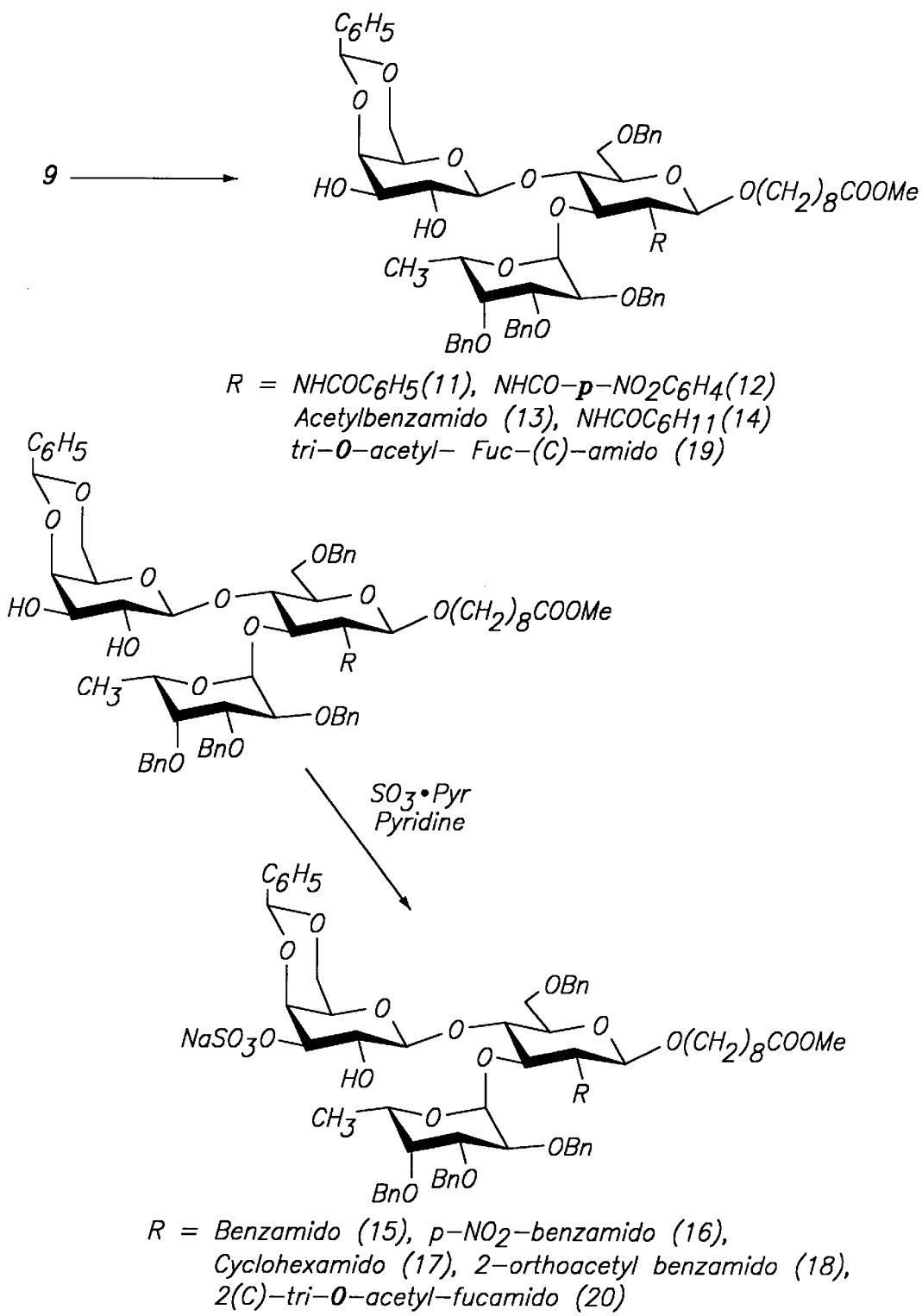
Figure 1D:
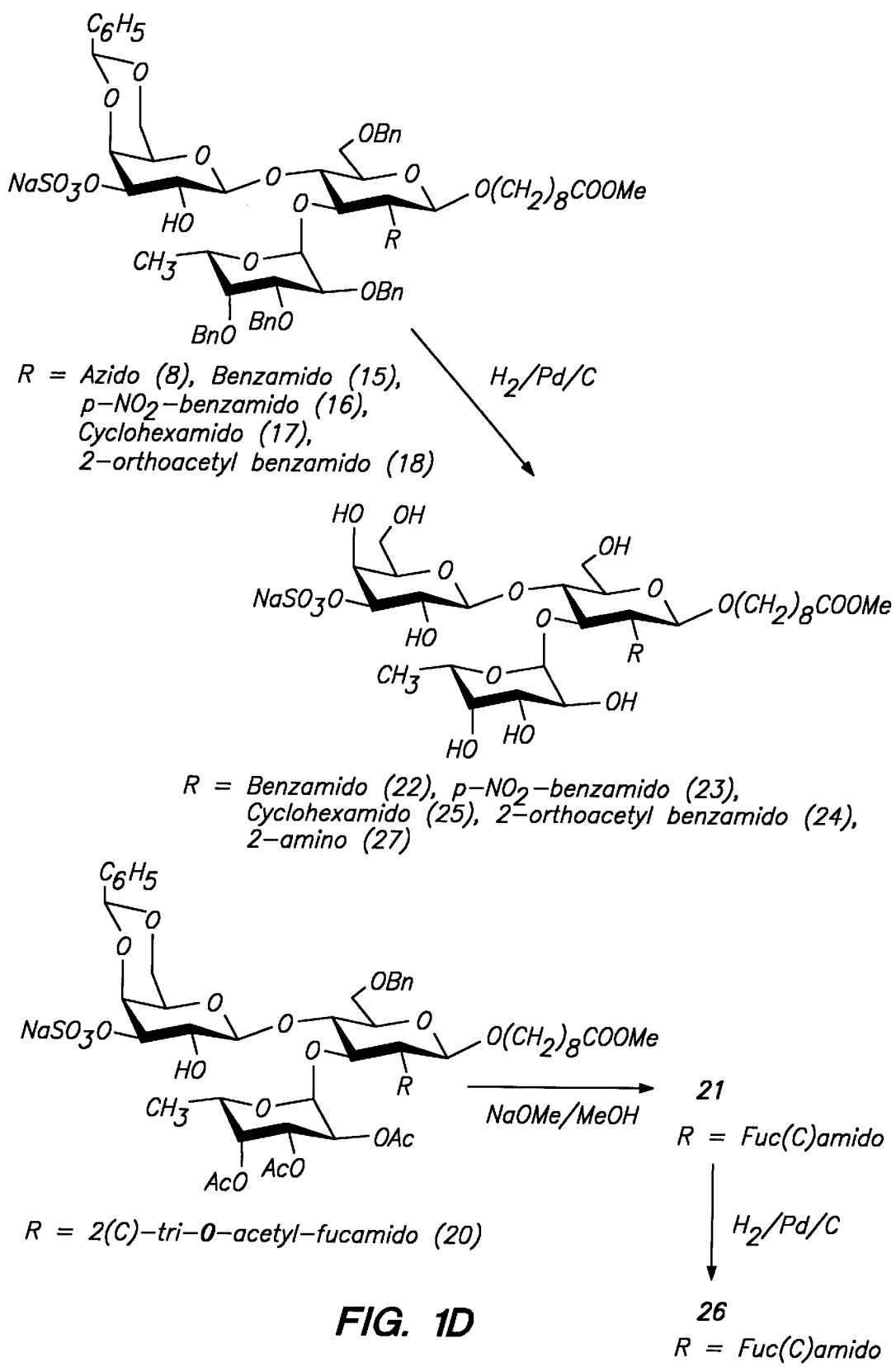

This invention is directed to novel oligosaccharide glycosides having mammalian immunosuppressive and tolerogenic properties.

However, prior to discussing this invention in further detail, the following terms will first be defined.

Definitions

As used herein the following terms have the definitions given below:

The term "cell-mediated immune response in a mammal" refers to those mammalian immune responses which are mediated by cell—cell interactions. Included within this term are cell mediated inflammatory responses to an antigen such as DTH responses as well as cell-mediated inflammatory responses arising from injury such as frost-bite injury, reperfusion injury, adult respiratory distress syndrome, and the like. Preferably, the cell-mediated immune response is a leucocyte-mediated response.

The term "antigen" refers to any protein, peptide, carbohydrate, nucleic acid or other non-endogenous substance which when exposed to a mammal induces an immune response in that mammal.

Disease conditions caused by antigen exposure include, by way of example, psoriasis, asthma, dermatitis, rheumatoid arthritis, delayed type hypersensitivity, inflammatory bowel disease, multiple sclerosis, viral pneumonia, bacterial pneumonia, and the like.

The term "sensitized mammal" or "antigen-sensitized mammal" refers to those mammals which have been previously exposed to an antigen and, accordingly, their immune systems have become educated to that antigen. Typically, initial exposure of an antigen to a mammal primes or educates the mammal's immune response to later exposure to that antigen with minimal inflammation during such initial exposure.

The term "secondary immune response" refers to the effector phase of a mammal's immune response to an antigen to which it has been previously been sensitized. A mammal's secondary immune response is typically accompanied by inflammation at the point of antigen exposure.

The term "period for maximal inflammation" refers to the period of time typically required to achieve maximal inflammation to a specific antigen exposure. This period of time depends on several factors such as the specific antigen to which the mammal has been exposed, the particular mammalian species exposed to the antigen, etc. Accordingly, the period of time required to effect maximal antigen induced inflammation in a sensitized mammal will vary for, by way of example, asthma as opposed to rheumatoid arthritis.

The term "Lewis$^x$" or "Le$^x$" refers to the trisaccharide βGal(1→4)βFuc(1→3)βGlcNAc.

The term "Lewis$^c$" or "Le$^c$" refers to the disaccharide βGal(1→3)βGlcNAc.

The term "aglycon of at least one carbon atom" refers to non-saccharide containing residues having at least one carbon atom. Preferably, the aglycon moiety, R, has from 1 to 20 carbon atoms or is selected from the group consisting of —(A)—Z wherein A represents a covalent bond, an alkylene group of from 2 to 10 carbon atoms, a moiety of the formula —(CH$_2$CR$^8$R$^8$)$_n$—, and a moiety of the formula —(CH$_2$CR$^8$R$^8$G)$_n$— wherein n is an integer equal to 1 to 5, each R$^8$ is independently selected from the group consisting of hydrogen, alkyl of from 1 to 6 carbon atoms, phenyl and phenyl substituted with 1 to 3 substituents selected from the group consisting of amine, hydroxyl, halo, alkyl of from 1 to 4 carbon atoms and alkoxy of from 1 to 4 carbon atoms and G is selected from the group consisting of —O—, —S— and —NH—; and Z is selected from the group consisting of hydrogen, methyl, phenyl, nitrophenyl, aminophenyl and, when G is not oxygen, sulfur or nitrogen and A is not a bond, then Z is also selected from the group consisting of —OH, —SH, —NH$_2$, —NHR$^9$, —N(R$^9$)$_2$, —C(O)OH, —C(O)OR$^9$, —C(O)NH—NH$_2$, —C(O)NH$_2$, —C(O)NHR$^9$, —C(O)N(R$^9$)$_2$, and —OR$^{10}$ wherein each R$^9$ is independently alkyl of from 1 to 4 carbon atoms and R$^{10}$ is an alkenyl group of from 3 to 10 carbon atoms.

Numerous aglycons are known in the art. For example, an aglycon comprising a para-nitrophenyl group (i.e., —YR= —OC$_6$H$_4$-p-NO$_2$) has been disclosed by Ekborg, et al.[10] At the appropriate time during synthesis, the nitro group is reduced to an amino group which can be protected as N-tifluoroacetamido. The trifluoroacetamido group can later be removed thereby unmasking the amino group which can then be used to further functionalize the aglycon group.

An aglycon containing sulfur is disclosed by Dahmen, et al.[11] Specifically, this aglycon is derived from a 2-bromoethyl group which, in a substitution reaction with thionucleophiles, has been shown to lead to aglycons possessing a variety of terminal functional groups such as —YCH$_2$CH$_2$SCH$_2$CO$_2$CH$_3$ and —YCH$_2$CH$_2$SC$_6$H$_4$-p-NH$_2$.

Rana, et al.12 discloses a 6-trifluoroacetamidohexyl aglycon (—Y—(CH$_2$)$_6$—NHCOCF$_3$) in which the trifluoroacetamido protecting group can be removed unmasking the primary amino group which can then be used to further functionalize the aglycon group.

Other exemplification of known aglycons include the 7-methoxycarbonyl-3,6-dioxaheptyl aglycon[13] (—YCH$_2$—CH$_2$)OCH$_2$CO$_2$CH$_3$; the 2-(4-methoxycarbonylbutanecarboxamido)ethyl[14] (—YCH$_2$CH$_2$NHC(O)(CH$_2$)$_4$CO$_2$CH$_3$); and the allyl aglycon[15] (—YCH$_2$CH=CH$_2$) which, by radical co-polymerization with an appropriate monomer, leads to co-polymers; other allyl aglycons[16] are known [e.g., —Y(CH$_2$CH$_2$O)$_2$CH$_2$CH=CH$_2$]. Additionally, allyl aglycons can be derivatized in the presence of 2-aminoethanethiol[17] to provide for aglycons —YCH$_2$CH$_2$CH$_2$SCH$_2$CH$_2$NH$_2$. Still other aglycons are illustrated hereinbelow.

Additionally, as shown by Ratcliffe et al.[31], the R group can be an additional saccharide-OR$^{11}$ or an oligosaccharide-OR$^{11}$ containing an aglycon at the reducing sugar terminus.

Still further, when Y is —NH—, the aglycon can be the residue of an amino acid or a peptide of from 2 to 10 amino acids in length. Amino acids include any of the naturally occurring amino acids, as well as synthetic analogs and derivatives thereof. α-Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine).

One of skill in the art will appreciate that the term "amino acid" can also include β-, γ-, δ-, and ω-amino acids, and the like. Unnatural amino acids are also known in the art, as set forth in, for example, Williams (ed.), *Synthesis of Optically Active α-Amino Acids*, Pergamon Press (1989); Evans et al., *J. Amer. Chem. Soc.*, 112:4011–4030 (1990); Pu et al., *J.*

*Amer. Chem. Soc.*, 56:1280–1283 (1991); and Williams et al., *J. Amer. Chem. Soc.*, 113:9276–9286 (1991) which are incorporated herein by reference in their entirety.

As used herein, the twenty conventional amino acids and their abbreviations follow conventional usage. Amino acid residues are abbreviated as follows: Phenylalanine is Phe or F; Leucine is Leu or L; Isoleucine is Ile or I; Methionine is Met or M; Norleucine is Nle; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any amino acid. Stereoisomers (e.g., D-amino acids) of the twenty conventional amino acids, unnatural amino acids such as $\alpha,\alpha$-disubstituted amino acids, N-alkyl amino acids, and other unconventional amino acids are also suitable components for compounds described herein. Examples of unconventional amino acids include: 4-hydroxyproline, O-phosphoserine, N-acetylserine, N-formylmethionine, 3-methylhistidine, 5-hydroxylysine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Preferably, the aglycon moiety is a hydrophobic group and most preferably, the aglycon moiety is a hydrophobic group selected from the group consisting of $-(CH_2)_8COOCH_3$, $-(CH_2)_5OCH_2CH=CH_2$ and $-(CH_2)_8CH_2OH$.

The term "oligosaccharide" refers to a carbohydrate structure having from 2 to about 7 saccharide units. The particular saccharide units employed are not critical and include, by way of example, all natural and synthetic derivatives of glucose, galactose, N-acetylglucosamine, N-acetylgalactosamine, fucose, sialic acid, 3-deoxy-D,L-octulosonic acid, and the like. In addition to being in their pyranose form, all saccharide units described herein are in their D form except for fucose which is in its L form.

The term "pharmaceutically acceptable salts" includes the pharmaceutically acceptable addition salts of the compounds of Formula I or Formula II derived from a variety of organic and inorganic counter salts well known in the art and include, by way of example only, sodium, potassium, calcium, magnesium, ammonium, tetralkylammonium, chloride, fluoride, bromide, hydroxide and the like.

The term "sulfate" refers to the $-O-S(O_2)-OH$ group, which readily forms pharmaceutically acceptable salts thereof.

The term "phosphate" refers to the group $-O-P(O)-OH_2$, which readily forms pharmaceutically acceptable salts thereof (e.g., $-O-P(O)-(O^-Na^+)_2$).

The term "removable blocking group" or "blocking group" or "protecting group" refers to any group which when bound to one or more hydroxyl and/or amine groups of oligosaccharide glycoside compounds and oligosaccharide glycoside related compounds prevents reactions from occurring at these hydroxyl and/or amine groups and which protecting group can be removed by conventional chemical or enzymatic steps to reestablish the hydroxyl or amine group. Typically, the particular removable blocking group employed is not critical and preferred removable hydroxyl blocking groups include conventional substituents such as benzyl, acetyl, benzoyl, chloroacetyl, benzylidene, t-butyldiphenylsilyl, t-butyldimethylsilyl and any other group that can be introduced either enzymatically or chemically onto a hydroxyl functionality and later selectively removed either by enzymatic or chemical methods in mild conditions compatible with the nature of the product. Preferred amine blocking groups include these well known in the art such as carboxybenzyloxy (CBZ), t-butyloxy carbonyl (t-Boc), and any other group that can be introduced either enzymatically or chemically onto an amine functionality and later selectively removed either by enzymatic or chemical methods in mild conditions compatible with the nature of the product.

"Alkyl" refers to monovalent alkyl groups having from 1 to 6 carbon atoms. This term is exemplified by groups such as methyl, ethyl, n-propyl, iso-propyl, n-butyl, iso-butyl, n-hexyl, and the like.

"Alkylene" refers to divalent alkylene groups preferably having from 1 to 10 carbon atoms and more preferably 2 to 10 carbon atoms. This term is exemplified by groups such as methylene ($-CH_2-$), ethylene ($-CH_2CH_2-$), the propylene isomers (e.g., $-CH_2CH_2CH_2-$ and $-CH(CH_3)CH_2-$) and the like.

"Alkaryl" refers to -alkylene-aryl groups of from 7 to 20 carbon atoms preferably having from 1 to 10 carbon atoms in the alkylene moiety and from 6 to 10 carbon atoms in the aryl moiety. Such alkaryl groups are exemplified by benzyl, phenethyl and the like.

"Alkoxy" refers to the group "alkyl—O—". Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like.

"Cycloalkyl" refers to cyclic alkyl groups of from 3 to 8 carbon atoms having a single cyclic ring or multiple condensed rings which can be optionally substituted with from 1 to 3 alkyl groups. Preferred cycloalkyl groups include those having from 3 to 6 carbon atoms. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

"Halo" or "halogen" refers to fluoro, chloro, bromo and iodo and preferably is either chloro or bromo.

"Heteroaryl" refers to a monovalent aromatic carbocyclic group of from 1 to 8 carbon atoms and 1 to 4 heteroatoms selected from oxygen, nitrogen and sulfur within the ring. Preferred heteroaryl groups have from 2 to 5 carbon atoms and 1 to 3 heteroatoms selected from oxygen, nitrogen and sulfur.

"Heterocycle" or "heterocyclic" refers to a monovalent saturated or unsaturated group having a single ring or multiple condensed rings, from 1 to 8 carbon atoms and from 1 to 4 hetero atoms selected from nitrogen, sulfur or oxygen within the ring.

Unless otherwise constrained by the definition for the heterocyclic substituent, such heterocyclic groups can be optionally substituted with 1 to 3 substituents selected from the group consisting of alkyl, alkoxy, aryl, aryloxy, halo, nitro, heteroaryl, thioalkoxy, thioaryloxy and the like. Such heterocyclic groups can have a single ring or multiple condensed rings.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline and the like.

"Thiol" refers to the group —SH.

"Thioalkoxy" refers to the groups —S-alkyl.

General Synthetic Methodology

Chemical methods for the synthesis of the oligosaccharides are known in the art. These oligosaccharides are generally assembled using suitably protected individual monosaccharides and/or suitably protected individual disaccharides intermediates.

The specific methods employed are generally adapted and optimized for each individual structure to be synthesized. In general, the chemical synthesis of all or part of these oligosaccharides first involves formation of a glycosidic linkage on the anomeric carbon atom of the reducing sugar. Specifically, an appropriately protected form of a naturally occurring or of a chemically modified glucose structure (the glycosyl donor) is selectively modified at the anomeric center of the reducing unit so as to introduce a leaving group comprising halides, trichloroacetimidate, acetyl, thioglycoside, etc. The donor is then reacted under catalytic conditions well known in the art with an aglycon or an appropriate form of a carbohydrate acceptor which possess one free hydroxyl, free thiol or primary/secondary amino group at the position where the glycosidic linkage is to be established. A large variety of aglycon moieties are known in the art and can be attached with the proper configuration to the anomeric center of the reducing unit. Appropriate use of compatible blocking groups, well known in the art of carbohydrate synthesis, will allow selective modification of the synthesized structures or the further attachment of additional sugar units or sugar blocks to the acceptor structures.

After formation of the glycosidic linkage, the saccharide glycoside can be used to effect coupling of additional saccharide unit(s) or chemically modified at selected positions or, after conventional deprotection, used in an enzymatic synthesis. In general, chemical coupling of a naturally occurring or chemically modified saccharide unit to the saccharide glycoside is accomplished by employing established chemistry well documented in the literature. See, for example, Okamoto et al.[25], Abbas et al.[26], Paulsen[27], Schmidt[28], Fugedi et al.[29], Kameyama et al.[30] and Ratcliffe, et al.[31]

The figures attached hereto illustrate a variety of complete chemical synthetic schemes used for preparing representative oligosaccharide glycosides of this invention. By necessity, these schemes illustrate the synthesis of specific compounds of this invention. However, it is well within the skill of those in the art to adapt these synthetic schemes to prepare any of the compounds of this invention. Moreover, it will be appreciated by those skilled in the art that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

A. 2-Amino and 2-Amido 3'-Sulfo Lewis$^x$-OR Derivatives

FIG. 1 illustrates the synthesis of 2-substituted 3'-sulfo Lewis$^x$ derivatives. As shown in this figure, 3'-sulfo-Lewis$^x$ derivatives having an amino or an amido substituent at the 2-position are prepared beginning with 3,4,6-tri-O-acetyl-2-azido-2-deoxy-α-D-glucopyranosyl bromide (1'), the synthesis of which is known in the art[19-20].

Compound 1' is first converted to the aglycon by reaction with from about 1.1 to about 5 equivalents of HYR, e.g., $HO(CH_2)_8COOCH_3$, by well known chemistry. In a preferred embodiment, compound 1' is reacted with 8-methoxycarbonyloctanol in anhydrous dichloromethane containing molecular sieves and a catalyst, such as silver carbonate, to provide intermediate 1" in 90% yield as a crystalline solid. This reaction is generally conducted at a temperature ranging from −20° C. to −10° C. for a period of 3 to 4 hours.

The 3, 4 and 6 hydroxyl groups of compound 1" are then deprotected by reaction of compound 1" with sodium methoxide in methanol to give 8-methoxycarbonyloctyl-2-azido-2-deoxy-β-D-glucopyranoside (1a).

The 4 and 6 hydroxy groups of compound 1a are then protected as the 4,6-O-benzylidene derivative by reaction of compound 1a with benzaldehyde dimethylacetal in the presence of an acid catalyst, such as p-toluenesulfonic acid, to give compound 1. This reaction is typically conducted at room temperature in an anhydrous inert solvent, such as acetonitrile, and is generally complete in about 0.5 to 5 hours.

The unprotected hydroxyl group of compound 1 is then glycosylated with p-chlorophenyl tribenzyl thiofucose (2). Compound 2 is well known in the art and may be prepared by the procedures described by Srivastava et al.[23] The glycosylation reaction is typically conducted by contacting compound 1 with about 1 to 2 equivalents, preferably 1.2 equivalents, of compound 2 in the presence of a cupric bromide/dimethylformamide catalyst and tetraethylammonium bromide. This reaction is generally conducted at room temperature in an anhydrous inert solvent, such dichloromethane, containing molecular sieves. The reaction is typically complete after about 7 to 15 hours and provides compound 3.

The 4,6-O-benzylidene group of compound 3 is then opened regioselectively to provide compound 4 having an unblocked hydroxyl group at the 4 position. Regioselective opening of the benzylidene group is affected by treatment of compound 3 with at least a molar equivalent, preferably an excess, of sodium cyanoborohydride or a similar hydride reducing agent, in the presence of an ethereal solution of hydrochloric acid. The reaction is typically conducted in a suitable inert solvent, such as tetrahydrofuran, and is preferably maintained under anhydrous conditions by, for example, the inclusion of molecular sieves. A pH indicator, such a methyl orange, is generally added to the reaction system and the reaction is generally conducted at a pH of about 3 or less. The reaction conditions are not critical and the conditions are selected so as to produce compound 4. In a preferred embodiment, about 2 to about 20, preferably 5 to 10 equivalents of sodium cyanoborohydride is employed at a reaction temperature of from about −15° C. to about 20° C. (preferably 0° C.) for a period of from about 1 to about 7 hours. The reaction generally provides compound 4 in about 60% yield.

Compound 4 is next converted to 8-methoxycarbonyloctyl-2-azido-3-O-(2,3,4-tri-O-benzyl-α-L-fucopyranosyl)-4-O-(β-D-galactopyranosyl)-6-O-benzyl-2-deoxy-β-D-glucopyranoside (7) by reaction with from about 1.1 to about 2 equivalents of O-(2,3,4,6-tetra-O-acetyl-α-D-galactopyranosyl)-trichloroacetirnidate (5) using conventional coupling conditions, followed by deacetylation of the resulting trisaccharide.

The coupling reaction is preferably conducted using an excess of boron trifluoride etherate relative to the galactose imidate and preferably using from about 1.1 to about 2 equivalents. The reaction is typically conducted at from about −30° C. to about 10° C. (preferably −10° C. to 0° C.) in a suitable anhydrous organic solvent such as dichloromethane or a 1:2 mixture of dichloromethane:ether.

Deacetylation is conducted using conventional reaction conditions, preferably using sodium methoxide in methanol, to provide compound 7.

The galactose unit of compound 7 is next converted to the 4,6-O-benzylidene derivative compound 8 by reaction of compound 7 with from about 1 to about 2 equivalents of benzaldehyde dimethylacetal. This reaction is preferably conducted in an inert organic solvent, such as acetonitrile, in the presence of an acidic catalyst, such as p-toluenesulfonic acid (pTSA). In a preferred embodiment, the reaction is conducted at a temperature of from about 0° C. to about 35° C. (preferably 15° C. to 25°) for from about 1 to about 5 hours. Standard work-up procedures provide compound 8 in about 76% yield.

The 2-azido group of compound 8 is then reduced to an amino group by contacting compound 8 with a saturated solution of hydrogen sulfide in a suitable solvent. In a preferred embodiment, the solvent comprises pyridine (2 parts), triethylamine (0.05 parts) and water (0.05 parts). This reaction is preferably conducted initially at 0° C. for about 2 hours and then at room temperature for about 5 to 15 hours, preferably for about 15 hours, to provide the amino derivative 9.

The amino group of 8-methoxycarbonyloctyl-2-amino-3-O-(2,3,4-tri-O-benzyl-α-L-fucopyranosyl)-4-O-[4,6-O-benzylidene-β-D-galactopyranosyl]-6-O-benzyl-2-deoxy-β-D-glucopyranoside (9) can then be acylated to form various 2-amido derivatives. Suitable acylating agents for use in this reaction include acyl halides, such as carboxylic acid chlorides and bromides; carboxylic acid anhydrides and carboxylic acids.

Preferred acylating agents are those having the formula W—C(O)R$^6$ where W is chloro or hydroxyl and R$^6$ is selected from the group consisting of alkyl of from 1 to 6 carbon atoms, cycloalkyl of from 3 to 8 carbon atoms, heterocyclic, aryl of from 6 to 14 carbon atoms, alkaryl of from 7 to 20 carbon atoms, heteroaryl of from 1 to 8 carbon atoms and from 1 to 4 hetero atoms selected from the group consisting of nitrogen, sulfur and oxygen, substituted alkyl of from 1 to 6 carbon atoms having one to three substituents independently selected from the group consisting of halo, nitro, cyano, carboxyl, amino, alkylamino of from 1 to 6 carbon atoms, alkoxy of from 1 to 6 carbon atoms, thiol, hydroxyl, thioalkoxy of from 1 to 6 carbon atoms and —C(O)R$^6$ where R$^6$ is selected from the group consisting of hydrogen and alkyl of from 1 to 6 carbon atoms, substituted aryl of from 6 to 14 carbon atoms having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^6$ where R$^6$ is selected from the group consisting of hydrogen and alkyl of from 1 to 6 carbon atoms, and substituted alkaryl having from 7 to 20 carbon atoms and having one to three substituents on the aryl moiety independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^6$ where R$^6$ is selected from the group consisting of hydrogen and alkyl of from 1 to 6 carbon atoms, substituted heteroaryl of from 2 to 5 carbon atoms and from 1 to 3 hetero atoms selected from the group consisting of nitrogen, sulfur and oxygen having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^6$ where R$^6$ is selected from the group consisting of hydrogen and alkyl of from 1 to 6 carbon atoms; is an alkyl group of from 1 to 6 carbon atoms.

Suitable acylating agents include, by way of example only, acetyl chloride, acetic anhydride, benzoyl chloride, p-nitrobenzoyl chloride, o-acetylbenzoic acid, cyclohexanecarboxylic acid, tri-O-acetyl-fucose(C)-carboxylic acid, azelaic acid, and stearic acid. Activated esters of such acids may also be employed.

When the acylating agent employed is an acyl halide, the acylation reaction is typically conducted by contacting compound 9 with about 1.5 to 5 equivalents of the acyl halide, such as benzoyl chloride, in a suitable solvent. A preferred solvent for this reaction is a mixture containing about 4 parts of methanol and 1 part of a saturated aqueous solution of sodium bicarbonate. The reaction is typically monitored by tlc and additional acyl halide may be added periodically until the reaction is complete. Generally, the reaction is conducted at a temperature of from about 0° to 22° C. for a period of about 1 to about 15 hours. When benzoyl chloride is employed as the acylating agent, the product of the reaction is compound 11; and when p-nitrobenzoyl chloride is employed, the product is compound 12.

Alternatively, the 2-amino group of compound 9 can be acylated using a carboxylic acid. This reaction is typically conducted by contacting compound 9 with about 1.5 to about 5 equivalents of the carboxylic acid in the presence of about 1.5 to about 5 equivalents of a coupling agent. Suitable coupling agents include, by way of example, 1-(3-dimethylaminopropyl)-3-ethylcarbodiimide hydrochloride and dicyclohexyl carbodiimide which provide for the activated ester. The reaction is generally conducted in an anhydrous inert solvent, such as dichloromethane, at room temperature for about 0.5 to about 24 hours. During this period, the reaction is typically monitored by tlc and additional amounts of the carboxylic acid and the coupling agent may be added periodically until the reaction is complete. When the carboxylic acid employed in this reaction is ortho-acetylbenzoic acid, the product is compound 13. When the carboxylic acid is cyclohexanecarboxylic acid or tri-O-acetyl-fucose(C)-carboxylic acid, the products are compounds 14 and 19, respectively.

The 2-amido derivatives of 8-methoxycarbonyloctyl-3-O-(2,3,4-tri-O-benzyl-α-L-fucopyranosyl)-4-O-[4,6-O-benzylidene-β-D-galactopyranosyl]-6-O-benzyl-2-deoxy-β-D-glucopyranoside, e.g. compounds 11, 12, 13, 14, and 19, are then selectively sulfonated to provide the corresponding 3'-O-sulfo derivatives. Selective sulfonation can be achieved by contacting the trisaccharide with about 1.0 to about 3 equivalents of a sulfur trioxide/pyridine complex in pyridine. Alternatively, sulfur trioxide complexes with dimethylformamide, triethylamine, dioxane or mixtures thereof may be employed. The conditions for the sulfonation reaction are selected to favor substitution only at the 3' position of the galactose unit which, in the case of sulfur trioxide in DMF includes reaction at from about −30° C. to about −50° C.; whereas for sulfur trioxide complexes with pyridine or triethylamine includes reaction temperatures of 0° C. to 30° C. In any event, the reaction is maintained at this temperature for a period of from about 1 to about 20 hours to provide for 3'-substitution of the trisaccharide derivative. The resulting 3'-O-sulfo derivatives are optionally converted to a salt thereof, e.g., compounds 15, 16, 17, 18, and 20, by contact with a suitable cation exchange resin.

Compounds 15, 16, 17, 18 and 20 or similar 2-amido 3'-O-sulfo derivatives are then deblocked using conventional deblocking methodology. The particular methodology employed is selected based on the blocking groups present in the molecule and it is well within the skill of the art to select a suitable deblocking methodology. For example, in the case of compound 15, deblocking is achieved by hydrogenolysis of the benzyl and benzylidene protecting groups which provides for 8-methoxycarbonyloctyl-2-benzamido-3-O-($\alpha$-L-fucopyranosyl)-4-O-(3-O-sulfo-$\beta$-D-galactopyranosyl)-2-deoxy-$\beta$-D-glucopyranoside, which can be converted to a salt by contact with a cation exchange resin. Formation of the sodium salt, for example, provides for compound 22. Compounds 16, 17 and 18 are similarly deblocked. Compound 20, which contains acetyl (Ac) protecting groups on the fuc(C)amido moiety, is. first treated with sodium methoxide in methanol to remove the acetyl groups to provide for compound 21 and then hydrogenolyzed to provide 8-methoxycarbonyloctyl-2-fuc(C)amido-3-O-($\alpha$-L-fucopyranosyl)-4-O-(3-O-sulfo-$\beta$-D-galactopyranosyl)-2-deoxy-$\beta$-D-glucopyranoside 26, which can be converted to a salt by contact with a cation exchange resin.

Using methodology similar to that described above for the 2-amido derivatives of 8-methoxycarbonyloctyl-3-O-($\alpha$-L-fucopyranosyl)-4-O-(3-O-sulfo-$\beta$-D-galactopyranosyl)-2-deoxy-$\beta$-D-glucopyranoside, the 2-amino derivative can be prepared by selectively sulfonating compound 8 using a sulfur trioxide-pyridine complex to provide compound 10 and then reducing the 2-azido group of compound 10 (while simultaneously removing the benzyl blocking groups) by hydrogenating compound 10 in the presence of a suitable catalyst, such as 5% palladium on carbon, to provide 8-methoxycarbonyloctyl-2-amino-3-O-($\alpha$-L-fucopyranosyl)-4-O-[3-O-sulfo-$\beta$-D-galactopyranosyl]-2-deoxy-$\beta$-D-glucopyranoside, which can be converted to a salt by contact with a cation exchange resin. Formation of the sodium salt, for example, provides for compound 27.

B. 2-Amido Lactosamine-OR Derivatives

Figure 2:
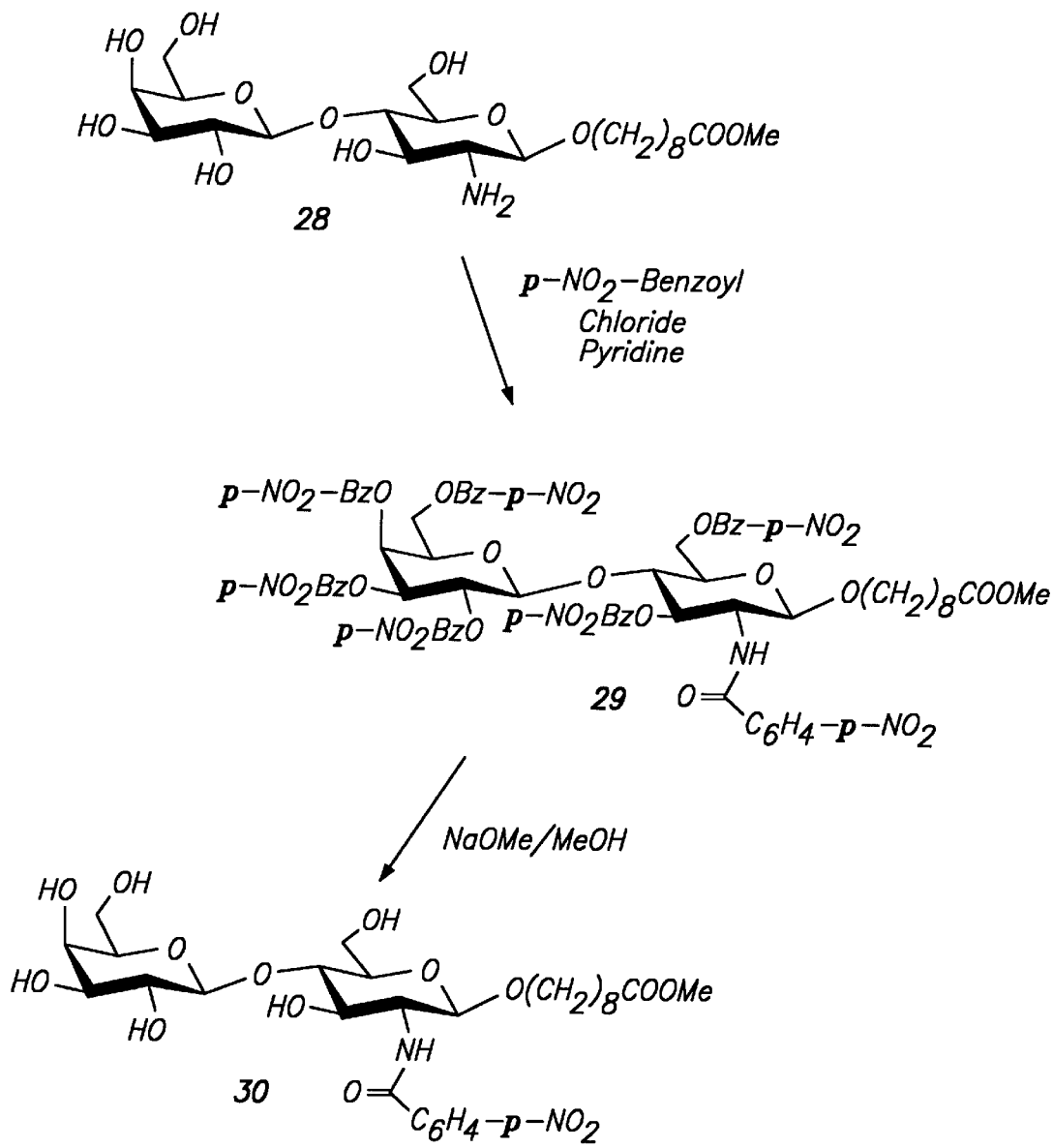
FIG. 2 illustrates a reaction scheme for the synthesis of 2-amido derivatives of lactosamine-OR compounds [R=—$(CH_2)_8CO_2CH_3$].

FIG. 2 illustrates the synthesis of the 2-p-nitrobenzamido derivative of 8-methoxycarbonyloctyl-4-O-($\beta$-D-galactopyranosyl)-2-deoxy-$\beta$-D-glucopyranose (e.g., compound 30). Specifically, in FIG. 2, 8-methoxycarbonyloctyl-2-amino-4-O-($\beta$-D-galactopyranosyl)-2-deoxy-$\beta$-D-glucopyranose (28) was prepared by glycosylation of 2-azido-2-deoxy-3,6,2',3',4',6'-hexa-O-acetyl-$\alpha$-D-lactopyranosyl bromide (described by Lemieux, et al.[22]) with 8-methoxycarbonyloctanol followed by reduction of the azido group with $H_2S$ in pyridine:triethylamine:water (4:1:0.1) and deacetylation. This compound is perbenzoylated with p-nitrobenzoyl chloride in pyridine to form intermediate 29.The conditions for this reaction are not critical and typically the reaction is conducted at a temperature of from about −10° C. to about 22° C. for about 5 to about 15 hours or until all of the hydroxyl and amino groups present in the oligosaccharide glycoside reactant have been acylated.

The hydroxyl groups of intermediate 29 are then selectively deblocked using conventional procedures, preferably using sodium methoxide in methanol, to provide 8-methoxycarbonyloctyl-2-p-nitrobenzamido-4-O-($\beta$-D-galactopyranosyl)-2-deoxy-$\beta$-D-glucopyranose (30). By employing acyl chlorides of the general formula Cl—C(O)$R^6$ ($R^6$ is defined as above) in place of p-nitrobenzoyl chloride, various 2-amido lactosamine-OR derivatives can be prepared.

C. 4'-Sulfo and 4'-Phospho Lactose-OR Derivatives

Figure 3A:
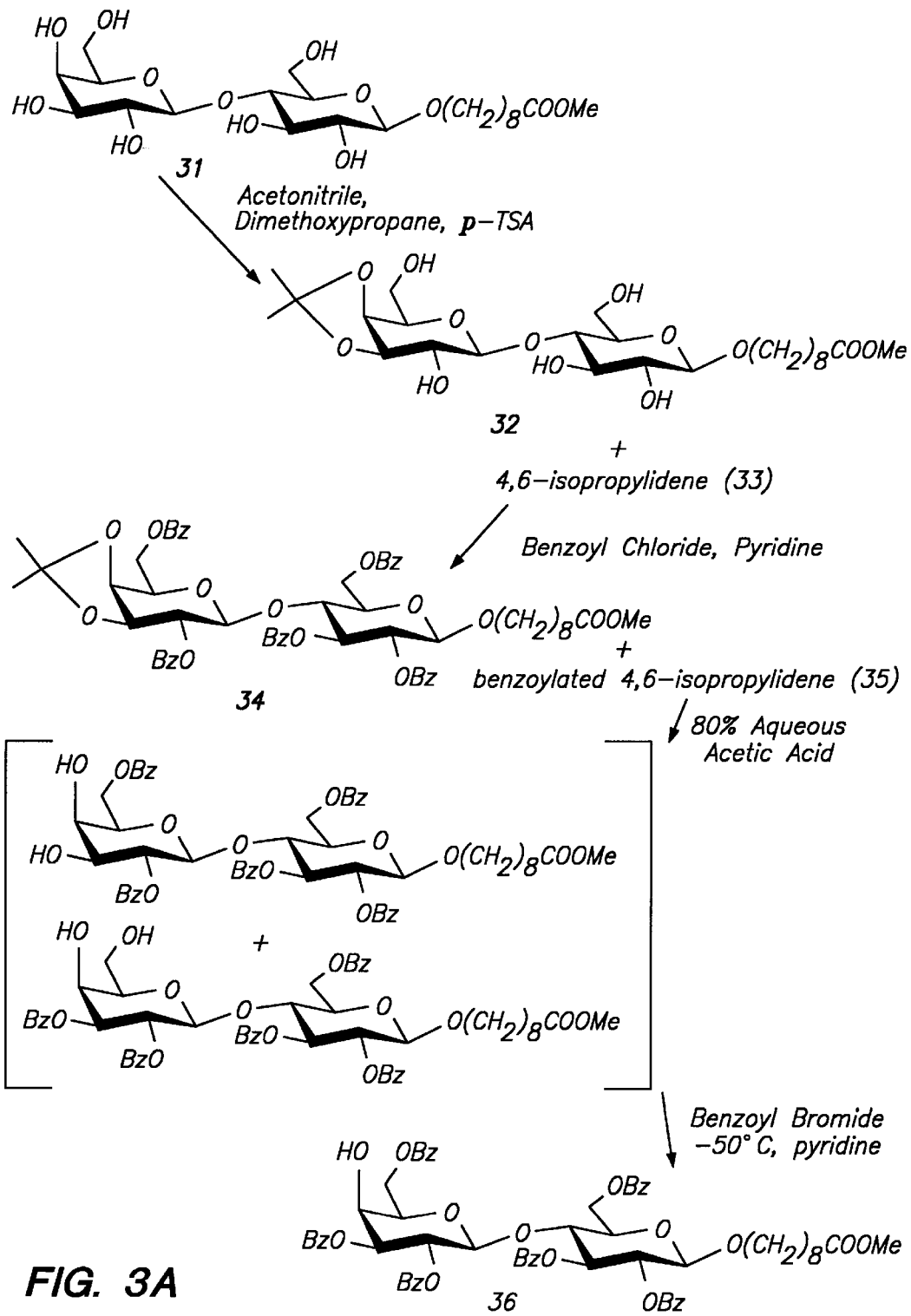
FIGS. 3A, and 3B (collectively FIG. 3) illustrate a reaction scheme for the synthesis of 4'-sulfo and 4'-phospho-lactose-OR compounds [R=—$(CH_2)_8CO_2CH_3$].
Figure 3B:
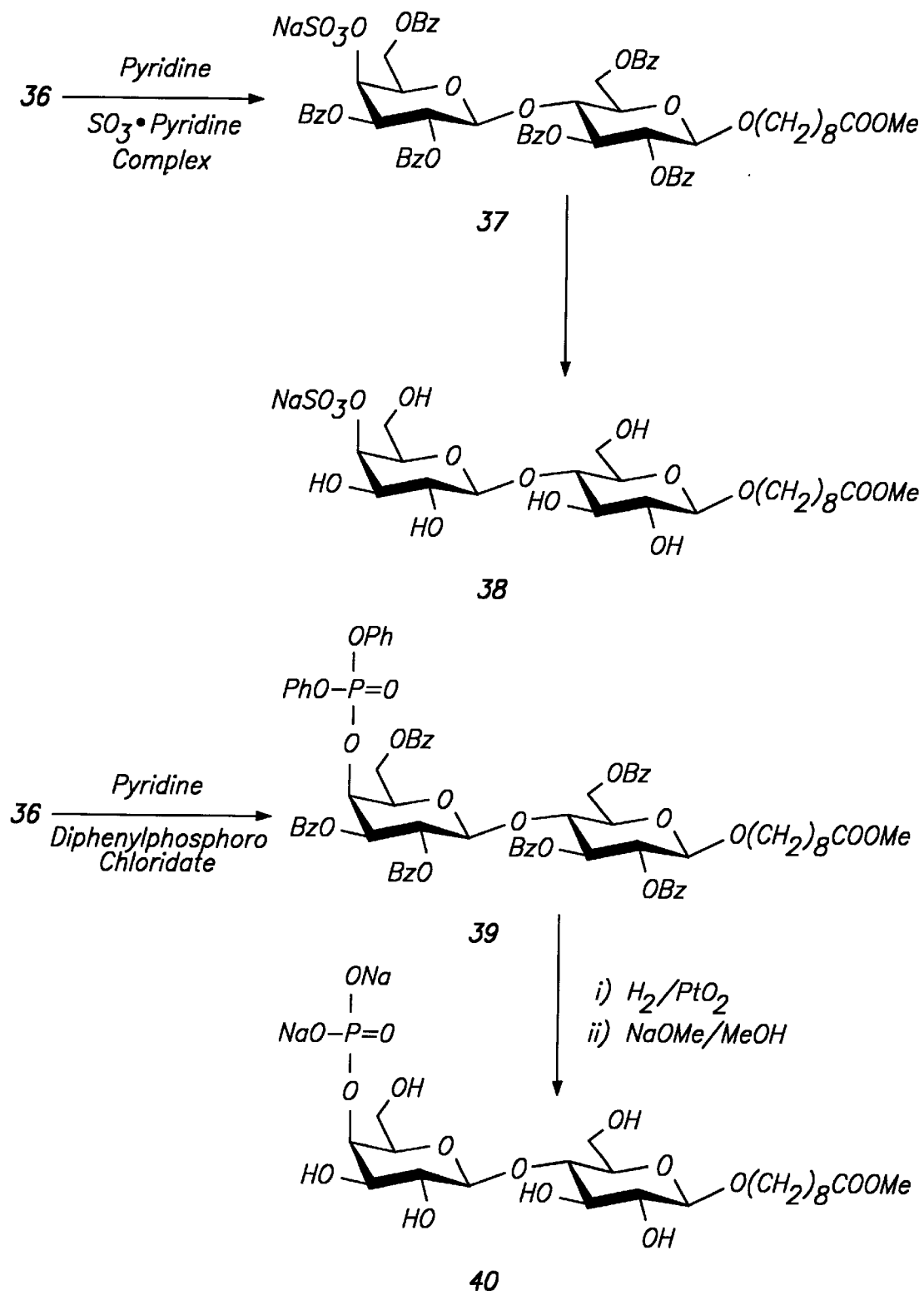

FIG. 3 illustrates the synthesis of the 4-O-sulfo- and 4-O-phospho-derivatives of 8-methoxycarbonyloctyl-4-O-($\beta$-D-galactopyranosyl)-$\beta$-D-glucopyranoside. Specifically, in FIG. 3, 8-methoxycarbonyloctyl lactose (31), prepared by the procedures described by Bundle and Banoub[24], is converted into a mixture of the 3,4-O— and 4,6-O-isopropylidene derivatives, compounds 32 and 33, respectively, by reaction with 2,2-dimethoxypropane in the presence of an acidic catalyst, such as p-toluenesulfonic acid. The mixture of compounds 32 and 33 is next benzoylated with an excess of benzoyl chloride to provide compounds 34 and 35. The isopropylidene blocking group of compounds 34 and 35 is then removed by contacting the mixture with aqueous acetic acid, preferably 80% aqueous acetic acid. The resulting diol is generally not isolated but is selectively benzoylated with benzoyl chloride at −50° C. to provide for compound 36. Compound 36 is then sulfonated using a sulfur trioxide/pyridine complex to provide the 4-O-sulfo derivative 37, after conversion to its sodium salt. Deblocking of compound 37 using conventional procedures, e.g. treatment with sodium methoxide in methanol, provides 8-methoxycarbonyloctyl-4-O-(4-O-sulfo-$\beta$-D-galactopyranosyl)-$\beta$-D-glucopyranoside (38), after conversion to its sodium salt.

Alternatively, intermediate 36 can be phosphorylated with diphenyl chlorophosphate and dimethylaminopyridine to give compound 39. Deblocking of the phosphate group of compound 39 by hydrogenolysis followed by deblocking of the hydroxyl groups using sodium methoxide in methanol affords 8-methoxycarbonyloctyl-4-O-(4-O-phospho-$\beta$-D-galactopyranosyl)-$\beta$-D-glucopyranoside (40), after conversion to its sodium salt.

D. 3',6'-Disulfo and 3',6'-Diphospho Lewis$^C$-OR Derivatives

Figure 4:
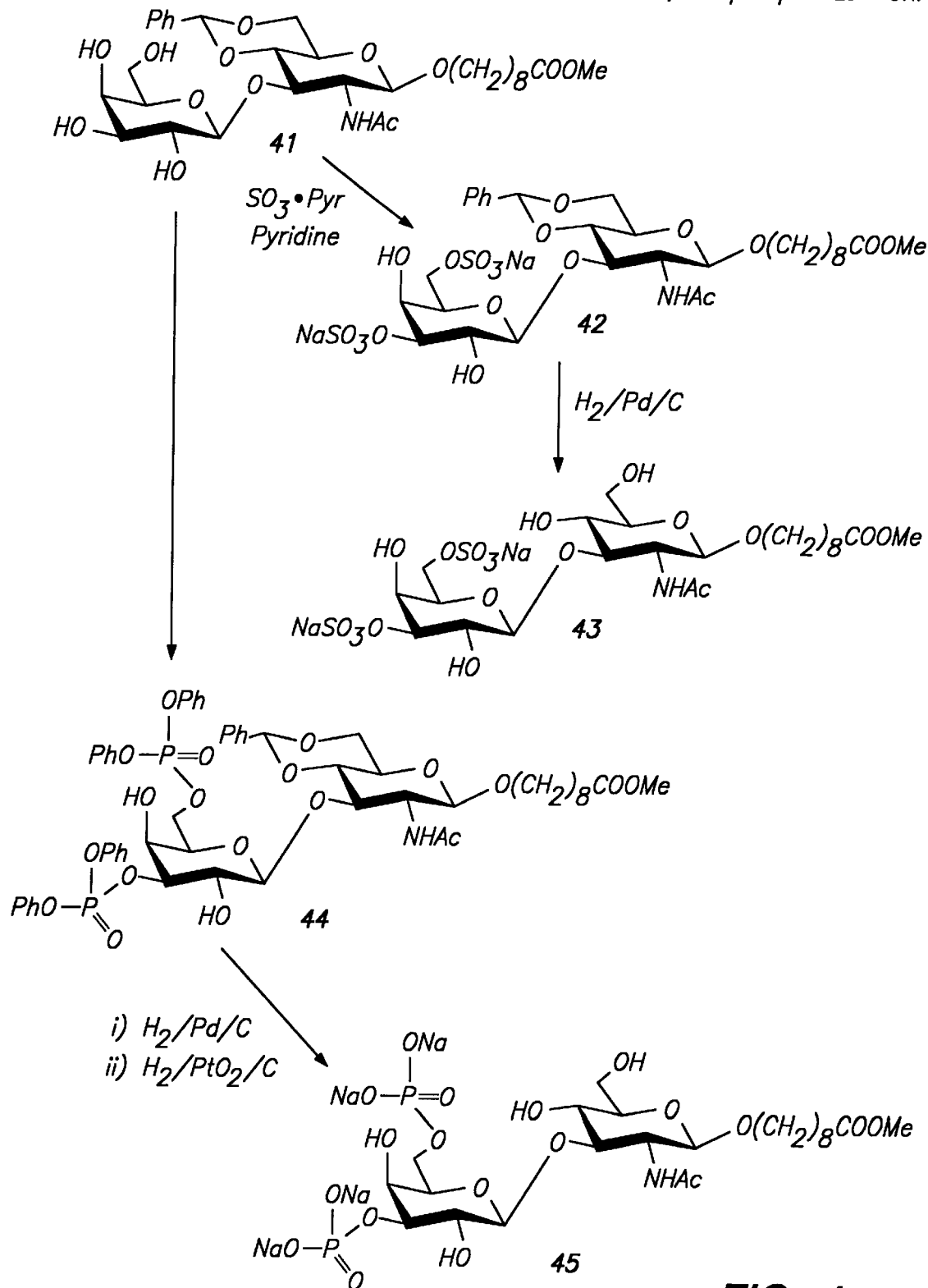
FIG. 4 illustrates a reaction scheme for the synthesis of 3',6'-disulfo and 3',6'-diphospho-Lewis$^C$-OR compounds [R=—$(CH_2)_8CO_2CH_3$].

FIG. 4 illustrates the synthesis of the 3',6'-disulfo- and 3',6'-diphospho-derivatives of 8-methoxycarbonyloctyl-2-acetamido-3-O-($\beta$-D-galactopyranosyl)- 2-deoxy-$\beta$-D-glucopyranoside, e.g., compounds 43 and 45. As shown in FIG. 4, 8-methoxycarbonyloctyl-2-acetamido-3-O-($\beta$-D-galactopyranosyl)-2-deoxy-4,6-O-benzylidene-$\beta$-D-glucopyranoside (41), prepared as described in the Examples set forth below, can be selectively disulfonated by treatment with about 2 to about 4 equivalents of a sulfur trioxide/pyridine complex in pyridine to afford the 3',6'-di-O-sulfo blocked intermediate 42. Preferably, this reaction is conducted at a temperature of from about 0° C. to about 20° C. for a period of about 3 to about 15 hours. Deblocking of compound 42 using conventional hydrogenolysis conditions provides 8-methoxycarbonyloctyl-2-acetamido-3-O-(3,6-di-O-sulfo-$\beta$-D-galactopyranosyl)-2-deoxy-$\beta$-D-glucopyranoside (43), after conversion to its sodium salt.

Additionally, the 3' and 6' hydroxyl groups of compound 41 can be selectively phosphorylated by treatment with about 2.0 to about 4.0 equivalents of diphenyl chlorophosphate and about 2.0 to about 4.0 equivalents of dimethylaminopyridine to provide intermediate 44. This reaction is preferably conducted in pyridine at a temperature of from about 0° C. to about 20° C. for about 1 to about 5 hours. Conventional deblocking of compound 44, e.g. hydrogenolysis, affords 8-methoxycarbonyloctyl-2- acetamido-3-O-(3,6-di-O-phospho-β-D-galactopyranosyl)-2-deoxy-β-D-glucopyranoside (45), after conversion to its sodium salt.

E. 3',4',6'-Trisulfo Lewis$^x$-OR Derivatives

Figure 5:
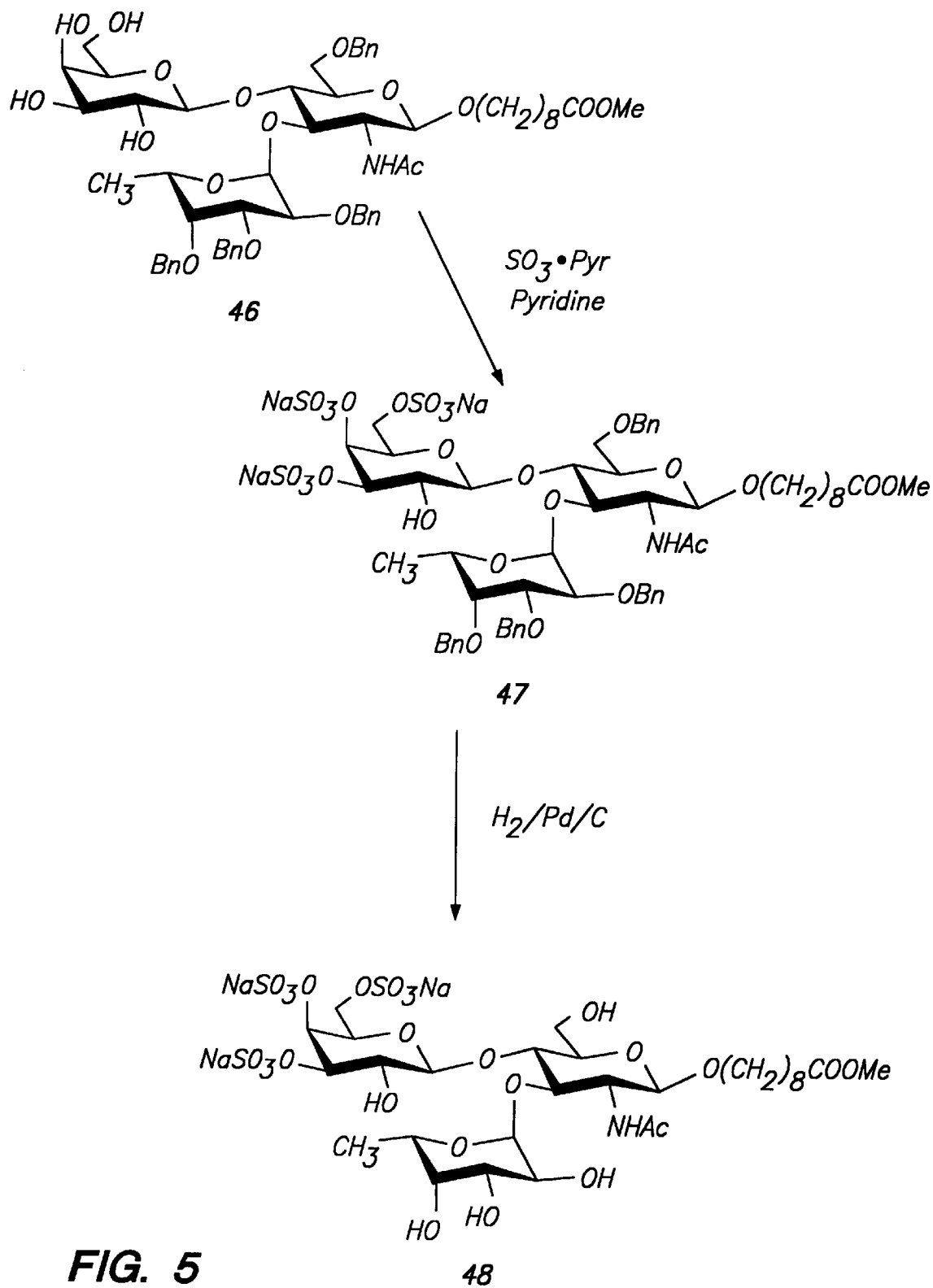
FIG. 5 illustrates a reaction scheme for the synthesis of 3',4',6'-trisulfo-Lewis$^x$-OR compounds [R=—$(CH_2)_8CO_2CH_3$].

FIG. 5 illustrates the synthesis of a 3',4',6'-trisulfo derivative of 8-methoxycarbonyloctyl-2-acetamido-3-O-(α-L-fucopyranosyl)-4-O-[β-D-galactopyranosyl]-2-deoxy-β-D-glucopyranoside. Specifically, in FIG. 5, compound 46, prepared by the procedure described by Srivastava et al.[23], is selectively tri-O-sulfonated by treatment with about 3.0 to about 6.0 equivalents of a sulfur trioxide/pyridine complex in pyridine to afford the 3',4',6'-tri-O-sulfo blocked intermediate 47. This reaction is preferably conducted at a temperature of from about 0° C. to about 20° for a period of about 5 to about 15 hours. Deblocking of compound 47 using conventional hydrogenolysis conditions provides 8-methoxycarbonyloctyl-2-acetamido-3-O-(α-L-fucopyranosyl)-4-O-[3,4,6-tri-O-β-D-galactopyranosyl]-2-deoxy-β-D-glucopyranoside (48), after conversion to its sodium salt.

F. 3'-Sulfo Y-Tetrasaccharide-OR Derivatives

Figure 6:
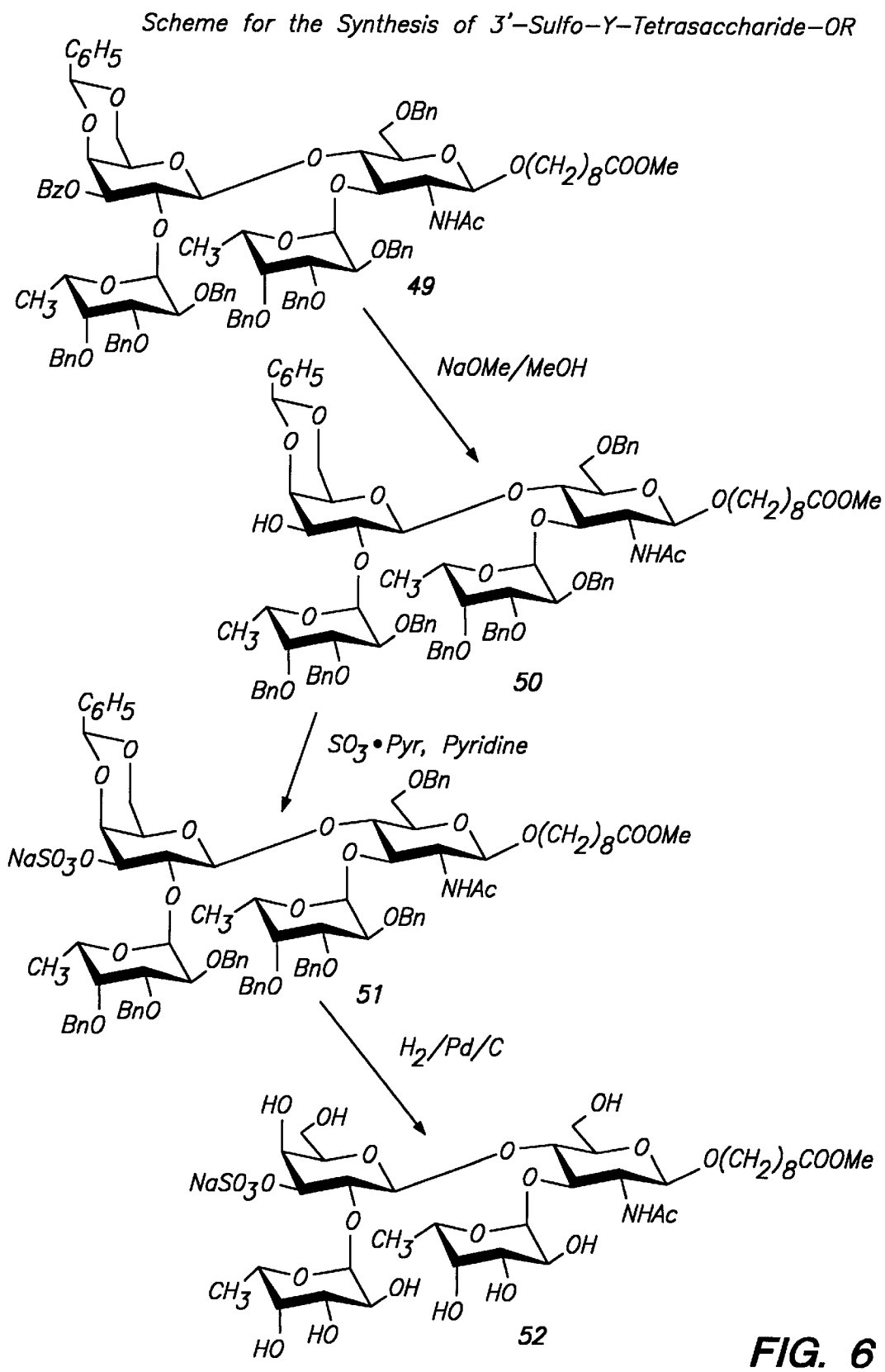
FIG. 6 illustrates a reaction scheme for the synthesis of 3'-sulfo Y-tetrasaccharide-OR compounds [R=—$(CH_2)_8CO_2CH_3$].

FIG. 6 illustrates the synthesis of 8-methoxycarbonyloctyl-2-acetamido-3-O-(α-L-fucopyranosyl)-4-O-[3-O-sulfo-2-O-(α-L-fucopyranosyl)-β-D-galactopyranosyl]-2-deoxy-β-D-glucopyranoside (52) beginning with blocked tetrasaccharide 49. Compound 49 can be prepared as set forth in the Examples below. Removal of the benzoyl blocking group from compound 49 by treatment with sodium methoxide in methanol provides compound 50 having an unblocked hydroxyl group in the 3 position of the galactose unit. Sulfonation of this hydroxyl group with a sulfur trioxide/pyridine complex provides intermediate 51 which is then deblocked under conventional hydrogenolysis conditions to afford compound 52, after conversion to its sodium salt.

G. Chloro, Dichloro, Deoxy and Dideoxy 3'-Sulfo Lewis$^x$-OR Derivatives

Figure 7A:
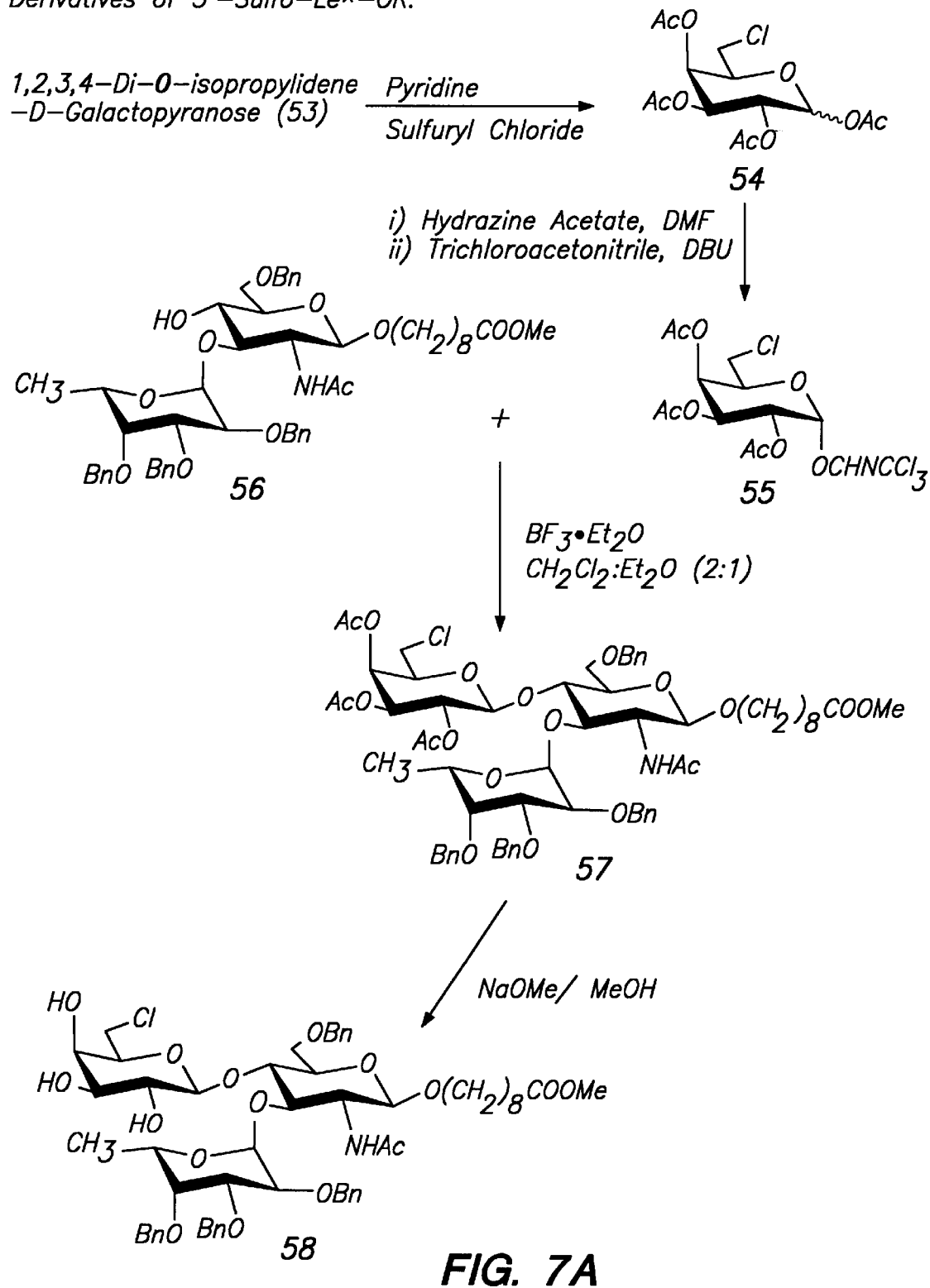
FIGS. 7A, 7B and 7C (collectively FIG. 7) illustrate a reaction scheme for the synthesis of 6'-chloro and 6'-deoxy-3'-sulfo-Lewis$^x$-OR compounds [R=—$(CH_2)_8CO_2CH_3$].
Figure 7B:
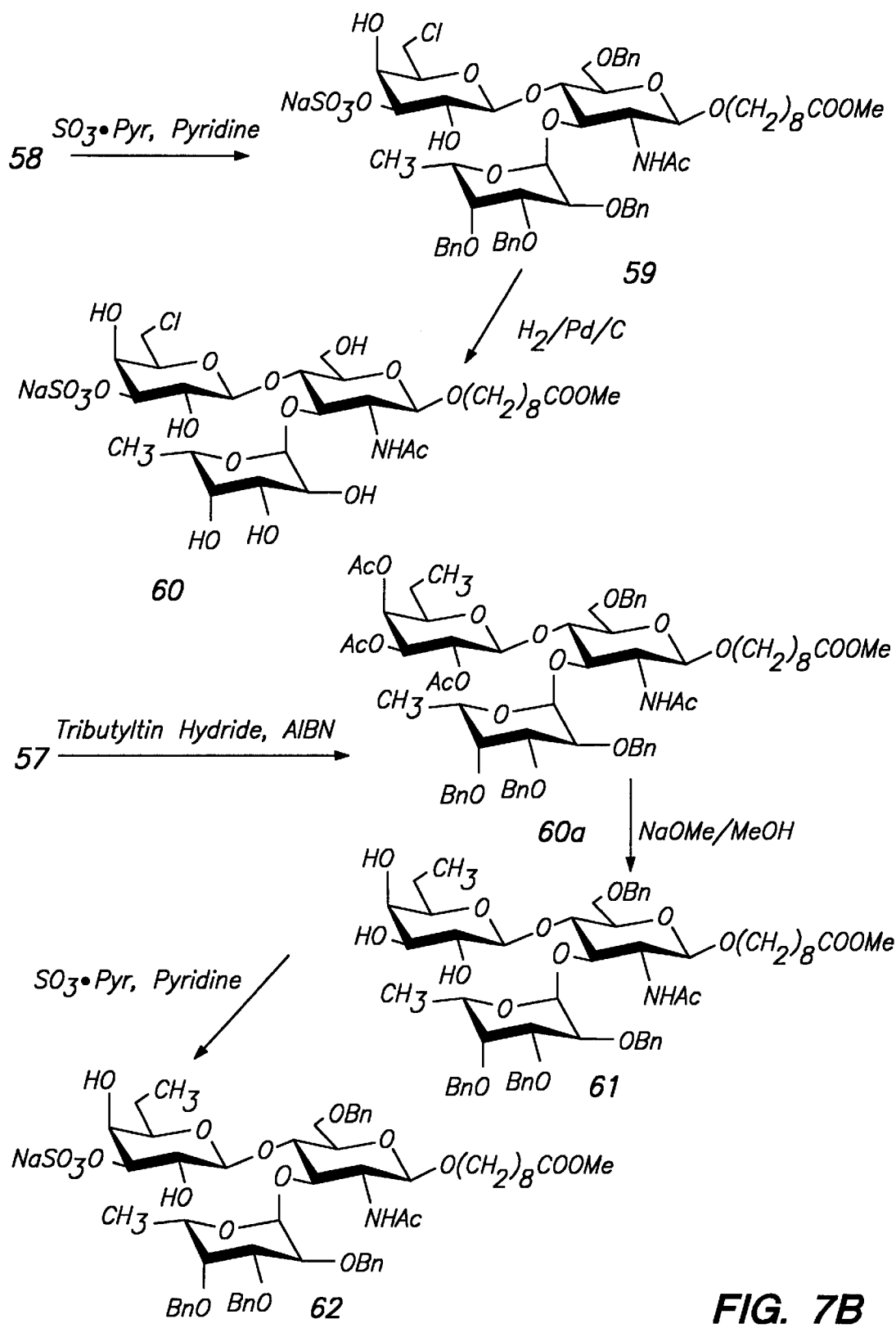
Figure 7C:
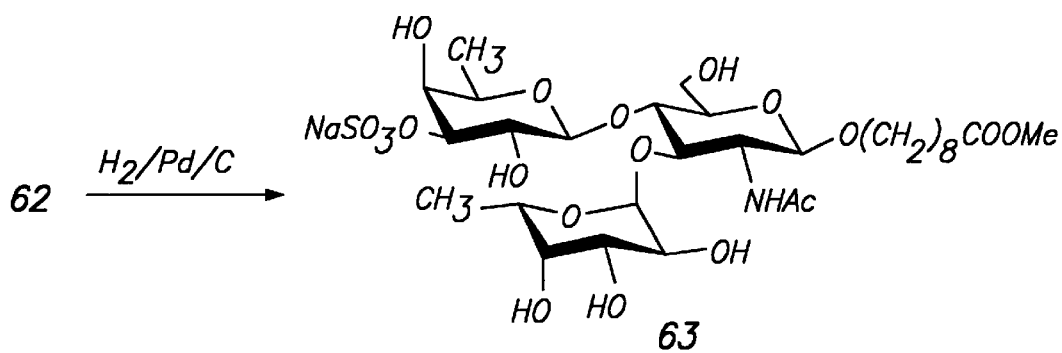

FIG. 7 illustrates the synthesis of 6'-chloro and 6'-deoxy 3'-sulfo-Le$^x$-OR derivatives. As shown in FIG. 7, the unblocked hydroxyl group of 1,2,3,4-di-O-isopropylidene-D-galactopyranose (53), obtained from Aldrich Chemical Company, Milwaukee, Wis., USA, is first converted into a chloro substituent by treatment of compound 53 with an inorganic acid halide, such as sulfuryl chloride, in a suitable solvent. In a preferred embodiment, compound 53 is contacted with an excess of sulfuryl chloride in pyridine. This reaction is typically conducted at a temperature in the range from about −40° C. to about 20° C., preferably at −40° C., for about 1 to about 15 hours. Subsequent hydrolysis of the isopropylidene blocking groups using 90% aqueous trifluoroacetic acid followed by acetylation of the resulting unblocked hydroxyl groups using conventional procedures, e.g., excess acetic anhydride in pyridine, affords intermediate 54.

Compound 54 is then converted in two steps into O-(2,3,4-tri-O-acetyl-6-chloro-6-deoxy-α-D-glucopyranosyl) trichloroacetimidate (55). First, the anomeric acetate group of compound 54 is selectively removed by reaction with hydrazine acetate. Preferably, this reaction is conducted by contacting compound 54 with from about 1.1 to about 1.5 equivalents of hydrazine acetate (prepared by known procedures from hydrazine and acetic anhydride) at a temperature of from about 0° C. to about 20° C. for about 5 to about 10 hours. Typically, the reaction is conducted in an anhydrous solvent, such as dimethylformamide. Treatment of the resulting product with trichloroacetonitrile in the presence of an amine, such as 1,8-diazabicyclo[5.4.0]undec-7-ene (DBU), provides compound 55. This reaction is typically conducted in an anhydrous inert organic solvent, such as dichloromethane, using an excess of trichloroacetonitrile.

Compound 55 is then coupled with 8-methoxycarbonyloctyl-2-acetamido-3-O-(2,3,4-tri-O-benzyl-α-L-fucopyranosyl)-6-O-benzyl-2-deoxy-β-D-glucopyranoside (56), prepared according to the procedures described by Srivastava et al.[23], using conventional coupling conditions to provide 8-methoxycarbonyloctyl-2-acetamido-3-O-(2,3,4-tri-O-benzyl-α-L-fucopyranosyl)-4-O-[6-chloro-6-deoxy-2,3,4-tri-O-acetyl-β-D-galactopyranosyl]-6-O-benzyl-2-deoxy-β-D-glucopyranoside (57). The coupling reaction is generally conducted by contacting compound 56 with from about 1.1 to about 2 equivalents of O-(6-chloro-6-deoxy-3,4,6-tri-O-acetyl-α-D-galactopyranosyl)-trichloroacetimidate (55) and an excess of boron trifluoride etherate relative to the galactose imidate. Preferably from about 1.1 to about 2 equivalents of boron trifluoride etherate are employed. The reaction is typically conducted at from about −30° C. to about 10° C. (preferably −10° C.) in a suitable anhydrous organic solvent such as dichloromethane or a 1:2 mixture of dichloromethane:ether.

Compound 57 is then deacetylated using conventional reaction conditions, preferably using sodium methoxide in methanol, to provide intermediate 58. Sulfonation of compound 58 using conventional procedures, e.g., treatment with a sulfur trioxide/pyridine complex, affords the 6'-chloro-3'-O-sulfo intermediate 59 which is deblocked using conventional hydrogenolysis conditions to provide 8-methoxycarbonyloctyl-2-acetamido-3-O-(α-L-fucopyranosyl)-4-O-[6-chloro-6-deoxy-3-O-sulfo-β-D-galactopyranosyl)]-β-D-glucopyranoside (60), after conversion to its sodium salt.

The 6'-deoxy-3'-sulfo-Lewis$^x$-OR derivative, compound 62, is readily prepared from the corresponding blocked 6'-chloro derivative, compound 57, by reduction (e.g. de-chlorination) with tributyltin hydride. This reaction is typically conducted by contacting compound 57 with about 1.0 to about 10.0 equivalents of tributyltin hydride, preferably about 10 equivalents, in the presence of a free radical initiator, such as azobisisobutyronitrile (AIBN). The reaction is generally conducted in an inert solvent, such as toluene, at a temperature of from about 20° C. to about 80° C. for a period of about 1.0 to about 10 hours. Reduction of compound 57 under these conditions affords compound 60a.

Compound 60a is then deacetylated, sulfonated and deblocked using conventional techniques to provide 8-methoxycarbonyloctyl-2-acetamido-3-O-(α-L-fucopyranosyl)-4-O-[6-deoxy-3-O-sulfo-β-D-galactopyranosyl)]-β-D-glucopyranoside (63), after conversion to its sodium salt.

Figure 8A:
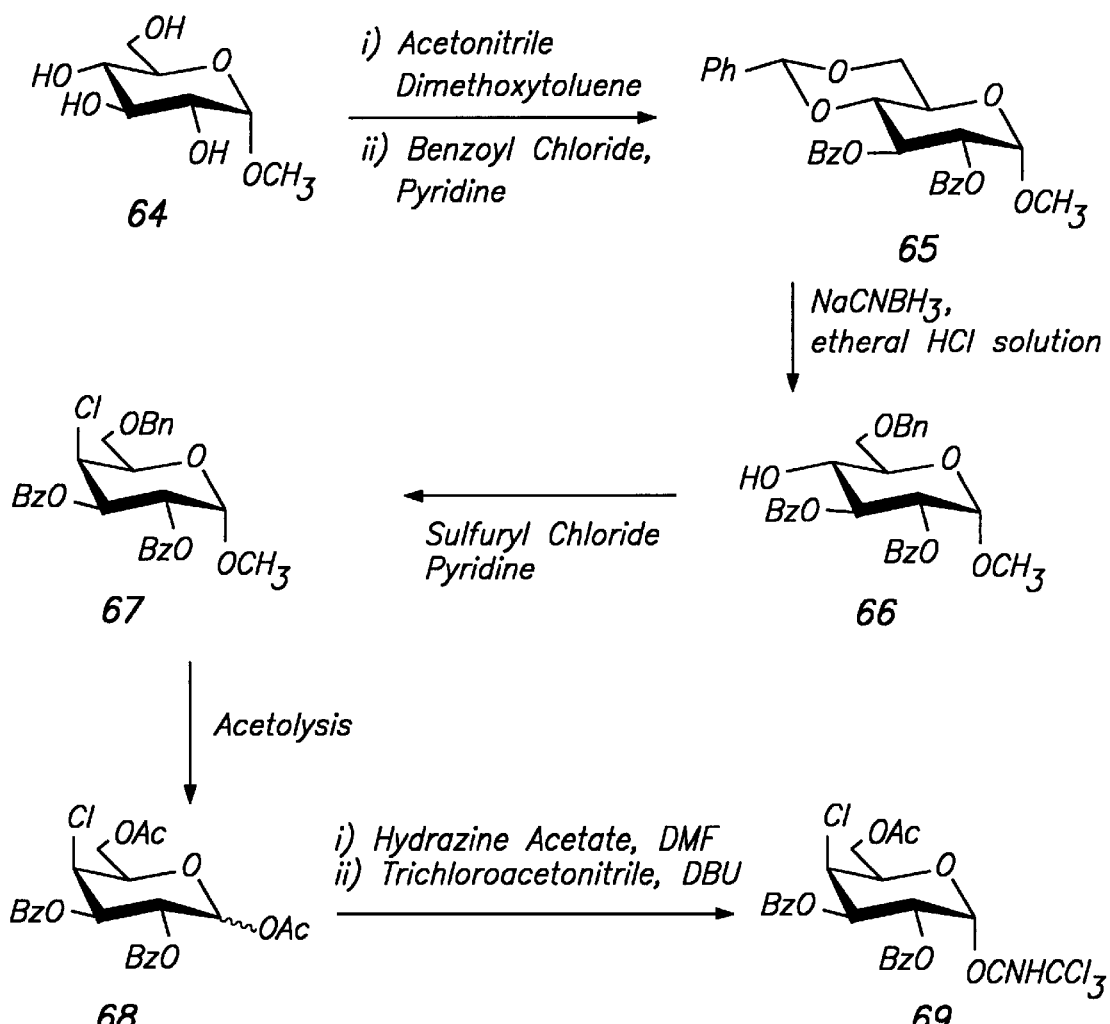
FIGS. 8A, 8B and 8C (collectively FIG. 8) illustrate a reaction scheme for the synthesis of 4'-chloro and 4'-deoxy-3'-sulfo-Lewis$^x$-OR compounds [R=—$(CH_2)_8CO_2CH_3$].
Figure 8B:
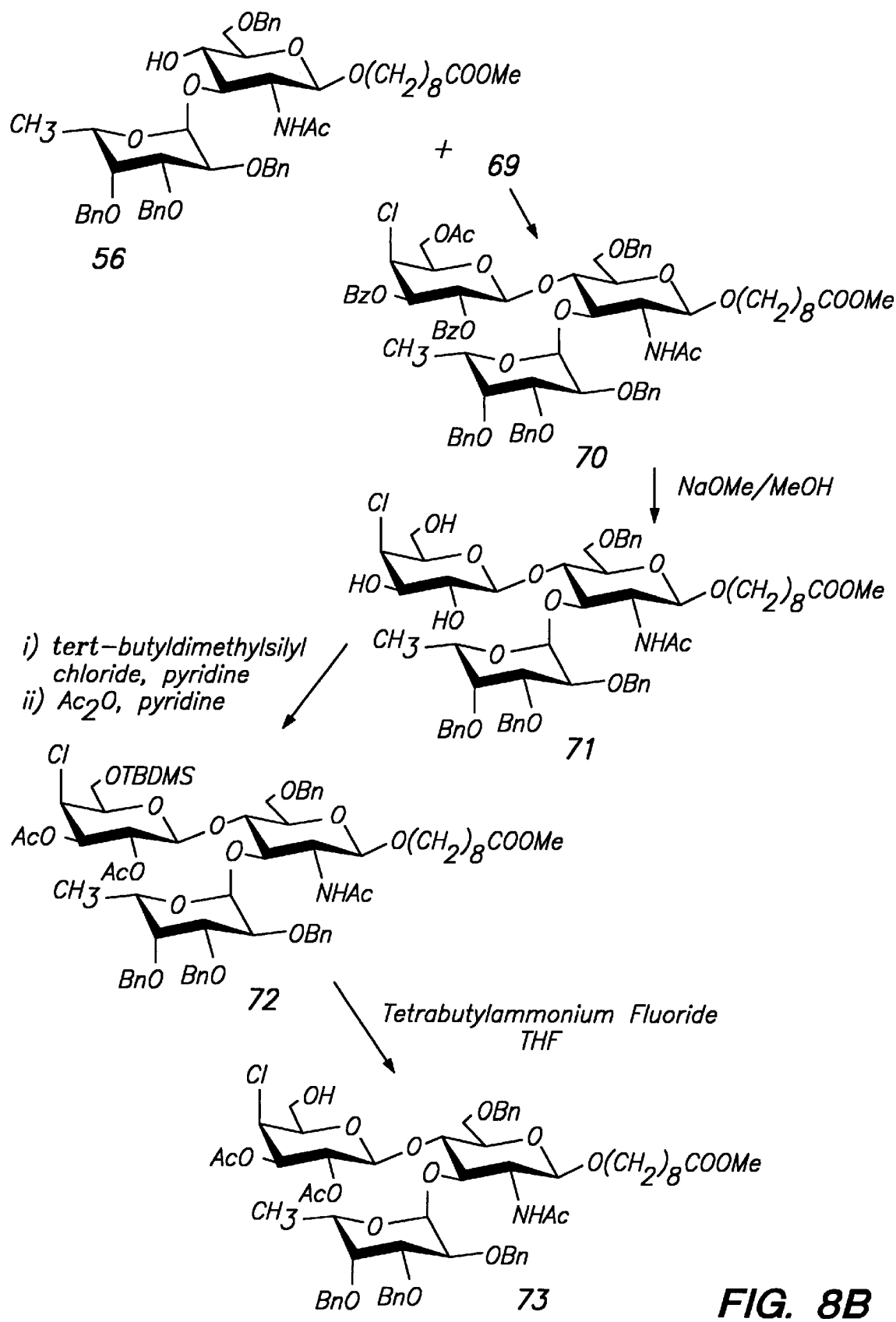
Figure 8C:
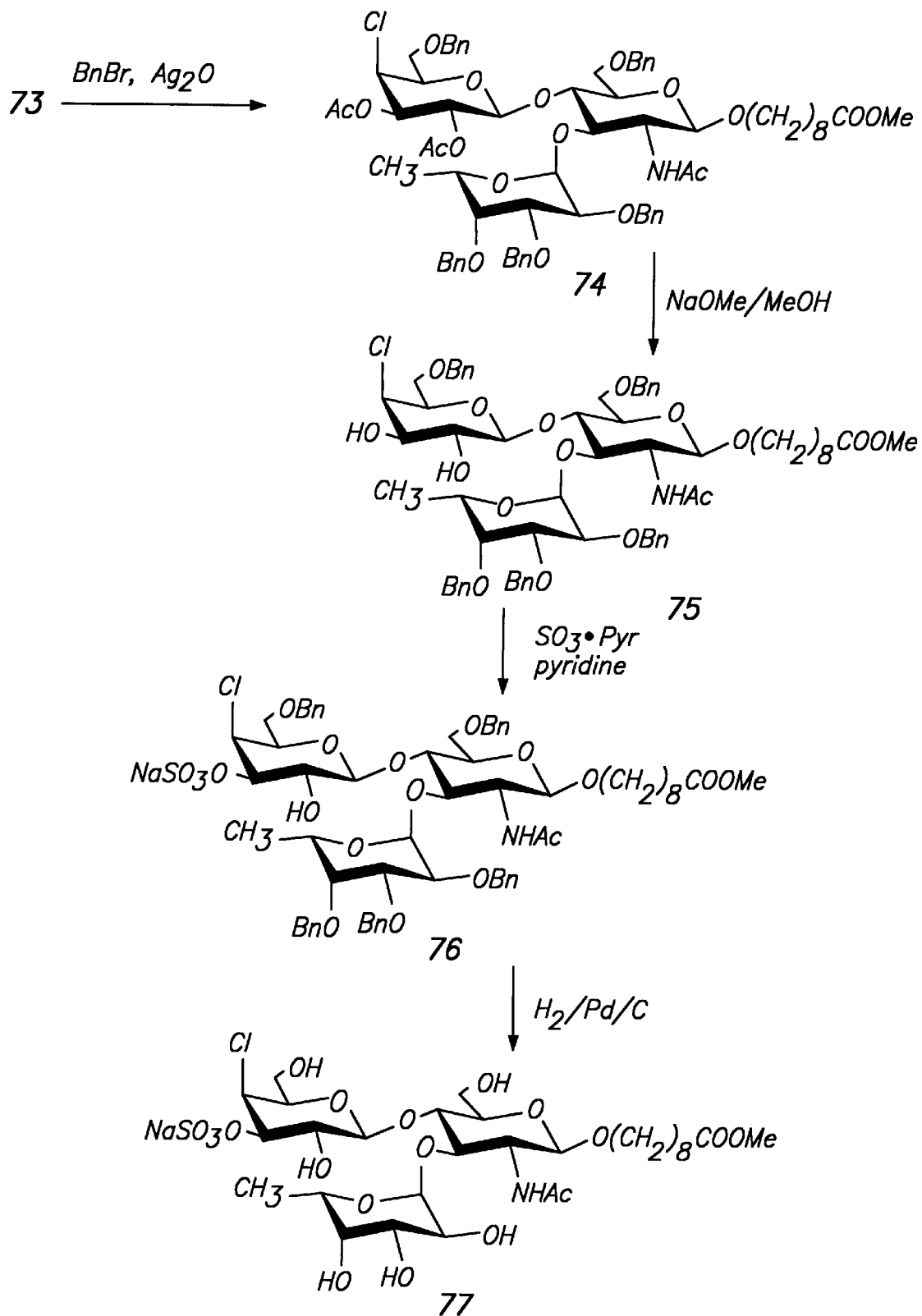

FIG. 8 illustrates the synthesis of 4'-chloro and 4'-deoxy 3'-sulfo-Lewis$^x$-OR derivatives. Specifically, in FIG. 8, methyl α-D-glucopyranoside (64) is selectively protected by first forming the 4,6-O-benzylidene derivative by reacting compound 64 with benzaldehyde dimethylacetal in the presence of an acidic catalyst, such as p-toluenesulfonic acid, and then benzoylating the benzylidene intermediate using benzoyl bromide in pyridine to provide methyl 4-6-O-benzylidene-2,3-di-O-benzyl-α-D-glucopyranoside (65).

The 4,6-O-benzylidene group of compound 65 is then opened regioselectively to provide methyl 6-O-benzyl-2,3-di-O-benzoyl-α-D-glucopyranoside (66), which has an unblocked hydroxyl group at the 4 position of the glucose unit. Regioselective opening of the benzylidene group is affected by treating compound 65 with at least a molar equivalent, preferably an excess, of sodium cyanoborohydride or a similar hydride reducing agent, in the presence of an ethereal solution of hydrochloric acid. The reaction is typically conducted in a suitable inert solvent, such as tetrahydrofuran and is preferably maintained under anhydrous conditions by, for example, the inclusion of molecular sieves. A pH indicator, such a methyl orange, is generally added to the reaction system and the reaction is generally conducted at a pH of about 3 or less. The reaction conditions are not critical and the conditions are selected so as to produce compound 66. In a preferred embodiment, about 2 to about 20, preferably 5 to 10 equivalents of sodium cyanoborohydride are employed at a reaction temperature of from about −15° C. to about 20° C. (preferably 0° C.) for a period of from about 1 to about 7 hours. The reaction provides compound 66 as a white solid.

Reaction of compound 66 with sulfuryl chloride in a suitable solvent, such as pyridine, then affords methyl 6-O-benzyl-2,3-di-O-benzoyl-4-chloro-4-deoxy-α-D-glucopyranoside (67). This reaction is typically conducted at a temperature in the range from about −40° to about 20° C., preferably at −40° C., using an excess of sulfuryl chloride. Subsequent acetolysis of compound 67 using acetic anhydride containing sulfuric acid provides acetyl 6-O-acetly-2,3-di-O-benzoyl-4-chloro-4-deoxy-α-D-galactopyranoside (68).

Compound 68 is next converted in two steps into α-(6-O-acetyl-2,3-di-O-benzoyl4-chloro-4-deoxy-α-D-galactopyranosyl)-trichloroacetimidate (69). First, the anomeric acetate group of compound 69 is selectively removed by reaction with hydrazine acetate. This reaction is preferably conducted by contacting compound 69 with from about 1.1 to about 1.5 equivalents of hydrazine acetate (prepared by known procedures from hydrazine and acetic anhydride) at a temperature of from about 0° C. to about 20° C. for about 5 to about 10 hours. Typically, the reaction is conducted in an anhydrous solvent, such as dimethylformamide. Treatment of the resulting product with trichloroacetonitrile in the presence of an amine, such as 1,8-diazabicyclo[5.4.0]undec-7-ene (DBU), provides compound 69. This reaction is typically conducted in an anhydrous inert organic solvent, such as dichloromethane, using an excess of trichloroacetonitrile.

Compound 69 is then coupled with 8-methoxycarbonyloctyl-2-acetamido-3-O-(2,3,4-tri-O-benzyl-α-L-fucopyranosyl)-6-O-benzyl-2-deoxy-β-D-glucopyranoside (56), prepared according to the procedures described by Srivastava et al.[23], using conventional coupling conditions to provide 8-methoxycarbonyloctyl-2-acetamido-3-O-(2,3,4-tri-O-benzyl-α-L-fucopyranosyl)-4-O-[6-O-acetyl-2, 3-di-O-benzyl-4-chloro-4-deoxy-β-D-galactopyranosyl]-2-deoxy-6-O-benzyl-β-D-glucopyranoside (70). The coupling reaction is generally conducted by contacting compound 56 with from about 1.1 to about 2 equivalents of trichloroacetimidate 69 and an excess of boron trifluoride etherate relative to the imidate. Preferably from about 1.1 to about 2 equivalents of boron trifluoride etherate are employed in this reaction. The reaction is typically conducted at from about −30° C. to about 10° C. (preferably −10° C.) in a suitable anhydrous organic solvent such as dichloromethane or a 1:2 mixture of dichloromethane:ether.

The blocking groups of compound 70 are then manipulated to allow the 3-hydroxyl group of the galactose unit to be selectively sulfonated. Specifically, the acetyl and benzoyl blocking groups of compound 70 are first removed using conventional procedures, preferably using sodium methoxide in methanol, to provide intermediate 71. The unblocked 6-hydroxyl group of the galactose unit of compound 71 is then re-blocked using a suitable protecting group. Preferably, this hydroxyl group is blocked as the tert-butyldimethylsilyl TBDMS) derivative by contacting compound 71 with excess tert-butyldimethylsilyl chloride in pyridine. Acylation of the remaining hydroxyl groups using conventional procedures, e.g., acetic anhydride, provides intermediate 72. The tert-butyldimethylsilyl blocking group is then removed by contacting compound 72 with tetrabutylammonium fluoride hydrate under conventional deblocking conditions to afford intermediate 73. The unblocked hydroxyl group of compound 73 is then re-blocked as the benzyl ether by reaction of compound 73 with excess benzyl bromide in the presence of silver oxide to provide compound 74. Compound 74 is then deacetylated using convention conditions, e.g. sodium methoxide in methanol, to afford 8-methoxycarbonyloctyl-2-acetamido-3-O-(2,3,4-tri-O-benzyl-α-L-fucopyranosyl)-4-O-[6-O-benzyl-4-chloro-4-deoxy-β-D-galactopyranosyl]-2-deoxy-6-O-benzyl-β-D-glucopyranoside (75).

Compound 75 is then sulfonated selectively on the 3-hydroxyl group of the galactose unit using a sulfur trioxide/pyridine complex to provide compound 76, which is then deblocked using conventional techniques, e.g., hydrogenolysis, to afford 8-methoxycarbonyloctyl-2-acetamido-3-O-(α-L-fucopyranosyl)-4-O-[4-chloro-4-deoxy-3-O-sulfo-β-D-galactopyranosyl)]-β-D-glucopyranoside (77), after conversion to its sodium salt.

Figure 9A:
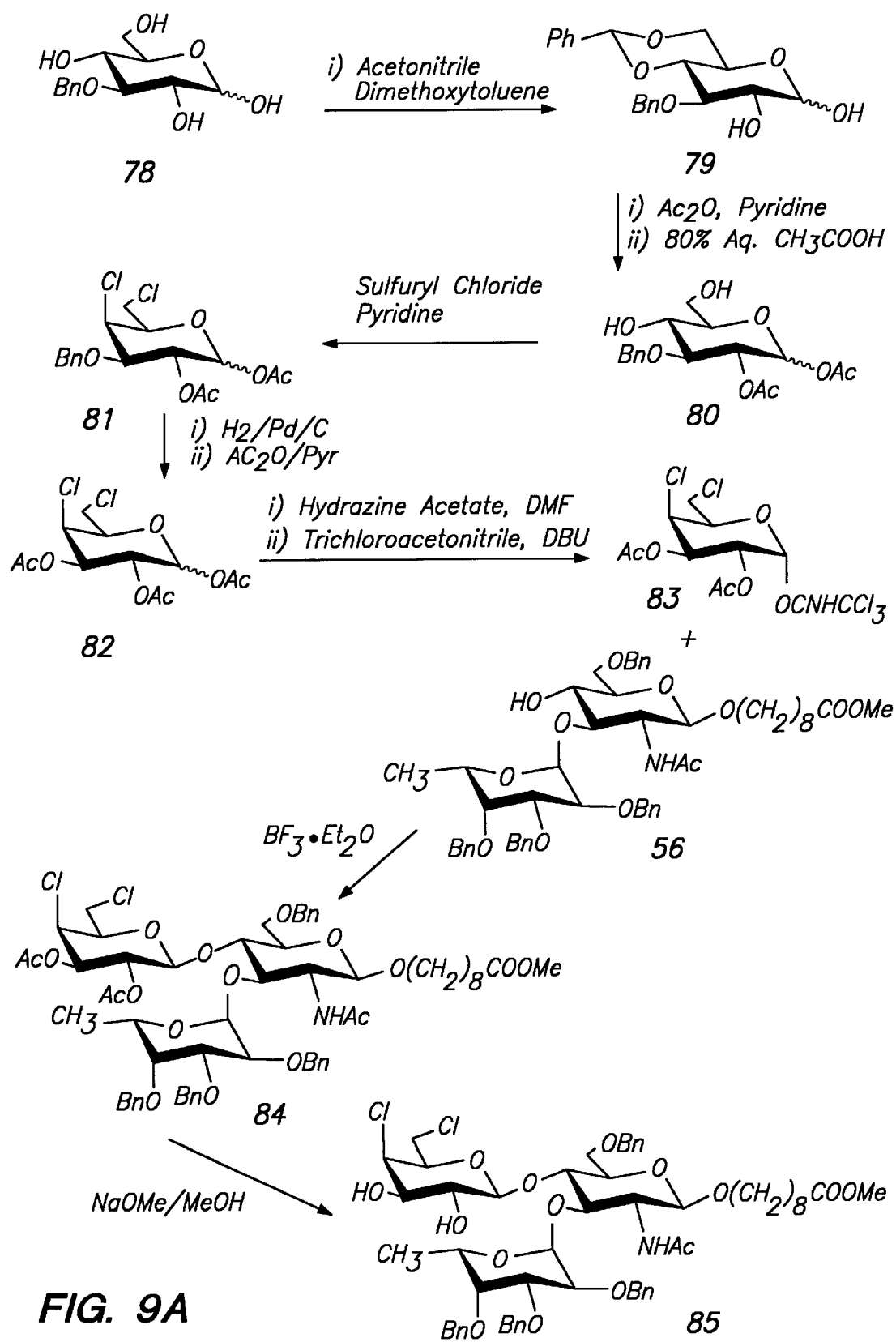
FIGS. 9A, 9B and 9C (collectively FIG. 9) illustrate a reaction scheme for the synthesis of 4',6'-dichloro and 4',6'-dideoxy-3'-sulfo-Lewis$^x$-OR compounds [R=—$(CH_2)_8CO_2CH_3$].
Figure 9B:
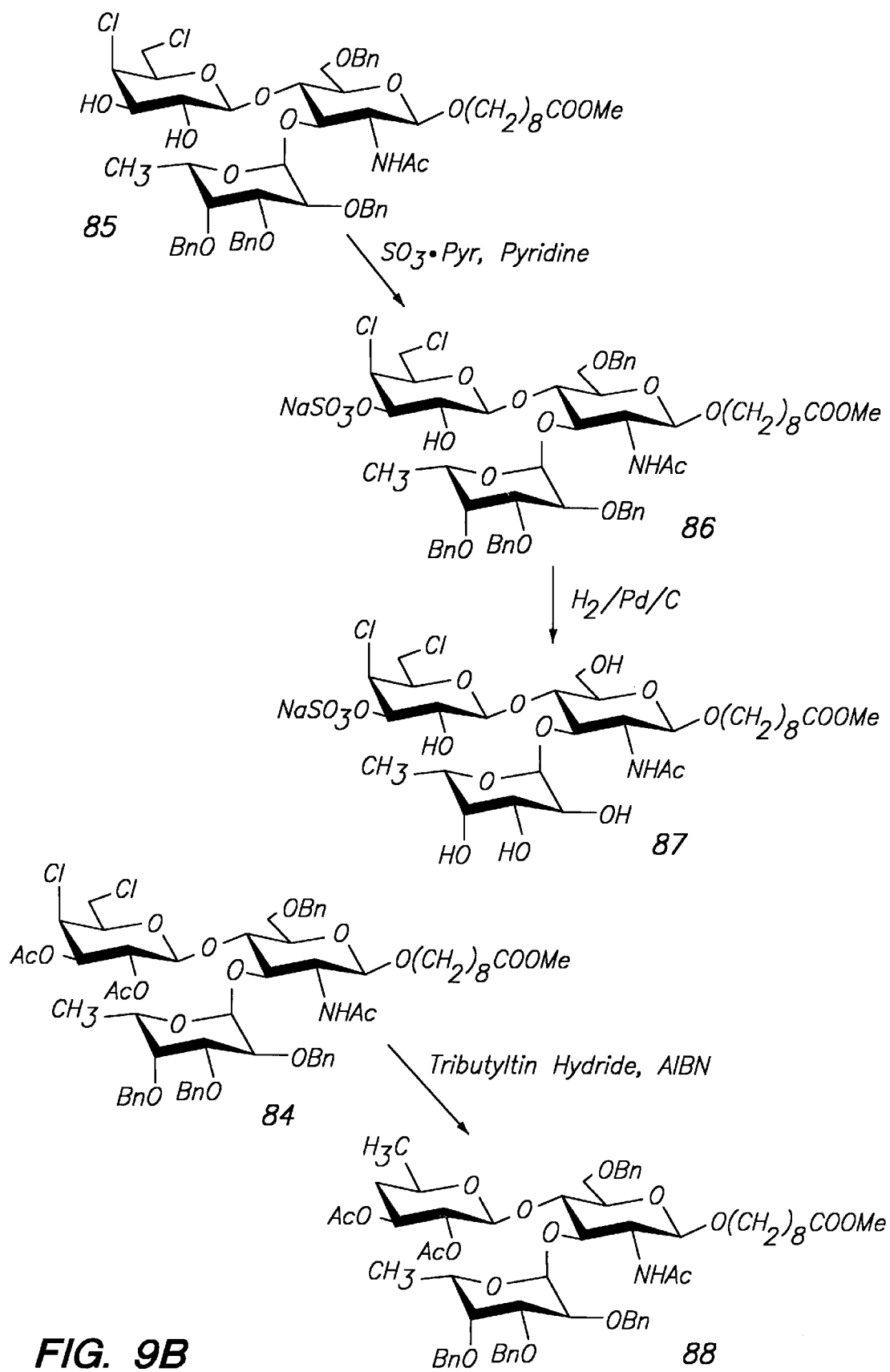
Figure 9C:
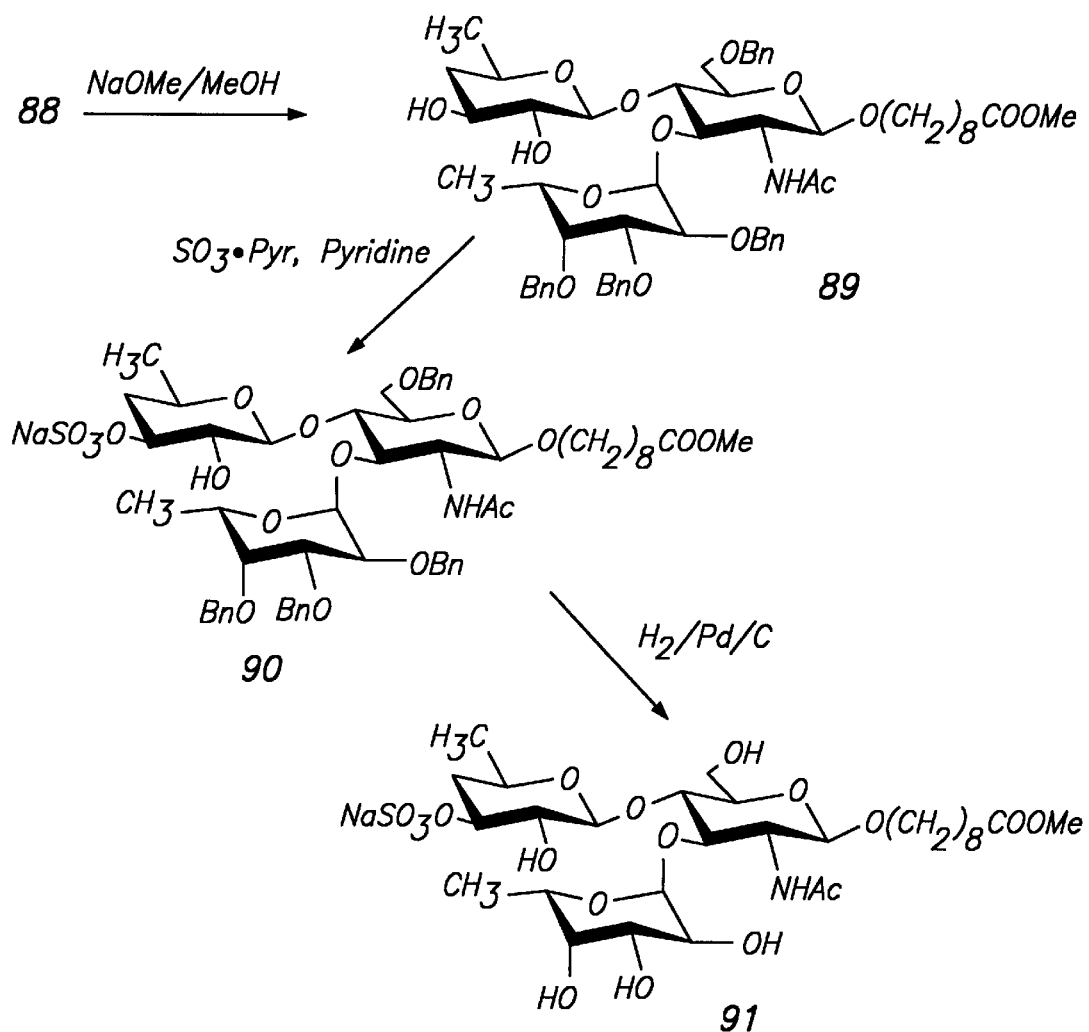

FIG. 9 illustrates the synthesis of 4',6'-dichloro- and 4',6'-dideoxy-3'-sulfo-Lewis$^x$-OR derivatives. Specifically, in FIG. 9, 3-O-benzyl-D-glucopyranose (78), prepared according to the procedure described by Finan, et al.[18], is converted into the 4,6-O-benzylidene derivative compound 79 using conventional procedures, e.g., reaction with benzaldehyde dimethylacetal (dimethoxytoluene) in the presence of an acidic catalyst, such as p-toluenesulfonic acid. Acetylation of compound 79, preferably using acetic anhydride in pyridine, followed by removal of the benzylidene blocking group using 80% aqueous acetic acid then provides compound 80, having unblocked hydroxyl groups at the 4 and 6 position of the glucose unit.

The unblocked hydroxyl groups of compound 80 are next converted to chloro substituents by treatment of compound 80 with a suitable chlorinating agent to provide acetyl 2-O-acetyl-3-O-benzyl-4,6-dichloro-4,6-dideoxy-glucopyranose (81). Preferably, compound 80 is contacted with sulfuryl chloride in a suitable solvent, such as pyridine. This reaction is typically conducted at a temperature in the range from about −40° C. to about 20° C., preferably at −40° C., using an excess of sulfuryl chloride.

The benzyl blocking group of compound 81 is then removed under conventional hydrogenolysis conditions and the resulting unblocked 3-hydroxyl group is acylated using acetic anhydride in pyridine to provide compound 82.

Compound 82 is next converted in two steps into α-(2, 3-di-O-acetyl-4,6-dichloro-4,6-dideoxy-α-D-glucopyranosyl)-trichloroacetimidate (83). First, the anomeric acetate group of compound 82 is selectively removed by reaction with hydrazine acetate. This reaction is preferably conducted by contacting compound 82 with from about 1.1 to about 1.5 equivalents of hydrazine acetate (prepared by known procedures from hydrazine and acetic anhydride) at a temperature of from about 0° C. to about 20° C. for about 5 to about 10 hours. Typically, the reaction is conducted in an anhydrous solvent, such as dimethylformamide. Treatment of the resulting product with trichloroacetonitrile in the presence of an amine, such as 1,8-diazabicyclo[5.4.0]undec-7-ene (DBU), provides compound 83. This reaction is typically conducted in an anhydrous inert organic solvent, such as dichloromethane, using an excess of trichloroacetonitrile.

Compound 83 is then coupled with 8-methoxycarbonyloctyl-2-acetamido-3-O-(2,3,4-tri-O-benzyl-α-L-fucopyranosyl)-6-O-benzyl-2-deoxy-β-D-glucopyranoside (56), prepared according to the procedures described by Srivastava et al.[23], using conventional coupling conditions to provide 8-methoxycarbonyloctyl-2-acetamido-3-O-(2,3,4-tri-O-benzyl-α-L-fucopyranosyl)4-O-[2,3-di-O-acetyl-4,6-dichloro-4,6-dideoxy-β-D-galactopyranosyl]-6-O-benzyl-2-deoxy-β-D-glucopyranoside (84). The coupling reaction is generally conducted by contacting compound 56 with from about 1.1 to about 2 equivalents of trichloroacetimidate 83 and an excess of boron trifluoride etherate relative to the imidate. Preferably from about 1.1 to about 2 equivalents of boron trifluoride etherate are employed in this reaction. The reaction is typically conducted at from about −30° C. to about 10° C. (preferably −10° C.) in a suitable anhydrous organic solvent such as dichloromethane or a 1:2 mixture of dichloromethane:ether.

Compound 84 is then deacetylated using convention conditions, e.g. sodium methoxide in methanol, to afford 8-methoxycarbonyloctyl-2-acetamido-3-O-(2,3,4-tri-O-benzyl-α-L-fucopyranosyl)-4-O-[4,6-dichloro-4,6-dideoxy-β-D-galactopyranosyl]-6-O-benzyl-2-deoxy-β-D-glucopyranoside (85)

Compound 85 is then sulfonated selectively on the 3-hydroxyl group of the galactose unit using a sulfur trioxide/pyridine complex to provide compound 86, which is then deblocked using conventional techniques, e.g., hydrogenolysis, to afford 8-methoxycarbonyloctyl-2-acetamido-3-O-(α-L-fucopyranosyl)-4-O-[4,6-dichloro-4,6-dideoxy-3-O-sulfo-β-D-galactopyranosyl)]-2-D-glucopyranoside (87), after conversion to its sodium salt.

The 4',6'-dideoxy-3'-sulfo-Lewis$^x$-OR derivative, compound 91, can be prepared fro m the corresponding blocked 4',6'-dichloro derivative, compound 84, by reduction (e.g. de-chlorination) with tributyltin hydride.

This reaction is typically conducted by contacting compound 84 with about 1.0 to about 10 equivalents of tributyltin hydride, preferably about 10 equivalents, in the presence of a free radical initiator, such as AIBN. The reaction is generally conducted in an inert solvent, such as toluene, at a temperature of from about 20° to about 80° C. for a period of about 1 to about 7 hours. Reduction of compound 84 under these conditions affords compound 88.

Compound 88 is then deacetylated, sulfonated and deblocked using conventional techniques to provide 8-methoxycarbonyloctyl-2-acetamido-3-O-(α-L-fucopyranosyl)-4-O-[4,6-dideoxy-3-O-sulfo-β-D-galactopyranosyl)]-β-D-glucopyranoside (91), after conversion to its sodium salt.

Figure 10:
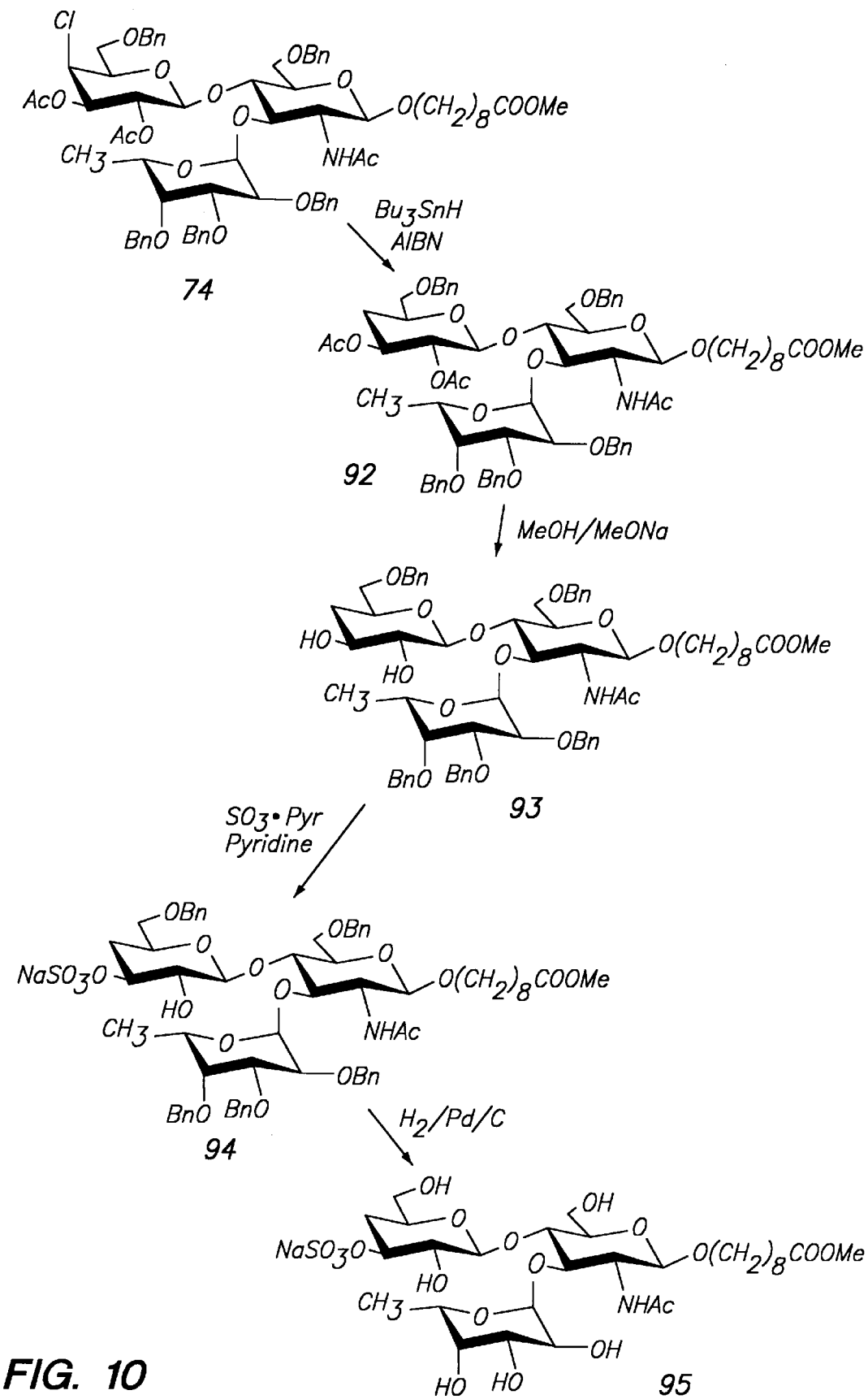
FIG. 10 illustrates a reaction scheme for the synthesis of 4'-deoxy-3'-sulfo-Lewis$^x$-OR compounds [R=—$(CH_2)_8CO_2CH_3$].

FIG. 10 illustrates the synthesis of 8-methoxycarbonyloctyl-2-acetamido-3-O-(α-L-fucopyranosyl)-4-O-[4-deoxy-3-O-Sulfo-β-D-galactopyranosyl-β-D-glucopyranoside sodium salt (95) from the blocked trisaccharide 74 described above. Specifically, reduction of the 4'-chloro group of compound 95 to the corresponding deoxy derivative is accomplished under conventional conditions using tributyltin hydride and azobisisobutyronitrile to provide for deoxy compound 92. Deacetylation of the acetyl groups at the 2' and 3' positions followed by selective sulfonation with sulfur dioxidedpyridine complex leads to the 3'-sulfo derivative, compound 94. Subsequent removal of the remaining blocking groups via conventional methods leads to the title compound 95.

H. 1-Azido Compounds and Derivatives Thereof

Figure 11A:
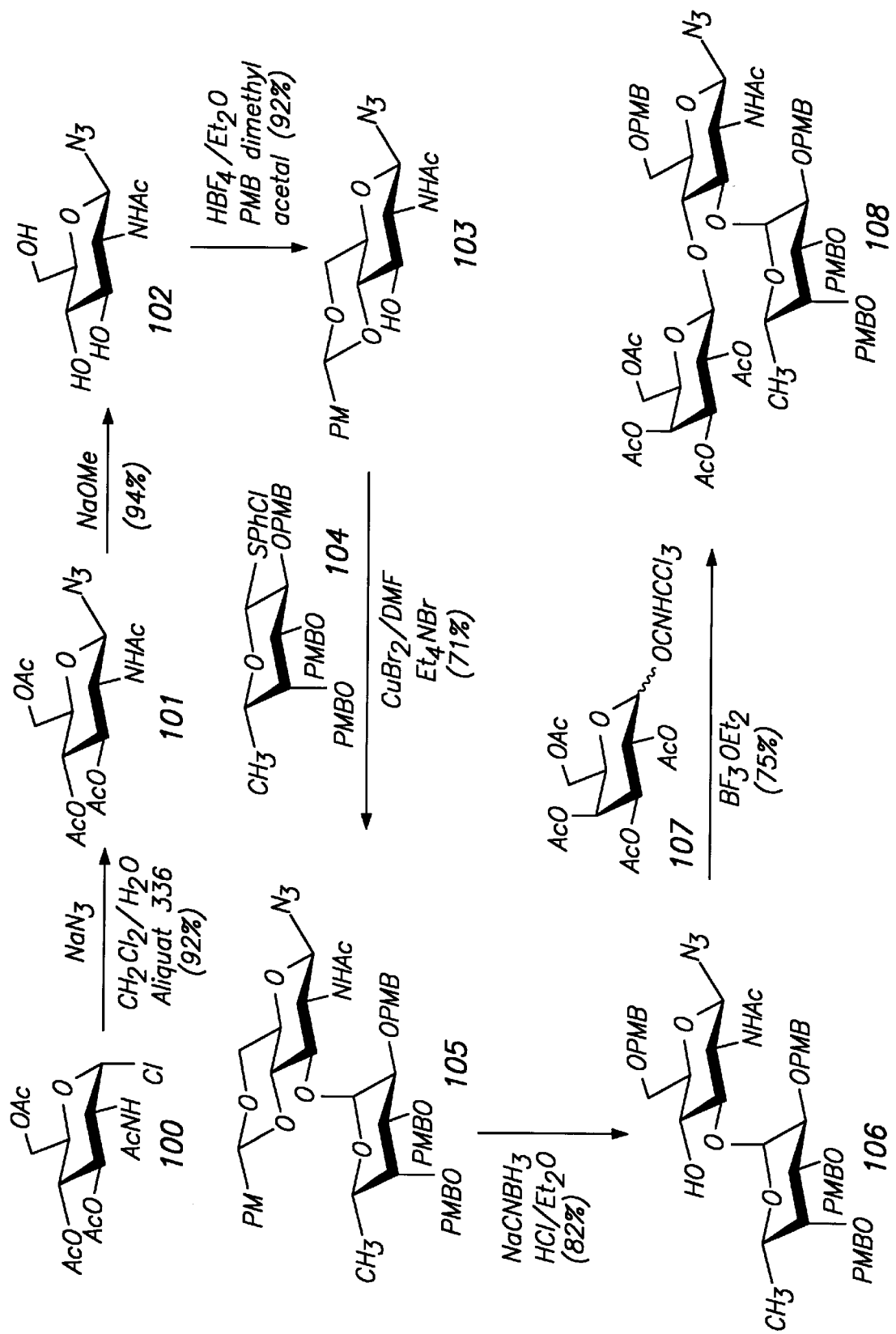
FIGS. 11A and 11B (collectively FIG. 11) illustrate a reaction scheme for the synthesis of 1-azido- 3'-sulfo-Lewis$^x$ compounds which can then be derivatized to 3'-sulfo-Lewis$^x$-NHR compounds.
Figure 11B:
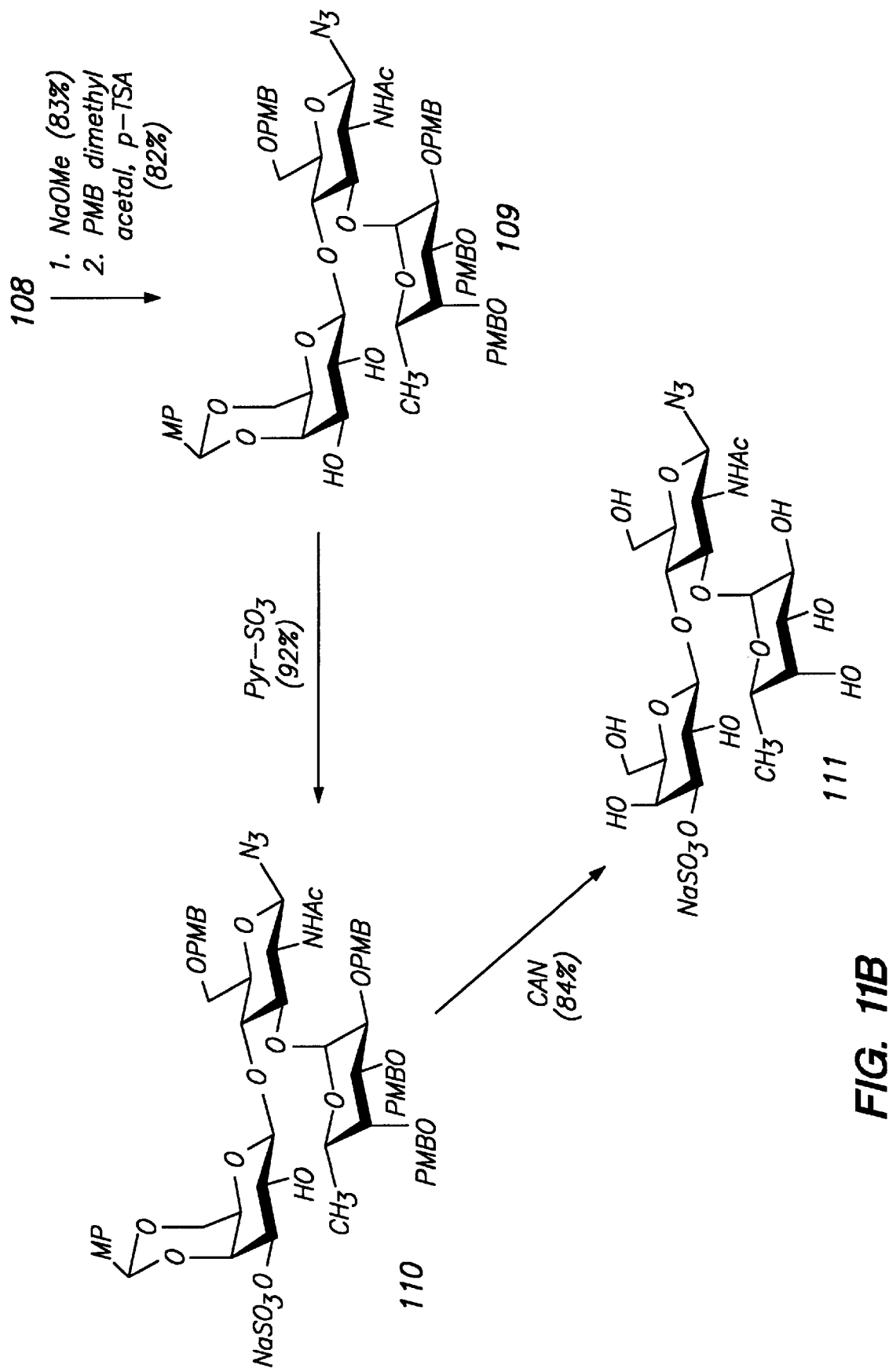

FIG. 11 illustrates a reaction scheme for the synthesis of 1-azido-3'-sulfo -Lewis$^x$compounds. Subsequent reduction of the azido group leads to the amino group which, in turn, leads to amino derivatives of the formula 3'-sulfo-Lewis$^x$-NHR compounds where R is as defined above.

Specifically, in FIG. 11, the known compound 3,4,6-triacetyl-2-acetamido-2-deoxy-α-D-glucopyranoside chloride 100 is converted to the 4,6-O-benzylidine-2-acetamido-2-deoxy-D-glucopyranoside azide, compound 103, by conventional conditions well known in the art and described by Unverzagt, et al.[35] Specifically, compound 100, as described by Srivastava, et al.[23], is first converted to the azido derivative by reaction with sodium azide in a suitable inert diluent such as dichloromethane:water in the presence of the phase transfer catalyst tri-n-capryl-methyl ammonium chloride (Aliquat 336) to provide for compound 101 which, in turn, is deacetylated by conventional Zemplen conditions (NaOMe/MeOH) and then treated under conventional conditions with p-methoxybenzyl dimethylacetal to provide for the 4,6-O-p-methoxybenzylidine derivative 103.

The 4,6-O-p-methoxybenzylidine derivative, compound 103, is then coupled with p-chlorophenyl 2,3,4-tri-O-p-methoxybenzyl-β-L-thiofucopyranoside, compound 104, under conventional coupling conditions to provide for disaccharide 105. Compound 104 is prepared in a manner disclosed in Example 1 of Srivastava, et al.[23] wherein the benzyl groups used in that example are replaced with p-methoxybenzyl groups.

The 4,6-O-benzylidene group of compound 105 is then opened regioselectively to provide for compound 106 having an unblocked hydroxyl group at the 4-position.

Subsequently, disaccharide 106 is converted to trisaccharide 108 by conventional coupling of O-(2,3,4,6-tetra-O-acetyl-α-D-galactopyranosyl)-trichloroacetimidate, compound 107, and deacetylation under conventional Zemplin conditions. The resulting compound is then selectively protected at the 4,6-positions by forming the 4,6-p-methoxybenzylidene derivative by reaction with p-methoxybenzaldehyde dimethylacetal in the presence of an acidic catalyst, such as pTSA, to provide for compound 109. Selective sulfonation, as described above, provides for compound 110 which is followed by conventional removal of the protecting groups to provide for 1-azido-3'-sulfo-Lewis$^x$ compound 111.

Compound 111 provides for a convenient route for the synthesis of other compounds. Specifically, the azido group of compound 111 can be reduced by conventional means (e.g., hydrogenation with palladium on carbon) to provide for the amino derivative which can then be acetylated, alkylated, etc. by conventional means to provide for —NHR derivatives as illustrated in Examples 21–27 below. Conventional amine reactions well known in the art permit a wide range of —NHR compounds. If desired, the reactions of the amino group can be conducted while the reactive hydroxyl groups on the trisaccharide are blocked with removable blocking groups to avoid unintended reactions at these positions.

I. Deoxy/Sulfo Compounds

Figure 12A:
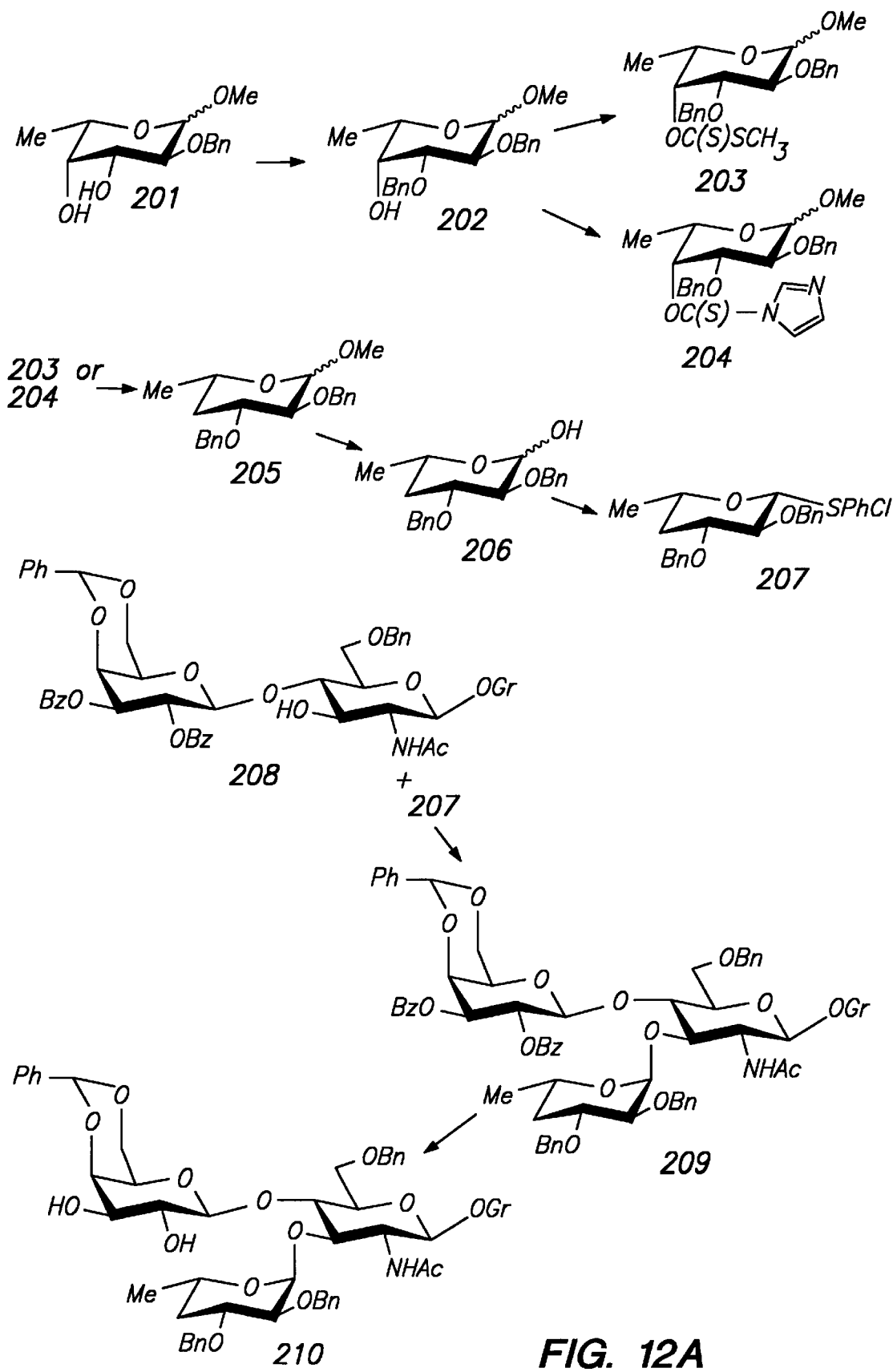
FIGS. 12A and 12B (collectively FIG. 12) illustrate a reaction scheme for the synthesis of 8-methoxycarbonyl 2-acetamido-2-deoxy-3-O-(4-deoxy-α-L-fucopyranosyl)-4-O-(3-O-sulfo-β-D-galactopyranosyl)-β-D-glucopyranoside (Gr=—$(CH_2)_8COOCH_3$).
Figure 12B:
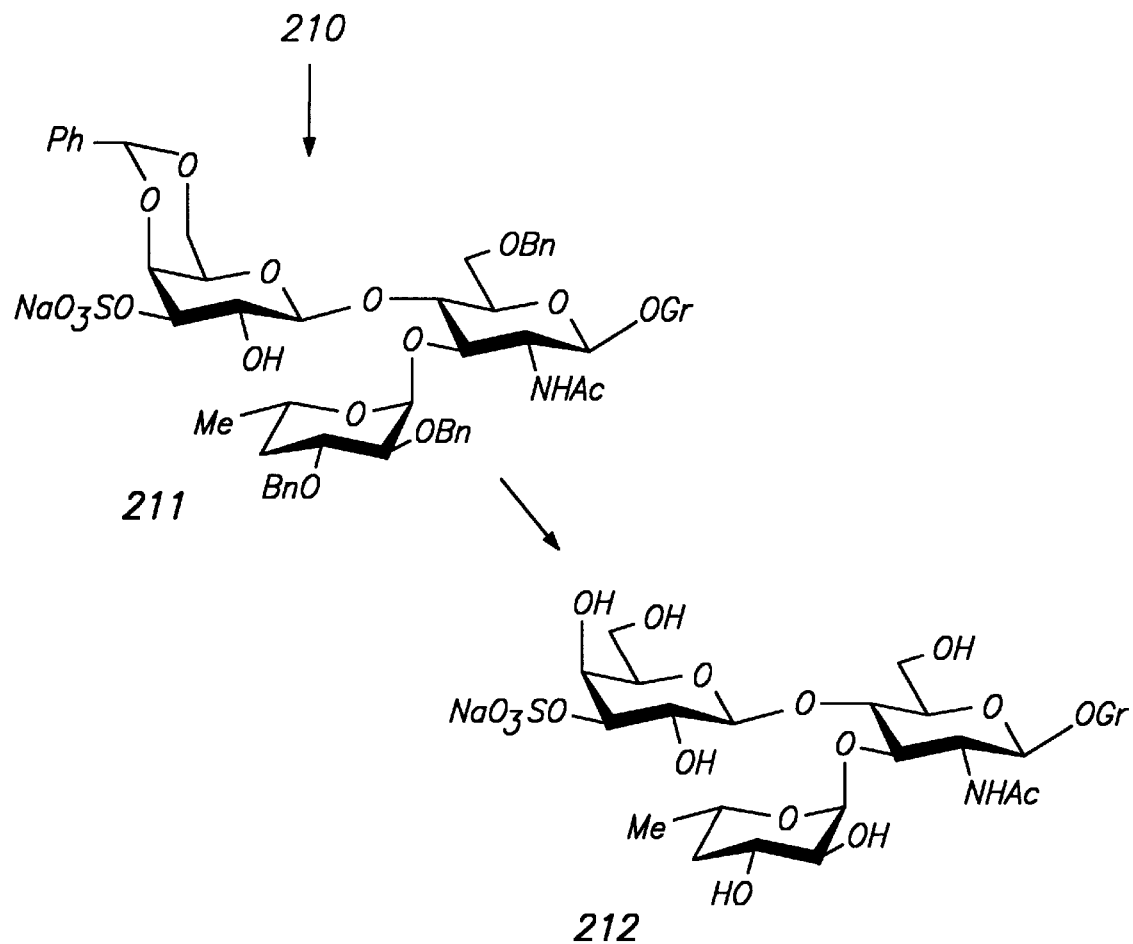
Figure 16A:
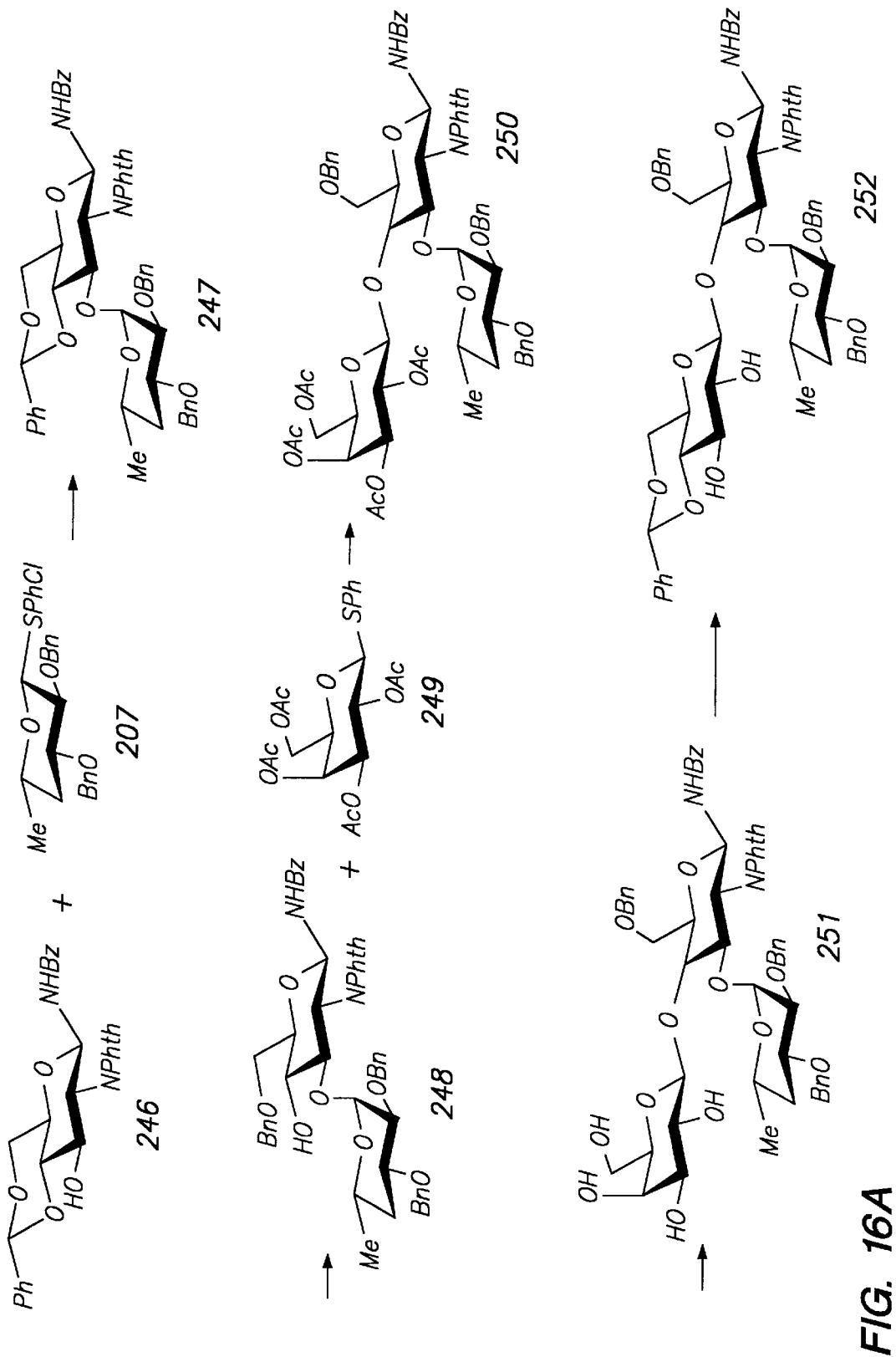
FIGS. 16A and 16B (collectively FIG. 16) illustrate a reaction scheme for the synthesis of 2-benzamido-2-deoxy-3-O-(4-deoxy-α-L-fucopyranosy)-4-O-(3-O-sulfo-β-D-galactopyranosyl)-(β-D-glucopyranosyl benzamide.
Figure 16B:
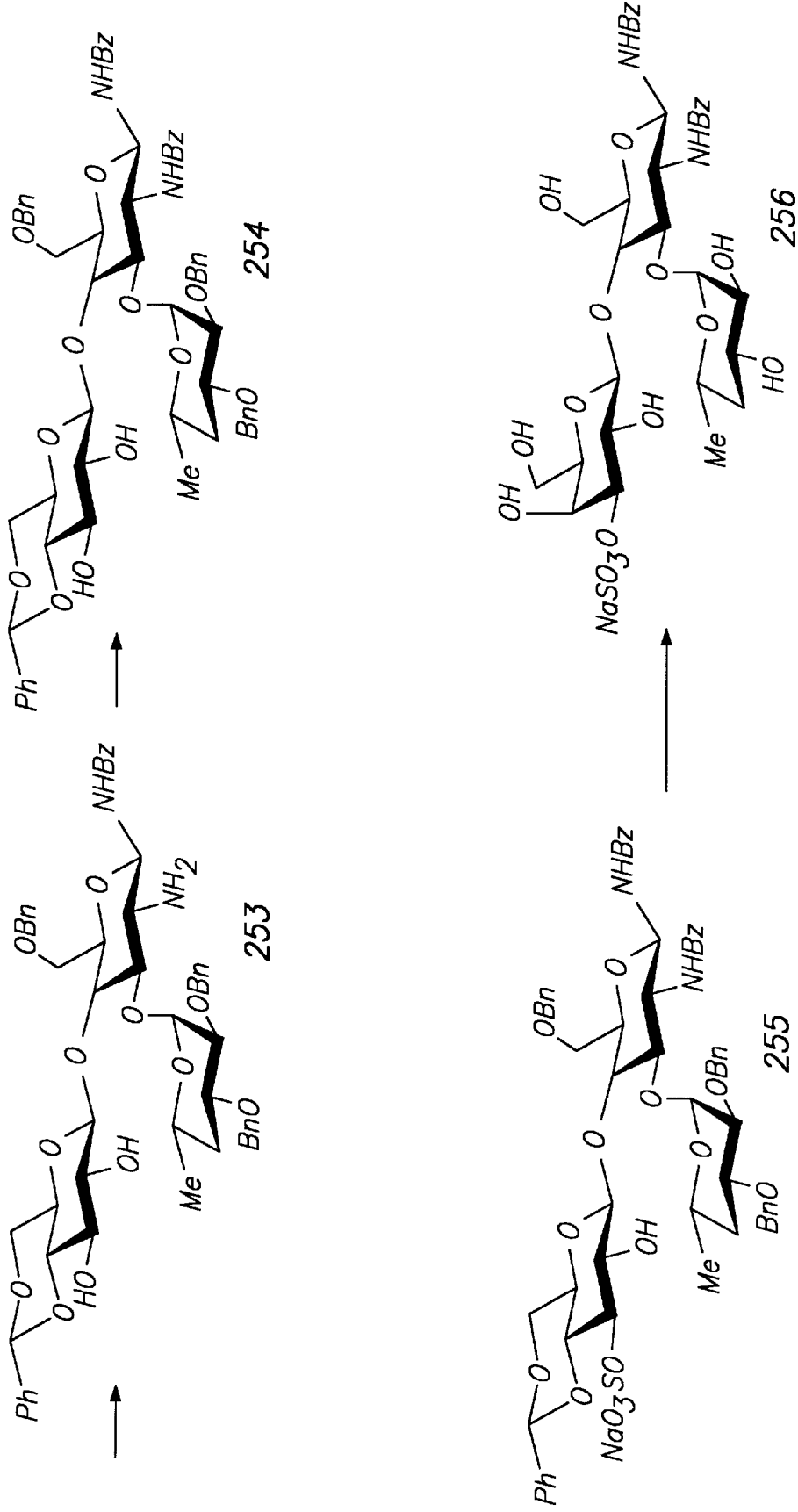

FIGS. 12 and 16 illustrate the synthesis of Lewis$^x$-YR compounds having a sulfo group on the galactose unit and further having one of the hydroxyl groups on the fucose unit being replaced with hydrogen.

The initial synthetic scheme provided in FIG. 12 illustrates the preparation of deoxyfucose compounds which can be incorporated into the Lewis$^x$ structures. Specifically, FIG. 12 illustrates the literature conversion of methyl 2-O-benzyl-L-fucopyranoside, compound 201, to methyl 2,3-di-O-benzyl-L-fucopyranoside, compound 202, as reported by Deter-Jusynski, et al.[36] The free hydroxy in compound 202 is then converted to the corresponding (methylthio) thiocarbonyl derivative 203 by reaction carbon disulfide and methyl iodide or the corresponding imidazolethiocarbonyl derivative 204 by reaction with 1,1'-thio-carbonyldiimidazole. Reduction of either compound 203 or 204 provides for the corresponding deoxy derivative 205 which is then demethylated under acidic conditions to provide for 2,3-di-O-benzyl-4-deoxy-L-fucopyranose, compound 206. In turn, compound 206 is treated with p-chlorothiophenol to provide for the corresponding p-chlorophenyl thiofucopyranoside, compound 207, which is now ready for coupling to the N-acetylglucosamine unit.

FIG. 12 illustrates one example of using compound 207 to couple with an N-acetylglucosamine unit. Specifically, compound 207 is coupled via conventional coupling conditions to disaccharide 208 disclosed in International Patent Application Serial No. PCT/US93/04909 to provide for fully protected trisaccharide 209. The benzoyl groups of compound 209 are differentially removed with sodium hydroxide to provide for trisaccharide diol 210. Selective sulfonation, as described above, provides for compound 211 which is followed by conventional removal of the protecting groups to provide for 8-methoxycarbonyloctyl 2-acetamido-2-deoxy-3-O-(4-deoxy-α-L-fucopyranosyl)-4-O-(3-O-sulfo-β-D-galactopyranosyl)-β-D-gluco-pyranoside, compound 212.

FIG. 16 illustrates another method for the preparation of Lewis$^x$ analogues wherein the —YR aglycon is —NHR. Specifically, the synthesis of FIG. 16 starts with compound 246 which was prepared in a manner similar to compound 103 with the exception that the N-acetyl group is replaced by N-phthalimido group and the azido group has been reduced to the amine and then converted to the —NHBz group by conventional methods. Compound 246 is then coupled to compound 207 to provide for disaccharide 247. The benzylidene group of disaccharide 247 is then ring opened to provide for monohydroxy derivative 248 which is coupled to monosaccharide 249 to provide for trisaccharide 250. Removal of the acetyl groups on the galactose unit of trisaccharide 250 provides for compound 251 which is then converted to the corresponding 4,6-di-O-benzylidene structure (compound 252). Conventional removal of the N-phthalimido group provides for amine 253 which is then converted to the corresponding N-benzamido derivative 254. Selective sulfonation, as described above, provides for compound 255 which is followed by conventional removal of the protecting groups to provide for compound 256.

J. 3',4"- and 3',3"-Disulfo-Lewis$^x$ Compounds

Figure 13A:
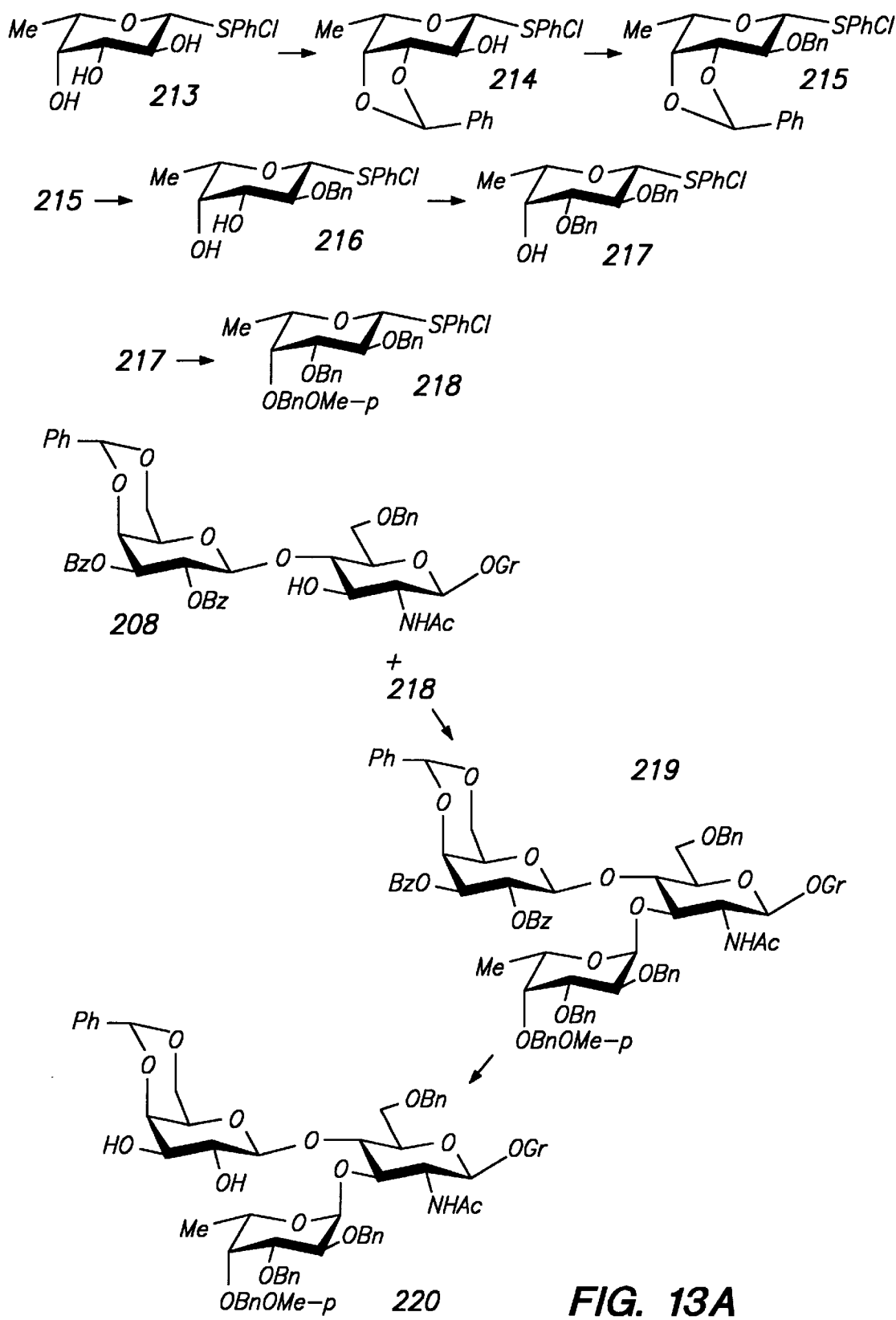
FIGS. 13A and 13B (collectively FIG. 13) illustrate a reaction scheme for the synthesis of 8-methoxycarbonyl 2-acetamido-2-deoxy-3-O-(4-O-sulfo-α-L-fucopyranosyl)-4-O-(3-O-sulfo-β-D-galactopyranosyl)-β-D-glucopyranoside.
Figure 13B:
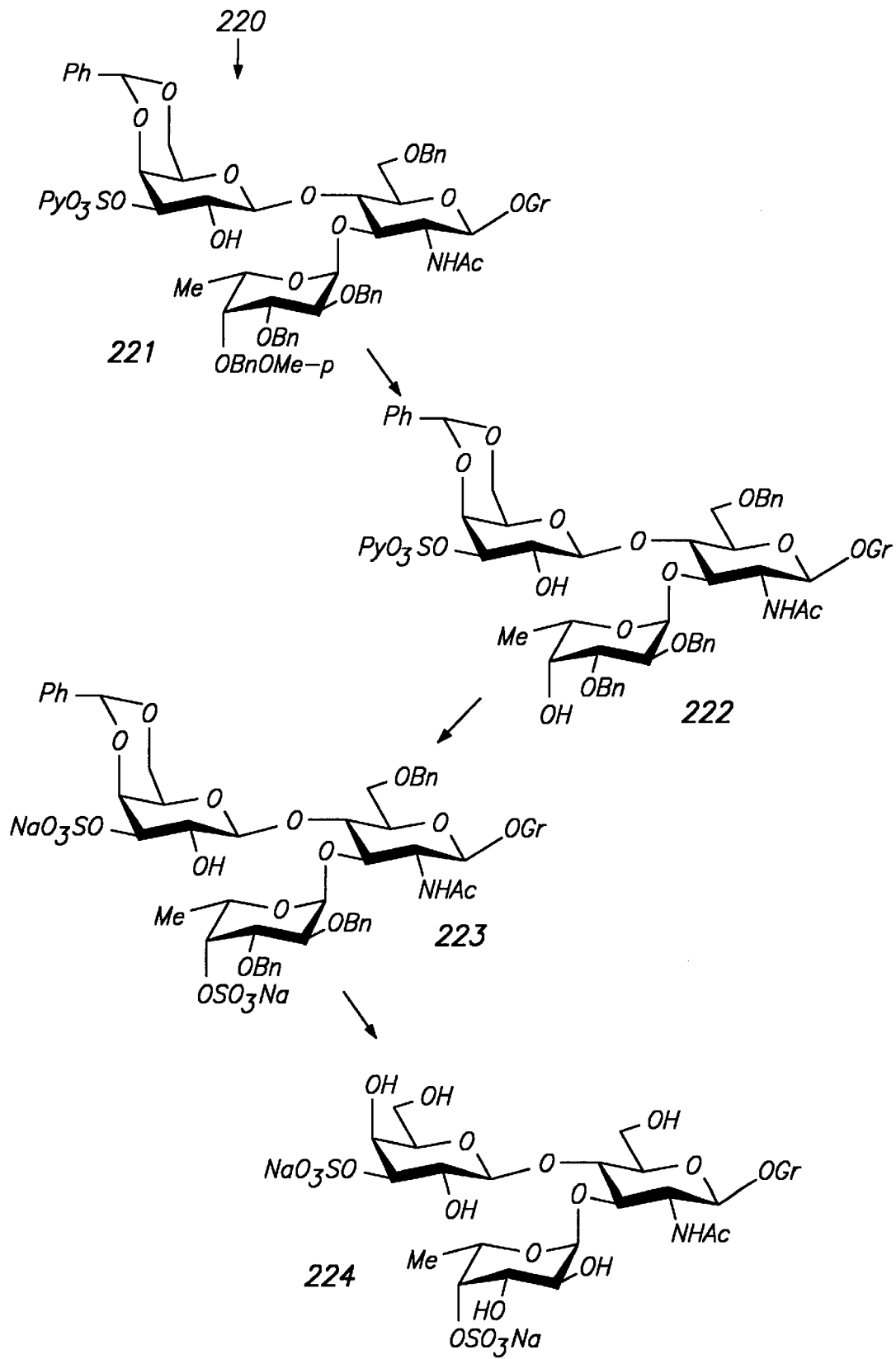

FIG. 13 illustrates the synthesis of 3',4"-disulfo-Lewis$^x$ compounds. Specifically, in this figure, known p-chlorophenyl β-L-thiofucopyranoside, 213, is converted to the corresponding protected 4,6-di-O-benzylidine structure, compound 214, and then the hydroxyl group at the 2-position is blocked with a benzyl group to provide for compound 215. Removal of the benzylidene group and selective benzylation of the 3-hydroxyl group leads to compound 217 which is then blocked at the remaining hydroxyl group with a p-methoxybenzyl group to provide for compound 218.

FIG. 13 also illustrates one example of using compound 218 to couple with an N-acetylglucosamine unit. Specifically, compound 218 is coupled via conventional coupling conditions to disaccharide 208 to provide for fully protected trisaccharide 219. The benzoyl groups of compound 219 are differentially removed with sodium hydroxide to provide for trisaccharide diol 220. Selective sulfonation, as described above, provides for compound 221 which is followed by conventional removal of the p-methoxybenzyl group to provide for diol 222. Again selective sulfonation of compound 222 as described above leads to compound 223 followed by removal of the protecting groups to provide for 8-methoxycarbonyloctyl 2-acetamido-2-deoxy-3-O-(4-O-sulfo-α-L-fucopyranosyl)-4-O-(3-O-sulfo-β-D-galactopyranosyl)-β-D-glucopyranoside, compound 224.

Figure 14A:
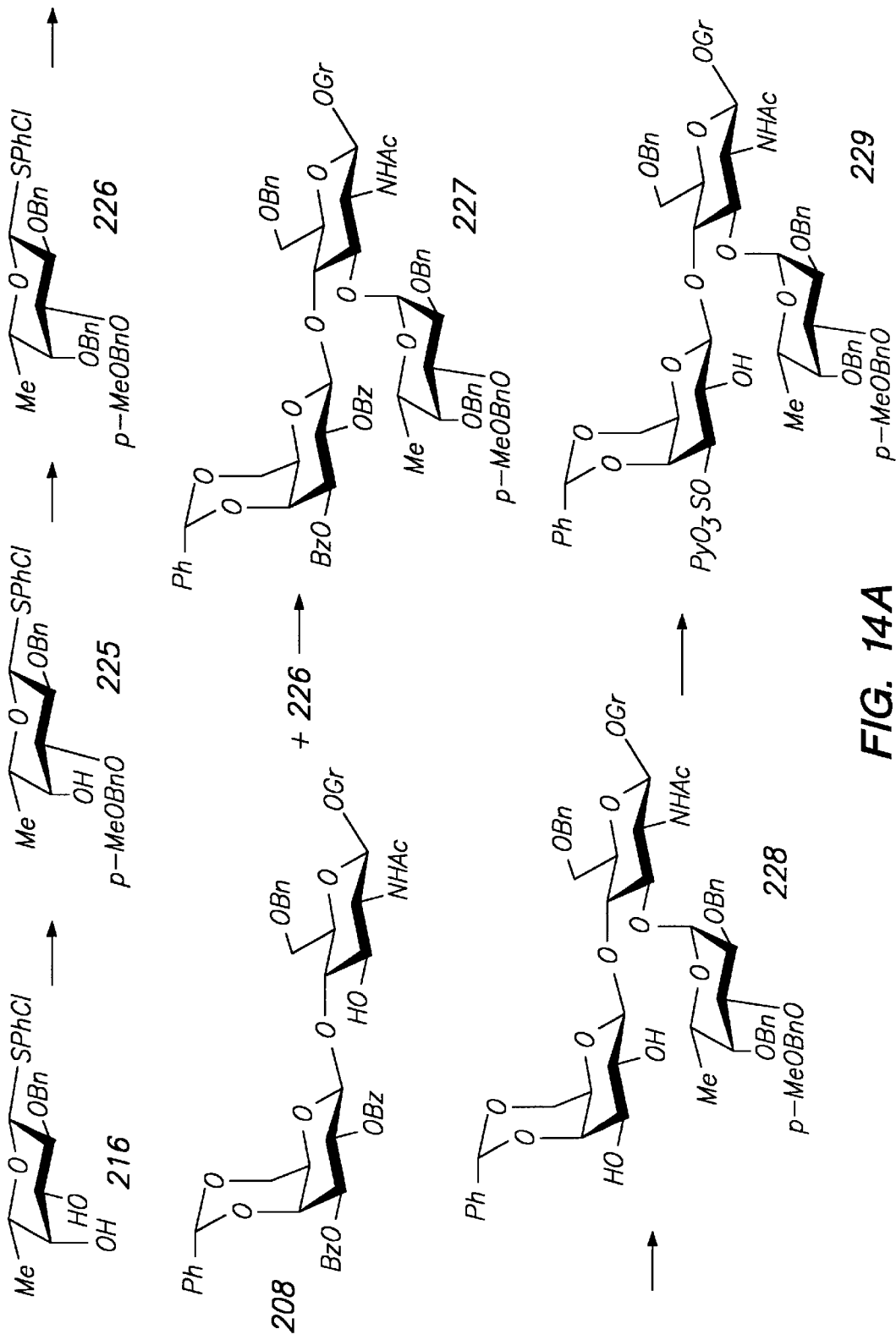
FIGS. 14A and 14B (collectively FIG. 14) illustrate a reaction scheme for the synthesis of 8-methoxycarbonyloctyl 2-acetamido-2-deoxy-3-O-(3-O-sulfo-α-L-fucopyranosyl)-4-O-(3-O-sulfo-β-D-galactopyranosyl)-β-D-glucopyranoside.
Figure 14B:
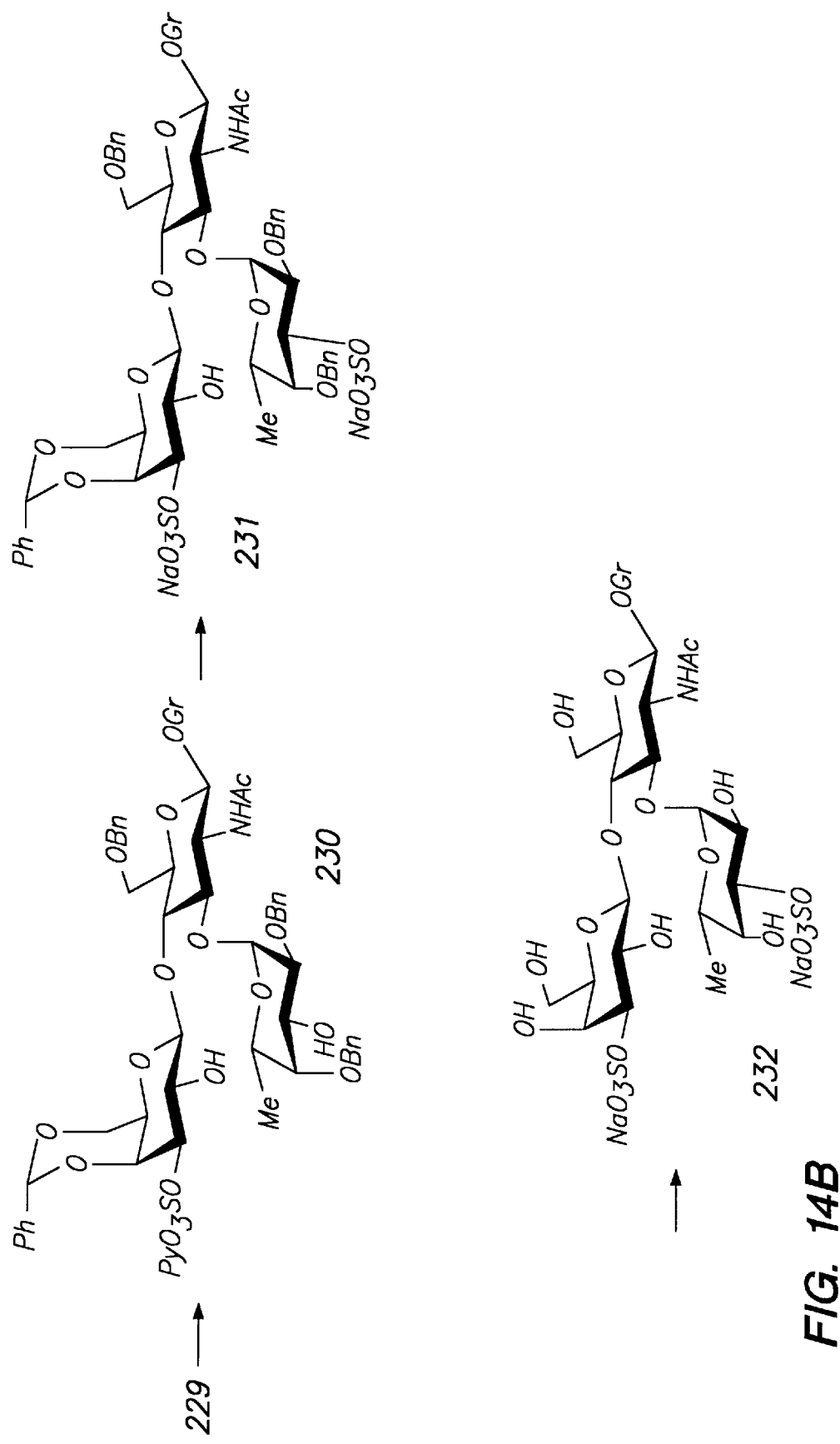

FIG. 14 illustrates the synthesis of 3',3"-disulfo-Lewis$^x$ compounds such as 8-methoxycarbonyloctyl 2-acetamido-2-deoxy-3-O-(3-O-sulfo-α-L-fucopyranosyl)-4-O-(3-O-sulfo-β-D-galactopyranosyl)-β-D-glucopyranoside, compound 232.

Specifically, in this figure, p-chlorophenyl 2-O-benzyl-β-L-thiofucopyranoside, compound 216 (as described above), is converted to the corresponding protected 3-O-p-methoxybenzyl derivative, compound 225, and then the hydroxyl group at the 4-position is blocked with a benzyl group to provide for compound 226.

FIG. 14 also illustrates one example of using compound 226 to couple with an N-acetylglucosamine unit. Specifically, compound 226 is coupled via conventional coupling conditions to disaccharide 208 to provide for fully protected trisaccharide 227. The benzoyl groups of compound 227 are differentially removed with sodium hydroxide to provide for trisaccharide diol 228. Selective sulfonation, as described above, provides for compound 229. Selective removal of the p-methoxybenzyl protecting group on the 3-position of the fucose provides for compound 230 which is then selectively sulfonated, again as described above, to provide for compound 231. Conventional removal of the remaining protecting groups provides for 8-methoxycarbonyloctyl 2-acetamido-2-deoxy-3-O-(3-O-sulfo-α-L-fucopyranosyl)-4-O-(3-O-sulfo-β-D-galactopyranosyl)-β-D-glucopyranoside, compound 232.

K. 3'-sulfo-3'-methoxy-Lewis$^x$ derivatives

Figure 15A:
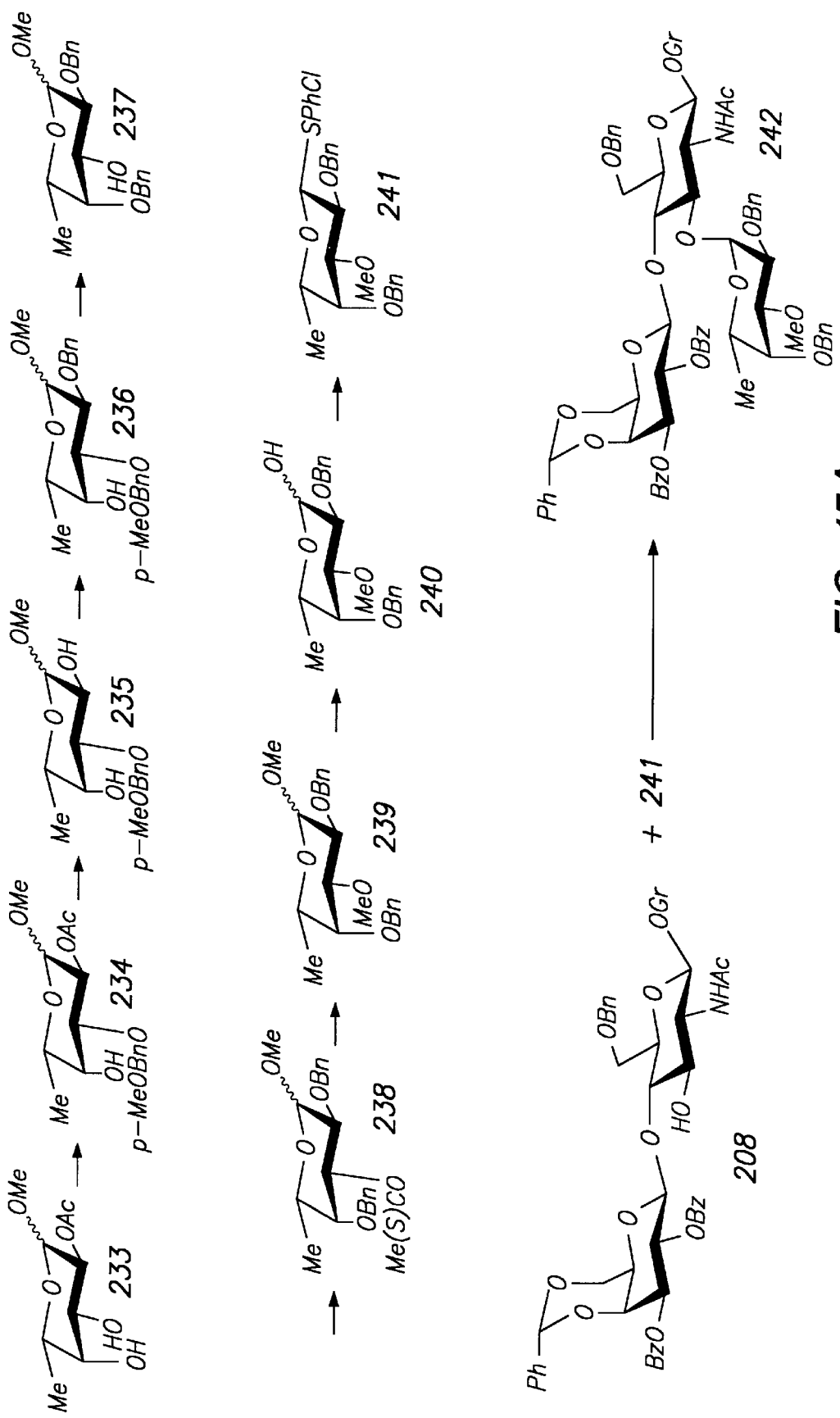

FIG. 15 illustrates the synthesis of 3'-sulfo-3"methoxy-Lewis$^x$ compounds such as 8-methoxycarbonyloctyl 2-acetamido-2-deoxy-3-O-(3-O-methyl-α-L-fucopyranosyl)-4-O-(3-O-sulfo-β-D-galactopyranosyl)-β-D-glucopyranoside, compound 245. Specifically, in this figure, known methyl 2-O-acetyl-L-fucopyranoside 233 (Zehavi, et al., J. Org. Chem., 37:13 (1977)) is converted to the corresponding protected 3-p-methoxybenzyl derivative, compound 234. The acetyl group at the 2 position is removed and the 2,4-hydroxyl groups are blocked with benzyl groups to provide for compound 236. Selective removal of the p-methoxybenzyl group at the 3-position provides for compound 237 which is then converted to the (methylthio) thiocarbonyl derivative, compound 238. Reduction of this compound provides for the methoxy derivative, compound 239 which is then treated under acidic conditions to provide for the reducing sugar (240) which is converted under conventional conditions to the corresponding p-chlorophenyl thiofucopyranoside (compound 241).

FIG. 15 also illustrates one example of using compound 241 to couple with an N-acetylglucosamine unit. Specifically, compound 241 is coupled via conventional coupling conditions to disaccharide 208 to provide for fully protected trisaccharide 242. The benzoyl groups of compound 242 are differentially removed with sodium hydroxide to provide for trisaccharide diol 243. Selective sulfonation, as described above, provides for compound 244 which is followed by conventional removal of the protecting groups to provide for 3'-sulfo-3"-methoxy-Lewis$^X$ compounds such as 8-methoxycarbonyloctyl 2-acetamido-2-deoxy-3-O-( 3-O-methyl-α-L-fucopyranosyl)-4-O-(3-O-sulfo-β-D-galactopyranosyl)-β-D-glucopyranoside, compound 245.

Additional compounds which can be prepared via similar methods are described in Examples 32–52 below the synthesis of which is illustrated in FIGS. 17–36.

Lewis$^A$ Analogues

The preparation of oligosaccharide glycosides having a 1→3 linkage between the galactose unit (or derivatized galactose unit) and the N-acetylglucosamine unit (or derivatized N-acetylglucosamine unit) as found in formula II above can be prepared by the procedures set forth above using appropriately protected N-acetylglucosamine compounds as described by, for example, Ippolito et al.[32]

Utility

Without being limited to any theory, it is believed that the oligosaccharide glycosides disclosed herein affect the cell mediated immune response in a number of ways. Specifically, these compounds can inhibit the ability of the immune response to become educated about a specific antigen when the compound is administered simultaneously with the first exposure of the immune system to the antigen.

Also, the oligosaccharide glycosides disclosed herein can inhibit the secondary immune response to an antigen in a sensitized mammal when administered after second or later exposures of the immune system to the same antigen. Additionally, the oligosaccharide glycosides disclosed herein can induce tolerance to antigens when administered at the time of second or later exposures of the immune system to the antigen.

The suppression of the inflammatory component of the secondary immune response by the oligosaccharide glycosides disclosed herein requires administering such compounds after initiation of the mammal's secondary immune response but at or prior to one-half the period required for maximal antigen induced inflammation. This criticality is disclosed in allowed U.S. patent application No. 08/081,214 entitled "Time Dependent Administration of Oligosaccharide Glycosides Related to Blood Group Determinants Having a Type I or Type II Core Structure in Reducing Inflammation in a Sensitized Mammal Arising from Exposure to an Antigen" which application is incorporated herein by reference in its entirety.

In this embodiment, the oligosaccharide glycosides of this invention are preferably administered to the patient at least about 0.5 hours after antigen exposure, more preferably, at least about 1 to 10 hour after antigen exposure, and still more preferably, from about at least about 1 to 5 hours after antigen exposure.

Similarly, in cell-mediated inflammatory responses arising from injuries (e.g., adult respiratory distress injury (lung injury)), administration of an oligosaccharide glycoside of this invention is also conducted after initiation of the immune response to this injury but at or prior to one-half the period required for maximal inflammation.

The oligosaccharide glycosides disclosed herein are effective in suppressing cell-mediated immune responses including cell-mediated immune response to an antigen (e.g., the inflammatory component of a DTH response) as well as in suppressing cell-mediated inflammatory responses to injury (e.g., lung injury) when administered at a dosage range of from about 0.5 mg to about 50 mg/kg of body weight per day, and preferably from about 0.5 to about 5 mg/kg of body weight per day. The specific dose employed is regulated by the particular cell-mediated immune response being treated as well as by the judgment of the attending clinician depending upon factors such as the severity of the adverse immune response, the age and general condition of the patient, and the like. The oligosaccharide glycosides of this invention are generally administered parenterally, such as intranasally, intrapulmonarily, transdermally and intravenously, although other forms of administration are contemplated.

In addition to providing suppression of a mammal's secondary immune response to an antigen, administration of the oligosaccharide disclosed herein also imparts a tolerance to later challenges from the same antigen provided that the compound is administered during the critical period discussed above. In this regard, re-challenge by the same antigen weeks after administration of the oligosaccharide glycoside results in a significantly reduced immune response.

Administration of the oligosaccharide glycosides disclosed herein simultaneously with first exposure to an antigen (i.e., a non-sensitized mammal) imparts suppression of a cell-mediated immune response to the antigen and tolerance to future challenges with that antigen. In this regard the term "reducing sensitization" means that the oligosaccharide glycoside, when administered to a mammal in an effective amount along with a sufficient amount of antigen to induce an immune response, reduces the ability of the immune system of the mammal to become educated and thus sensitized to the antigen administered at the same time as the oligosaccharide glycoside. An "effective amount" of this compound is that amount which will reduce sensitization (immunological education) of a mammal, including humans, to an antigen administered simultaneously as determined by a reduction in a cell-mediated response to the antigen such as DTH responses as tested by the footpad challenge test. Preferably the reduction in sensitization will be at least about 20% and more preferably at least about 30% or more. Generally, the oligosaccharide glycosides disclosed herein are effective in reducing sensitization when administered at a dosage range of from about 0.5 mg to about 50 mg/kg of body weight per day, and preferably from about 0.5 mg to about 5 mg/kg of body weight per day. The specific dose employed is regulated by the sensitization being treated as well as the judgement of the attending clinician depending upon the age and general condition of the patient and the like. "Simultaneous" administration of the compound with the antigen with regard to inhibiting sensitization means that the compound is administered once or continuously throughout a period of time within 3 hours of the administration of an antigen, more preferably the compound is administered within 1 hour of the antigen.

The methods of this invention are generally achieved by use of a pharmaceutical composition suitable for use in the parenteral administration of an effective amount of a oligosaccharide glycoside of this invention. These compositions comprise a pharmaceutically inert carrier such as water, buffered saline, etc. and an effective amount of a oligosaccharide glycoside so as to provide the above-noted dosage of these compounds when administered to a patient. Preferably, the pharmaceutical compositions comprise from about 1 to 99 weight percent of said inert carrier and from 99 to 1 weight percent of the oligosaccharide glycoside(s) described herein. It is contemplated that suitable pharmaceutical compositions can additionally contain optional components such as a preservative, etc.

It is also contemplated that other suitable pharmaceutical compositions can include oral compositions, transdermal compositions or bandages etc., which are well known in the art. Therefore, the compositions can be in the form of tablets, pills, powders, lozenges, sachets, cachets, elixirs, suspensions, emulsions, solutions, syrups, aerosols, ointments, soft and hard gelatin capsules, suppositories, sterile injectable solutions and sterile packaged powders. It is still further contemplated that the oligosaccharide glycoside compound can be incorporated as a part of a liposome or a micelle which can then be formulated into a pharmaceutical composition.

It is also contemplated that mixtures of these compounds can be used.

EXAMPLES

The following examples are set forth to illustrate the claimed invention and are not to be construed as a limitation thereof.

Examples 1–52 illustrate synthetic procedures for representative oligosaccharide glycosides of the present invention. Example A illustrates the suppression of antigen-induced inflammation in a mammal by administering the oligosaccharide glycoside compounds of Examples 7, 8, 9, 11, 12 and 13.

In these examples, the following abbreviations have the following meanings. If not defined, any abbreviation used in this application has its generally accepted meaning.

Ac=acetyl
AIBN=azobisisobutyronitrile
aq.=aqueous
Bn=benzyl
Bz=benzoyl
CAN=ceric ammonium nitrate
° C.=degrees Celsius
d=doublet
DBU=1,8-diazabicyclo[5.4.0]undec-7-ene
DMF=dimethylformamide
DTH=delayed type hypersensitivity
EDTA=ethylene diamine tetraacetic acid
eq.=equivalents
g=gram
Gr=—(CH$_2$)$_8$COCH$_3$
$^1$H-nmr=proton nuclear magnetic resonance
kg=kilogram
L=liter
m=multiplet
M=molar
mg=milligrams
mL=milliliter
mmol=millimolar
MP=p-methoxy
N=normal
PMB=p-methoxybenzyl
s=singlet
THF=tetrahydrofuran
tlc=thin-layer chromatography
TR=trityl
μg=microgram
μL=microliter Example 1

Synthesis of 8-Methoxycarbonyloctyl-2-benzamido3-O-(α-L-fucopyranosyl)-4-O-[3-O-sulfo-β-D-galactopyranosyl]-2-deoxy-β-D-glucopyranoside sodium salt (compound 22)

The synthesis of compound 22 is illustrated in FIG. 1.
Step (A)—Preparation of 8-Methoxycarbonyloctyl-2-azido-2-deoxy-β-D-glucopyranoside (compound 1a)

3,4,6-Tri-O-acetyl-2-azido-2-deoxy-α-D-glucopyranosyl bromide (synthesized according to the procedure described by Paulsen, et al.[19] and BeMiller, et al.[20]) (5 g, 12.6 mmol) in dichloromethane (5 mL) was added dropwise over a period of 0.5 hours to a stirred mixture of 8-methoxycarbonyloctanol (5.0 g), molecular sieves 4A (7.5 g, crushed) and dry silver carbonate (4.5 g) in dichloromethane (5 mL) at −20° C. The mixture was warmed to −10° C. and stirred for 3–4 hours at which time analysis of the mixture by tlc (hexane-ethyl acetate; 60:40) indicated that the reaction was complete. The mixture was then diluted with dichloromethane and filtered on Celite which had been washed twice with water. The solution was then evaporated and the resulting crude product was dissolved in pyridine (30 mL) and acetylated with acetic anhydride (1.5 mL) at 22° C. for 48 hours. Methanol was added to the mixture which was then diluted with dichloromethane, washed with water, a solution of sodium bicarbonate, water and brine. The crude product was chromatographed on silica gel, eluting with hexane-ethyl acetate (75:25), to give 8-methoxycarbonyloctyl-2-azido-2-deoxy-3,4,6-tri-O-acetyl-β-D-glucopyranoside (compound 1") (5.5 g, 87%). The product was crystallized from ethanol. $[α]_D^{22}$ −13.2° (C1.0, chloroform); m.p. 59°–61° C.; $^1$H-nmr (CDCl$_3$) δ=5.00(m, 2H, H-3 and H-4), 4.39 (d, 1H, J$_{1,2}$ 7.5 Hz, H-1), 3.45–4.45 [m incl. OCH$_3$ (s, 3.67)], 2.10, 2.05 (2s, 6H, 2 OAc); Anal. Calc. for C$_{22}$H$_{35}$O$_{10}$N$_3$: C, 52.68; H, 7.03; N, 8.38, Found: C, 52.74; H, 6.90: N, 8.42.

A 0.2N solution of sodium methoxide in methanol (0.5 mL) was syringed into a flask containing the triacetate compound 1" (5.5 g, 11.0 mmol) in methanol (160 mL). After 1 day at 22° C., Dowex(H$^+$) resin was added to the solution and the mixture was stirred, filtered and evaporated to give 8-methoxycarbonyloctyl-2-azido-2-deoxy-β-D-glucopyranoside (compound 1a) which was used directly in the next step without characterization.

Step (B)—Preparation of 8-Methoxycarbonyloctyl-2-azido-4,6-O-benzylidene-2-deoxy-β-D-glucopyranoside (compound 1)

Compound 1a (7.72 g, 20.6 mmol) from step (A) was dissolved in anhydrous acetonitrile (80 mL). Benzaldehyde dimethylacetyl (6.2 mL, 41.1 mmol) and a catalytic amount of p-toluenesulfonic acid (pTSA) were added and the reaction mixture was stirred at room temperature for 5 hours. The reaction mixture was then neutralized with triethylamine and evaporated. The resulting syrup was chromatographed on silica gel using hexane-ethyl acetate (4:1) as the eluent to provide for compound 1 (7.0 g, 73%).

Step (C)—Preparation of 8-Methoxycarbonyloctyl-2-azido-3-O-(2,3,4tri-O-benzyl-α-L-fucopyranosyl)-4,6-O-benzylidene-2-deoxy-β-D-glucopyranoside (compound 3)

To a suspension of cupric bromide (12.31 g, 55.12 mmol) and molecular sieves (11.0 g) in dry dichloromethane (20 mL) under nitrogen were added DMF (8.5 mL, 110.3 mmol) and tetraethylammonium bromide (2.32 g, 11.03 mmol).

After stirring the dark green mixture for approximately 30 minutes at room temperature, 8-methoxycarbonyloctyl-2-azido-4,6-O-benzylidene-2-deoxy-β-D-glucopyranoside (compound 1—5.11 g, 11.03 mmol) was added. After stirring for 5 minutes, p-chlorophenyl tri-O-benzyl-fucose thioglycoside (compound 2—11.92 g, 21.2 mmol), was added and the mixture was stirred for 15 hours at room temperature. The reaction mixture was then diluted with dichloromethane (500 mL) and filtered. The filtrate was washed with 5% EDTA solution (5×500 mL) and water (2×500 mL) and evaporated to give a syrup. Chromatography of the syrup on Iatrobeads, eluting with hexane-ethyl acetate (5:1), provided compound 3 (5.41 g, 55%).

Step (D)—Preparation of 8-Methoxycarbonyloctyl-2-azido-3-O-(2,3,4tri-O-benzyl-α-L-fucopyranosyl)-6-O-benzyl-2-deoxy-β-D-glucopyranoside (compound 4)

Blocked disaccharide (compound 3—5.0 g, 5.68 mmol), was dissolved in dry THF (20 mL) at room temperature. The reaction mixture was cooled and molecular sieves were added (500 mg, 3A). Sodium cyanoborohydride (5.27 g, 83.9 mmol) was then added along with a small amount of methyl orange (a few crystals). The reaction mixture was stirred for 15 minutes at 0° C. and then an etheral solution of hydrochloric acid was added until the mixture was acidic (pH~3). The reaction mixture was stirred for 1 hours at 0° C. at which time all the starting material had been completely consumed and converted to the product. The reaction mixture was then diluted with dichloromethane (500 mL) and triethylamine was added to neutralize (pH~6–7) the mixture. The resulting mixture was filtered and the precipitate was washed thoroughly with dichloromethane (500 mL). The combined filtrates were then washed sequentially with a saturated solution of sodium bicarbonate (5×1 L) and water (2×1 L), and then evaporated to provide for compound 4 (3 g, 60%) as a syrup.

Step (E)—Preparation of 8-Methoxycarbonyloctyl-2-azido-3-O-(2,3,4-tri-O-benzyl-α-L-fucopyranosyl)-4-O-[2,3,4,6-tetra-O-acetyl-β-D-galactopyranosyl]-6-O-benzyl-2-deoxy-β-D-glucopyranoside (compound 6)

Disaccharide acceptor (compound 4—3.39 g, 3.84 mmol), and imidate donor (compound 5—5.6 g, 11.35 mmol) were dissolved in a mixture of diethyl ether and dichloromethane (30 mL, 2:1) and stirred at −10° C. for 15 minutes. Boron trifluoride etherate (2.33 mL, 18.92 mmol) was added and the reaction mixture was stirred under nitrogen for 15 hours at 0° C. The reaction mixture was then diluted with dichloromethane (500 mL), filtered and washed successively with a saturated solution of sodium bicarbonate (2×500 mL) and water (2×500 mL). Evaporation of the solvent gave a syrup which was purified by chromatography on Iatrobeads, eluting with hexane-ethyl acetate, to provide for compound 6 (3.5 g, 75%).

Step (F)—Preparation of 8-Methoxycarbonyloctyl-2-azido-3-O-(2,3,4-tri-O-benzyl-α-L-fucopyranosyl)-4-O-[β-D-galactopyranosyl]-6-O-benzyl-2-deoxy-β-D-glucopyranoside (compound 7)

Trisaccharide 6 (4.81 g, 3.97 mmol) was dissolved in methanol (50 mL) and a catalytic amount of sodium methoxide (0.5M solution) in methanol was added. The reaction mixture was stirred for 5 hours at room temperature and then neutralized with IR-120(H⁺) ion exchange resin and filtered. The filtrate was then evaporated and the resulting residue was purified by chromatography on silica gel, eluting with hexane-ethyl acetate (1:4), to provide tetrol trisaccharide 7 (4.0 g, 96.5 %).

Step (G)—Preparation of 8-Methoxycarbonyloctyl-2-azido-3-O-(2,3,4-tri-O-benzyl-α-L-fucopyranosyl)-4-O-[4,6-O-benzylldene-β-D-galactopyranosyl]-6-O-benzyl-2-deoxy-β-D-glucopyranoside (compound 8)

To a solution of tetrol trisaccharide 7 (1.81 g, 1.73 mmol) dissolved in anhydrous acetonitrile (20.0 mL) was added benzaldehyde dimethylacetate (520.3 μL, 3.47 mmol) and a catalytic amount of p-toluenesulfonic acid. The reaction mixture, which had a pH of ~3, was monitored by tlc. After stirring the reaction mixture for 5 hours at room temperature, tlc indicated that the starting material had been completely consumed and a new spot having a higher Rf was observed. The reaction mixture was then neutralized with triethylamine (1.0 mL) and evaporated. The resulting residue was chromatographed on silica gel, eluting with hexane-ethyl acetate (1:2), to provide diol 8 (1.5 g, 77%).

Step (H)—Preparation of 8-Methoxycarbonyloctyl-2-amino-3-O-(2,3,4-tri-O-benzyl-α-L-fucopyranosyl)-4-O-[4,6-O-benzylidene-β-D-galactopyranosyl]-6-O-benzyl-2-deoxy-β-D-glucopyranoside (compound 9)

A solution of diol 8 (1.5 g, 1.32 mmol) in a mixture of pyridine, triethylamine and water (2:0.5:0.05, 20 mL) was saturated with a stream of hydrogen sulfide, initially at 0° C. for 2 hours and then at room temperature for 15 hours. After stirring the reaction mixture for 15 hours at room temperature, the solvents were evaporated and then co-evaporated with toluene under high vacuum to remove pyridine. The resulting material was chromatographed on silica gel, eluting with hexane-ethyl acetate (1:2) and (1:4), to provide compound 9 (1.4 g, 96%).

Step (I)—Preparation of 8-Methoxycarbonyloctyl-2-benzamido-3-O-(2,3,4tri-O-benzyl-α-L-fucopyranosyl)-4-O-[4,6-O-benzylidene-β-D-galactopyranosyl]-6-O-benzyl-2-deoxy-β-D-glucopyranoside (compound 11).

To a solution of amino sugar 9 (5.59 g, 5.05 mmol) in methanol (50 mL) was added a saturated sodium hydrogen carbonate solution (100 mL). The reaction mixture was then stirred at 0° C. for 10 minutes. Benzoyl chloride (1.15 mL, 9.94 mmol) was then added and stirring was continued for 1 hour at room temperature by which time the starting material had been completely consumed. The reaction mixture was then diluted with dichloromethane (500 mL), filtered and evaporated. The residue was chromatographed on an Iatrobeads column, eluting with hexane-ethyl acetate (2:1), to provide compound 11 (5.0 g, 82%).

Step (J)—Preparation of 8-Methoxycarbonyloctyl-2-benzamido-3-O-(2,3,4-tri-O-benzyl-α-L-fucopyranosyl)-4-O-[4,6-O-benzylidene-3-O-sulfo-β-D-galactopyranosyl]-6-O-benzyl-2-deoxy-β-D-glucopyranoside sodium salt (compound 15)

To a solution of diol 11 (370 mg, 0.31 mmol) in pyridine (5.0 mL) at 0° C. was added SO₃-pyridine complex (97.3 mg, 0.62 mmol) and the resulting reaction mixture was allowed to warm at room temperature. After stirring for 1 hour, tlc indicated that the starting material was not completely consumed so additional SO₃-pyridine complex (1 eq) was added and stirring was continued for 2 hours. At this time, tlc indicated that there was no remaining starting material. The mixture was then quenched with methanol (5.0 mL) and evaporated to dryness. The residue was chromatographed on Iatrobeads, eluting with dichloromethane-methanol-pyridine (95:5:0.5), to provided compound 15 (310 mg, 76%).

Step (K)—Preparation of 8-Methoxycarbonyloctyl-2-benzamido-3-O-(α-L-fucopyranosyl)-4-O-[3-O-sulfo-β-D-galactopyranosyl]-2-deoxy-β-D-glucopyranoside sodium salt (compound 22).

A mixture of compound 15 (330 mg, 0.25 mmol) and 5 % palladium on carbon (330 mg) in methanol (5.0 mL) was stirred under one atmosphere of hydrogen for 5 hours. The mixture was then filtered through a pad of Celite to remove the catalyst and the Catalyst/Celite was washed with methanol (100 mL). The filtrate and washings were combined and evaporated after adding a trace of pyridine (5.0 mL). The resulting product was chromatographed on Iatrobeads, eluting with isopropanol-water-ammonia (7:15:0.5), to provide compound 22 (150 mg, 70%) after conversion to the sodium salt by passage through Dowex-50-x-8-($Na^+$) resin.

Example 2

Synthesis of 8-Methoxycarbonyloctyl-2-p-nitrobenzamido-3-O-(α-L-fucopyranosyl)-4-O-[3-O-sulfo-β-D-galactopyranosyl]-2-deoxy-β-D-glucopyranoside sodium salt (compound 23)

The synthesis of compound 23 is illustrated in FIG. 1.

Step (A)—Preparation of 8-Methoxycarbonyloctyl-2-p-nitrobenzamido-3-O-(2,3,4-tri-O-benzyl-α-L-fucopyranosyl)-4-O-[4,6-O-benzylidene-β-D-galactopyranosyl]-6-O-benzyl-2-deoxy-β-D-glucopyranoside (compound 12)

To a solution of amino sugar 9 (310 mg, 0.28 mmol) (prepared as described in Example 1) in methanol (4.0 mL) was added a saturated solution of sodium bicarbonate (1.0 mL). The reaction mixture was stirred for 15 minutes at room temperature, cooled to 0° C., and then p-nitrobenzoyl chloride (104 mg, 0.56 mmol) was added. After 15 minutes, tlc indicated that 75% of starting material had been consumed. Additional 4-nitrobenzoyl chloride (150.0 mg) was added and the reaction mixture was stirred at room temperature for 15 hours. At this time, tlc indicated the reaction was essentially complete. The mixture was then diluted with dichloromethane (100 mL) and washed with a saturated solution of sodium bicarbonate (2×100 mL) and water (2×100 mL). Evaporation of the solvent gave a residue which was purified by chromatography on Iatrobeads, eluting with hexane-ethyl acetate (1:2), to provide compound 12 (250 mg, 71%).

Step (B)—Preparation of 8-Methoxycarbonyloctyl-2-p-nitro-benzamido-3-O-(2,3,4-tri-O-benzyl-α-L-fucopyranosyl)-4-O-[4,6-O-benzylidene-3-O-sulfo-β-D-galactopyranosyl]-2-deoxy-6-O-benzyl-β-D-glucopyranoside sodium salt (compound 16)

To a solution of diol 12 (277 mg, 0.22 mmol) in pyridine (3.0 mmol) at 0° C. was added $SO_3$-pyridine complex (52.7 mg, 0.33 mmol). The reaction mixture was stirred for 0.5 hours at 0° C. and then for 2 hours at room temperature. An additional amount of $SO_3$-pyridine complex (1 eq) was then added and stirring was continued for 2 hours at room temperature. The excess reagent was destroyed by adding methanol and the mixture was evaporated. The resulting syrup was purified by chromatography on Iatrobeads, eluting with dichloromethane-methanol-pyridine (95:5:0.5), to provide compound 16 (250 mg, 84%).

Step (C)—Preparation of 8-Methoxycarbonyloctyl-2-p-nitrobenzamido-3-O-(α-L-fucopyranosyl)-4-O-[3-O-sulfo-β-D-galactopyranosyl]-2-deoxy-β-D-glucopyranoside sodium salt (compound 23)

Compound 16 (350 mg, 0.26 mmol) was hydrogenolyzed in the presence of 5% palladium on carbon (350 mg) using the procedure described in Example 1, Step K for compound 15. Conversion of the resulting product to its sodium salt by passage through Dowex-50-x-8 ($Na^+$) resin provided compound 23 (180 mg, 76%) after lyophilization.

Example 3

Synthesis of 8-Methoxycarbonyloctyl-2-ortho-acetyl-benzamido-3-O-(α-L-fucopyranosyl)-4-O-[3-O-sulfo-β-D-galactopyranosyl]-2-deoxy-β-D-glucopyranoside sodium salt (compound 24)

The synthesis of compound 24 is illustrated in FIG. 1.

Step (A)—Preparation of 8-Methoxycarbonyloctyl-2-ortho-acetylbenzamido-3-O-(2,3,4-tri-O-benzyl-α-L-fucopyranosyl)-4-O-[4,6-O-benzylidene-β-D-galactopyranosyl]-6-O-benzyl-2-deoxy-β-D-glucopyranoside (compound 13)

To a solution of amino sugar 9 (270 mg, 0.24 mmol) (prepared as described in Example 1) in dichloromethane (5.0 mL) at room temperature was added 2-o-acetylbenzoic acid (80 mg, 0.49 mmol) and 1-(3-dimethylaminopropyl)-3-ethylcarbodiimide hydrochloride (145 mg, 0.49 mmol). The reaction mixture was then stirred at room temperature overnight. Tlc indicated that some starting material remained so 1 additional equivalent of both reagents were added and stirring was continued for 15 hours. The reaction mixture was then diluted with dichloromethane, washed with water, dried over anhydrous sodium sulfate and evaporated. Chromatography of the residue on Iatrobeads, eluting with toluene-ethanol (95:5), provided compound 13 (250 mg, 83%).

Step (B)—Preparation of 8-Methoxycarbonyloctyl-2-ortho-acetylbenzamido-3-O-(2,3,4-tri-O-benzyl-α-L-fucopyranosyl)-4-O-[4,6-O-benzylidene-3-O-sulfo-β-D-galactopyranosyl]-6-O-benzyl-2-deoxy-β-D-glucopyranoside sodium salt (compound 18).

To a solution of diol 13 (300 mg, 0.24 mmol) in pyridine (3.0 mL) at 0° C. was added $SO_3$-pyridine complex (75.2 mg, 0.47 mmol). The reaction mixture was stirred at 0° C. for 1 hour and then at room temperature for 2 hours. Additional $SO_3$-pyridine complex (0.5 eq) was then added and stirring was continued for an additional 3 hours at room temperature. The excess $SO_3$-pyridine complex was destroyed by adding methanol and the solution was evaporated. The residue was chromatographed on a silica gel, eluting with dichloromethane-methanol-pyridine (95:5:05), to provide compound 18 (250 mg, 77%) after conversion to a sodium salt by passage through Dowex 50-X-8 ($Na^+$) resin.

Step (C)—Preparation of 8-Methoxycarbonyloctyl-2-ortho-acetylbenzamido-3-O-(α-L-fucopyranosyl)-4-O-[3-O-sulfo-β-D-galactopyranosyl]-2-deoxy-β-D-glucopyranoside sodium salt (compound 24)

Compound 18 (300 mg, 0.22 mmol) was hydrogenolyzed in the presence of 5% palladium on carbon (300 mg) using the procedure described in Example 1, Step K for compound 15. Conversion of the resulting product to its sodium salt by passage through Dowex-50-x-8 ($Na^+$) resin provided compound 24 (150 mg, 75%) after lyophilization.

Example 4

Synthesis of 8-Methoxycarbonyloctyl-2-cyclohexamido-3-O-(α-L-fucopyranosyl)-4-O-[3-O-sulfo-β-D-galactopyranosyl]-2-deoxy-β-D-glucopyranoside sodium salt (compound 25)

The synthesis of compound 25 is illustrated in FIG. 1.

Step (A)—Preparation of 8-Methoxycarbonyloctyl-2-cyclohexamido-3-O-(2,3,4-tri-O-benzyl-α-L-fucopyranosyl)-4-O-[4,6-O-benzylidene-β-D-galactopyranosyl]-6-O-benzyl-2-deoxy-β-D-glucopyranoside (compound 14)

To a solution of amino sugar 9 (270 mg, 0.24 mmol) (prepared as described in Example 1) in dichloromethane (50 mL) at room temperature was added cyclohexanecarboxylic acid (31.27 mg, 0.49 mmol) and 1-(3-dimethylaminopropyl)-3-ethylcarbodiimidate hydrochloride (145 mg, 0.49 mmol). The reaction mixture was stirred for 15 hours at room temperature and then an additional 0.49 mmol amount of each reagent was added and stirring was continued overnight. The mixture was then diluted with dichloromethane (100 mL) and the dichloromethane layer washed with water (2×100 mL), dried and evaporated. The residue was chromatographed on Iatrobeads, eluting with dichloromethane-methanol (97:3), to provided compound 14 (230 mg, 79%).

Step (B)—Preparation of 8-Methoxycarbonyloctyl-2-cyclohexamido-3-O-(2,3,4-tri-O-benzyl-α-L-fucopyranosyl)-4-O-[4,6-O-benzylidene-3-O-sulfo-β-D-galactopyranosyl]-6-O-benzyl-2-deoxy-β-D-glucopyranoside sodium salt (compound 17)

To a solution of compound 14 (231.5 mg, 0.19 mmol) in dry pyridine (3.0 mL) at 0° C. was added $SO_3$-pyridine complex (45.5 mg, 0.29 mmol). The solution was allowed to warm at room temperature by which time tlc indicated that all the starting material had been consumed. The excess $SO_3$-pyridine complex was destroyed by adding methanol (1 mL) and the reaction mixture was evaporated. The resulting residue was chromatographed on an Iatrobeads column eluting with dichloromethane-methanol-pyridine (95:5:0.5), to provide compound 17 (225 mg, 90%) after conversion to a sodium salt by passage through Dowex 50-X-8 ($Na^+$) resin.

Step (C)—Preparation of 8-Methoxycarbonyloctyl-2-cyclohexamido-3-O-(α-L-fucopyranosyl)-4-O-[3-O-sulfo-β-D-galactopyranosyl]-2-deoxy-β-D-glucopyranoside sodium salt (compound 25)

Compound 17 (216 mg, 0.16 mmol) was hydrogenolyzed in the presence of 5% palladium on carbon (200 mg) using the procedure described in Example 1, Step K for compound 15. Conversion of the resulting product to its sodium salt by passage through Dowex-50-x-8 ($Na^+$) resin provided compound 25 (120 mg, 86%) after lyophilization.

Example 5

Synthesis of 8-Methoxycarbonyloctyl-2-fuc(C)amido-3-O-(α-L-fucopyranosyl)-4-O-[3-O-sulfo-β-D-galactopyranosyl]-2-deoxy-β-D-glucopyranoside sodium salt (compound 26)

The synthesis of compound 26 is illustrated in FIG. 1.
Step (A)—Preparation of C-Fucoside To a stirred mixture of 1-allyl-1-deoxy-2,3,4-tri-O-acetyl-α-L-fucopyranose (10 g, 31.9 mmols) (prepared as described by Luengo, et al.[33]) in a solvent mixture of acetonitrile:carbon tetrachloride:water (80 mL:80 mL:120 mL)), was added 28.0 g (131.2 mmole) of sodium periodate followed by ruthenium trichloride hydrate (145 mg) in the manner described by Carlsen et al.[34] The reaction became exothermic after 10 minutes and was stirred overnight at room temperature. The mixture was diluted with water (300 mL) and extracted with dichloromethane (2×300 mL). The combined organic layer was washed with water (100 mL) and concentrated. The residual oil was dissolved in ethyl acetate (200 mL) and extracted with saturated sodium bicarbonate (30 mL). The organic layer was washed again with water (20 mL) which was combined with the sodium bicarbonate solution extracts. This combined aqueous extract was acidified with 6N hydrochloric acid solution to pH 1 and extracted with dichloromethane (2×200 mL). The combined organic extracts were washed with water (100 mL), followed by saturated sodium chloride solution, dried over sodium sulfate, filtered and concentrated to give 6.9 g (20.8 mmole, 65%) of (1-deoxy-2,3,4-tri-O-acetyl-α-L-fucopyranoside) acetic acid. Deacetylation of this compound provides for fucose(C)carboxylic acid.

If desired, the fucose(C)carboxylic acid can be converted to its NHS-C-fucoside via conventional methods. For example, (1-deoxy-2,3,4-tri-O-acetyl-α-L-fucopyranoside) acetic acid (1.97 g, 6.16 mmol) was dissolved in dichloromethane (25 mL) and N-hydroxysuccinimide (NHS, 1.0 g, 8.69 mmol) was added to the solution, and the solution was warmed to dissolve the NHS. Dicyclohexylcarbodiimide (DCC, 1.41 g, 6.83 mmol) was dissolved in dichloromethane (5 mL) and added to the reaction mixture with stirring. After 5 hours, the reaction mixture was cooled to 4° C., filtered and evaporated. The syrupy residue was taken up in ethyl acetate (50 mL), filtered and washed with water (2×25 mL). The ethyl acetate layer was dried over anhydrous sodium sulfate, filtered and evaporated. After drying under high vacuum, 2.5 g (94%) of an amorphous white solid (1-deoxy-2,3,4-tri-O-acetyl-α-L-fucopyranosyl) acetic acid N-hydroxysuccinimide ester was obtained.

Step (B)—Preparation of 8-Methoxycarbonyloctyl-2-(2,3,4-tri-O-acetyl-fuc-(C)-amido)-3-O-(2,3,4-tri-O-benzyl-α-L-fucopyranosyl)-4-O-[4,6-O-benzylidene-β-D-galactopyranosyl]-6-O-benzyl-2-deoxy-β-D-glucopyranoside (compound 19)

To a solution of amino sugar 9 (270 mg, 0.24 mmol) (prepared as described in Example 1) in dichloromethane (2.0 mL) at room temperature was added fucose(C) carboxylic acid (443 mg) and 1-(3-dimethylaminopropyl)-3-ethylcarbodiimidate hydrochloride (443 mg). The reaction mixture was stirred for 15 hours at room temperature and then diluted with dichloromethane (100 mL). The organic layer was washed with water (3×100 mL), dried over anhydrous sodium sulfate and evaporated. The residue was then chromatographed on Iatrobeads, eluting with dichloromethane-methanol (95:5), to provided compound 19 (286 mg, 84%).

Step (C)—Preparation of 8-Methoxycarbonyloctyl-2-(2,3,4-tri-O-acetyl-fuc(C)amido)-3-O-(2,3,4-tri-O-benzyl-α-L-fucopyranosyl)-4-O-[4,6-O-benzylidene-3-O-sulfo-β-D-galactopyranosyl]-6-O-benzyl-2-deoxy-β-D-glucopyranoside sodium salt (compound 20)

To a solution of diol 19 (286 mg, 0.2 mmol) in anhydrous dichloromethane (3.0 mL) at 0° C. was added $SO_3$-pyridine complex (2 eq). The reaction mnixture was allowed to warm to room temperature and was stirred for 3 hours. The excess $SO_3$-pyridine complex was destroyed by adding methanol (1.0 mL) and the solution was then evaporated. The resulting residue was chromatographed on an Iatrobead column, eluting with dichloromethane-methanol-pyridine (95:5:0.5), to provided compound 20 (250 mg, 82%) after conversion to the sodium salt by passage through Dowex 50-X-8 ($Na^+$) resin.

Step (D)—Preparation of 8-Methoxycarbonyloctyl-2-fuc(C)amido-3-O-(2,3,4-tri-O-benzyl-α-L-fucopyranosyl)-4-O-[4,6-O-benzylidene-3-O-sulfo-β-D-galactopyranosyl]-6-O-benzyl-2-deoxy-β-D-glucopyranoside sodium salt (compound 21)

To a solution of compound 20 (240 mg, 0.158 mmol) in methanol (5.0 mL) was added sodium methoxide in methanol (0.5M solution). The resulting solution was stirred for 5 hours at room temperature and then neutralized with IR-120 ($H^+$) ion exchange resin, filtered (the filtered residue was washed with methanol) and evaporated. The resulting residue was chromatographed on Iatrobeads, eluting with dichloromethane-methanol-pyridine (95:5:0.5), to provide compound 21 (180 mg, 82%) after conversion to the sodium salt by passage through Dowex 50-X-8 ($Na^+$) resin.

Step (E)—Preparation of 8-Methoxycarbonyloctyl-2-fuc(C)amido-3-O-(α-L-fucopyranosyol)-4-O-[3-O-sulfo-β-D- galactopyranosyl]-2-deoxy-β-D-glucopyranoside sodium salt (compound 26)

Compound 21 (250 mg, 0.179 mmol) was hydrogenolyzed in the presence of 5% palladium on carbon (250 mg) using the procedure described in Example 1, Step K for compound 15. Conversion of the resulting product to its sodium salt by passage through Dowex-50-x-8 (Na$^+$) resin provided compound 26 (150 mg, 88%) after lyophilization.

Example 6

Synthesis of 8-Methoxycarbonyloctyl-2-amino-3-O-(α-L-fucopyranosyl)-4-O-[3-O-sulfo-β-D-galactopyranosyl]-2-deoxy-β-D-glucopyranoside sodium salt (27)

The synthesis of compound 27 is illustrated in FIG. 1.
Step (A)—Preparation of 8-Methoxycarbonyloctyl-2-azido-3-O-(3,4,6-tri-O-benzyl-α-L-fucopyranosyl)-4-O-[4,6-O-benzylidene-3-O-sulfo-β-D-galactopyranosyl]-6-O-benzyl-2-deoxy-β-D-glucopyranoside sodium salt (compound 10)

To a solution of diol 8 (5.0 g, 4.42 mmol)(prepared as described in Example 1) dissolved in pyridine (50.0 mL) at 0° C. was added SO$_3$-pyridine complex (1.05 g, 6.62 mmol). The reaction mixture was stirred for 0.5 hours at 0° C. and then for 1 hour at room temperature. The reaction was not complete, so additional SO$_3$-pyridine complex (500 mg) was added and stirrng was continued for an additional 2 hours. The reaction mixture was then quenched with methanol and the solvent evaporated. Chromatography of the resulting syrup using dichloromethane-methanol-pyridine (95:5:0.5) as eluent provided compound 10 (4.0 g, 73 %) after sodium ion exchange column.
Step (B)—Preparation of 8-Methoxycarbonyloctyl-2-amino-3-O-(α-L-fucopyranosyl)-4-O-[3-O-sulfo-β-D-galactopyranosyl]-2-deoxy-β-D-glucopyranoside sodium salt (compound 27)

Compound 10 (250 mg, 0.2 mmol) was dissolved in methanol (5.0 mL) containing 0.1% HCl in MeOH and 5 % palladium on carbon (250 mg) was added. The reaction mixture was stirred for 6 hours at room temperature and then the catalyst was removed by filtration. Pyridine was added and the solution was evaporated. Conversion of the resulting product into its sodium salt by passage through Dowex-50-x-8 (Na$^+$) resin provided compound 27 (120 mg, 78%) as a white powder after lyophilization.

Example 7

Synthesis of 8-Methoxycarbonyloctyl-2-p-nitrobenzamido-4O-(β-D-galactopyranosyl)-2-deoxy-β-D-glucopyranose (30)

The synthesis of compound 30 is illustrated in FIG. 2.
8-methoxycarbonyloctyl-2-amino-4-O-(β-D-galactopyranosyl)-2-deoxy-β-D-glucopyranose (28) (250 mg, 0.489 mmol), prepared by glycosylation of 2-azido-2-deoxy-3,6,2',3',4',6'-hexa-O-acetyl-α-D-lactopyranosyl bromide[22] with 8-methoxycarbonyloctanol followed by reduction with H$_2$S in pyridine:triethylamine:water (4:1:0.1) and deacetylation, was added to pyridine (5 mL) followed by addition of p-nitrobenzoyl chloride (2.5 g). The reaction mixture was stirred for 15 hours at room temperature and then excess p-nitrobenzoyl chloride was destroyed by adding methanol (5 mL). The mixture was evaporated and the residue was diluted with dichloromethane (100 mL). This solution was washed with a 5% solution of hydrochloric acid (2×100 mL), aqueous sodium bicarbonate (2×100 mL) and water (2×100 mL), then dried over sodium sulfate, filtered and evaporated to dryness to give compound 29 which was used without further purification.

Compound 29 was debenzoylated by dissolving the compound in sodium methoxide (0.5M solution) in methanol and stirring the resulting mixture for 15 hours at room temperature. The reaction mixture was then neutralized by adding IR-120(H+) ion exchange resin and the resin was removed by filtration. The filtrate was evaporated to dryness and the resulting residue was purified by chromatography on Iatrobeads, eluting with dichloromethane-methanol-water (80:20:2), to provide compound 30 (210 mg, 68% based on compound 28).

Example 8

Synthesis of 8-methoxycarbonyloctyl-4-O-(4-O-sulfo-β-D-galactopyranosyl)-β-D-glucopyranoside sodium salt (compound 38)

The synthesis of compound 38 is illustrated in FIG. 3.
Step (A)—Preparation of 8-Methoxycarbonyloctyl-4-O-(2,3,6-tri-O-benzoyl-β-D-galactopyranosyl)-2,3,6-tri-O-benzoyl-β-D-glucopyranoside (compound 36)

To a solution of 8-methoxycarbonyloctyl lactopyranoside (compound 31) (9.5 g, 18.5 mmol) (prepared as described in Banoub, et al.[24]) in acetonitrile (100 mL) at room temperature was added 2,2-dimethoxypropane (4.56 mL, 37 mmol) and p-toluenesulfonic acid (95 mg). After stirring for 3 hours at room temperature, the reaction mixture was neutralized by adding trimethylamine (1.0 mL). The mixture was then evaporated to dryness and the residue filtered through silica gel using dichloromethane-methanol (80:20) to provide the 3,4- and 4,6-O-isopropylidene derivatives 32 and 33.

The mixture of compounds 32 and 33 prepared above was dissolved in pyridine and dichloromethane (50 mL) (1:9) and cooled to 0° C. Benzoyl chloride (10.0 mL) was added dropwise at 0° C. and resulting mixture was stirred for 15 hours at room temperature. The excess benzoyl chloride was then neutralized by adding methanol (5.0 mL) and the reaction mixture evaporated. The residue was diluted with dichloromethane (250 mL), washed with 5% aq. hydrochloric acid (2×250 mL), saturated sodium bicarbonate (2×250 mL) and water (2×250 mL), dried over anhydrous sodium sulfate, filtered and evaporated. The resulting residue was chromatographed on silica gel, eluting with dichloromethane-methanol (98:2) and (95:5), to provide a mixture of compounds 34 and 35 (14.5 g).

The mixture of compounds 34 and 35 prepared above was dissolved in 80% aqueous acetic acid and this solution was stirred at room temperature for 15 hours. The mixture was then evaporated and co-evaporated with toluene to dryness. The resulting residue was then benzoylated by adding benzoyl chloride (1.3 eq) in a mixture of dichloromethane-pyridine (9:1) at −50° C. Standard work-up procedures gave a residue (one major spot by tlc) which was chromatographed on silica gel, eluting with hexane-ethyl acetate (2:1), to provide compound 36 (11.5 g).
Step (B)—Preparation of 8-Methoxycarbonyloctyl-4-O-(4-O-sulfo-2,3,6-tri-O-benzoyl-β-D-galactopyranosyl)-2,3,6-tri-O-benzoyl-β-D-glucopyranoside sodium salt (compound 37)

To a solution of compound 36 (50 mg, 0.44 mmol) in pyridine (2.0 mL) was added SO$_3$-pyridine complex (14 mg, 0.88 mmol). The resulting mixture was stirred for 1 hour at room temperature. Additional SO$_3$-pyridine complex (36 mg) was then added and stirring was continued for 3 hours. The reaction mixture was quenched with methanol (1.0 mL)

and evaporated to dryness. The residue was chromatographed on silica gel, eluting with dichloromethane-methanol-pyridine (95:5:0.5), to provide compound 37 (50 mg, 92%) after conversion to sodium salt by passage through Dowex-50-x-8 (Na$^+$) resin.

Step (C)—Preparation of 8-Methoxycarbonyloctyl-4-O-(4-O-sulfo-β-D-galactopyranosyl)-β-D-glucopyranoside sodium salt (compound 38)

To a solution of compound 37 (50 mg, 0.04 mmol) in methanol (5.0 mL) was added a 0.5 molar solution of sodium methoxide in methanol. The resulting solution was stirred at room temperature for 15 hours. The mixture was then neutralized by adding IR-120 (H$^+$) resin, filtered and evaporated to dryness. The residue was chromatographed on silica gel, eluting with dichloromethane-methanol-water-pyridine (80:20:2:2), to provide compound 38 (20.0 mg, 81 %) after sodium exchange and lyophilization.

Example 9

Synthesis of 8-Methoxycarbonyloctyl-4-O-(4-O-phospho-β-D-galactopyranosyl)-β-D-glucopyranoside disodium salt (compound 40)

The synthesis of compound 40 is illustrated in FIG. 3.

Step (A)—Preparation of 8-Methoxycarbonyloctyl-4-O-(4-O-phospho-2,3,6-tri-O-benzoyl-β-D-galactopyranosyl)-2,3,6-tri-O-benzoyl-β-D-glucopyranoside disodium salt (compound 39)

To a solution of compound 36 (1.0 g, 0.88 mmol) in dry pyridine (5.0 mL) at 0° C. was added dimethylaminopyridine (161 mg, 1.32 mmol) and diphenylphosphorochloride (365 μL, 1.76 mmol). The resulting mixture was stirred at 0° C. for 1 hour and then at room temperature for 5 hours by which time tlc showed complete consumption of the starting material. The mixture was then diluted with dichloromethane (250 mL), washed with cold 5% HCl solution (2×250 mL), saturated sodium bicarbonate solution (2×250 mL) and water (2×250 mL), and evaporated to dryness. The residue was chromatographed on a silica gel, eluting with dichloromethane-methanol (95:5), to provided compound 39 (1.0 g, 83%).

Step (B)—Preparation of 8-Methoxycarbonyloctyl-4-O-(4-O-phospho-β-D-galactopyranosyl)-β-D-glucopyranoside disodium salt (compound 40)

A solution of compound 39 (750 mg, 0.55 mmol) in methanol (20.0 mL) containing PtO$_2$ on carbon (750 mg) was hydrogenolysed for 15 hours at 1 atmosphere of hydrogen. The catalyst was filtered and the solution was evaporated after adding pyridine (1.0 mL). The residue was saponified by reacting with sodium methoxide (0.5 molar solution) in methanol using standard conditions and workup. The debenzoylated product was chromatographed on an Iatrobeads column, eluting with isopropanol-water-ammonia (7:3:1), to provide compound 40 (300 mg, 86%).

Example 10

Synthesis of 8-Methoxycarbonyloctyl-2-acetamido-3-O-(3,6-di-O-sulfo-β-D-galactopyranosyl)-2-deoxy-β-D-glucopyranoside disodium salt (compound 43)

The synthesis of compound 43 is illustrated in FIG. 4.

Step (A)—Preparation of 8-Methoxycarbonyloctyl-2-acetamido-3-O-(β-D-galactopyranosyl)-2-deoxy-4,6-O-benzylidene-β-D-glucopyranoside (compound 41)

8-Methoxycarbonyloctyl-2-acetamido-3-O-(β-D-galactopyranosyl)-2-deoxy-4,6-O-benzylidene-β-D-glucopyranoside, compound 41, was prepared by coupling with thiobenzyl-2,3,4,6-tetraacetyl-β-D-galactopyranoside (reported by Ippolito et al.[32]) with the 8-methoxycarbonyloctyl-2-acetamido-4,6-O-benzylidene-2-deoxy-β-D-glucopyranoside (also reported by Ippolito et al.[32]). Specifically, 1.5 equivalents of n-iodosuccinimide, 1 equivalent of 8-methoxycarbonyloctyl-2-acetamido-4,6-O-benzylidene-2-deoxy-β-D-glucopyranoside (glycosyl donor), 1.5 equivalents of thiobenzyl-2,3,4,6-tetraacetyl-β-D-galactopyranoside (glycosyl acceptor) and molecular sieves were first combined in dichloromethane and then stirring the mixture for 0.5 hours at −20° C. Then, 1 to 1.5 equivalents of trifluoromethane sulfonic acid was added and the reaction mixture stirred for 3 hours at −20° C. The reaction mixture was quenched by adding triethylamine until neutral pH was reached. The reaction solution was filtered, washed with sodium bicarbonate and water. The organic layer was dried over sodium sulfate and the solvent evaporated to provide for the fully protected 8-methoxycarbonyloctyl-3-O-(2,3,4,6-tetra-O-acetyl-β-D-galactopyranosyl)-2-acetamido-4,6-O-benzylidene-2-deoxy-β-D-glucopyranoside which was then subjected to Zemplen conditions (sodium methoxide/methanol) to provide for 8-methoxycarbonyloctyl-2-acetamido-3-O-(β-D-galactopyranosyl)-2-deoxy-4,6-O-benzylidene-β-D-glucopyranoside, compound 41.

Step (B)—Preparation of 8-Methoxycarbonyloctyl-2-acetamido-3-O-(3, 6-di-O-sulfo-β-D-galactopyranosyl)-2-deoxy-4,6-O-benzylidene-β-D-glucopyranoside disodium salt (compound 42)

To a solution of 8-methoxycarbonyloctyl-2-acetamido-3-O-(β-D-galactopyranosyl)-2-deoxy-4,6-O-benzylidene-β-D-glucopyranoside (compound 41) (1.5 g, 2.34 mmol) (prepared as described above) in pyridine (7.5 mL) at 0° C. was added SO$_3$-pyridine complex (4.0 equivalent). The reaction mixture was stirred for 5 hours at room temperature, quenched by adding methanol (2 mL), and evaporated to dryness. The residue was chromatographed on Iatrobeads, eluting with dichloromethane-methanol-pyridine (9:1:0.5), to provide compound 42 (700 mg, 35%) after conversion to a sodium salt using the procedures described earlier.

Step (C)—Preparation of 8-Methoxycarbonyloctyl-2-acetamido-3-O-(3,6-di-O-sulfo-β-D-galactopyranosyl)-2-deoxy-β-D-glucopyranoside disodium salt (compound 43)

Compound 42 (550 mg, 0.65 mmol) was dissolved in methanol (50 mL) and hydrogenolysed in the presence of 5 % palladium on carbon (550 mg) using the procedure described previously. The mixture was filtered, evaporated and chromatographed on an Iatrobeads column, eluted with dichloromethane-methanol-water-pyridine (80:20:2:2), to provide compound 43 (350 mg, 71 %) after conversion to the sodium salt as described above.

Example 11

Synthesis of 8-Methoxycarbonyloctyl-2-acetamido-3-O-(3,6-diphospho-β-D-galactopyranosyl)-2-deoxy-β-D-glucopyranoside tetrasodium salt (compound 45)

The synthesis of compound 45 is illustrated in FIG. 4.

To a solution of compound 41 (1.2 g, 1.87 mmol) (prepared as described above) in pyridine (10.0 mL) at 0° C. was added dimethylaminopyridine (1.5 eq) and diphenylphosphorochloride (4.0 eq). The resulting mixture was stirred at 0° C. for 5 hours and then diluted with dichloromethane (100 mL), washed with cold 5% HCl solution (2×100 mL), saturated sodium bicarbonate solution (2×100 mL) and water (2×100 mL), dried over sodium sulfate, filtered and evaporated to dryness. The residue was chromatographed on silica gel, eluting with dichloromethane-methanol (95:5), to provide compound 44 (850 mg, 41 %).

Compound 44 (750 mg, 0.68 mmol) was hydrogenolyzed in the presence of $PtO_2$ on carbon (750 mg) in methanol using standard procedures and work-up conditions to provide deblocked phospho-$Le^c$, compound 45 (400 mg, 73%).

Example 12

Synthesis of 8-Methoxycarbonyloctyl-2-acetamido-3-O-(α-L-fucopyranosyl)-4-O-[3,4,6-tri-O-sulfo-β-D-galactopyranosyl]-2-deoxy-β-D-glucopyranoside trisodium salt (compound 48)

The synthesis of compound 48 is illustrated in FIG. 5.
Step (A)—Preparation of 8-Methoxycarbonyloctyl-2-acetamido-3-O-(2,3,4-tri-O-benzyl-α-L-fucopyranosyl)-4-O-[3,4,6-tri-O-sulfo-β-D-galactopyranosyl]-2-deoxy-6-O-benzyl-β-glucopyranoside trisodium salt (compound 47)

To a solution of 8-methoxycarbonyloctyl-2-acetamido-3-O-(2,3,4-tri-O-benzyl-α-L-fucopyranosyl)-4-O-[-β-D-galactopyranosyl]-6-O-benzyl-2-deoxy-β-D-glucopyranoside (46) (2.5 g, 2.36 mmol) (prepared as described by Srivastava, et al.[23]) in pyridine (15.0 mL) at 0° C. was added $SO_3$-pyridine complex (5 eq). This reaction mixture was stirred at 0° C. for 0.5 hours and then overnight at room temperature. The mixture was then quenched with methanol (5.0 mL), evaporated and the residue chromatographed on Iatrobeads using dichloromethane-methanol-pyridine (9:1:0.5) and dichloromethane-methanol-water-pyridine (80:20:2:0.5) as an eluent to provide compound 47 (1.0 g, 31%) as a syrup.

Step (B)—Preparation of 8-Methoxycarbonyloctyl-2-acetamido-3-O-(α-L-fucopyranosyl)-4-O-([3,4,6-tri-O-sulfo-β-D-galactopyranosyl]-2-deoxy-β-D-glucopyranoside trisodium salt (compound 48)

Compound 47 (800 mg, 0.59 mmol) was hydrogenolyzed with palladium on carbon (800 mg) using the procedures and work-up conditions as described above to provide compound 48 (400 mg, 67%) as the sodium salt.

Example 13

Synthesis of 8-Methoxycarbonyloctyl-2-acetamido-3-O-(α-L-fucopyranosyl)-4-O-[3-O-sulfo-2-O-(-α-L-fucopyranosyl)-β-D-galactopyranosyl]-2-deoxy-β-D-glucopyranoside sodium salt (compound 52)

The synthesis of compound 52 is illustrated in FIG. 6.
Step (A)—Preparation of 8-Methoxycarbonyloctyl-2-acetamido-3-O-(3,4,6-tri-O-benzyl-α-L-fucopyranosyl)-4-O-[3-benzoyl-4,6-O-benzylidene-2-O-(3,4,6-tri-O-benzyl-α-L-fucopyranosyl)-β-D-galactopyranosyl]-6-O-benzyl-2-deoxy-β-D-glucopyranoside (compound 49)

Compound 49 was prepared by selective benzoylation at the 3' of 8-methoxycarbonyloctyl-2-acetamido-3-O-(3,4,6-tri-O-benzyl-α-L-fucopyranosyl)-4-O-[4,6-O-benzylidene-β-D-galactopyranosyl]-6-O-benzyl-2-deoxy-β-D-glucopyranoside (prepared as described by Srivastava[31]) followed by fucosylation at the 2' position using $CuBr_2$/DMF catalyzed reaction conditions and tribenzyl thiofucose as the glycosyl donor in methylene chloride.

Step (B)—Preparation of 8-Methoxycarbonyloctyl-2-acetamido-3-O-(3,4,6-tri-O-benzyl-α-L-fucopyranosyl)-4-O-[4,6-O-benzylidene-2-O-(3,4,6-tri-O-benzyl-α-L-fucopyranosyl)-β-D-galactopyranosyl]-6-O-benzyl-2-deoxy-β-D-glucopyranoside (compound 50)

To a solution of 8-methoxycarbonyloctyl-2-acetamido-3-O-(3,4,6-tri-O-benzyl-α-L-fucopyranosyl)-4-O-[3-O-benzoyl-4,6-O-benzylidene-2-O-(3,4,6-tri-O-benzyl-α-L-fucopyranosyl)-β-D-galactopyranosyl]-6-O-benzyl-2-deoxy-β-D-glucopyranoside (compound 49) (1.45 g, 0.87 mmol) (prepared by as above) (1.45 g, 0.87 mmol) in dichloromethane was added sodium methoxide (0.5M solution) in methanol and the resulting solution was stirred for 5 hours at room temperature. The mixture was then neutralized with resin, filtered and evaporated to dryness to obtain compound 50 (1.2 g, 88%) which was used without further purification.

Step (C)—Preparation of 8-Methoxycarbonyloctyl-3-O-(3,4,6-tri-O-benzyl-α-L-fucopyranosyl)-4-O-[4,6-O-benzylidene-3-O-sulfo-2-O-(3,4,6-tri-O-benzyl-α-L-fucopyranosyl)-β-D-galactopyranosyl]-6-O-benzyl-2-deoxy-β-D-glucopyranoside sodium salt (compound 51)

To a solution of compound 50 (150 mg, 0.096 mmol) in pyridine (2.0 mL) at 0° C. was added $SO_3$-pyridine complex (30.5 mg, 0.19 mmol). The resulting mixture was stirred for 20 minutes at 0° C. and then overnight at room temperature. Standard work-up procedures as described above gave a residue which was chromatographed on Iatrobeads, eluting with dichloromethane-methanol-pyridine (95:5:0.5), to provide compound 51 (135 mg, 84%).

Step (D)—Preparation of 8-Methoxycarbonyloctyl-2-acetamido-3-O-(α-L-fucopyranosyl)-4-O-[3-O-sulfo-2-O-(α-L-fucopyranosyl)-β-D-galactopyranosyl]-2-deoxy-β-D-glucopyranoside sodium salt (compound 52)

Blocked sulfo-tetrasaccharide 51 (120 mg, 0.072 mmol) was hydrogenolyzed over palladium on carbon (120 mg) using the procedures and work-up conditions described above to provide for compound 52 (54 mg, 79%).

Example 14

Synthesis of 8-Methoxycarbonyloctyl-2-acetamido-3-O-(α-L-fucopyranosyl)-4-O-[6-chloro-6-deoxy-3-O-sulfo-β-D-galactopyranosyl)]-β-D-glucopyranoside sodium salt (compound 60)

The synthesis of compound 60 is illustrated in FIG. 7.
Step (A)—Preparation of 6-Chloro-6-deoxy-1,2,3,4-tetra-O-acetyl-glucose (compound 54)

1,2,3,4-Di-O-isopropylidene-D-galactopyranose (compound 53) (11.33 g, 43.6 mmol) was dissolved in 200 mL of dry pyridine and cooled to −40° C. Sulfuryl chloride (11 mL) was added and the reaction mixture was stirred at −40° C. for 1 hour. The reaction was then warmed to room temperature and stirring was continued for 3 hours at room temperature. Dichloromethane (1 L) was added and the resulting solution was washed with a saturated solution of sodium bicarbonate and twice with water. The solvent was evaporated and the residue was chromatographed on a silica gel column using hexane-ethyl acetate (5:1) as the eluent. The isolated product was dissolved in 200 mL of 90% trifluoroacetic acid and the resulting mixture was stirred at room temperature for 1 hour and then evaporated and co-evaporation with toluene. The residue was then acetylated in a mixture of pyridine-acetic anhydride (1:1, 300 mL) for 20 hrs. After standard work-up conditions, the residue was chromatographed, eluting with hexane-ethyl acetate (3:1), to provide tetra-O-acetyl-6-chloro-6-deoxy-D-galactopyranose (compound 54) (6.36 g, 40%) as a foam.

Step (B)—Preparation of O-(2,3,4Tri-O-acetyl-6-Chloro-6-deoxy-α-D-glucopyranosyl) Trichloroacetimidate (compound 55)

To a solution of tetra-O-acetyl-6-chloro-6-deoxy-D-galactopyranose (compound 54) (6.36 g, 17.3 mmol) in DMF (60 mL) was added hydrazine acetate (2.4 g, 26.0 mmol). The mixture was stirred for 1 hour at room temperature and then 1 L of dichloromethane was added and the resulting solution washed 4 times with water. The organic layer was dried over anhydrous sodium sulfate and evaporated. Flash column chromatography using hexane-ethyl acetate (1:1) as the eluent gave 2,3,4-tri-O-acetyl-6-chloro-6-deoxy-α-D-galactopyranose (5.79 g). This material was dissolved in 50 mL of dichloromethane and cooled to 0° C. Trichloroacetonitrile (8.93 mL, 89.2 mmol) was added followed by DBU (1.33 mL, 8.9 mmol). This solution was stirred for 1.5 hours and then evaporated. The residue was chromatographed on a silica gel column, eluting with hexane-ethyl acetate (2:1), to provide compound 55 (4.1 g, 51%) as a foam.

Step (C)—Preparation of 8-Methoxycarbonyloctyl-2-acetamido-3-O-(2,3,4-tri-O-benzyl-α-L-fucopyranoysl)-4-O-[6-chloro-6-deoxy-2,3,4-tri-O-acetyl-β-D-galactopyranosyl]-6-O-benzyl-2-deoxy-β-D-glucopyranoside (compound 57)

To a solution of compound 56 (9.7 g, 10.8 mmol) (prepared by the procedure described by Srivastava, et al.[23]) in 35 mL of dichloromethanediethyl ether (1:2), stirred under nitrogen, was added imidate 55 (10.3 g 21.9 mmol) and then an additional 10 mL of dichloromethane-ether (1:2). The resulting mixture was cooled to −10° C. to −15° C. at which temperature a gel type mass formed. Dichloromethane was added until the solution became clear and then 3.5 mL of BF$_3$-etherate solution was added dropwise and stirring was continued for 1 hour at low temperature. The reaction mixture was then diluted with dichloromethane and washed with water, saturated NaHCO$_3$ solution and water. The resulting solution was dried over anhydrous sodium sulfate and evaporated. The residue was chromatographed on a silica gel column, eluting with hexane-ethyl acetate (1:1), to provide compound 57 (12.09 g, 93%) as a white foam.

Step (D)—Preparation of 8-Methoxycarbonyloctyl-2-acetamido-3-O-(2,3,4tri-O-benzyl-α-L-fucopyranosyl)-4-O-[6-chloro-6-deoxy-β-D-galactopyranosyl]-6-O-benzyl-2-deoxy-β-D-glucopyranoside (compound 58)

To a solution of compound 57 (5 g, 4.12 mmol) in 160 mL of methanol was added 10 mL of a 0.5N solution of sodium methoxide in methanol. The resulting mixture was stirred at room temperature overnight and then neutralized with Amberlite IR-120 (H$^+$) resin, filtered and evaporated. The residue was chromatographed on a silica gel column, eluting with dichloromethane-methanol (97:3), to provide compound 58 (3.93 g, 87%).

Step (E)—Preparation of 8-Methoxycarbonyloctyl-2-acetamido-3-O-(2,3,4-tri-O-benzyl-α-L-fucopyranosyl)-4-O-[6-chloro-6-deoxy-3-O-sulfo-β-D-galactopyranosyl]-6-O-benzyl-2-deoxy-β-D-glucopyranoside sodium salt (compound 59)

To a solution of compound 58 (3.92, 3.63 mmol) in pyridine (50 mL) at 0° C. was added SO$_3$-pyridine complex (860 mg, 1.5 eq). The resulting mixture was stirred at 0° C. for 0.5 hours and then allowed to warm to room temperature while stirring. After 0.5 hours at room temperature, 0.5 eq. of SO$_3$-pyridine complex was added. An additional 0.5 eq. of SO$_3$-pyridine complex was added after 1.5 hours. After 3 hours, the reaction was terminated by adding methanol. The solvent was evaporated and the resulting residue was chromatographed on a silica gel column, eluting with dichloromethane-methanol-pyridine (95:5:05). After evaporation, the product was dissolved in methanol and passed through Bio-Rex® 70 resin (100–200 mesh, sodium form) using methanol as an eluent to provide compound 59 (2.82 g, (66%).

Step (F)—Preparation of 8-Methoxycarbonyloctyl-2-acetamido-3-O-(α-L-fucopyranosyl)-4-O-[6-chloro-6-deoxy-3-O-sulfo-β-D-galactopyranosyl)]-β-D-glucopyranoside sodium salt (compound 60)

To a solution of compound 59 (537 mg, 0.46 mmol) in methanol (50 mL) was added (530 mg) of 5% Pd/C. The resulting mixture was hydrogenolyzed at room temperature for 2.5 hours at atmospheric pressure and then filtered and evaporated. The residue was chromatographed on an Iatrobead column, eluting with dichloromethane-methanol-water-pyridine (80:20:2:0.5). The fractions were pooled and evaporated and passed through Bio-Rex® 70 Resin (100–200 mesh, sodium form) using methanol as an eluent. Freeze-drying gave compound 60 (285 mg, 76%) as a white solid.

Example 15

Synthesis of 8-Methoxycarbonyloctyl-2-acetamido-3-O-(α-L-fucopyranosyl)-4-O-[6-deoxy-3-O-sulfo-β-D-galactopyranosyl]-2-deoxy-β-D-glucopyranoside sodium salt (compound 63)

The synthesis of compound 63 is illustrated in FIG. 7.
Step (A)—Preparation of 8-Methoxycarbonyloctyl-2-acetamido-3-O-(2,3,4-tri-O-benzyl-α-L-fucopyranosyl)-4-O-[6-deoxy-β-D-galactopyranosyl]-6-O-benzyl-2-deoxy-β-D-glucopyranoside (compound 61)

A mixture of compound 57 (6.1 g, 5.1 mmol), tributyltin hydride (13.6 mL, 10 eq) and AIBN (115 mg) in toluene (250 mL) was heated at 90° C. for 4 hours. The reaction mixture was then evaporated and the residue was chromatographed on a silica gel column, eluting with hexane-ethyl acetate (1:1), to provide crude compound 60a as a foam (~6.2 g with some impurities and tin residue). This crude material was dissolved in a mixture of methanol (100 mL) and dichloromethane (20 mL) and 10 mL of a 0.5N solution of sodium methoxide in methanol was added. The reaction mixture was stirred overnight at room temperature and neutralized with Amberlite IR-120(H$^+$) resin, filtered and evaporated. The residue was chromatographed on a silica gel column, eluting with dichloromethane-methanol (95:5), to provide compound 61 (4.42 g, 83%) as a white foam.

Step (B)—Preparation of 8-Methoxycarbonyloctyl-2-acetamido-3-O-(2,3,4-tri-O-benzyl-α-L-fucopyranosyl)-4-O-[6-deoxy-3-O-sulfo-β-D-galactopyranosyl]-6-benzamido-2-deoxy-β-D-glucopyranoside sodium salt (compound 62)

To a solution of compound 61 (4.42 g, 4.2 mmol) in 50 mL of pyridine at 0° C. was added SO$_3$-pyridine complex (1 g, 1.5 eq). The reaction mixture was stirred for 0.5 hours at 0° C. and then allowed to warm to room temperature. After 0.5 hours at room temperature, 0.5 eq. of SO$_3$-pyridine complex was added followed by an additional 0.5 eq. after 1.5 hours. After 3 hours, the reaction was terminated by adding methanol and the solvents were evaporated. The residue was chromatographed on a silica gel column, eluting with dichloromethane-methanol (95:5) containing 2 mnL of pyridine per 1 L of solvent, and the resulting product was passed through Bio-Rex® 70 Resin (100–200 mesh, sodium form) using methanol as an eluent to provide compound 62 (2.65, 55%).

Step (C)—Preparation of 8-Methoxycarbonyloctyl-2-acetamido-3-O-(α-L-fucopyranosyl)4-O-[6-deoxy-3-O-sulfo-β-D-galactopyranosyl]-2-deoxy-β-D-glucopyranoside sodium salt (compound 63)

A mixture of compound 62 (562 mg, 0.49 mmol) and 560 mg of 5% Pd/C in 50 mL of methanol was hydrogenolyzed for 2 hours under standard conditions. The mixture was then filtered, evaporated and chromatographed on an Iatrobead column, eluting with dichloromethane-methanol-water (80:20:2) containing pyridine (2 mL per 1 L of eluent), to provide a product which was then passed through Bio-Rex® 70 Resin (100–200 mesh, sodium form) using water as an eluent. The resulting solution was freeze-dried to provide compound 63 (216 mg, 56%).

Example 16

Synthesis of 8-Methoxycarbonyloctyl-2-acetamido-3-O-(α-L-fucopyranosyl)-4-O-[4-chloro-4-deoxy-3-O-sulfo-β-D-galactopyranosyl]-2-deoxy-β-D-glucopyranoside sodium salt (compound 77)

The synthesis of compound 77 is illustrated in FIG. 8.

Step (A)—Preparation of Methyl 4,6-O-Benzylidene-2,3-di-O-benzoyl-α-D-glucopyranoside (compound 65)

To a mixture of 25 g (0.13 mmol) of methyl-α-D-glucopyranoside (64) (commercially available from Aldrich Chemical Co., Milwaukee, Wis., USA) in 750 mL of acetonitrile was added αα-dimethoxytoluene (20 mL) and p-toluenesulfonic acid (600 mg). The resulting mixture was stirred at room temperature for 20 hours and then neutralized with triethylamine and evaporated. The residue was dissolved in pyridine (200 mL) and cooled in an ice bath. Benzoyl chloride (5 eq) was then added and the mixture was stirred overnight at room temperature. After standard work-up procedures, compound 65 (44.2 g, 70%) was crystallized from a mixture of ethyl acetate and ether.

Step (B)—Preparation of Methyl 6-O-Benzyl-2,3-di-O-benzoyl-α-D-glucopyranoside (compound 66)

A mixture of methyl 4,6-O-benzylidene-2,3-di-O-benzoyl-β-D-glucopyranoside (compound 65) (16.3 g, 33.2 mmol), sodium cyanoborohydride (42.9 g, 0.68 mmol), 3A molecular sieves and crystals of methyl orange in 500 mL of tetrahydrofuran was stirred at 0° C. while diethyl ether saturated with hydrogen chloride was added until the solution became pink and evolution of gas ceased. After 1 hour, tlc indicated that the starting material had been consumed. The reaction mixture was then poured into a cold mixture of dichloromethane and a saturated aqueous solution of sodium bicarbonate. The organic layer was separated and washed with saturated sodium bicarbonate solution and water (5 times), then dried over anhydrous sodium sulfate and evaporated to provide crude methyl 6-O-benzyl-2,3-di-O-benzoyl-α-D-glucopyranoside (compound 66) as a white solid which was used in the next step without further purification.

Step (C)—Preparation of Methyl 6-O-Benzyl-2, 3-di-O-benzoyl-4-chloro-4-deoxy-α-D-glucopyranoside (compound 67)

To a solution of crude methyl 6-O-benzyl-2,3-di-O-benzoyl-α-D-glycopyranoside (compound 66) (from previous step) in 300 mL of pyridine at −40° C. was added sulfuryl chloride (15 mL). After 1 hour, the cooling bath was removed and stirring was continued at room temperature for 3 hours. Dichloromethane was then added and the resulting solution was washed with saturated sodium bicarbonate solution and water, dried over anhydrous sodium sulfate and evaporated. The residue was chromatographed on a silica gel, eluting with dichloromethane, to provide methyl 6-O-benzyl-2,3-di-O-benzoyl-4-chloro-4-deoxy-α-D-galactopyranoside (compound 67) (15.3 g, 90.0% —based on compound 65) as a syrup.

Step (D)—Preparation of Acetyl 6-O-acetyl-2,3-di-O-benzoyl-4-chloro-4-deoxy-D-galacopyranoside (compound 68)

To a solution of methyl 6-O-benzyl-2,3-di-O-benzoyl-4-chloro-4-deoxy-α-D-galactopyranoside (compound 67) (14.4 g, 28.2 mmol) in 75 mL of acetic anhydride was added a mixture of acetic anhydride and concentrated sulfuric acid (60 mL, 13 μL of conc. $H_2SO_4$ per 1 mL of acetic anhydride). The resulting mixture was stirred at room temperature overnight and then the solvent was evaporated under high vacuum. The residue was dissolved in dichloromethane and this solution was washed with saturated sodium bicarbonate solution and water, and evaporated. The residue was chromatographed on a silica gel column, eluting with hexane-ethyl acetate (3:1), to provide acetyl 6-O-acetyl-2,3-di-O-benzoyl-4-chloro-4-deoxy-D-galactopyranoside (compound 68) (8.53 g, 62%).

Step (E)—Preparation of α-(6-O-acetyl-2,3-di-O-benzoyl-4-chloro-4-deoxy-α-D-galactopyranosyl)-trichloroacetimidate (compound 69)

A solution of acetyl 6-O-acetyl-2,3-di-O-benzoyl-4-chloro-4-deoxy-D-galactopyranoside (68) (8.53 g, 17.4 mmol) and hydrazine acetate (2.4 g, 26.0 mmol, 1.5 eq) in 70 mL of DMF was stirred for 1 hour at room temperature. The reaction mixture was then evaporated, washed with water (5 times) and evaporated. The residue was chromatographed on a silica gel, eluting with hexane-ethyl acetate (2:1), to provide 6-O-acetyl-2,3-di-O-benzoyl-4-chloro-4-deoxy-D-galactopyranose (7.44 g, 95.3%). This material was dissolved in dichloromethane (50 mL) and the resulting solution was cooled to 0° C. Trichloroacetonitrile (8.3 mL, 82.9 mmol) was added and the mixture was stirred for 2 hours. The solvent was then evaporated and the residue was chromatographed on a silica gel column, eluting with hexane-ethyl acetate (3:1), to give imidate 69 (6.3 g, 64%).

Step (F)—Preparation of 8-Methoxycarbonyloctyl-2-acetamido-3-O-(2,3,4-tri-O-benzyl-α-L-fucopyranosyl)-4-O-[6-O-acetyl-2,3-di-O-benzoyl-4-chloro-4-deoxy-β-D-galactopyranosyl]-6-O-benzyl-2-deoxy-β-D-galacopyranoside (compound 70)

To a solution of compound 56 (1.98 g 2.2 mmol) (prepared by the procedure described by Srivastava, et al.[23]) in 10 mL of dichloromethane-ether (1:2) was added imidate 69 (2.45 g, 4.13 mmol) and 4 mL of dichloromethane-diethyl ether (1:2). The reaction mixture was then cooled to −15° C. to −10° C. and $BF_3$-etherate (0.7 mL) was added. This mixture was stirred for 1 hour and then diluted with dichioromethane. The resulting solution was washed with sodium bicarbonate solution and water, and then evaporated to give a syrup. The syrup was chromatographed on silica gel, eluting with hexane-ethyl acetate (2:1) and (1:1), to give trisaccharide 70 (1.42 g, 49%) as a white solid.

Step (G)—Preparation of 8-Methoxycarbonyloctyl-2-acetamido-3-O-(2,3,4-tri-O-benzyl-α-L-fucopyranosyl)-4-O-[4-chloro-4-deoxy-galactopyranosyl]-6-O-benzyl-2-deoxy-β-D-glucopyranoside (compound 71)

To a solution of compound 70 (1.42 g 1.1 mmol) in 20 mL of methanol was added 5 mL of 0.5N sodium methoxide in methanol. The reaction mixture was stirred at room temperature for 5 hours and then neutralized with Amberlite IR-120 ($H^+$) resin, filtered and evaporated. The residue was chromatographed on a silica gel column, eluting with dichloromethane-methanol (95:5), to provide compound 71 (1.11 g, 94%).

Step (H)—Preparation of 8-Methoxycarbonyloctyl-2-acetamido-3-O-(2,3,4-tri-O-benzyl-α-L-fucopyranosyl)4-O-[2,3-di-O-acetyl-4-chloro-4-deoxy-6-tert-butyl-dimethylsiyl-β-D-galactopyranosyl]-6-O-benzyl-2-deoxy-β-D-glucopyranoside (compound 72)

A solution of compound 71 (1.05 g, 0.97 mmol) and tert-butyldimethylsilyl chloride (296 mg, 1.96 mmol) in pyridine (10 mL) was stirred overnight at room temperature. Acetic anhydride (5 mL) was added at 0° C. and stirring was continued for 3 hours at room temperature. The solution was worked-up followed by chromatography using hexane-ethyl acetate (1:1) as an eluent gave compound 72 (1.08 g, 87%).
Step (I)—Preparation of 8-Methoxycarbonyloctyl-2-acetamido-3-O-(2,3,4-tri-O-benzyl-α-L-fucopyranosyl)-4-O-[2,3-di-O-acetyl-4-chloro4-deoxy-β-D-galactopyranosyl]-2-deoxy-6-O-benzyl-β-5 D-glucopyranoside (compound 73)

To a solution of compound 72 (1.07 g , 0.84 mmol) in 25 mL of THF was added tetrabutylammonium fluoride hydrate (399 mg 1.26 mmol). The resulting mixture was stirred at room temperature for 1 hour and then diluted with dichloromethane (100 mL), washed with water (2×100 mL) and evaporated. The residue was chromatographed, eluting with hexane-ethyl acetate (1:1), to provide compound 73 (815 mg, 84%).
Step—(J) Preparation of 8-Methoxycarbonyloctyl-2-acetamido-3-O-(2,3,4-tri-O-benzyl-α-L-fucopyranosyl)-4-O-[2,3-di-O-acetyl-6-O-benzyl-4-chloro-4-deoxy-β-D-galactopyranosyl]-6-O-benzyl-2-deoxy-β-D-glucopyranoside (compound 74)

To a solution of compound 73 (815 mg, 0.7 mmol) in 10 mL of toluene was added benzyl bromide (167 mL, 1.4 mmol) and silver oxide (715 mg, 3.5 mmol). The reaction mixture was stirred at room temperature for 24 hours and then filtered and evaporated. The residue was chromatographed on a silica gel column, eluting with hexane-ethyl acetate (1:1), to provide compound 74 (471 mg, 54%).
Step (K)—Preparation of 8-Methoxycarbonyloctyl-2-acetamido-3-O-(2,3,4-tri-O-benzyl-α-L-fucopyranosyl)-4-O-[6-O-benzyl-4-chloro-4-deoxy-β-D-galactopyranosyl]-6-O-benzyl-2-deoxy-β-D-glucopyranoside (compound 75)

To a solution of compound 74 (467 mg, 0.34 mmol) in 10 mL of methanol was added 5 mL of 0.5N sodium methoxide in methanol. The resulting mixture was stirred for 3 hours at room temperature and then neutralized with Amberlite IR-120(H$^+$) resin, filtered and evaporated. The residue was chromatographed on a silica gel, eluting with dichloromethane-methanol (98:2), to provide compound 75 (390 mg, 90%).
Step (L)—Preparation of 8-Methoxycarbonyloctyl-2-acetamido-3-O-(2,3,4-tri-O-benzyl-α-L-fucopyranosyl)-4-O-[6-O-benzyl-4-chloro-4-deoxy-3-O-sulfo-β-D-galactopyranosyl]-6-O-benzyl-2-deoxy-β-D-glucopyranoside sodium salt (compound 76)

To a solution of compound 75 (390 mg, 0.34 mmol) in pyridine (1 mL) at 0° C. was added SO$_3$-Pyridine complex (80 mg, 0.5 mmol). The reaction mixture was allowed to warm to room temperature and additional SO$_3$-pyridine complex was added after 0.5 hours (0.5 eq) and 1 hour (0.5 eq). The reaction was terminated after 2 hour by adding methanol and the solvents were then evaporated. The residue was chromatographed on a silica gel column, eluting with dichloromethane-methanol (95:5) containing 2 mL of pyridine per 1 L of solvent, to provide compound 76 (241 mg, 57%) after Bio-Rex® 70 Resin (sodium form) ion exchange.
Step (M)—Preparation of 8-Methoxycarbonyloctyl-2-acetamido-3-O-(α-L-fucopyranosyl)-4-O-[4-chloro-4-deoxy-3-O-sulfo-β-D-galactopyranosyl]-2-deoxy-β-D-glucopyranoside sodium salt (compound 77)

A solution of compound 76 (241 mg, 0.19 mmol) in methanol (20 mL) containing 240 mg of 5% Pd/C was hydrogenolyzed at room temperature for 1.5 hours. The reaction mixture was then filtered and evaporated. The residue was chromatographed, eluting with dichloromethane-methanol (80:20) containing 2 mL of pyridine per 1 L of solvent, to provide a product which was passed through a Bio-Rex®70 Resin (sodium form) column using water as an eluent. The resulting solution was freeze-dried to give compound 77 (135 mg, 87%).

Example 17

Synthesis of 8-Methoxycarbonyloctyl-2-acetamido-3-O-(α-L-fucopyranosyl)-4-O-[4,6-dichloro-4,6-dideoxy-3-O-sulfo-β-D-galactopyranosyl]-β-D-glucopyranoside sodium salt (compound 87)

The synthesis of compound 87 is illustrated in FIG. 9.
Step (A)—Preparation of 3-O-Benzyl-4,6-O-benzylidene glucopyranose (compound 79)

A solution of 3-O-benzyl-D-glucopyranose (78) (12.8 g, 47.4 mmol) (prepared by the procedure described by Finan, et al.[18]), α,α-dimethoxy-toluene (10 mL) and p-toluenesulfonic acid (265 mg) in 500 mL of acetonitrile was stirred at room temperature for 1.5 hours. The mixture was then neutralized with triethylamine and evaporated. The residue was chromatographed, eluting with dichloromethane-methanol, to provide compound 79 (5.21 g, 31%).
Step (B)—Preparation of Acetyl 2-O-acetyl-3-O-benzyl-D-glucopyranose (compound 80)

3-O-Benzyl-4,6-O-benzylidene-D-glucopyranose (compound 79) (5.21 g, 14.5 mmol) was acetylated in a mixture of pyridine (40 mL) and acetic anhydride (140 mL) at room temperature for 2 hours. After standard work-up procedures and evaporation of the solvent, the residue was heated with 80% aqueous acetic acid (500 mL) for 17 hours. Flash column chromatography using hexane-ethyl acetate (1:2) as an eluent gave acetyl 2-O-acetyl-3-O-benzyl-D-glucopyranoside (compound 80) (3.5 g, 68%).
Step (C)—Preparation of Acetyl 2-O-Acetyl-3-O-benzyl-4, 6-dichloro-4,6-dideoxy-glucopyranose (compound 81)

To a solution of acetyl 2-O-acetyl-3-O-benzyl-D-glucopyranose (compound 80) (3.5 g, 9.88 mmol) in pyridine at −40° C. was added a solution of SO$_2$Cl$_2$ (100 mL) in 100 mL of pyridine. The reaction mixture was allowed to warm to room temperature and was stirred for 3 hours. The mixture was then diluted with dichloromethane (500 mL) and this solution was washed with water (2×500 mL), saturated sodium bicarbonate solution and water (2×500 mL), dried over anhydrous sodium sulfate and evaporated. The residue was chromatographed on a silica gel column, eluting with hexane-ethyl acetate (5:1), to provide acetyl 2-O-acetyl-3-O-benzyl-4,6-dichloro-4,6-dideoxy-D-galactopyranoside (compound 81) (2.89 g, 75%).
Step (D)—Preparation of Acetyl-2, 3-di-O-acetyl-4,6-dichloro-4,6-dideoxy-glucopyranose (compound 82)

A solution of acetyl-2-O-acetyl-3-O-benzyl-4,6-dichloro-4,6-dideoxy-D-galactopyranoside (compound 81) (2.89 g, 7.4 mmol) in 60 mL of methanol was hydrogenolyzed in the presence of 1.4 g of 5% Pd/C for 3 hours. The solution was then filtered and evaporated and the residue was acetylated in a mixture of pyridine (10 mL) and acetic anhydride (10 mL). Standard work-up procedures and column chromatography using hexane-ethyl acetate (2:1) as an eluent provided acetyl 2, 3-di-O-acetyl-4,6-dichloro-4,6-dideoxy-D-galactopyranose (compound 82) (2.34 g, 92%).
Step (E)—Preparation of α-(2,3-Di-O-acetyl-4,6-dichloro-4,6-dideoxy-α-D-glucopyranosyl)-trichloroacetimidate (compound 83)

A solution of acetyl 2,3-di-O-acetyl-4,6-dichloro-4,6-dideoxy-D-galactopyranose (compound 82) (2.24 g, 6.5 mmol) and hydrazine acetate (903 mg) in DMF (22 mL) was stirred for 2 hours at room temperature. The reaction mixture was then diluted with dichloromethane (250 mL) and washed 4 times with water (4×250 mL), dried over anhydrous sodium sulfate and evaporated. Flash chromatography using hexane-ethyl acetate (1:1) as an eluent gave 2,3-di-O-acetyl-4,6-dichloro-4,6-dideoxy-D-galactopyranose (~6.88 mmol). This compound was then dissolved in dichloromethane (20 mL) cooled to 0° C., and trichloroacetonitrile (3.35 mL, 34.4 mmol) was added. After stirring at 0° C. for 40 minutes, the solvent was evaporated and the residue was chromatographed on a silica gel column, eluting with hexane-ethyl acetate (5:1), to give imidate 83 (1.14 g, 39%) as a white solid.

Step (F)—Preparation of 8-Methoxycarbonyloctyl-2-acetamido-3-O-(2,3,4tri-O-benzyl-α-L-fucopyranosyl)-4-O-[2,3-di-O-acetyl-4,6-dichloro-4,6-dideoxy-β-D-galactopyranosyl]-6-O-benzyl-2-deoxy-β-D-glucopyranoside (compound 84)

To a solution of compound 56 (990 mg, 1.10 mmol) in dichloromethane-diethyl ether (1:2) (5 mL), stirred under nitrogen, was added dichloro imidate 83 (997 mg, 2.94 mmol) followed by additional dichloromethane-diethyl ether (1:2) (2 mL). The solution was cooled to −10° C. to −15° C. over 1 hour, at which temperature a gel-type mass formed. Dichloromethane was added until solution became clear and then BF$_3$-etherate solution (350 μL) was added dropwise. The reaction mixture was stirred for 1 hour and then diluted with dichloromethane (250 mL), washed with NaHCO$_3$ solution (2×250 mL) and water (2×250 mL), dried over anhydrous sodium sulfate and evaporated. The residue was chromatographed on a silica gel, eluting with hexane-ethyl acetate (2:1) and (1:1), to provide compound 84 (853 mg, 66%).

Step (G)—Preparation of 8-Methyoxycarbonyloctyl-2-acetamido-3-O-(2,3,4-tri-O-benzyl-α-L-fucopyranosyl)-4-O-[4,6-dichloro-4,6-dideoxy-β-D-galactopyranosyl]-6-O-benzyl-2-deoxy-β-D-glucopyranoside (compound 85)

To a solution of compound 84 (402 mg, 0.34 mmol) in 20 mL of methanol was added 2 mL of 0.5N sodium methoxide in methanol. The resulting mixture was stirred at room temperature for 1 hour and then neutralized with Amberlite IR-120(H$^+$) resin, filtered, evaporated under high vacuum. The residue was chromatographed on a silica gel column, eluting with dichloromethane-methanol (95:5), to provide compound 85 (358 mg, 96%).

Step (H)—Preparation of 8-Methoxycarbonyloctyl-2-acetamido-3-O-(2,3,4-tri-O-benzyl-α-L-fucopyranosyl)-4-O-[4,6-dichloro-4,6-dideoxy-3-O-sulfo-β-D-galactopyranosyl]-6-O-benzyl-2-deoxy-β-D-glucopyranoside sodium salt (86)

To a solution of compound 85 (356 mg, 0.32 mmol) in pyridine (7 mL) at 0° C. was added SO$_3$-pyridine complex (70 mg, 0.44 mmol). The reaction mixture was stirred for 30 minutes at 0° C. then the cooling bath was removed and stirring was continued at room temperature. Additional SO$_3$-pyridine complex was added after 1 hour (0.5 eq), 2.5 hours (0.5 eq), 3.5 hours (0.5 eq) and 4 hours (1.5 eq). The reaction was then terminated after 5.5 hours by adding methanol. The solvents were evaporated and the residue was chromatographed on a silica gel column, eluting with dichloromethane-methanol (95:5) containing 2 mL of pyridine per 1 L of solvent, to provide compound 86 (240 mg, 63%) after Bio-Rex® 70 Resin (sodium form).

Step (I)—Preparation of 8-Methoxycarbonyloctyl-2-acetamido-3-O-(α-L-fucopyranosyl)-4-O-[4,6-dichloro-4,6-dideoxy-3-O-sulfo-β-D-galactopyranosyl]-β-D-glucopyranoside sodium salt (compound 87)

A solution of compound 86 (215 mg, 0.18 mmol) in 20 mL of methanol containing 215 mg of 5% Pd/C was hydrogenolyzed at room temperature and atmospheric pressure for 6 hours. The solution was then filtered and evaporated. The residue was chromatographed on an latrobead column using dichloromethane-methanol-water (80:20:2) containing pyridine (12 mL per 1 L of solvent) as eluent. The collected material was passed through Bio-Rex® 70 Resin (sodium form) using water as an eluent and the resulting solution was freeze-dried to provide compound 87 (128 mg, 85%).

Example 18

Synthesis of 8-Methoxycarbonyloctyl-2-acetamido-3-O-(α-L-fucopyranosyl)-4-O-[4,6-dideoxy-3-O-sulfo-β-D-galactopyranosyl]-2-deoxy-β-D-glucopyranoside sodium salt (compound 91)

The synthesis of compound 91 is illustrated in FIG. 9.

Step (A)—Preparation of 8-Methoxycarbonyloctyl-2-acetamido-3-O-(2,3,4-tri-O-benzyl-α-L-fucopyranosyl)-4-O-[2,3-di-O-acetyl-4,6-dideoxy-β-D-galactopyranosyl]-6-O-benzyl-2-deoxy-β-D-glucopyranoside (compound 88)

A mixture of blocked di-chloro trisaccharide (compound 84) (412 mg, 0.35 mmol), tributyltin hydride (1.88 mL, 6.98 mmol) and AIBN (20 mg) in 20 mL of toluene was heated at 90° C. for 3 hours. The solvent was then evaporated and the residue was chromatographed on a silica gel column, eluting with hexane-ethyl acetate (2:1), to provide compound 88 (298 mg, 77%).

Step (B)—Preparation of 8-Methoxycarbonyloctyl-2-acetamido-3-O-(2,3,4-tri-O-benzyl-α-L-fucopyranosyl)-4-O-[4,6-dideoxy-β-D-galactopyranosyl]-6-O-benzyl-2-deoxy-β-D-glucopyranoside (compound 89)

To a solution of compound 88 (298 mg, 0.27 mmol) in methanol (10 mL) and dichloromethane (2 mL) was added a 0.5N solution of sodium methoxide in methanol (5 mL). After 2 hours at room temperature, the reaction mixture was neutralized with Amberlite IR-120(H$^+$) resin, filtered and evaporated. The residue was chromatographed on a silica gel column, eluting with dichloromethane-methanol (95:5), to provide compound 89 (253 mg, 91%).

Step (C)—Preparation of 8-Methoxycarbonyloctyl-2-acetamido-3-O-(2,3,4tri-O-benzyl-α-L-fucopyranosyl)-4-O-[4,6-dideoxy-3-O-sulfo-β-D-galactopyranosyl]-6-O-benzyl-2-deoxy-β-D-glucopyranoside sodium salt (compound 90)

To a solution of compound 89 (253 mg, 0.23 mmol) in 5 mL of pyridine at 0° C. was added SO$_3$-pyridine complex (59 mg, 0.37 mmol). After 0.5 hours at 0° C., the cooling bath was removed and stirring was continued at room temperature. Additional SO$_3$-pyridine complex was added after 1.5 hours (0.75 eq), 2.5 hours (0.75 eq) and 3.5 hours (0.75 eq). After 5 hours, the reaction was terminated by adding methanol. The solvents were evaporated and the residue was chromatographed on a silica gel column, eluting with dichloromethane-methanol (95:5) containing pyridine (2 mL per 1 L of solvent), to provide compound 90 (227 mg, 87%) after passing the recovered product through Bio-Rex® 20 Resin (sodium form) using methanol as an eluent.

Step (D)—Preparation of 8-Methoxycarbonyloctyl-2-acetamido-3-O-(α-L-fucopyranosyl)-4-O-[4,6-dideoxy-3-O-sulfo-β-D-galactopyranosyl]-2-deoxy-β-D-glucopyranoside sodium salt (compound 91)

A solution of compound 90 (225 mg, 0.20 mmol) in 20 mL of methanol containing 225 mg of 5% Pd/C was hydrogenolyzed for 2 hours at room temperature. The solution was then filtered and evaporated. The residue was chromatographed on an Iatrobeads column, eluting with dichloromethane-methanol-water (80:20:2) containing 2 mL of pyridine per liter of solvent, to provide a product which was converted into its sodium salt by passage through Bio-Rex® 70 Resin (sodium form) using water as an eluent. The resulting solution was freeze-dried to give compound 91 (147 mg, 96%).

Example 19

Synthesis of 8-methoxycarbonyloctyl-2-acetamido-3-O-(α-L-fucopyranosyl)-4O-[4-deoxy-3-O-sulfo-13-D-galactopyranosyl-2-deoxy-β-D-glucopyranoside sodium salt (95)

The synthesis of compound 95 is illustrated in FIG. 10.
Step (A) Preparation of 8-methoxycarbonyloctyl-2-acetamido-3-O-(2,3,4-tri-O-benzyl-α-L-fucopyranosyl)-4-O-[2,3-di-O-acetyl-4-deoxy-6-O-benzyl-β-D-galactopyranosyl]-6-O-benzyl-2-deoxy-β-D-glucopyranoside (compound 92)

A mixture of blocked trisaccharide (compound 74) (374 mg, 0.30 mmol), tributyltin hydride (1.7 mL) and AIBN (10 mg) in 20 mL of toluene was heated at 90° C. for 3–5 hours. The solvent was evaporated and the residue was chromatographed on a silica gel column eluting with hexane-ethyl acetate (1:1) to provide for compound 92 (325 mg, 89%).
Step (B) Preparation of 8-methoxycarbonyloctyl-2-acetamido-3-O-(2,3,4-tri-O-benzyl-α-α-L-fucopyranosyl)-4O-[4-deoxy-6-O-benzyl-β-D-galactopyranosyl]-6-O-benzyl-2-deoxy-α-D-glucopyranoside (93)

A 0.5M solution of sodium methoxide in methanol (5.0 mL) was added to a soltuion of compound 92 (325 mg, 0.27 mmol) in methanol (10 mL). After stirring for 3 hours at room temperature, the reaction mixture was neutralized with Amberlite IR-120 (H$^+$) resin, filtered and the solvent evaporated. The residue was chromatographed on a silica gel column eluting with dichloromethane-methanol (97:3) to provide compound 93 (289 mg, 95.5%).
Step (C) Preparation of 8-methoxycarbonyloctyl-2-acetamido-3-O-(2,3,4tri-O-benzyl-α-L-fucopyranosyl)-4-O-[4-deoxy-3-O-sulfo-6-O-benzyl-β-D-galactopyranosyl]-6-O-benzyl-2-deoxy-β-D-glucopyranoside sodium salt (94)

To a solution of compound 93 (289 mg, 0.26 mmol) in 5 mL of pyridine at 0° C. was added SO$_3$-pyridine complex (51 mg, 0.38 mmol) and the reaction mixture was stirred for 15 minutes at 0° C. and then 2–5 hours at room temperature. Additional amounts of SO$_3$-pyridine complex were added (0.7 equivalents) after 1 and 2 hours. After 5.5 hours, the reaction was terminated by adding methanol. The solvents were evaporated and the residue was chromatographed on a silica gel column, eluting with dichloromethane-methanol (95:5) containing pyridine (2 mL per 1 L of solvent), to provide compound 94 (266 mg, 84.4%), after passing the recovered product through Bio-Rex® 70 Resin (sodium form) using methanol as eluent.
Step (D) Preparation of 8-methoxycarbonyloctyl-2-acetamido-3-O-(α-L-fucopyranosyl)-4-O-[4-deoxy-3-O-sulfo-β-D-galactopyranosyl]-2-deoxy-β-D-glucopyranoside sodium salt (95)

A solution of compound 94 (266 mg, 0.22 mmol) in 10 mL of methanol containing 266 mg of 5% palladium on carbon was hydrogenolyzed for 2 hours at room temperature. The solution was then filtered and evaporated. The residue was chromatographed on an Iatrobead column, eluting with dichloromethane-methanol-water (80:20:2) containing a bit of pyridine (2 mL/1 L of the solvent mixture) to provide a product which was converted into a sodium salt by passage through BioRex® 70 Resin (sodium form) using water as the eluent. The residue was freeze dried to give compound 95 (145 mg, 86.9%).

Example 20

Preparation of 2-Acetamido-2-deoxy-3-O-[α-L-fucopyranosyl]-4-O-[3-O-sulfo-β-D-galactopyranosyl]-β-D-glucopyranosyl azide sodium salt (compound 111)

The synthesis of compound 111 is illustrated in FIG. 11.
Step (A) Preparation of 2-Acetamido-2-deoxy-3-O-[2,3,4-tri-O-p-methoxybenzyl-α-L-fucopyranosyl]-4,6-O-p-methoxybenzylldine-β-D-gIucopyranosyl azide (compound 105)

Copper (II) bromide (59.7 g, 0.268 mol, 5.0 eq.) and pulverized 4A molecular sieves (100 g) were added to a reaction vessel. Dry dichloromethane (120 mL) was syringed into the flask followed by dry DMF (47 mL, 10 eq.). Tetraethylammonium bromide (11.2 g, 0.0535 mol. 1.0 eq.) was added to the reaction flask and the greenish-black mixture was stirred for 30 minutes. The acceptor 2-N-acetamido-2-deoxy-4,6-O-p-methoxybenzylidene-β-D-glucopyranosyl azide, compound 103 (19.5 g, 0.0535 mol, 1.0 eq.), was added to the reaction, followed by the donor p-chlorothiophenyl 2,3,4-tri-O-p-methoxybenzyl-β-L-fucopyranoside, compound 104 (43.5 g, 0.0668 mol, 1.25 eq.). The mixture was stirred for three hours at room temperature before being quenched with triethylamine until neutral (3 mL, pH=7). The reaction was filtered through Celite and washed with 800 mL of dichloromethane. The organic layer was washed 4×1 L with a 5% EDTA solution (made by mixing 150 g tetrasodium EDTA salt with 75 g of fully protonated EDTA, pH=7).

The organic layer was washed once with 1.5 L of water, dried (MgSO$_4$), filtered and concentrated to give a golden syrup. This syrup was recrystallized from ethyl acetate/hexane to give 33.1 g of compound 105 (71%). MW 870.97 (C$_{46}$H$_{54}$O$_{13}$N$_4$).
Step (B) Preparation of 2-Acetamido-2-deoxy-3-O-[2,3,4-tri-O-p-methoxybenzyI-α-L-fueopyranosyl]-6-O-p-methoxybenzyl-β-D-glucopyranosyl azide (compound 106)

The benzylidene acetal (compound 105—23.2 g, 26.6 mmol, 1 eq.), sodium cyanoborohydride (16.7 g, 266 mmol, 10 eq.), 3A molecular sieves (50 g), and methyl orange (2 mg) were charged to a round bottom flask. THF (350 mL) was poured into the flask and the mixture was cooled to 0° C. A solution of hydrochloric acid in ether was added in a dropwise fashion to the reaction mixture until a pink color persisted. After 3 hours, the reaction was quenched by pouring the mixture into 600 mL of saturated sodium bicarbonate solution. Dichloromethane (600 mL) was added and the organic layer was separated. The organic layer was washed with 3×500 mL of bicarbonate solution, 1×500 mL water and 1×500 mL of a saturated solution of sodium chloride. The organic layer was dried (MgSO$_4$), filtered and concentrated. The golden syrup was recrystallized from isopropanol to give 19 g (82%) of compound 106 as a white solid. MW 872.98 (C$_{46}$H$_{56}$O$_{13}$N$_4$).
Step (C) Preparation of 2-Acetamido-2-deoxy-3-O-[2,3,4-tri-O-p-methoxybenzyl-(α-L-fucopyranosyl]-4-O-[β-D-galactopyranosyl]-6-O-p-methoxybenzyl-β-D-glucopyranosyl azide The acceptor 2-Acetamido-2-deoxy-3-O-[2,3,4-tri-O-p-methoxybenzyl-α-L-fucopyranosyl]-6-O-p-methoxybenzyl-β-D-glucopyranosyl azide (compound 106—15.0 g, 0.017 mol) and the donor 2,3,4,6-tetra-O-acetyl-β-D-galactopyranosyl trichloroacetimidate (compound 107—12.5 g, 0.025 mol, 1.5 eq.) were added to a round bottomed flask. Dichloromethane, 200 mL, was poured into the round bottomed flask and the mixture was cooled to 0° C. Boron trifluoride etherate (1.05 mL, 8.5 mmol, 0.5 eq.) was syringed into the mixture. The reaction continued for eight hours and was quenched with triethylamine (0.6 mL). The final pH of the reaction mixture was 7. The reaction was concentrated and purified by silica gel chromatography. The eluent used was a step gradient (25%–60% ethyl acetate in hexane). Compound 108 (15.5 g, 75%) was obtained as a yellowish foam. MW 1203.28 ($C_{60}H_{74}O_{22}N_4$).

The tetraacetylated galactose intermediate (compound 108—15.5 g, 0.0129 mol) was dissolved in 200 mL of methanol. A sodium methoxide in methanol solution (5 mL of a 0.5M solution, 2.5 mmol, 0.2 eq) was syringed into the mixture. The mixture was stirred overnight and neutralized with Amberlite IR-120 ($H^+$) resin. The neutralized mixture was filtered and concentrated. The product was purified by silica gel chromatography. The eluent used was 3–5% methanol in dichloromethane. The product (11.2 g, 83%) was obtained as a white solid. MW 1035.13 ($C_{52}H_{66}O_{22}N_4$).

Step (D) Preparation of 2-Acetamido-2-deoxy-6-O-p-methoxybenzyl-3-O-[2,3,4-tri-O-p-methoxybenzyl-α-L-fucopyranosyl]-4-O-[4,6-O-p-methoxybenzylidene-β-D-galactopyranosyl]-β-D-glucopyranosyl azide (compound 109)

2-Acetamido-2-deoxy-3-O-[2,3,4-tri-O-p-methoxybenzyl-α-L-fucopyranosyl]-4-O-[β-D-galactopyranosyl]-6-O-p-methoxybenzyl-β-D-glucopyranosyl azide (11.2 g, 10.8 mmol, 1 eq.) was dissolved in 150 mL of acetonitrile. Anisaldehyde dimethyl acetal (3.7 mL, 22 mmol, 2 eq.) was syringed into the stirred mixture. Toluene sulfonic acid (50 mg) was added to the reaction mixture ensuring a pH of 2–3. The reaction was stirred at pH 2–3 for 30 minutes at room temperature. The reaction was quenched by neutralization with triethylamine. The solution was concentrated and purified by silica gel chromatography. The chromatography eluent was 2% methanol in dichloromethane. The product, compound 109, obtained was a white solid (10.2 g, 82%). MW 1153.26 ($C_{60}H72O_{19}N_4$).

Step (E) Preparation of 2-Acetamido-2-deoxy-3-O-(2,3,4-tri-O-p-methoxybenzyl-α-L-fucopyranosyl)-4-O-[4,6-O-p-methoxybenzylidene-3-O-sulfo-β-D-galactopyranosyl]-6-O-p-methoxybenzyl-β-D-glucopyranosyl azide sodium salt (compound 110)

2-Acetamido-2-deoxy-3-O-(2,3,4-tri-O-p-methoxybenzyl-α-L-fucopyranosyl)-4-O-[4,6-O-p-methoxybenzylidene-β-D-galactopyranosyl]-6-O-p-methoxybenzyl-β-D-glucopyranosyl azide (compound 109—4.02 g, 3.49 mmol, 1 eq.) was dissolved in pyridine (40 mL) and cooled to 0° C. Sulfur trioxide pyridine complex (1.11 g, 6.97 mmol, 2 eq) was added to the reaction mixture. The reaction was slowly allowed to reach room temperature. After 90 minutes another portion of sulfur trioxide pyridine complex was added (0.28 g, 0.5 eq.). After a total reaction time of three hours, the reaction was quenched by the addition of 2 mL of methanol. The solution was concentrated and purified by silica gel chromatography. The chromatographic eluent was 5% methanol in dichloromethane with 0.5% added pyridine. After purification, the product was concentrated and passed through 50 g of analytical grade $Na^+$ ion exchange resin using methanol as the eluent. The product was concentrated to give compound 110 as a white solid (3.98 g, 92%). MW 1255.30 ($C_{60}H_{71}O_{22}N_4SNa$).

Step (F) Preparation of 2-Acetamido-2-deoxy-3-O-(α-L-fucopyranosyl)-4-O-[3-O-sulfo-β-D-galactopyranosyl]-β-D-glucopyranosyl azide sodium salt (compound 111)

2-N-Acetamido-2-deoxy-3-O-(2,3,4-tri-O-p-methoxybenzyl-α-L-fucopyranosoyl)-4-O-[4,6-O-p-methoxybenzylidene-3-O-sulfo-β-D-galactopyranosyl]-6-O-p-methoxybenzyl-β-D-glucopyranosyl azide sodium salt (1.0 g, 0.797 mmol) was dissolved in 30 mL of 90% aqueous acetonitrile. The reaction mixture was cooled to 0° C. and ceric ammonium nitrate (3.5 g, 6.4 mmol, 8 eq.) was added to the mixture all at once. The reaction was gradually warmed to room temperature and quenched at 6.5 hours by the addition of pyridine. The reaction required 1.7 mL of pyridine for complete neutralization. The product was concentrated, and purified by column chromatography using Iatrobead silica gel. The chromatographic eluent was 70:30:3:1 dichloromethane:methanol:water:pyridine. The product was concentrated to dryness and passed through 40 g of analytical grade $Na^+$ ion exchange resin. The product was then filtered through a 0.22μ Millipore filter and lyophilized. The product, compound 111, was isolated as a fluffy white solid (443 mg, 85%). MW 656.56 ($C_{20}H_{33}O_{17}N_4SNa$).

Example 21

Preparation of 2-Acetamido-2-deoxy-3-O-(α-L-fucopyranosyl)-4-O-[3-O-sulfo-β-D-galactopyranosyl]-β-D-glucopyranosyl amine Procedure A.

2-Acetamido-2-deoxy-3-O-(2,3,4-tri-O-p-methoxybenzyl-α-L-fucopyranosyl)-4-O-[4,6-O-p-methoxybenzylidene-3-O-sulfo-β-D-galactopyranosyl]-6-O-p-methoxybenzyl-β-D-glucopyranosyl azide (compound 110—500 mg, 0.398 mmol) was weighed into a reaction flask. The vessel was then flushed with nitrogen and 500 mg of 5% palladium on charcoal was added to the flask. Dry methanol (6.0 mL) was syringed into the flask followed by 4.0 mL of a 0.37% methanolic hydrochloric acid solution. The mixture was then purged with hydrogen gas and remained under hydrogen atmosphere for four hours at room temperature. At this time, another 1.0 mL of acidic solution was added to the reaction (total mmols of HCl=0.51, 1.28 eq.). The reaction was stirred an additional four hours and quenched by the addition of pyridine until the pH of the solution was basic. The reaction solution was then filtered and the catalyst washed well with water and methanol. The solution was concentrated on a rotary evaporator (water bath<25° C.) and purified by column chromatography (Iatrobeads 85:10:5 isopropanol:water:ammonia was the eluant). The total time the product was in contact with silica gel was three hours. The product was collected, pyridine added to the collection flask and concentrated as noted above. The product was then loaded onto 8 g of $Na^+$ analytical grade ion exchange resin and lyophilized to yield 191 mg (75%) of a fluffy white powder. MW of sodium salt 630.55 ($C_{20}H_{35}O_{17}N_2SNa$). NMR revealed the product was 20–30% decomposed. It was found that the lifetime of the product could be enhanced by using the reaction mixture immediately after hydrogenation. MW (pyridinium salt) 687.68 ($C_{25}H_{41}O_{17}N_3S^-$).

Procedure B.

2-Acetamido-2-deoxy-(3-O-α-L-fucopyranosyl)-4-O-[3-O-sulfo-β-D-galactopyranosyl)-β-D-glucopyranosyl azide (compound 111—150 mg, 0.22 mmol) and 5% palladium on charcoal (200 mg) were added to a reaction vessel and purged with nitrogen. Dry methanol (10 mL) was syringed into the flask and the reaction contents were cooled to 0° C. The reaction vessel was then purged with hydrogen gas and stirred at 0° C. for two hours. The reaction was quenched by the addition of pyridine, filtered and concentrated. Caution was used to maintain all procedures at or below room temperature to reduce risk of product decomposition. The crude product was used directly for further chemical manipulations without any characterization. Tlc of the reaction mixture when complete indicates a major product spot at Rf=0.30 (75:20:5 isopropanol:water:ammonia) with a minor spot at Rf=0.20 (approximately 20% as intense as the product spot by sulfuric acid charring).

Example 22

Preparation of 2-Acetamido-2-deoxy-3-O-(α-L-fucopyranosyl)-4-O-[3-O-sulfo-β-D-galactopyranosyl]-β-D-glucopyranosyl benzamide sodium salt The crude glycosyl amine (190 mg, 0.28 mmol—pyridinium salt from Example 21—Procedure A) was dissolved in 8.5 mL of methanol and 3.0 mL of a saturated solution of sodium bicarbonate. The reaction mixture was cooled to 0° C. and benzoyl chloride (0.175 mL, 1.5 mmol, 5.4 eq.) was syringed into the mixture all at once. The reaction was complete within 5 minutes, as indicated by an increase in Rf on tlc (Rf starting material=0.31, product= 0.53 in 75:20:5 isopropanol:water:ammonia). A few drops of pyridine were added to the reaction mixture and it was concentrated under reduced pressure. The product was isolated by Iatrobead column chromatography using 70:30:3:1 dichloromethane:methanol:water:pyridine as eluent. Concentration of the product was followed by ion exchange chromatography using 10 g of analytical grade $Na^+$ resin. Lyophilization yielded 122 mg of product (59%) as a fluffy white powder. MW 734.66 ($C_{27}H_{39}O_{18}N_2SNa$).

Example 23

Preparation of 2-Acetamido-2-deoxy-3-O-(α-L-fucopyranosyl)-4O-[3-O-sulfo-β-D-galactopyranosyl]-β-D-glucopyranosyl p-nitrobenzamide sodium salt The crude glycosyl amine (335 mg, 0.49 mmol—pyridinium salt from Example 21—Procedure A) was dissolved in 15 mL of methanol and 5 mL of a saturated solution of sodium bicarbonate. The reaction mixture was cooled to 0° C. and p-nitrobenzoyl chloride (698 mg, 3.8 mmol, 7.7 eq.) was added to the reaction mixture. Acetone (1 mL) was syringed into the mixture to enhance the solubility of the acid chloride. The reaction was stirred overnight at room temperature. A few drops of pyridine was added to the reaction and the mixture was concentrated. The product was purified as described for the preparation of the benzamido product (Example 22). The chromatography eluent was 70:30:3:1 dichloromethane:methanol:water:pyridine. The product, 88 mg (23%), was obtained as a fluffy white solid. MW 779.66 ($C_{27}H_{38}O_{20}N_3SNa$).

Example 24

Preparation of 2-Acetamido-2-deoxy-3-O-(α-L-fucopyranosyl)-4-O-[3-O-sulfo-β-D-galactopyranosyl]-β-D-glucopyranosyl butyramide sodium salt The crude glycosyl amine (292 mg, 0.42 mmol—pyridinium salt from Example 21—Procedure A) was dissolved in 12 mL of methanol and 4 mL of a saturated solution of sodium bicarbonate. The reaction mixture was cooled to 0° C. and butyric anhydride (0.39 mL, 2.4 mmol, 5.7 eq.) was added to the reaction mixture. After 5 minutes, a few drops of pyridine was added to the reaction and the mixture was concentrated. The product was purified as described for the preparation of the benzamido product (Example 22). The chromatography eluent was 70:30:2:1 dichloromethane:methanol:water:pyridine. A second column using 85:10:5 isopropanol:water:ammonia was used to repurify the product. The product, 90 mg (30%), was obtained as a fluffy white solid. MW 700.65 ($C_{24}H_{41}O_{18}N_2SNa$).

Example 25

Preparation of 2-Acetamido-2-deoxy-3-(α-L-fucopyranosyl)-40-[3-O-sulfo-β-D-galactopyranosyl]-β-D-glucopyranosyl acetamide sodium salt The crude glycosyl amine (135 mg, 0.20 mmol—pyridinium salt from Example 21—Procedure A) was dissolved in 4.5 mL of methanol and 1.5 mL of a saturated solution of sodium bicarbonate. The reaction mixture was cooled to 0° C. and acetic anhydride (0.095 mL, 1.0 mmol, 5 eq.) was added to the reaction mixture. After several hours, a few drops of pyridine were added to the reaction and the mixture was concentrated. The product was purified as described for the preparation of the benzamido product (Example 22). The chromatography eluent was 85:11:4 isopropanol:water:ammonia. A second column was used to repurify the product (eluent was 70:30:2.5:1 dichloromethane:methanol:water:pyridine). The product, 118 mg (88%), was obtained as a fluffy white solid. MW 672.59 ($C_{22}H_{37}O_{18}N_2SNa$).

Example 26

Preparation of 2-Acetamido-2-deoxy-3-O-(α-L-fucopyranosyl)-4-O-[3-O-sulfo-β-D-galactopyranosyl]-β-D-glucopyranosyl stearamide sodium salt Stearic acid (564 mg, 2.0 mmol, 9 eq.) and dicyclohexylcarbodiimide (590 mg, 2.9 mmol, 13 eq.) were weighed into a reaction flask. Methanol (70 mL) was added to the flask and the mixture was stirred at 0° C. for 30 minutes. The crude glycosyl amine (158 mg, 0.23 mmol, 1 eq.—pyridinium salt from Example 21—procedure B) was dissolved in 2×5 mL of methanol and added to the reaction flask. The reaction was stirred overnight at room temperature and then a few drops of pyridine were added to the reaction flask. The mixture was then concentrated and purified as described for the preparation of the benzamido product (Example 22). The chromatography eluent was 80:20:2 dichloromethane:methanol:pyridine. The product, 62 mg (30%), was obtained as a fluffy white solid. MW 897.02 ($C_{38}H_{69}O_{18}N_2SNa$).

Example 27

Preparation of 2-Acetamido-2-deoxy-3-O-(α-L-fucopyranosyl)-4-O-[3-O-sulfo-β-D-galactopyranosyl]-β-D-glucopyranosyl L-serine sodium salt N-Benzyloxycarbonyl-L-serine (450 mg, 1.9 mmol, 9 eq.) and EDC (560 mg, 2.9 mmol, 14 eq.) were weighed into a reaction flask. Methanol (65 mL) was added to the flask and the mixture was stirred at 0° C. for 30 minutes. The crude glycosyl amine (142 mg, 0.21 mmol, 1 eq—pyridinium salt from Example 21 procedure B) was dissolved in 2×5 mL of methanol and added to the reaction flask. The reaction was stirred overnight at room temperature and then a few drops of pyridine were added to the reaction flask. The mixture was then concentrated and purified as described for the preparation of the benzamido product (Example 22). The chromatography eluent was 70:30:2:0.1 dichloromethane:methanol:water:pyridine. The benzyloxycarbonyl protected product, 115 mg (64%), was obtained as a fluffy white solid. MW 851.77 ($C_{31}H_{46}O_{21}N_3SNa$).

The benzyloxycarbonyl protected product (115 mg, 0.13 mmol) was added to a reaction flask followed by 200 mg of 5% palladium on charcoal. The flask was argon purged and then methanol (10 mL) was added. The reaction flask was then purged with hydrogen for one hour at room temperature. Tlc of the reaction after one hour indicated the reaction was complete. Several drops of pyridine were added to the reaction and the catalyst was removed by filtration. The filtrate was concentrated and purified as described for the preparation of the benzamido product (Example 22). The chromatography eluent was 65:35:4:0.1 dichloromethane:methanol:water:pyridine. The glucopyranosyl serine product was obtained after lyophilization as a fluffy white solid (60 mg, 62%). MW 717.64 ($C_{23}H_{40}O_{19}N_3SNa$).

Example 28

Preparation of 8-methoxycarbonyloctyl-2-acetamido-2-deoxy-3-O-(4-deoxy-α-L-fucopyranosyl)-4-O-(3-O-sulfo-β-D-galactopyranosyl)-β-D-glucopyranoside sodium salt (compound 212)

The synthesis of this compound is illustrated in FIG. 12.
Step A—Preparation of Methyl 2-O-benzyl-L-fucopyranoside, compound 201
The title compound, compound 201, was prepared according to Deter-Jusynski, et al.[36]
Step B—Preparation of Methyl 2,3-di-O-benzyl-L-fucopyranoside (compound 202)
A mixture of compound 201 (7 g, 26.089 mmol), di-n-butyltin oxide (7 g, 28.12 mmol) in anhydrous benzene (300 mL) was boiled under reflux with azetropic removal of water for 6 hours and then concentrated to 50 mL. Tetrabutylammonium fluoride monohydrate (9.8 g, 37.48 mmol), 4A molecular sieves (23 g) and benzyl bromide (9.25 mL, 77.77 mmol) were then added and the mixture was kept at room temperature overnight. Column chromatography on silica gel (hexane-ethyl acetate, 2:1) gave compound 202 (9.1 g, 97%).
Step C—Preparation of Methyl 2,3-di-O-benzyl-4-O-(methylthio)thiocarbonyl-L-fucopyranoside (compound 203)
Sodium hydride (428 mg, 60% in mineral oil, 10.7 mmol) and imidazole (10 mg) were added to compound 202 (750 mg, 2.092 mmol) in THF (16 mL). The reaction mixture was heated at 50° C. for 0.5 hours and carbon disulfide (16 mL) was added. In another 1 hour, methyl iodide (16 mL) was added. Heating was continued for 1 more hour and the mixture was cooled to room temperature and methanol was added. Concentration and then column chromatography (hexane-ethyl acetate, 3:1) gave compound 203 (850 mg, 90%).
Step D—Preparation of Methyl 2,3-di-O-benzyl-4-O-(imidazole)thiocarbonyl-L-fucopyranoside (compound 204)

A mixture of compound 202 (8 g, 22.32 mmol) and 1,1'-thiocarbonyldiimidazole (9 g, 50.50 mmol) in 1,2-dichloroethane (100 mL) was refluxed for 4 hours and then concentrated. Column chromatography of the residue (hexane-ethyl acetate, 2:1, 1:1) yielded compound 204 (10.1 g, 96%).
Step E—Preparation of Methyl 2,3-di-O-benzyl-4-deoxy-L-fucopyranoside (compound 205)
Preparation A (from compound 203)
Compound 203 (850 mg, 1.895 mmol) in anhydrous toluene (20 mL) was heated at 80° C. AIBN (350 mg, 2.142 mmol) was added followed by tributyltin hydride (8 mL, 29.74 mmol). Heating was continued for 2 hours and the mixture was concentrated and chromatographed (hexane-ethyl acetate, 3:1) to give compound 205 (620 mg, 95%).
Preparation B (from compound 204)
Compound 204 (10 g, 21.3 mmol) in anhydrous toluene (160 mL) was heated at 100° C. AIBN (2.6 g, 15.912 mmol) and tributyltin hydride (50 g, 171.8 mmol) were then added. Heating was continued for 2 hours and the mixture was concentrated and chromatographed (hexane-ethyl acetate, 6:1) to give compound 205 (5.4 g, 74%).
Step F—Preparation of 2,3-Di-O-benzyl-4-deoxy-L-fucopyranose (compound 206)
Compound 205 (10 g, 29.2 mmol) in glacial acetic acid (180 mL) and 6N HCl (36 mL) was heated at 65° C. for 3 hours and evaporated. The crude product, compound 206, was used in the next reaction without purification.
Step G—Preparation of p-Chlorophenyl 2,3-di-O-benzyl-4-deoxy-β-L-thiofucopyranoside (compound 207)
A mixture of compound 206 (29.2 mmol), anhydrous NaOAc (2.5 g, 30.48 mmol) and acetic anhydride (53 mL) in 1,2-dichloroethane (90 mL) was heated at 60° C. for 3 hours and cooled to room temperature. Water was added and the organic layer was separated and washed with water and aqueous sodium bicarbonate. After concentration, the dried residue was dissolved in dichloromethane (100 mL) and the mixture was cooled at 0° C. p-Chlorothiophenol (4.5 g, 31.116 mmol) was added followed by $BF_3$-ether (7.3 mL). The reaction mixture was allowed to reached room temperature and kept there for 1.5 hours. It was then poured into ice-$NaHCO_3$ and extracted with dichloromethane. Column chromatography (hexane-ethyl acetate, 6:1) of the residue on evaporation gave compound 207 (10.5 g, 79% 3-steps).
Step H—Preparation of 8-Methoxycarbonyloctyl 2-acetamido-6-O-benzyl-4-O-(2,3-di-O-benzoyl-4,6-O-benzylidene-β-D-galactopyranosyl)-2-deoxy-β-D-glucopyranoside (compound 208)
Compound 208 was prepared according to the procedures provided in International patent application Ser. No. PCT/US93/04909 which is incorporated herein by reference in its entirety.
Step I—Preparation of 8-Methoxycarbonyloctyl 2-acetamido-6-O-benzyl-2-deoxy-3-O-(2,3-di-O-benzyl-4-deoxy-α-L-fucopyranosyl)-4-O-(2,3-di-O-benzoyl-4,6-O-benzylidene-β-D-galactopyranosyl)-β-D-glucopyranoside (compound 209)
DMF (3 mL) and tetraethylammonium bromide (768 mg, 3.654 mmol) were added to a suspension of copper bromide (4.17 g, 18.669 mmol) and 4A molecular sieves (7.2 g) in dichloromethane (6 mL). After string at room temperature for 0.5 hours, a solution of compound 208 (3.6 g, 3.83 mmol) in dichloromethane (7 mL) was added followed by compound 207 (4 g, 8.79 mmol) in dichloromethane (6 mL). The mixture was then kept in the dark for 16 hours and pyridine (1 mL) was added. The resulting solution was filtered through Celite, concentrated and column chromatographed (hexane-acetone, 5:2) to give compound 209 (3.5 g, 73%)

Step J—Preparation of 8-Methoxycarbonyloctyl 2-acetamido-6-O-benzyl-3-O-(2,3-di-O-benzyl-4-deoxy-α-L-fucopyranosyl)-4-O-(4,6-O-benzylidene-β-D-galactopyranosyl)-2-deoxy-β-D-glucopyranoside (compound 210)

Compound 209 (3.3 g, 2.64 mmol) was treated with 0.06N methanolic sodium methoxide (90 mL) for 16 hours. It was neutralized by Amberlite IR 120 (H$^+$), filtered and evaporated. Column chromatography of the residue (hexane-acetone, 2:1) provided for compound 210 (2.5 g, 91%).

Step K—Preparation of 8-Methoxycarbonyloctyl 2-acetamido-6-O-benzyl-3-O-(2,3-di-O-benzyl-4-deoxy-α-L-fucopyranosyl)-4-O-(4,6-O-benzylidene-3-O-sulfo-β-D-galactopyranosyl)-2-deoxy-β-D-glucopyranoside sodium salt (compound 211)

Sulfur trioxide-pyridine complex (687 mg, 4.32 mmol) was added to compound 210 (2.5 g, 2.4 mmol) in pyridine (16 mL) at 0° C. The reaction mixture was allowed to reach room temperature and more sulfur trioxide-pyridine complex (300 mg, 1.885 mmol) was added. Stirring was continued for 1 more hour and methanol was added. After evaporation of the solvent, the residue was applied to a column of silica gel (methanol-dichloromethane, 1:9, 0.1% pyridine). The product obtained was then passed through a column of Amberlite IR-120 Na$^+$ (MeOH) to give compound 211 (2.2 g, 80%).

Step L—Preparation of 8-Methoxycarbonyloctyl 2-acetamido-2-deoxy-3-O-(4-deoxy-α-L-fucopyranosyl)-4-O-(3-O-sulfo-β-D-galactopyranosyl)-β-D-glucopyranoside sodium salt (compound 212)

Compound 211 (1.5 g, 1.311 mmol) and palladium on carbon (5%, 2.2 g) in MeOH (80 mL) were hydrogenated for 3 hours and pyridine was added. After filtration of the catalyst and evaporation of the solvent, the crude product was purified by chromatography on silica gel (dichloromethane-methanol-water, 80:20:2, 0.2% pyridine) and then a column of Bio-Rex® 70 (Na$^+$ form) to provide for compound 212 (750 mg, 73%).

Example 29

Preparation of 8-Methoxycarbonyloctyl 2-acetamido-2-deoxy-3-O-(4-O-sulfo-α-L-fucopyranosyl)-4-O-(3-O-sulfo-β-D-galactopyranosyl)-β-D-glucopyranoside sodium salt (compound 224)

The synthesis of this compound is illustrated in FIG. 13.

Step A—Preparation of p-Chlorophenyl 3,4-O-benzylidene-β-L-thiofucopyranoside (compound 214)

A mixture of compound 213 (1.8 g, 6.19 mmol), p-toluenesulfonic acid (20 mg) and α,α-dimethoxytoluene (1.6 mL, 10.66 mmol) in acetonitrile (10 mL) was kept at room temperature overnight and concentrated to 6 mL. It was then heated at 55° C. for 2 hours and neutralized by triethylamine and evaporated to give crude compound 214 which was used in the next reaction.

Step B—Preparation of p-Chlorophenyl 2-O-benzyl-3,4-O-benzylidene-β-L-thiofucopyranoside (compound 215)

Sodium hydride (383 mg, 60% in mineral oil, 9.575 mmol) was added in small portions to compound 214 (3.1 mmol) in DMF (4 mL) which was cooled in dry ice. After 0.5 hours, benzyl bromide (1.2 mL) was added and the reaction mixture was allowed to reach room temperature and kept there for 2 hours. Methanol was added to destroy the remaining NaH and the solvent were then removed by evaporation. The residue was taken up in dichloromethane, filtered through Celite and evaporated to leave crude compound 215 as a syrup.

Step C—Preparation of p-Chlorophenyl 2-O-benzyl-β-L-thiofucopyranoside (compound 216)

Compound 215 (3.0 mmol) in 80% acetic acid (20 mL) was heated at 50° C. for 2 hours. It was evaporated and co-evaporated with toluene. Chromatography of the residue (hexane-ethyl acetate, 1:1) provided compound 216 (720 mg, 63%, 3 steps).

Step D—Preparation of p-Chlorophenyl 2,3-di-O-benzyl-β-L-thiofucopyranoside (compound 217)

A mixture of compound 216 (700 mg, 1.838 mmol) and di-n-butyltin oxide (495 mg, 1.988 mmol) in benzene (40 mL) was boiled under reflux with azetropic removal of water for 6 hours and then concentrated to 5 mL. Tetrabutylammonium fluoride monohydrate (700 mg, 2.67 mmol), 4A molecular sieves (1.7 g) and benzyl bromide (0.7 mL, 5.89 mmol) were then added and the mixture was kept at room temperature overnight. Column chromatography on silica gel (hexane-ethyl acetate, 3:1) gave compound 217 (810 mg, 93%).

Step E—Preparation of p-Chlorophenyl 2,3-di-O-benzyl-4-O-(4-methoxybenzyl)-β-L-thiofucopyranoside (compound 218)

A solution of compound 217 (660 mg, 1.401 mmol) in DMF (6 mL) was cooled in dry ice and sodium hydride (584 mg, 60% in mineral oil, 14.6 mmol) was added in small portions. After 0.5 hours, p-methoxybenzyl chloride (1.83 mL, 13.50 mmol) was added and the reaction mixture was then kept at room temperature for 3 hours. Methanol was then added. After evaporation, the residue was applied to a column of silica gel (hexane-ethyl acetate, 10:1) and the appropriate fractions collected to provide for compound 218 (605 mg, 73%).

Step F—Preparation of 8-Methoxycarbonyloctyl 2-acetamido-6-O-benzyl-2-deoxy-3-O-(2,3-di-O-benzyl-4-O-(4-methoxybenzyl)-α-L-fucopyranosyl)-4-O-(2,3-di-O-benzoyl-4,6-O-benzylidene-β-D-galactopyranosyl)-β-D-glucopyranoside (compound 219)

DMF (0.39 mL) and tetraethylammonium bromide (106 mg, 0.505 mmol) were added to a suspension of copper bromide (552 mg, 2.473 mmol) and 4A molecular sieves (880 mg) in dichloromethane (1 mL). After stirring at room temperature for 0.5 hours, a solution of compound 208 (490 mg, 0.521 mmol) in dichloromethane (1 mL) was added followed by compound 218 (440 mg, 0.745 mmol) in dichloromethane (1 mL). The mixture was then kept in the dark for 24 hours and pyridine (0.3 mL) was added. It was filtered through Celite, concentrated and column chromatographed (hexane-acetone, 5:2) to give compound 219 (680 mg, 94%).

Step G—Preparation of 8-Methoxycarbonyloctyl 2-acetamido-6-O-benzyl-2-deoxy-3-O-(2,3-di-O-benzyl-4-O-(4-methoxybenzyl)-α-L-fucopyranosyl)-4-O-[4,6-O-benzylidene-β-D-galactopyranosyl]-β-D-glucopyranoside (compound 220)

Compound 219 (670 mg, 0.483 mmol) was treated with 0.06N methanolic sodium methoxide (15 mL) for 16 hours. It was neutralized by Amberlite IR 120 (H$^+$), filtered and evaporated. Column chromatography of the residue (hexane-acetone, 1:1) provided compound 220 (550 mg, 97%).

Step H—Preparation of 8-Methoxycarbonyloctyl 2-acetamido-6-O-benzyl-3-O-(2,3-di-O-benzyl-4-O-(4methoxybenzyD)-α-L-fucopyranosyl)-4-O-[4,6-O-benzylidene-3-O-sulfo-β-D-galactopyranosyl]-2-deoxy-β-D-glucopyranoside (compound 221)

Sulfur trioxide pyridine complex (119 mg, 0.747 mmol) was added to compound 220 (550 mg, 0.467 mmol) in pyridine (2 mL) at 0° C. The reaction mixture was allowed to reach room temperature. Stirring was continued for 1 more hour and methanol was added. After evaporation of the solvent, the crude product, compound 221, was used in the next reaction.

Step I—Preparation of 8-Methoxycarbonyloctyl 2-acetamido-6-O-benzyl-3-O-(2,3-di-O-benzyl-α-L-fucopyranosyl)-4-O-[4,6-O-benzylidene-3-O-sulfo-β-D-galactopyranosyl]-2-deoxy-β-D-glucopyranoside (compound 222)

A mixture of compound 221 (0.336 mmol) and CAN (460 mg, 0.839 mmol) in acetonitrile-water (9:1, 10 mL) was kept at room temperature for 1 hour and pyridine (0.6 mL) was added followed by dichloromethane. The organic layer was separated and washed with water. After evaporation of the solvent, the residue was applied to a column of silica gel (dichloromethane-methanol, 85:15, 0.2% pyridine) to provide for compound 222 (350 mg, 87%, 2 steps).

Step J—Preparation of 8-Methoxycarbonyloctyl 2-acetamido-6O-benzyl-3-O-(2,3-di-O-benzyl-4-O-sulfo-α-L-fucopyranosyl)-4-O-[4,6-O-benzylidene-3-O-sulfo-β-D-galactopyranosyl]-2-deoxy-β-D-glucopyranoside disodium salt (compound 223)

Sulfur trioxide-pyridine complex (80 mg, 0.502 mmol) was added to compound 222 (350 mg, 0.291 mmol) in pyridine (2.4 mL) at 0° C. The reaction mixture was allowed to reach room temperature and more sulfur trioxide-pyridine complex (120 mg, 0.753 mmol) was added in small portions. Stirring was continued for 3 hours and methanol was added. After evaporation of the solvent, the residue was applied to a column of silica gel (water-methanol-dichloromethane, 2:20:80, 0.2% pyridine used as eluent). The product obtained was then passed through a column of Amberlite R-120 Na$^+$ (MeOH) to give compound 223 (180 mg, 49%).

Step K—Preparation of 8-Methoxycarbonyloctyl 2-acetamido-2-deoxy-3-O-(4-O-sulfo-α-L-fucopyranosyl)-4-O-[3-O-sulfo-β-D-galactopyranosyl]-β-D-glucopyranoside disodium salt (compound 224)

Compound 223 (150 mg, 0.119 mmol) and palladium on carbon (5%, 280 mg) in MeOH (8 mL) were hydrogenated for 2 hours and pyridine (0.8 mL) was added. After filtration of the catalyst and evaporation of the solvent, the crude product was purified by chromatography on silica gel (dichloromethane-methanol-water, 70:30:3, 0.2% pyridine) and then a column of Bio-Rex® 70 (Na$^+$ form) to provide for compound 224 (81 mg, 76%).

Example 30

Preparation of 8-Methoxycarbonyloctyl 2-acetamido-2-deoxy-3-O-(3-O-sulfo-α-L-fucopyranosyl)-4-O-(3-O-sulfo-β-D-galactopyranosyl)-β-D-glucopyranoside disodium salt (compound 232)

The synthesis of compound 232 is illustrated in FIG. 14.
Step A—Preparation of p-Chlorophenyl 2-O-benzyl-3-O-(4-methoxybenzyl)-β-L-thiofucopyranoside (compound 225)

A mixture of compound 216 (660 mg, 1.732 mmol) and di-n-butyltin oxide (495 mg, 1.988 mmol) in benzene (60 mL) was boiled under reflux with azetropic removal of water for 6 hours and then concentrated to 10 mL. Tetrabutylammonium fluoride monohydrate (660 mg, 2.524 mmol), 4A molecular sieves (1.7 g) and 4-methoxybenzyl chloride (0.77 mL, 5.66 mmol) were then added and the mixture was kept at room temperature overnight. Column chromatography on silica gel (hexane-ethyl acetate, 3:1) gave compound 225 (770 mg, 89%).

Step B—Preparation of p-Chlorophenyl 2,4-di-O-benzyl-3-O-(4-methoxybenzyl)-β-L-thiofucopyranoside (compound 226)

A solution of compound 225 (750 mg, 1.497 mmol) in DMF (5 mL) was cooled in dry ice and sodium hydride (600 mg, 60% in mineral oil, 15 mmol) was added in small portions. After 0.5 hours, benzyl bromide (1.7 mL, 14 mmol) was added and the reaction mixture was then kept at room temperature for 2 hours. Methanol was added. After evaporation, the residue was applied to a column of silica gel (hexane-ethyl acetate, 6:1) to provide for compound 226 (705 mg, 80%).

Step C—Preparation of 8-Methoxycarbonyloctyl 2-acetamido-6-O-benzyl-2-deoxy-3-O-(2,4-di-O-benzyl-3-O-(4-methoxybenzyl)-α-L-fucopyranosyl)-4-O-[2,3-di-O-benzoyl-4,6-O-benzylidene-β-D-galactopyranosyl]-β-D-glucopyranoside (compound 227)

DMF (0.34 mL) and tetraethylammonium bromide (106 mg, 0.504 mmol) were added to a suspension of copper bromide (477 mg, 2.137 mmol) and 4A molecular sieves (760 mg) in dichloromethane (1 mL). After stirring at room temperature for 0.5 hours, a solution of compound 208 (300 mg, 0.319 mmol) in dichloromethane (1.5 mL) was added followed by compound 226 (380 mg, 0.642 mmol) in dichloromethane (1.5 mL). The mixture was then kept in the dark for 5 hours and pyridine (0.5 mL) was added. It was filtered through Celite, concentrated and column chromatographed (hexane-acetone, 5:2) to give compound 227 (360 mg, 81%).

Step D—Preparation of 8-Methoxycarbonyloctyl 2-acetamido-6-O-benzyl-3-O-(2,4-di-O-benzyl-3-O-(4-methoxybenzyl)-α-L-fucopyranosyl)-4-O-[4,6-O-benzylidene-β-D-galactopyranosyl]-2-deoxy-β-D-glucopyranoside (compound 228)

Compound 227 (330 mg, 0.237 mmol) was treated with 0.06N methanolic sodium methoxide (8 mL) for 16 hours. It was neutralized by Amberlite IR 120 (H$^+$), filtered and evaporated. Column chromatography of the residue (hexane-acetone, 1:1) provided for compound 228 (255 mg, 91%).

Step E—Preparation of 8-Methoxycarbonyloctyl 2-acetamido-6-O-benzyl-3-O-(2,4-di-O-benzyl-3-O-(4-methoxybenzyl)-α-L-fucopyranosyl)-4-O-[4,6-O-benzylidene-3-O-sulfo-β-D-galactopyranosyl]-2-deoxy-β-D-glucopyranoside (compound 229)

Sulfur trioxide-pyridine complex (50 mg, 0.314 mmol) was added to compound 228 (245 mg, 0.207 mmol) in pyridine (1.6 mL) at 0° C. The reaction mixture was allowed to reach room temperature and more sulfur trioxide-pyridine complex (20 mg) was added. Stirring was continued for 0.5 more hours and methanol was added. After evaporation of the solvent, the crude product, compound 229, was used in the next reaction.

Step F—Preparation of 8-Methoxycarbonyloctyl 2-acetamido-6-O-benzyl-3-O-(2,4di-O-benzyl-α-L-fucopyranosyl)-4-O-[4,6-O-benzylidene-3-O-sulfo-β-D-galactopyranosyl]-2-deoxy-β-D-glucopyranoside (compound 230)

A mixture of compound 229 (0.207 mmol) and CAN (400 mg, 0.730 mmol) in acetonitrile-water (9:1, 10 mL) was kept at room temperature for 3 hours and pyridine (0.6 mL) was added followed by dichloromethane. The organic layer was separated and washed with water. After evaporation of the solvent, the residue was applied to a column of silica gel (dichloromethane-methanol, 85:15, 0.2% pyridine) to yield compound 230 (190 mg, 76%, 2 steps).

Step G—Preparation of 8-Methoxycarbonyloctyl 2-acetamido-6-O-benzyl-3-O-(2,4-di-O-benzyl-3-O-sulfo-α-L-fucopyranosyl)-4-O-[4,6-O-benzylidene-3-O-sulfo-β-D-galactopyranosyl]-2-deoxy-β-D-glucopyranoside disodium salt (compound 231)

Sulfur trioxide-pyridine complex (80 mg, 0.502 mmol) was added to compound 230 (140 mg, 0.116 mmol) in pyridine (1 mL) at 0° C. The reaction mixture was allowed to reach room temperature and more sulfur trioxide-pyridine complex (70 mg) was added in small portions. Stirring was continued for 1.5 hours and methanol was added. After evaporation of the solvent, the residue was applied to a column of silica gel (methanol-dichloromethane, 15:85, 0.2% pyridine). The product obtained was then passed through a column of Amberlite IR-120 Na$^+$ (MeOH) to give compound 231 (110 mg, 75%).

Step H—Preparation of 8-Methoxycarbonyloctyl 2-acetamido-2-deoxy-3-O-(3-O-sulfo-α-L-fucopyranosyl)-4-O-[3-O-sulfo-β-D-galactopyranosyl]-β-D-glucopyranoside disodium salt (compound 232)

Compound 231 (110 mg, 0.087 mmol) and palladium on carbon (5%, 150 mg) in MeOH (4 mL) were hydrogenated for 2 hours and pyridine (2 mL) was added. After filtration of the catalyst and evaporation of the solvent, the crude product was purified by chromatography on silica gel (dichloromethane-methanol-water, 70:30:3, 0.2% pyridine) and then a column of Bio-Rex® 70 (Na$^+$ form) to provide for compound 232 (68 mg, 87%).

Example 31

Preparation of 8-Methoxycarbonyloctyl 2-acetamido-2-deoxy-3-O-(3-O-methyl-α-L-fucopyranosyl)-4-O-(3-O-sulfo-β-D-galactopyranosyl)-β-D-glucopyranoside sodium salt (compound 245)

The synthesis of compound 245 is illustrated in FIG. 15.

Step A—Preparation of Methyl 2-O-Acetyl-3-O-(4-methoxybenzyl)-L-fucopyranoside (compound 234)

A mixture of compound 233 (2.1 g, 9.5 mmol), di-n-butyltin oxide (2.6 g, 10.446 mmol) in anhydrous benzene (100 mL) was boiled under reflux with azetropic removal of water for 6 hours and then concentrated to 20 mL. Tetrabutylammonium fluoride monohydrate (3.638 g, 13.914 mmol), 4A molecular sieves (8.664 g) and p-methoxybenzyl chloride (4 mL, 29.5 mmol) were then added and the mixture was kept at room temperature overnight. Column chromatography on silica gel (hexane-ethyl acetate, 3:2) gave compound 234 (2.7 g, 83%).

Step B—Preparation of Methyl 3-O-(4-methoxybenzyl)-L-fucopyranoside (compound 235)

Compound 234 (900 mg, 2.64 mmol) was treated with 0.06N methanolic sodium methoxide (12 mL) for 2 hours. It was then neutralized by Amberlite IR 120 (H$^+$), filtered and evaporated to give compound 235 (785 mg, 100%).

Step C—Preparation of Methyl 2,4-di-O-benzyl-3-O-(4-methoxybenzyl)-L-fucopyranoside (compound 236)

Sodium hydride (480 mg, 50% in mineral oil, 10 mmol) was added in small portions to compound 235 (774 mg, 2.6 mmol) in DMF (6 mL) which was cooled in dry ice. After 0.5 hours, benzyl bromide (1.05 mL, 8.8 mmol) was added and the reaction mixture was allowed to reach room temperature and kept there for 1 hour. Methanol was added to destroy the remaining sodium hydride and it was then evaporated. The residue was S taken up in dichloromethane, filtered through Celite and the filtrate was washed with water. Evaporation then gave crude compound 236.

Step D—Preparation of Methyl 2,4di-O-benzyl-L-fucopyranoside (compound 237)

A mixture of 236 (2.6 mmol) and CAN (2.85 g, 5.2 mmol) in acetonitrile-water (9:1, 12 mL) was kept at room temperature for 1.5 hours and dichloromethane was added. The organic layer was separated and washed with water. After evaporation of the solvent, the residue was applied to a column of silica gel (hexane-ethyl acetate, 3:1) to yield compound 237 (670 mg, 72%, 2 steps).

Step E—Preparation of Methyl 2,4-di-O-benzyl-3-O-(methylthio)thiocarbonyl-L-fucopyranoside (compound 238)

Sodium hydride (428 mg, 60% in mineral oil, 10.7 mmol) and imidazole (10 mg) were added to compound 237 (640 mg, 1.787 mmol) in THF (16 mL). The reaction mixture was heated at 50° C. for 0.5 hours and carbon disulfide (12 mL) was added. In another 1 hour, methyl iodide (12 mL) was added. Heating was continued for 1 more hour and the mixture was then cooled to room temperature and methanol was added. Concentration followed by column chromatography (hexane-ethyl acetate, 4:1) gave compound 238 (790 mg, 98%).

Step F—Preparation of Methyl 2,4di-O-benzyl-3-O-methyl-L-fucopyranoside (compound 239)

Compound 238 (780 mg, 1.738 mmol) in anhydrous toluene (20 mL) was heated at 80° C. AIBN (330 mg, 2.02 mmol) was added followed by tributyltin hydride (7.2 mL, 26.7 mmol). Heating was continued for 2 hours and the mixture was then concentrated and chromatographed (hexane-ethyl acetate, 3:1) to give compound 239 (450 mg, 70%).

Step G—Preparation of 2,4-Di-O-benzyl-3-O-methyl-L-fucopyranose (compound 240)

Compound 239 (520 mg, 1.395 mmol) in glacial acetic acid (11 mL) and 6N HCl (2.3 mL) was heated at 65° C. for 1.5 hours and evaporated, co-evaporated with toluene. The crude product 240 was used in the next reaction without purification.

Step H—Preparation of p-Chlorophenyl 2,4-di-O-benzyl-3-O-methyl-β-L-thiofucopyranoside (compound 241)

A mixture of compound 240 (490 mg, 1.367 mmol), anhydrous NaOAc (160 mg) and acetic anhydride (3.8 mL) in 1,2-dichloroethane (5 mL) was heated at 60° C. for 3.5 hours and cooled to room temperature. Water was added and the organic layer was separated and washed with water and aqueous sodium bicarbonate. After concentration, the dried residue was dissolved in dichloromethane (10 mL) and the mixture was cooled at 0° C. p-Chlorothiophenol (237 mg, 1.639 mmol) was added followed by BF$_3$-ether (0.5 mL). The reaction mixture was allowed to reach room temperature and kept there for 1.5 hours. It was then poured into ice-NaHCO$_3$ and extracted with dichloromethane. Column chromatography (hexane-ethyl acetate, 6:1) of the residue on evaporation gave compound 241 (440 mg, 66%).

Step I—Preparation of 8-Methoxycarbonyloctyl 2-acetamido-6-O-benzyl-3-O-(2,4-di-O-benzyl-3-O-methyl-α-L-fucopyranosyl)-4-O-[2,3-di-O-benzoyl-4,6-O-benzylidene-β-D-galactopyranosyl]-2-deoxy-β-D-glucopyranoside (compound 242)

DMF (0.5 mL) and tetraethylammonium bromide (160 mg, 0.76 mmol) were added to a suspension of copper bromide (870 mg, 3.90 mmol) and 4A molecular sieves (1.5 g) in dichloromethane (1 mL). After stirring at room temperature for 0.5 hours, a solution of compound 208 (480 mg, 0.51 mmol) in dichloromethane (2 mL) was added followed by compound 241 (550 mg, 1.13 mmol) in dichloromethane (2 mL). The mixture was then kept in the dark for 1 day and pyridine (1 mL) was added. The system was filtered through Celite, concentrated and column chromatographed (hexane-acetone, 5:2) to give compound 242 (430 mg, 66%).

Step J—Preparation of 8-Methoxycarbonyloctyl 2-acetamido-6-O-benzyl-3-O-(2,4-di-O-benzyl-3-O-methyl-α-L-fucopyranosyl)-4-O-[4,6-O-benzylidene-β-D-galactopyranosyl]-2-deoxy-β-D-glucopyranoside (compound 243)

Compound 242 (420 mg, 0.328 mmol) was treated with 0.06N methanolic sodium methoxide (8 mL) for 16 hours. The reaction system was then neutralized by Amberlite IR 120 (H$^+$), filtered and evaporated. Column chromatography of the residue (hexane-acetone, 1:1) provided compound 243 (315 mg, 90%).

Step K—Preparation of 8-Methoxycarbonyloctyl 2-acetamido-6-O-benzyl-3-O-(2,4di-O-benzyl-3-O-methyl-α-L-fucopyranosyl)-4-O-[4,6-O-benzylidene-3-O-sulfo-β-D-galactopyranosyl]-2-deoxy-β-D-glucopyranoside sodium salt (compound 244)

Sulfur trioxide-pyridine complex (70 mg, 0.44 mmol) was added to compound 243 (300 mg, 0.279 mmol) in pyridine (1.7 mL) at 0° C. The reaction mixture was allowed to reach room temperature. Stirring was continued for 1 more hour and methanol was added. After evaporation of the solvent, the residue was applied to a column of silica gel (methanol-dichloromethane, 15:85, 0.2% pyridine). The product obtained was then passed through a column of Amberlite IR-120 Na$^+$ (MeOH) to give compound 244 (296 mg, 90%).

Step L—Preparation of 8-Methoxycarbonyloctyl 2-acetamido-2-deoxy-3-O-(3-O-methyl-α-L-fucopyranosyl)-4-O-(3-O-sulfo-β-D-galactopyranosyl)-β-D-glucopyranoside sodium salt (compound 245)

Compound 244 (212 mg, 0.18 mmol) and palladium on carbon (5%, 220 mg) in MeOH (6 mL) were hydrogenated for 2 hours and pyridine was then added. After filtration of the catalyst and evaporation of the solvent, the crude product was purified by chromatography on silica gel [(a) ethyl acetate-methanol-aqueous ammonia, 70:30:3, (b) isopropanol-water-aqueous ammonia, 80:6:2, (c) dichloromethane-methanol-water, 70:30:3, 0.2% pyridine) and then a column of Bio-Rex® 70 (Na$^+$ form) to provide for compound 245 (99 mg, 68%).

Example 32

Preparation of 2-benzamido-2-deoxy-3-O-(4-deoxy-α-L-fucopyranosyl)-4-O-(3-O-sulfo-β-D-galactopyranosyl)-β-D-glucopyranosyl benzamide sodium salt (compound 256)

The synthesis of compound 256 is illustrated in FIG. 16.

Step A—Preparation of Compound 247

DMF (0.85 mL) and tetraethylammonium bromide (240 mg, 1.14 mmol) were added to a suspension of copper bromide (1305 mg, 5.85 mmol) and 4A molecular sieves (1.7 g) in dichloromethane (1 mL). After stirring at room temperature for 0.5 hours, a solution of compound 246 (400 mg, 0.8 mmol) in dichloromethane (1.6 mL) was added followed by compound 207 (1100 mg, 2.418 mmol) in dichloromethane (1.6 mL). The mixture was then kept in the dark for 6 hours and pyridine (1 mL) was added. The solution was filtered through Celite, concentrated and column chromatographed (hexane-acetone, 3:1) to give compound 247 (629 mg, 97%).

Step B—Preparation of Compound 248

Diethyl ether saturated with HCl was added to a mixture of 247 (600 mg, 0.741 mmol), sodium cyanoborohydride (900 mg, 14.322 mmol), a few crystals of methyl orange and 3A molecular sieves (0.5 g) in dry THF (10 mL) at 0° C. until the color of the indicator turned red. Then stirring was continued for 1.5 hours and the reaction mixture was neutralized with triethylamine and filtered. The filtrate was washed with water, aqueous sodium bicarbonate and concentrated. The residue was dissolved in dichloromethane-methanol (1:1, 6 mL) and deionized by Amberlite MB-1 (2 g). Chromatography on silica gel (hexane-acetone, 5:2) yielded compound 248 (460 mg, 77%).

Step C—Preparation of Compound 250

A mixture of compound 248 (400 mg, 0.492 mmol), compound 249 (432 mg, 0.981 mmol) and 4A molecular sieves (1.4 g) was stirred at –20° C. N-Iodosuccinimide (317 mg, 1.412 mmol) was added followed by TfOH (42 µL). Stirring was continued for 1 hour at –20° C. and pyridine (1 mL) was added. After concentration of the reaction mixture, the residue was applied to a column of silica gel (hexane-ethyl acetate, 3:2) to provide for compound 250 (360 mg, 64%).

Step D—Preparation of Compound 251

Compound 250 (400 mg, 0.35 mmol) was treated with 0.06N methanolic sodium methoxide (3 mL) at 0° C. for 2 hours. It was neutralized by Amberlite IR 120 (H$^+$), filtered and evaporated. The crude product, compound 251, was used in the next reaction without further purification.

Step E—Preparation of Compound 252 p-Toluene sulfonic acid (20 mg) was added to a solution of compound 251 (0.35 mmol) in acetonitrile (3 mL) followed by α,α-dimethoxytoluene (0.1 mL, 0.67 mmol). After 0.5 hours at room temperature, the reaction mixture was neutralized with triethylamine and concentrated. Chromatography of the residue (hexane-acetone, 1:1) gave compound 252 (250 mg, 67%, 2 steps).

Step E—Preparation of Compound 253

A solution of compound 252 (220 mg, 0.205 mmol) in methanol (6 mL) and hydrazine hydrate (1 mL) was refluxed overnight and evaporated, co-evaporated with toluene and then dried on vacuum. The crude product, compound 253, was used in the next reaction without any further purification.

Step F—Preparation of Compound 254

Compound 253 was dissolved in a mixture of methanol (6 mL) and saturated aqueous sodium bicarbonate (4 mL). Benzoyl chloride (0.25 mL) was added to this mixture at 0° C. After 0.5 hours, dichloromethane was added and the organic layer was separated. The residue, after evaporation of the solvent, was chromatographed (methanol-dichloromethane, 5:95) to yield compound 254 (150 mg, 70%—2-steps).

Step G—Preparation of Compound 255

Sulfur trioxide-pyridine complex (40 mg, 0.251 mmol) was added to compound 254 (150 mg, 0.143 mmol) in pyridine (1.5 mL) at 0° C. The reaction mixture was allowed to reach room temperature and more sulfur trioxide-pyridine complex (20 mg) was added. Stirring was continued for 1 more hour and methanol was added. After evaporation of the solvent, the residue was applied to a column of silica gel (methanol-dichloromethane, 10:90, 15:85, 0.2% pyridine). The product obtained was then passed through a column of Amberlite IR-120 Na$^+$ (MeOH) to give compound 255 (120 mg, 73%).

Step H—Preparation of Compound 256

Compound 255 (100 mg, 0.087 mmol) and Pd-C (5%, 200 mg) in MeOH (4 mL) were hydrogenated for 3.5 hours and pyridine (1.5 mL) was then added. After filtration of the catalyst and evaporation of the solvent, the crude product was purified by chromatography on silica gel (dichloromethane-methanol-water, 75:25:2.5, 0.2% pyridine) and then a column of Bio-Rex® 70 (Na⁺ form) to provide for compound 256 (40 mg, 60%).

Example 33

Preparation of phenyl alanine amido-2-fuc(C)-amido-4-O-(3-O-sulfo-β-D-galactopyranosyl)-β-D-glucopyranoside (compound 315)

Figure 17:
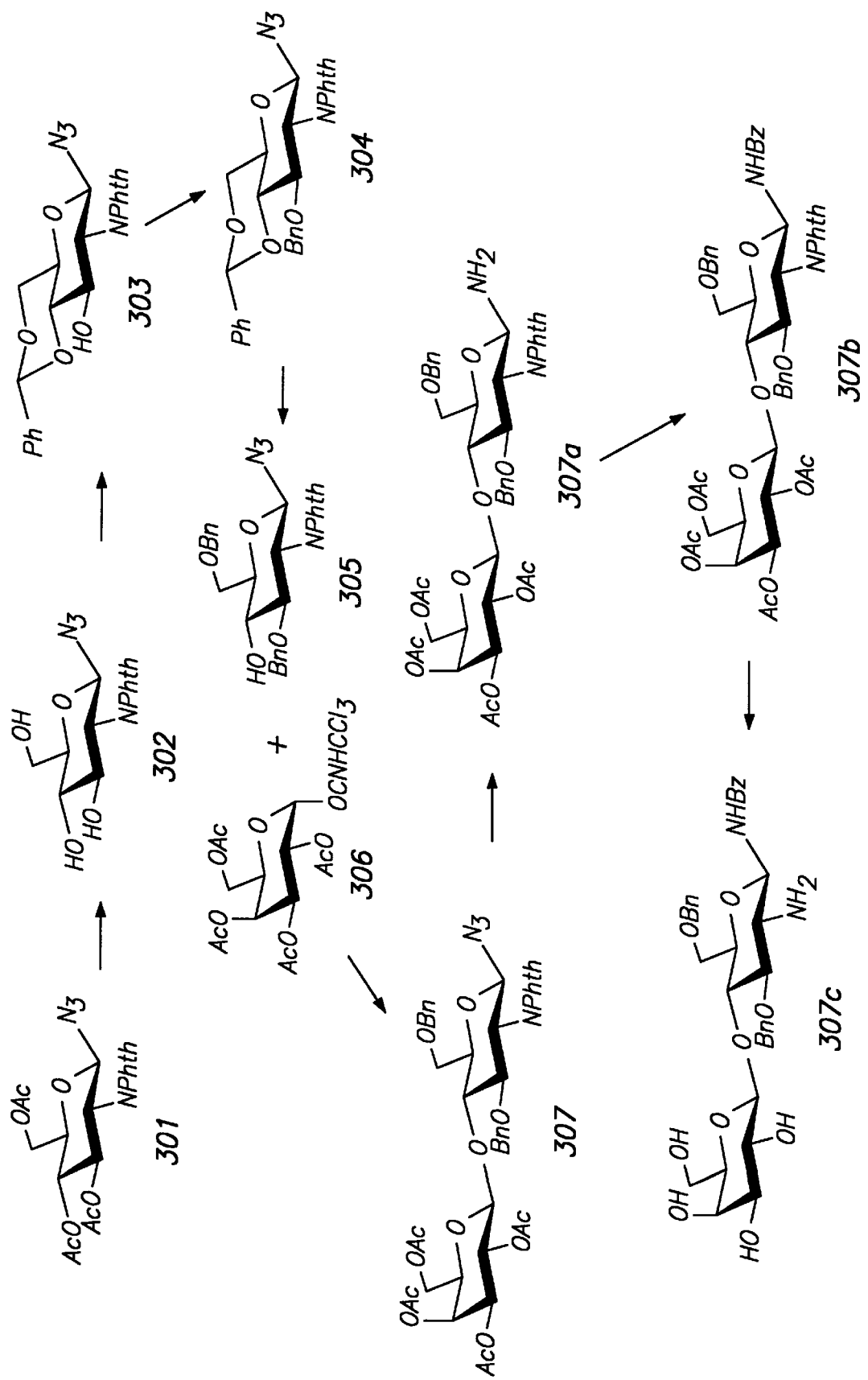
FIG. 17, FIG. 18, FIGS. 19A and 19B (collectively FIG. 19), FIGS. 20A and 20B (collectively FIG. 20), FIG. 21, FIG. 22, FIG. 23, FIG. 24, FIG. 25, FIGS. 26A and 26B (collectively FIG. 26)
Figure 18:
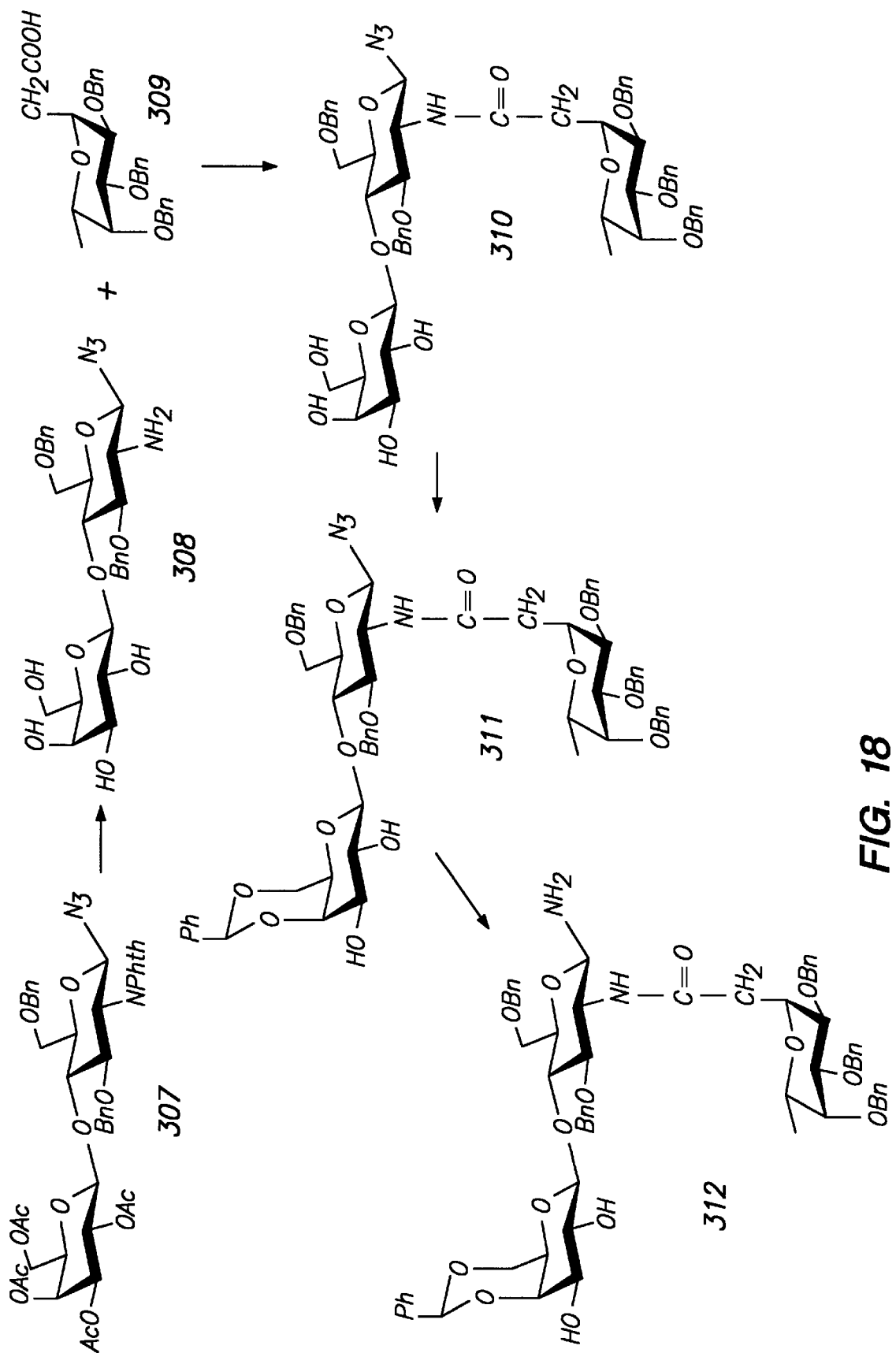
Figure 19A:
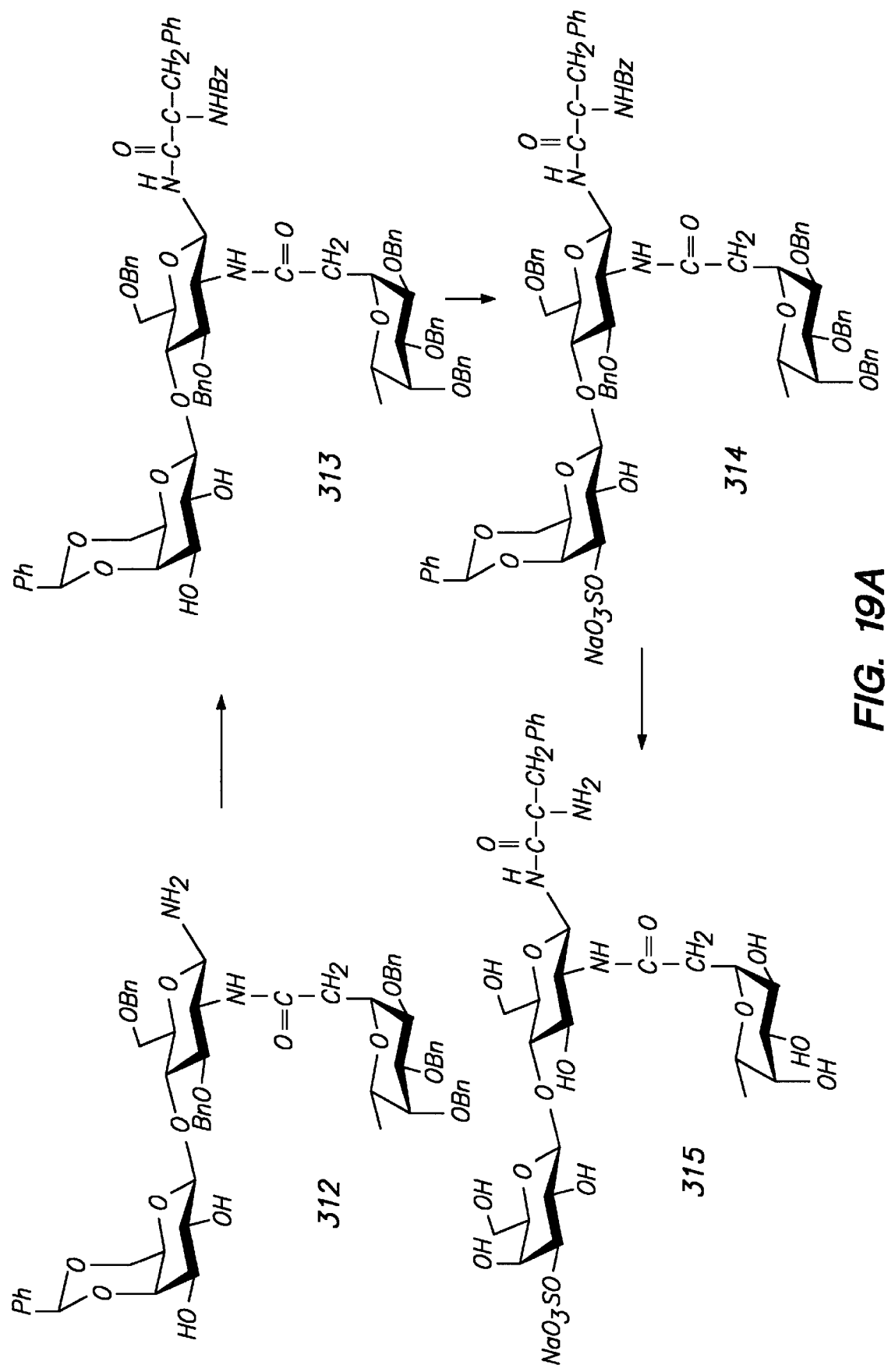
Figures 19B, 20A:
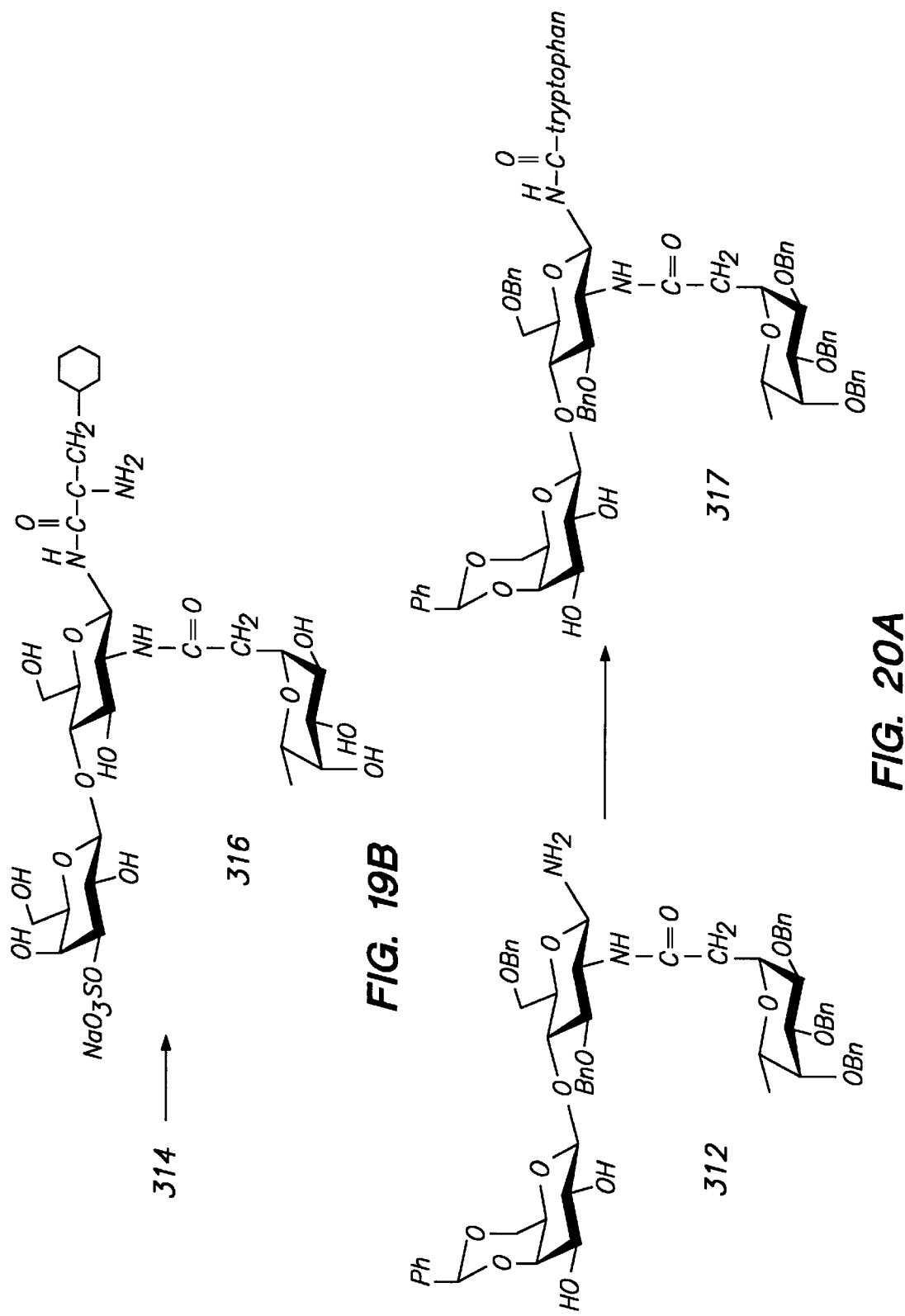

The synthesis of compound 315 is illustrated in FIGS. 17–19.

Step A—Preparation of 4,6-O-Benzylidene-2-deoxy-2-phthalimido-β-D-glucopyranosyl azide (compound 303)

To a solution of compound 301 (19.0 g, 41.3 mmol), was added 20 mL of a 0.5N solution of sodium methoxide in methanol. The resulting mixture was stirred for 2 hours at room temperature and then neutralized with Amberlite IR-120 (H⁺) resin, filtered and evaporated to obtain compound 302 which was directly converted into its 4,6-O-benzylidene derivative by dissolving the crude mass in acetonitrile (260 mL) and α,α-dimethoxy-toluene (15.0 mL), followed by addition of p-toluenesulfonic acid (1.3 g) and stirring the mixture overnight at room temperature. Neutralize the reaction mixture with triethylamine and evaporate. The crude mass was purified by chromatography on silica gel column, using hexane-ethyl acetate (2:1) as eluent to provide for compound 303 (14.5 g, 85.5%).

Step B—Preparation of 3-O-Benzyl-4,6-O-benzylidene-2-deoxy-2-phthalimido-β-D-glucopyranosyl azide (compound 304)

Compound 303 (13.0 g, 30.9 mmol) was dissolved in toluene (110 mL) and benzyl bromide (7.3 mL, 2.0 eq.) and silver oxide (31.4 g, 5.0 eq.) were added and the reaction mixture stirred for 24 hours at room temperature. The reaction solution was filtered and the solvent evaporated. The residue was purified by chromatography on silica gel using hexane-ethyl acetate (4:1) as eluent to provide for compound 304 (11.9 g, 75%).

Step C—Preparation of 2,6-Di-O-benzyl-2-deoxy-2-phthalimido-β-D-glucopyranosyl azide (compound 305)

Compound 304 (9.9 g, 19.4 mmol) was dissolved in dry THF (150 mL) at room temperature. The reaction mixture was cooled to 0° C. and molecular sieves were added (10 g, 3A). Sodium cyanoborohydride (12.2 g, 194.0 mmol) was then added along with a small amount of methyl orange (a few crystals). The reaction mixture was stirred for 15 minutes at 0° C. and then an etheral solution of hydrochloric acid was added until the mixture was acidic (pH~3). The reaction mixture was stirred for 2 hours at 0° C. at which time all the starting material had been completely consumed and converted to the product. The reaction mixture was then diluted and filtered and the precipitate was washed thoroughly with dichloromethane (1.0 L). The combined filtrates were then washed sequentially with a saturated solution of sodium bicarbonate (3×1.0 L) and water (3×1.0 L), dried over sodium sulfate, filtered and evaporated. The product was purified by chromatography on silica gel using hexane-ethyl acetate (2:1) as eluent to give compound 305 (5.2 g, 52%).

Step D—Preparation of 3,6-Di-O-benzyl-2-phthalimido-2-deoxy-4-O-(2,3,4,6-tetra-O-acetyl-β-D-galactopyranosyl)-β-D-glucopyranosyl azide (compound 307)

Monosaccharide acceptor compound 305 (2.0 g, 3.9 mmol) and imidate donor compound 306 (4.8 g, 9.7 mmol), disclosed in Srivastava et al.²³, were dissolved in a mixture of ether and dichloromethane (20 mL, 2:1) and stirred at −10° C. for 15 minutes. Boron trifluoride ethereate (1.34 mL, 10.9 mmol) was added and the reaction mixture was stirred under nitrogen at −10° C. for 1.5 hours. After completion, the reaction medium was diluted with dichloromethane (250 mL), filtered and washed successively with a saturated solution of sodium bicarbonate (2×250 mL) and water (2×250 mL). Evaporation of the solvent gave a syrup which was purified by chromatography on silica gel column using hexane-ethyl acetate (2:1) as eluent to provide for compound 307 (1.9 g, 58.4%).

Step E—Preparation of 1-Benzamido 3,6-Di-O-benzyl-2-phthalimido-4-O-(2,3,4,6-tetra-O-acetyl-β-D-galactopyranosyl)-2-deoxy-β-D-glucopyranoside (compound 307b)

3,6-Di-O-benzyl-2-phthalimido-4-O-(2,3,4,6-tetra-O-acetyl)-β-D-galactopyranosyl)-2-deoxy-β-D-glucopyranosyl azide, compound 307 (10.4 g, 12.3 mmol), was dissolved in a mixture of pyridine:water:triethylamine (4:1:0.1). The mixture was cooled to 0° C. over 10 minutes and then hydrogen sulfide was passed through the reaction mixture over 1 hour at 0° C. The color of the solution turned to brownish-yellow and tlc indicated that the reaction was complete. After a 30 minute nitrogen purge was employed to remove hydrogen sulfide and the solvent was evaporated and then co-evaporated with toluene (200 mL) twice to dryness. The residue was passed through a short silica gel column (70–230 mesh), using hexane:ethyl acetate (1:1) as the eluent to provide for compound 307a.

Compound 307a was then dissolved in a mixture of dry dichloromethane (200 mL) and pyridine (5 mL) and then benzoyl chloride (5 mL, 43 mmol) was added. The mixture was stirred for 10 minutes at room temperature. Tlc indicated that the reaction was complete. The reaction mixture was washed with water and dried over anhydrous sodium sulfate, and then the solvent evaporated. The crude product was then chromatographed on silica gel (230–400 mesh) using hexane:ethyl acetate (2:1) as the eluent to provide 11 g of compound 307b (yield 96%).

Step F—Preparation of 1-Benzamido 2-amino-3,6-Di-O-benzyl-4O-(β-D-galactopyranosyl)-2-deoxy-β-D-glucopyranoside (compound 307c)

3,6-Di-O-benzyl-2-phthalimido-4-O-(2,3,4,6-tetra-O-acetyl-β-D-galactopyranosyl)-2-deoxy-β-D-glucopyranosyl azide, compound 307a, (7.8 g, 8.45 mmol) was dissolved in methanol (200 mL) and then hydrazine hydrate (5 mL) was added. The mixture was heated to reflux for 2 hours and, then, tlc indicated that the reaction was complete. The solvent was evaporated and then co-evaporated with toluene (200 mL) twice to dryness. The residue was passed through a short silica gel column (70–230 mesh), using dichloromethane: methanol (5:1) as the eluent to provide for 2.8 g of compound 307c as a white solid (yield 53%).

Step G—Preparation of 2-amino-2-deoxy-3,6-Di-O-benzyl-4-O-(β-D-galactopyranosyl)-β-D-glucopyranosyl azide (compound 308)

Compound 307 (11.5 g, 13.6 mmol) was dissolved in methanol (20 mL) and a solution of hydrazine hydrate (8 mL, 164.6 mmol) was added. The reaction mixture was refluxed for 15 hours and then the solvent was evaporated to dryness. The residue was purified by chromatography on silica gel column using dichloromethane-methanol (80:20) as eluent to yield compound 308 (6.1 g, 82%).

Step H—Preparation of 3,6-di-O-benzyl-2-(2,3,4-tri-O-benzyl-Fuc(C)-amido)-4O-[βL-D-galactopyranosyl]-2-deoxy-β-D-glucopyranosyl azide (compound 310)

To a solution of compound 308 (3.9 g, 7.0 mmol) in dichloromethane (60.0 mL) at room temperature was added 2,3,4-tri-O-benzylfucose carboxylic acid, compound 309

(5.9 g, 12.3 mmol) and 1-(3-dimethylaminopropyl)-3-ethyl-carbodiimide hydrochloride (4.7 g, 24.6 mmol). The reaction mixture was stirred for 2 hours at room temperature and then the solvent was evaporated. The residue was purified on silica gel column chromatography using dichloromethane-methanol (95:5) as eluent to obtain compound 310 (5.7 g, 80%).

Step I—Preparation of 3,6-Di-O-benzyl-2-(2,3,4tri-O-benzyl-fuc-(C)-amido)-4-O-[4,6-O-benzylidene-β-D-galactopyranosyl]-2-deoxy-β-D-glucopyranosyl azide (compound 311)

To a solution of compound 310 (7.8 g, 7.8 mmol) dissolved in anhydrous acetonitrile (200 mL) was added benzaldehyde dimethylacetal (15.0 mL) and a catalytic amount of p-toluene sulfonic acid (350 mg). The reaction mixture was stirred for 15 hours at room temperature and neutralized with triethylamine. After evaporation, the residue was chromatographed on silica gel column eluting with dichloromethane-methanol (97.5:2.5) to provide for compound 311 (5.5 g, 65%).

Step J—Preparation of 1-phenylalanineamido 3,6-di-O-benzyl-2-(2,3,4tri-O-benzyl-fuc(C)-amido)-4-O-[4,6-O-benzylidene-β-D-galactopyranosyl]-2-deoxy-β-D-glucopyranoside (compound 313)

Compound 311 (500 mg, 0.46 mmol) was dissolved in a mixture of isopropanol-water (9:1, 40 mL) and hydrogenated with Raney nickel (100 mg) under atmospheric pressure for 1.5 hours. The catalyst was filtered and the solvent evaporated to obtain compound 312 which was directly converted into its phenylalanine amido derivative by dissolving in dichloromethane (7.0 mL) and reacting with N-CBz-L-phenylalanine (500 mg, 1.67 mmol) and EDC-HCl (500 mg, 2.6 mmol) for 0.5 hours. The solvent was evaporated and the residue chromatographed on silica gel using chloroform-ethyl acetate (2:3) as eluent to obtain compound 313 (426 mg, 69%).

Step K—Preparation of 1-phenylalanineamido 3,6-di-O-benzyl-2-(2,3,4-tri-O-benzyl-fuc(C)-amido)-4-O-[4,6-O-benzylidene-3-O-sulfo-β-D-galactopyranosyl]-2-deoxy-β-D-glucopyranoside sodium salt (compound 314)

Compound 313 (362 mg, 0.27 mmol) was added to pyridine (6.0 mL) at 0° C. $SO_3$-pyridine complex (64 mg, 0.4 mmol) was added and stirring was continued for 0.5 hours at 0° C. and 2 hours at room temperature. An additional amount of $SO_3$-pyridine complex (0.5 eq) was added and the mixture stirred for 3.5 hours and quenched with methanol (1.5 mL) and evaporated to dryness. The residue was chromatographed on a silica gel column eluting with dichloromethane-methanol-pyridine (95:5:0.1) to provide compound 314 (321 mg, 82.4%) after conversion to its sodium salt by passage through Dowex-50-X-8 ($Na^+$) resin.

Step L—Preparation of 1-phenylalanine amido-2-(fuc(C)-amido)-4-O-[3-O-sulfo-β-D-galactopyranosyl]-β-D-glucopyranoside sodium salt (compound 315)

A mixture of compound 314 (321 mg, 0.22 mmol) and 5% palladium on carbon (330 mg) in methanol (30.0 mL) was stirred under one atmosphere of hydrogen for 5 hours. The mixture was then filtered through a pad of a Celite to remove the catalyst and the catalyst-Celite was washed with methanol (100 mL). The filtrate and washings were combined and evaporated after adding a trace of pyridine (5.0 mL). The resulting product was chromatographed on Iatrobeads eluting with isopropanol-water-ammonia (7:1.5:0.3) to provide compound 315 (70 mg, 41%) after conversion to the sodium salt by passage through Dowex-50-X-8 ($Na^+$) resin.

Example 34

Preparation of 1-cyclohexylalanine amido-2-N-(fuc (C)-amido)-4-O-[3-O-sulfo-β-D-galactopyranosyl]-β-D-glucopyranoside sodium salt (compound 316)

The synthesis of compound 316 is illustrated in FIG. 19.

Compound 314 (320 mg, 0.22 mmol) was hydrogenated in methanol (30 mL) using 20% $Pa(OH)_2$/C (1.5 g) for 4 days as described earlier to provide for compound 316 (17.0 mg, 10%) after purification by chromatography on silica gel using isopropanol-water-ammonia (7:1.5:0.5) as eluent and converting to sodium salt by passage through Dowex-50-X-8 ($Na^+$) resin.

Example 35

Preparation of 1-tryptophanamido-2-(fuc(C)-amido) -4-O-(3-O-sulfo-β-D-galactopyranosyl)-β-D-glucopyranoside (compound 319)

Figure 20B:
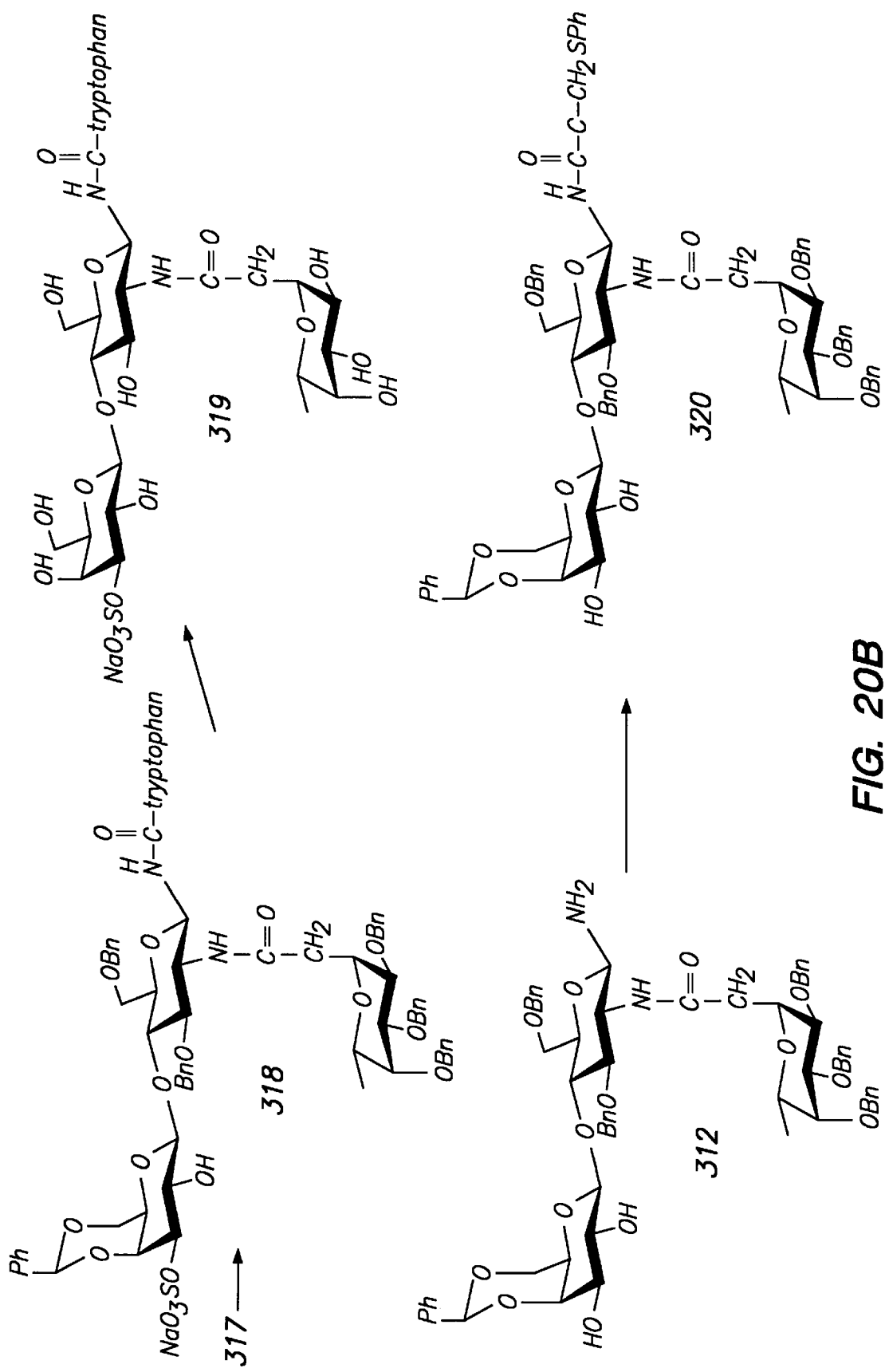

The synthesis of compound 319 is illustrated in FIG. 20.

Step A—Preparation of 1-tryptophanamido-2-(2,3,4-tri-O-benzyl-fuc(C)-amido)-4-O-[4,6-O-benzylidene-β-D-galactopyranosyl]-2-deoxy-3,6-di-O-benzyl-β-D-glucopyranoside (compound 317).

Compound 311 (500 mg, 0.46 mmol) was dissolved in a mixture of isopropanol-water (9:1, 50 mL) and hydrogenated with Raney nickel (100 mg) under atmospheric pressure for 45 minutes. The catalyst was filtered and the solvent evaporated to dryness. The residue without purification was dissolved in dichloromethane (7.0 mL) and reacted with EDC-HCl (500 mg, 2.61 mmol) and Z-2-tryptophan for 1 hour. The reaction mixture was evaporated and the residue chromatographed on a silica gel column using dichloromethane-methanol (98:2) as eluent to provide for compound 317 (378 mg, 60%) after sodium exchange.

Step B—Preparation of 1-tryptophanamido-2-(2,3,4-tri-O-benzyl-fuc(C)-amido)-4-O-[4,6-O-benzylidene-3-O-sulfo-β-D-galactopyranosyl]-2-deoxy-3,6-di-O-benzyl-β-D-glucopyranoside sodium salt (compound 318)

Compound 317 (378 mg, 0.27 mmol) was dissolved in pyridine (6.0 mL) and to this mixture was added $SO_3$-pyridine complex (66 mg, 0.42 mmol) at 0° C. and reaction mixture was allowed to warm to room temperature. After 1 hour, another portion of $SO_3$-pyridine complex (0.5 eq) was added and addition was continued at the same rate at every 1.5, 2.5 and 3 hours until all the starting material was completely converted into product. The reaction was quenched by the addition of methanol. Evaporation and co-evaporation provided a syrup which was purified by chromatography on silica gel column using dichloromethane-methanol-pyridine (95:5:0.1) as eluent to provide for pure compound 318 (260 mg, 64%) after sodium exchange.

Step C—Preparation of 1-tryptophanamido-2-(fuc(C)-amido)-4-O-[3-O-sulfo-β-D-galactopyranosyl]-β-D-glucopyranoside sodium salt (compound 319)

Compound 318 (260 mg, 0.17 mmol) was hydrogenated for 6 hours in methanol (0.25 mL) and 5% palladium on carbon (750 mg) using hydrochloric acid (1.2 eq) to provide for compound 319 (40 mg, 28%) after purification with chromatography on silica gel using isopropanol-water-ammonia (7:1.5:0.5) as eluent followed by its conversion into sodium salt.

Example 36

Preparation of 1-acetamido-2-(fuc(C)-amido-4-O-[3-O-sulfo-β-D-galactopyranosyl)-2-deoxy-β-D-glucopyranoside (compound 322)

The synthesis of compound 322 is illustrated in FIGS. 18–21.

Step A—Preparation of 1-thiophenyl acetamido-2-(2,3,4tri-O-benzyl-fuc(C)-amido)-4-O-[4,6-O-benzylidene-β-D- galactopyranosyl]-2-deoxy-3,6-di-O-benzyl-β-D-glucopyranoside (compound 320)

Compound 311 (400 mg, 0.37 mmol) was dissolved in a mixture of pyridine-water-triethylamine (13:2:0.4). Hydrogen sulfide gas was bubbled through the solution at 0° C. for 1 hour and then allowed to warm to room temperature for 1.5 hours. Evaporation of the mixture provided crude amine which was dissolved in pyridine (8.0 mL) and then (phenylthio)acetylchloride (117 μL, 0.79 mmol) was added at 0° C. and the resulting mixture stirred for 0.5 hours at room temperature before evaporation and chromatography of the residue on silica gel using dichloromethane-methanol (98:2) as eluent to provide compound 320 (177.6 mg, 40%).

Step B—Preparation of 1-thiophenyl acetamido-2-(2,3,4-tri-O-benzyl-fuc(C)-amido)-4-O-[4,6-O-benzylidene-3-O-sulfo-β-D-galactopyranosyl]-2-deoxy-3,6-di-O-benzyl-β-D-glucopyranoside sodium salt (compound 321)

Compound 320 (177.6 mg, 0.15 mmol) was dissolved in pyridine (4 mL) and cooled to 0° C. SO₃-pyridine complex (40 mg, 0.25 mmol) was added to the reaction mixture and then the reaction mixture was allowed to warm to room temperature. An additional amount of SO₃-pyridine complex (2 eq, 0.5 eq. portions after every 0.5 hours) was added and the mixture stirred for 4 hours at room temperature. After addition of methanol (2 mL), the solvent was evaporated and the residue was chromatographed on a silica gel column using dichloromethane-methanol-pyridine (95:5:0.1) as eluent to obtain compound 321 (172.3 mg, 90% after sodium exchange column).

Step C—Preparation of 1-acetamido-2-(fuc(C)-amido)-4-O-[3-O-sulfo-β-D-galactopyranosyl)-2-deoxy-β-D-glucopyranoside (compound 322)

Compound 321 (172.8 mg, 0.13 mmol) was hydrogenated under atmospheric pressure using methanol (30 mL) and 20% Pd(OH)₂/C (200 mg) as described earlier to provide compound 322 (23.2 mg, 16%) after chromatography on silica gel using isopropanol-water-ammonia (7:1.5:0.5) as eluent followed by Na⁺ ion exchange column.

Example 37

Preparation of 1-Benzamido 2-(fuc(C)-amido)-4-O-[3-O-sulfo-β-D-galactopyranosyl])-2-deoxy-β-D-glucopyranoside (compound 326)

Figure 21:
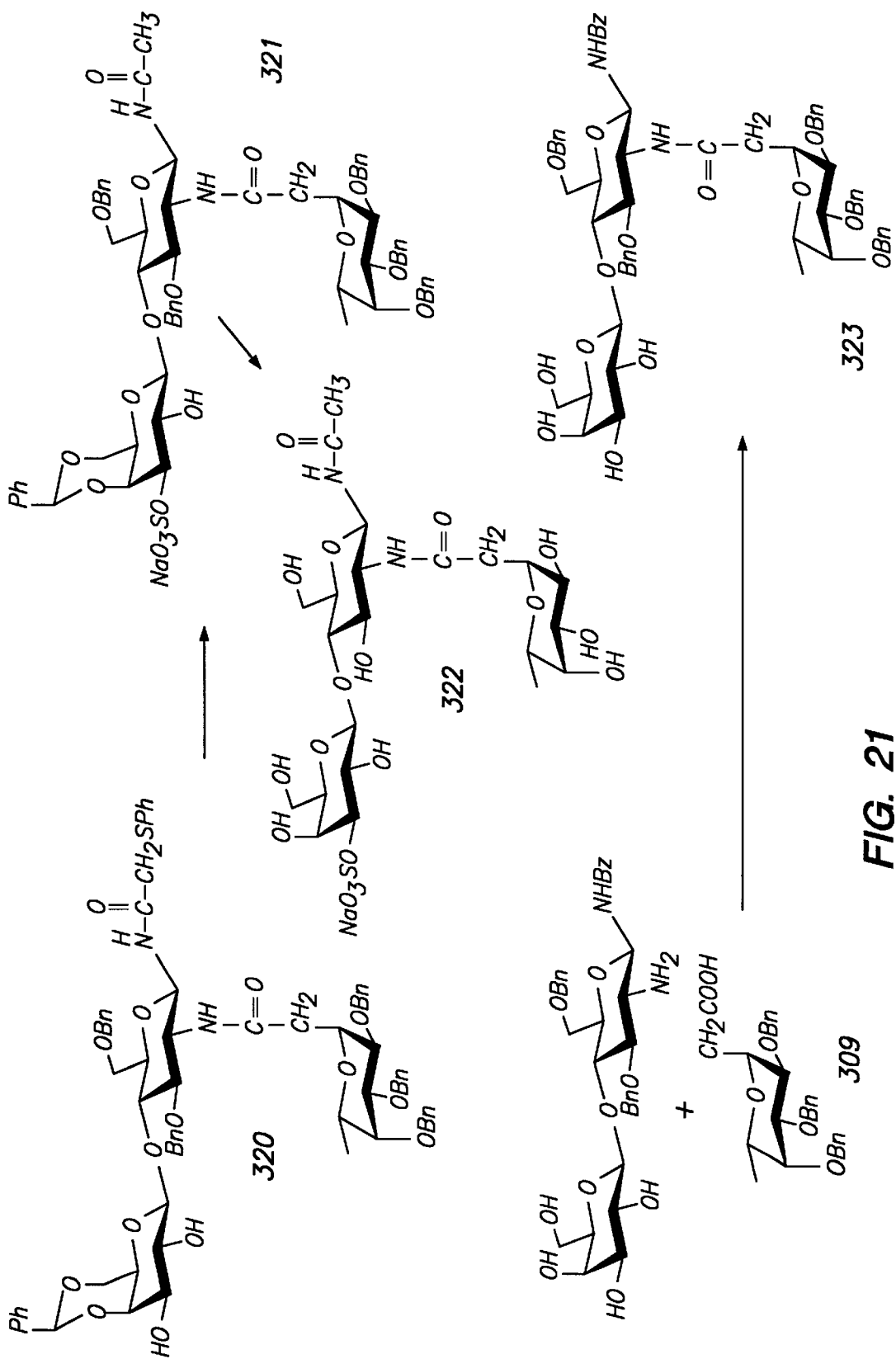
Figure 22:
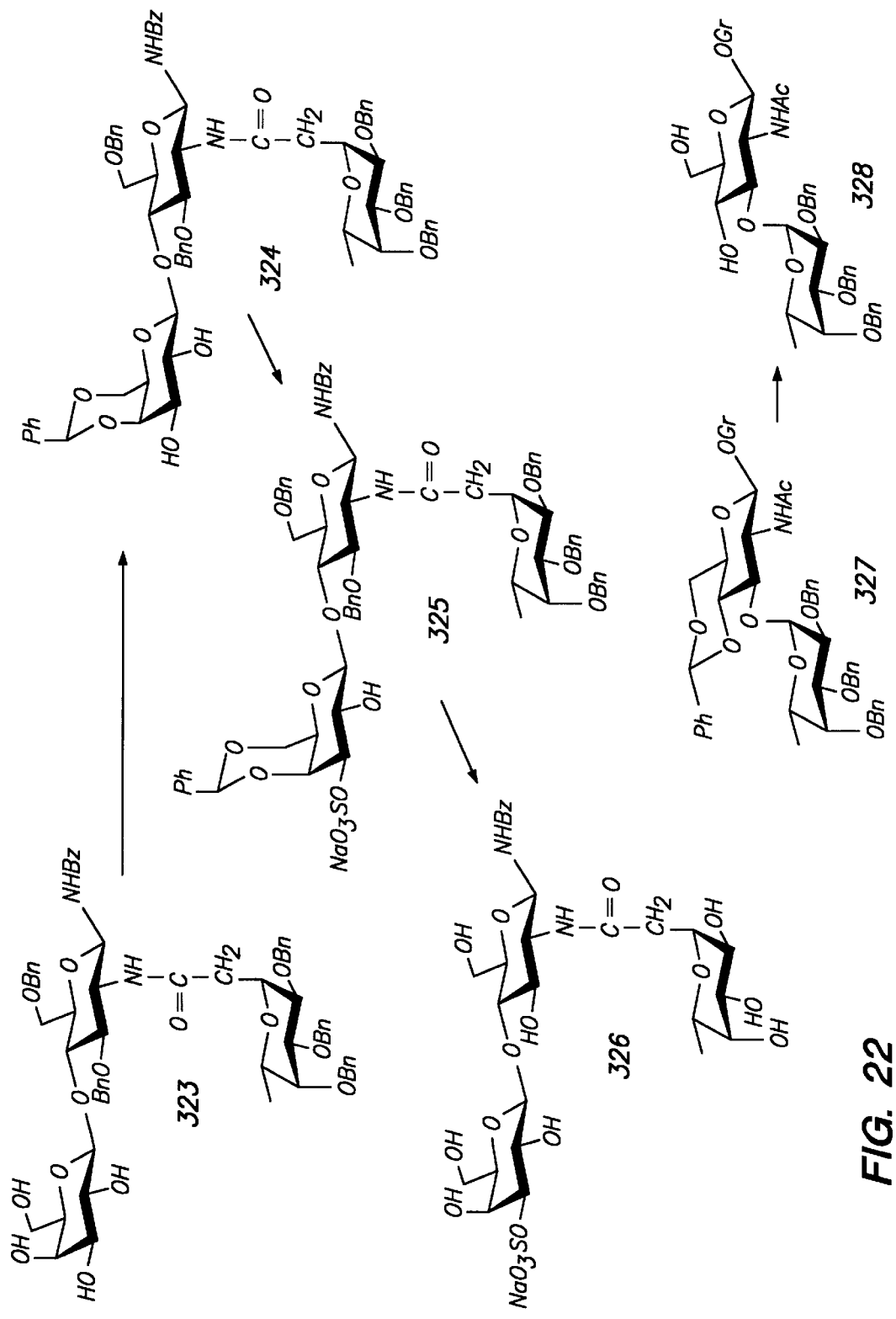

The synthesis of compound 326 is illustrated in FIGS. 21 and 22.

Step A—Preparation of 1-Benzamido 3,6-di-O-benzyl-2-(2,3,4-tri-O-benzyl-fuc(C)-amido)-4-O-[3-D-galactopyranosyl]-2-deoxy-β-D-glucopyranoside (compound 323).

Compound 307c (325 mg, 0.52 mmol) was dissolved in dichloromethane (6.0 mL) and tri-O-benzyl-fucose-(C)-carboxylic acid (495 mg, 1.04 mmol) and EDC-HCl (398 mg, 2.1 mmol) were added thereto. The resulting mixture was stirred for 1 hour at room temperature. The solvent was evaporated and the residue chromatographed on silica gel using dichloromethane-methanol (95:5) as eluent to provide compound 323 (508 mg, 90%).

Step B—Preparation of 1-Benzamido-3,6-di-O-benzyl-2-(2,3,4-tri-O-benzyl-fuc(C)-amido)-4-O-[4,6-O-benzylidene-β-D-galactopyranosyl]-2-deoxy-β-D-glucopyranoside (compound 324)

Compound 323 (508 mg, 0.47 mmol) was dissolved in dry acetonitrile (15.0 mL) and α,α-dimethoxytoluene (1.0 mL) was added thereto followed by p-toluene sulfonic acid (20.0 mg) and the reaction mixture was stirred for 45 minutes at room temperature, neutralized with triethylamine and the solvent evaporated. The residue was purified by chromatography on silica gel using dichloromethane-methanol (97.5:2.5) as eluent to provide compound 24 (298 mg, 54.2%).

Step C—Preparation of 1-Benzamido 3,6-di-O-benzyl-2-(2,3,4-tri-O-benzyl-fuc(C)-amido)-40-[4,6-O-benzylidene-3-O-sulfo-β-D-galactopyranosyl]-2-deoxy-β-D-glucopyranoside (compound 325).

Compound 324 (298 mg, 0.25 mmol) was dissolved in pyridine (5.0 mL) and cooled to 0° C. SO₃-pyridine complex (61 mg, 0.38 mmol) was added to the reaction mixture and the reaction mixture was then allowed to warm to room temperature. After 1 hour, SO₃-pyridine complex (1.0 eq) was again added and the reaction mixture stirred for 2 hours at room temperature. Methanol (2.0 mL) was added and the solvent was evaporated to dryness. The residue was purified by chromatography on silica gel using dichloromethane-methanol-pyridine (95:5:0.1) as eluent to provide for compound 325 (228 mg, 70.4%).

Step D—Preparation of 1-benzamido-2-(fuc(C)-amido)-4-O-[3-O-sulfo-β-D-galactopyranosyl]-2-deoxy-β-D-glucopyranoside sodium salt (compound 326).

Compound 325 (228 mg, 0.18 mmol) was dissolved in methanol (25 mL) and hydrogenated with 5% palladium on carbon (250 mg) as described earlier to provide for compound 326 (105 mg, 80%) after conversion to its sodium salt.

Example 38 reparation of 8-methoxycarbonyloctyl-2-acetamido-3-O-(α-L-fucopyranosyl)-4-O-[3-O-sulfo-β-D-galactopyranosyl]-6-O-sulfo-β-D-glucopyranoside (compound 335)

Figure 23:
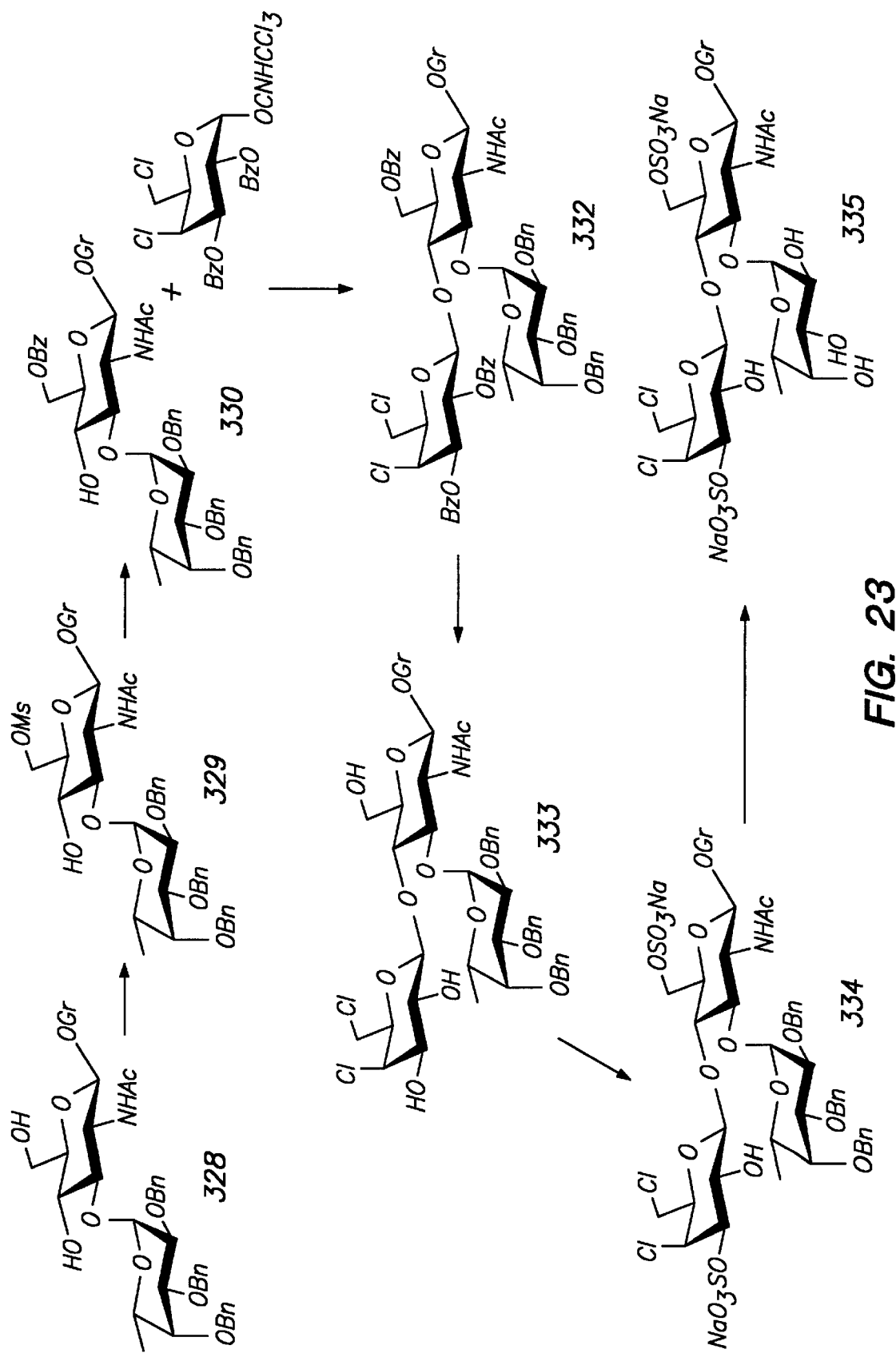

The synthesis of compound 335 is illustrated in FIGS. 22 and 23.

Step A—Preparation of 8-methoxyearbonyloctyl-2-acetamido-3-O-(2,3,4-tri-O-benzyl-α-L-fucopyranosyl)-2-deoxy-β-D-glucopyranoside (compound 328)

Compound 327 (10.0 g), disclosed in Srivastava, et al.[23], was dissolved in a mixture of acetic acid-water (4:1, 100 mL) and heated to 40° C. for 15 hours. Only 50% reaction was complete. The reaction mixture was stirred for an additional 3 hours at 55° C. and the solvent was was evaporated to dryness. The residue was redissolved in dichloromethane (150 mL) and washed with water (2×250 mL), 6% sodium hydrogen carbonate (2×250 mL) and water (2×250 mL), dried over sodium sulfate, filtered and the solvent evaporated. The syrup was purified by chromatography on silica gel using dichloromethane-methanol (9:1) as eluent to provide for compound 328 quantitatively.

Step B—Preparation of 8-methoxycarbonyloctyl-2-acetamido-6-O-mesyl-3-O-(2,3,4-tri-O-benzyl-α-L-fucopyranosyl)-2-deoxy-β-D-glucopyranoside (compound 329)

Compound 328 (10.0 g, 12.377 mmol) was dissolved in pyridine (90 mL) and mesyl chloride (1.14 mL, 14.8 mmol) was dropwise added thereto at 0° C. Stirring was continued for 2 hours at this temperature. Afterwards, the solvent was removed and the residue was chromatographed on a silica gel column using dichloromethane-methanol (97.5:2.5) as eluent to provide for compound 329 (10.05 g, 91.6%).

Step C—Preparation of 8-methoxycarbonyloctyl-2-acetamido-6-O-benzoyl-3-O-(2,3,4-tri-O-benzyl-α-L-fucopyranosyl)-2-deoxy-β-D-glucopyranoside (compound 330)

Compound 329 (1.0 g, 1.129 mmol) was dissolved in DMF (20.0 mL). Sodium benzoate (0.81 mg, 5.6 mmol) was added thereto and the resulting mixture stirred at 100° C. for 24 hours by which time there was a complete consumption of starting material. After evaporation of the solvent, the residue was chromatographed on silica gel column using hexane-ethyl acetate (3:2) as eluent to provide for compound 330 (650 mg, 59%).

S Step D—Preparation of 8-methoxycarbonyloctyl-2-acetamido-6O-benzoyl-3-O-(2,3,4tri-O-benzyl ∝-L-fucopyranosyl)-4O-[2,3-di-O-benzoyl-4,6-dichloro-4,6dideoxy-β-D-galactopyranosyl]-2-deoxy-β-D-glucopyranoside (compound 332)

To a solution of compound 330 (605 mg, 0.663 mmol) in a mixture of dichloromethane-ether (1:2, 5.0 mL) stirred under nitrogen, was added dichloro dibenzoyl imidate (905 mg, 1.6 mmol) and the resulting mixture was cooled to −10° C. to −15° C. $BF_3$-ethereate solution (200 14L, 1.63 mmol) was added dropwise and stirring was continued for 1 hour at −10° C. The reaction mixture was then diluted with dichloromethane and washed with water saturated $NaHCO_3$ solution and water. The resulting solution was dried over anhydrous sodium sulfate and evaporated. The residue was chromatographed on a silica gel column, eluting with hexane-ethyl acetate (2:1) as eluent to provide compound 332, 485 mg (55.6%).

Step E—Preparation of 8-methoxycarbonyloctyl-2-acetamido-3-O-(2,3,4-tri-O-benzyl-∝-L-fucopyranosyl)-4-O-[4,6-dichloro-dideoxy-β-D-galactopyranosyl]-2-deoxy-β-D-glucopyranoside (compound 333)

To a solution of compound 332 (485 mg, 0.372 mmol) in dry methanol (20.0 mL) was added sodium methoxide (5 mL, 0.5M) solution in methanol and the resulting solution was stirred at room temperature for 5 hours. The mixture was then neutralized with resin, filtered and evaporated to dryness to provide for compound 333 (340 mg, 91.8%) after purification by chromatography on silica gel using dichloromethane-methanol (95:5) as eluent.

Step F—Preparation of 8-methoxycarbonyloctyl-2-acetamido-3-O-[2,3,4tri-O-benzyl-∝-L-fucopyranosyl]-4-O-[4,6-dichloro-dideoxy-3-O-sulfo-β-D-galactopyranosyl]-2-deoxy-6-O-sulfo-β-D-glucopyranoside sodium salt (compound 334)

To a solution of compound 333 (340 mg, 0.338 mmol) in pyridine (5.0 mL) at 0° C. was added $SO_3$-pyridine complex (248 mg, 1.56 mmol). The sulfonation reaction was stirred at room temperature for 3 hours and methanol was added before evaporation and co-evaporation with toluene (3×20 TL). The residue was purified by chromatography on silica gel using dichloromethane-methanol-pyridine (93:7:0.1) as eluent to provide for compound 334 (320 mg, 78%) after sodium column.

Step G—Preparation of 8-methoxycarbonyloctyl-2-acetamido-3-O-(∝-L-fucopyranosyl)-4-O-[3-O-sulfo-β-D-galactopyranosyl]-2-deoxy-6-O-sulfo-β-D-glucopyranoside disodium salt (compound 335).

Disulfo trisaccharide 334 (320 mg, 0.264 mmol) was hydrogenated over palladium on carbon (350 mg) in methanol (20.0 mL) as described earlier to provide for compound 335 (194 mg, 79%) after conversion to its sodium salt.

Example 39

Preparation 8-methoxycarbonyloctyl 2-acetamido-3-O-[α-L-fucopyranosyl]-4-O-[4,6-dichloro-dideoxy-3-O-sulfo-β-D-galactopyranosyl]-6-benzamido-2,6-dideoxy-β-D-glucopyranoside (compound 341)

Figure 24:
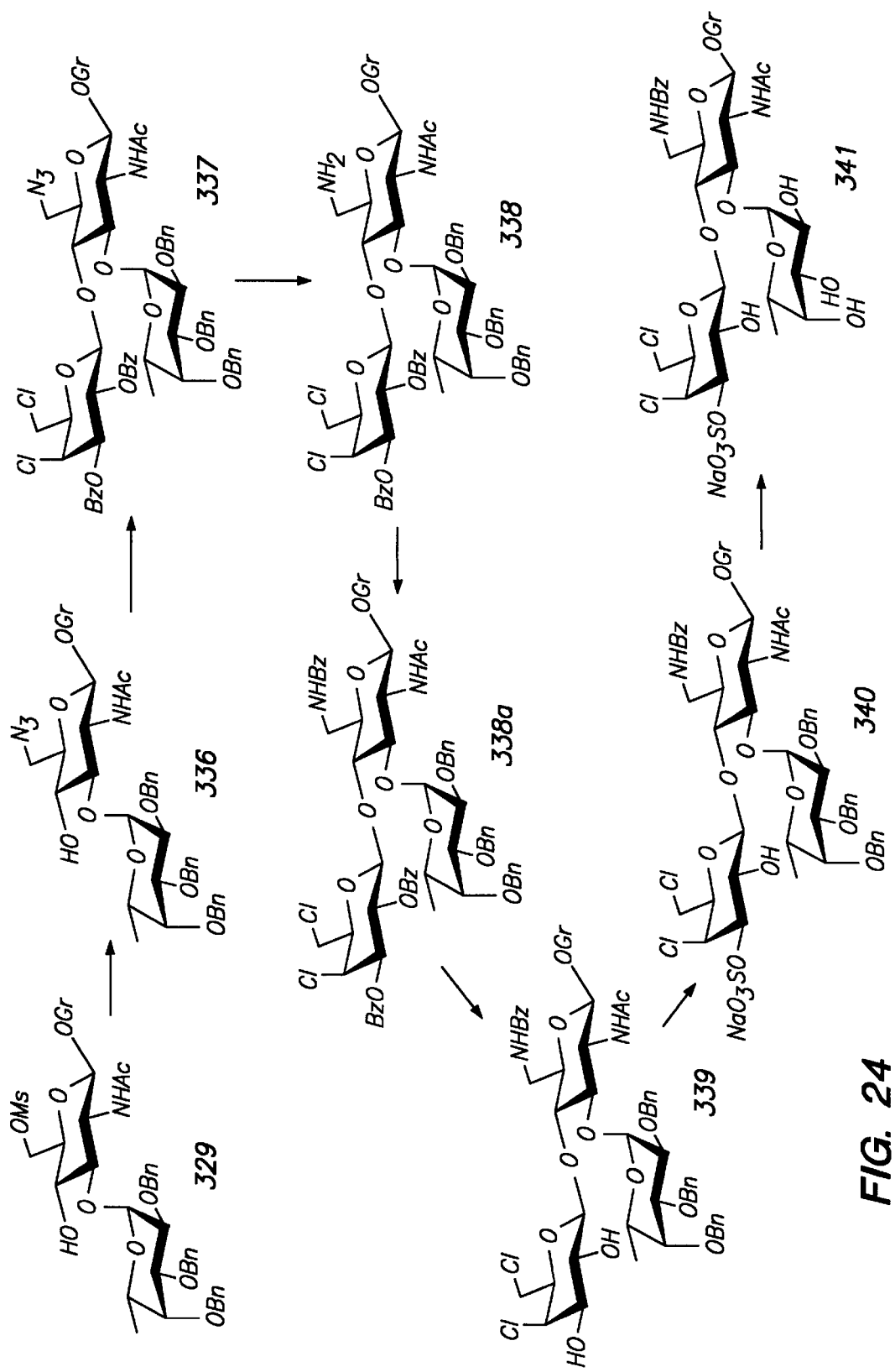

The synthesis of compound 341 is illustrated in FIG. 24.
Step A—Preparation of 8-methoxycarbonyloctyl-2-acetamido-3-O-(2,3,4-tri-O-benzyl-∝-L-fucopyranosyl)-6-azido-2,6-dideoxy-β-D-glucopyranoside (compound 336)

Compound 329 (1.0 g, 1.13 mmol) was dissolved in dry DMF (10.0 mL) and sodium azide (550 mg, 7.7 mmol) was added thereto. The resulting solution was heated at 80° C. under nitrogen for 3 days by which time most of the starting material was completely converted into product. The solvent was evaporated and the residue dissolved in dichloromethane (25.0 mL). The organic layer was washed with water (2×25 mL), dried over $Na_2SO_4$ and evaporated to give a yellow solid which was purified by chromatography on silica gel using hexane-ethyl acetate-methanol (1:1:0.05) as eluent to provide for compound 336 (657 mg, 70.0%).

Step B—Preparation of 8-methoxycarbonyloctyl-2-acetamido-3-O-(2,3,4-tri-O-benzyl-∝-L-fucopyranosyl)-4-O-[2,3-di-O-benzoyl-4,6-dichloro-dideoxy-β-D-galactopyranosyl]-6-azido-2,6-dideoxy-β-D-glucopyranoside (compound 337)

Compound 336 (2.73 g, 3.28 mmol) as a glycosyl acceptor and dichloro dibenzoyl imidate (4.67 g, 8.20 mmol) were dissolved in a mixture of dichloromethane-ether (40 mL, 1:1) and stirred at 0° C. for 0.5 hours. A solution of $BF_3$-ethereate (1.1 mL, 8.9 mmol) was added dropwise at this temperature and the reaction was then stirred overnight at 0° C. The reaction solution was then diluted with dichloromethane (150 mL) and worked successively with water (2×150 mL), 6% solution of sodium hydrogen carbonate (2×50 mL) and water (2×150 mL), dried over sodium sulfate, filtered and the solvent evaporated to dryness. The residue was purified by chromatography on silica gel using hexane-ethyl acetate (2:1) as eluent to yield compound 337 (1.68 g, 43%).

Step C—Preparation of 8-methoxycarbonyloctyl-2-acetamido-3-O-(2,3,4-tri-O-benzyl-∝-L-fucopyranosyl)-4-O-[2,3-di-O-benzoyl-4,6-dichloro-dideoxy-β-D-galactopyranosyl]-6-amino-2,6-dideoxy-β-D-glucopyranoside (compound 338).

Compound 337 (1.68 g, 1.35 mmol) was dissolved in a mixture of pyridine-water-triethylamine (13:2:0.4) and a stream of hydrogen sulfide gas was bubbled at 0° C. for 1 hour. The reaction mixture was then stirred for 15 hours at room temperature. Solvents were evaporated and the residue, compound 338, was used directly without further purification. The yield of compound 338 was quantitative at this stage.

Step D—Preparation of 8-methoxycarbonyloctyl-2-acetamido-3-O-(2,3,4-tri-O-benzyl-∝-L-fucopyranosyl)-4-O-[2,3-di-O-benzoyl-4,6-dichloro-dideoxy-β-D-galactopyranosyl]-6-benzamido-2,6-dideoxy-β-D-glucopyranoside (compound 338a)

The crude amine, compound 338—obtained from Step C above, was dissolved in methanol (20 mL) and then a 6% solution of $NaHCO_3$ (29 mL) was added followed by addition of benzoyl chloride (0.62 mL, 5.3 mmol). The reaction mixture was stirred for 1 hour at room temperature and then the solvent was evaporated. The residue was dissolved in dichloromethane (100 mL) and washed with water (2×100 mL), dried over $Na_2SO_4$ before evaporation to a syrup which was purified by chromatography on silica gel using dichloromethane:methanol (98:2) as eluent to provide for compound 338a (1.11 g, 62% based on the azido compound).

Step E—Preparation of 8-methoxycarbonyloctyl-2-acetamido-3-O-(2,3,4-tri-O-benzyl-∝-L-fucopyranosyl)-4-O-[4,6-dichloro-dideoxy-β-D-galactopyranosyl]-6-benzamido-2,6-dideoxy-β-D-glucopyranoside (compound 339)

Compound 338a (501 mg, 0.38 mmol) was dissolved in methanol (20.0 mL) and a solution of sodium methoxide in methanol (5.0 mL, 0.5M) Was added thereto. The reaction mixture was stirred for 3 hours. The reaction mixture was then neutralized with Amberlite IR-120 (H⁺) resin, filtered and evaporated. The crude product was purified by chromatography on silica gel using dichloromethane:methanol (98:2) as eluent to provide for compound 339 (357 mg, 84.6%).

Step F—Preparation of 8-methoxycarbonyloctyl-2-acetamido-3-O-(2,3,4-tri-O-benzyl-α-L-fucopyranosyl)-4O-[4,6-dichloro-dideoxy-3-O-sulfo-β-D-galactopyranosyl]-6-benzamido-2,6-dideoxy-β-D-glucopyranoside sodium salt (compound 340)

Compound 339 (357 mg, 0.32 mmol) was dissolved in pyridine (6.0 mL) and SO₃-pyridine complex (284 mg, 1.77 mmol) was added thereto at 0° C. The reaction mixture was stirred for 0.5 hours at this temperature and 5.5 hours at room temperature. Afterwards, methanol (2.0 mL) was added and the reaction mixture evaporated and the residue purified by chromatography on silica gel using dichloromethane-methanol-pyridine (95:5:0.1) as eluent to provide for compound 340 (333 mg, 85.4%, after sodium exchange resin).

Step G—Preparation 8-methoxycarbonyloctyl 2-acetamido-3-O-[α-L-fucopyranosyl]-4-O-[4,6-dichloro-dideoxy-3-O-sulfo-β-D-galactopyranosyl]-6-benzamido-2,6-dideoxy-β-D-glucopyranoside sodium salt (compound 341)

Hydrogenation of compound 340 (333 mg, 0.27 mmol) for 1 hour in methanol (20.0 mL) using 5% palladium on carbon (340 mg) as a catalyst provided for compound 341 (207 mg, 80%) after workup (as described above) and purification on Iatrobeads using dichloromethane-methanol-water-pyridine (80:20:2:0.1) as eluent followed by sodium exchange to effect conversion to the sodium salt.

Example 40

Preparation 8-methoxycarbonyloctyl-2-acetamido-3-O-(α-L-fucopyranosyl)-4-O-[4,6-dideoxy-3-O-sulfo-β-D-galactopyranosyl]-6-benzamido-2,6-dideoxy-β-D-glucopyranoside (compound 345)

Figure 25:
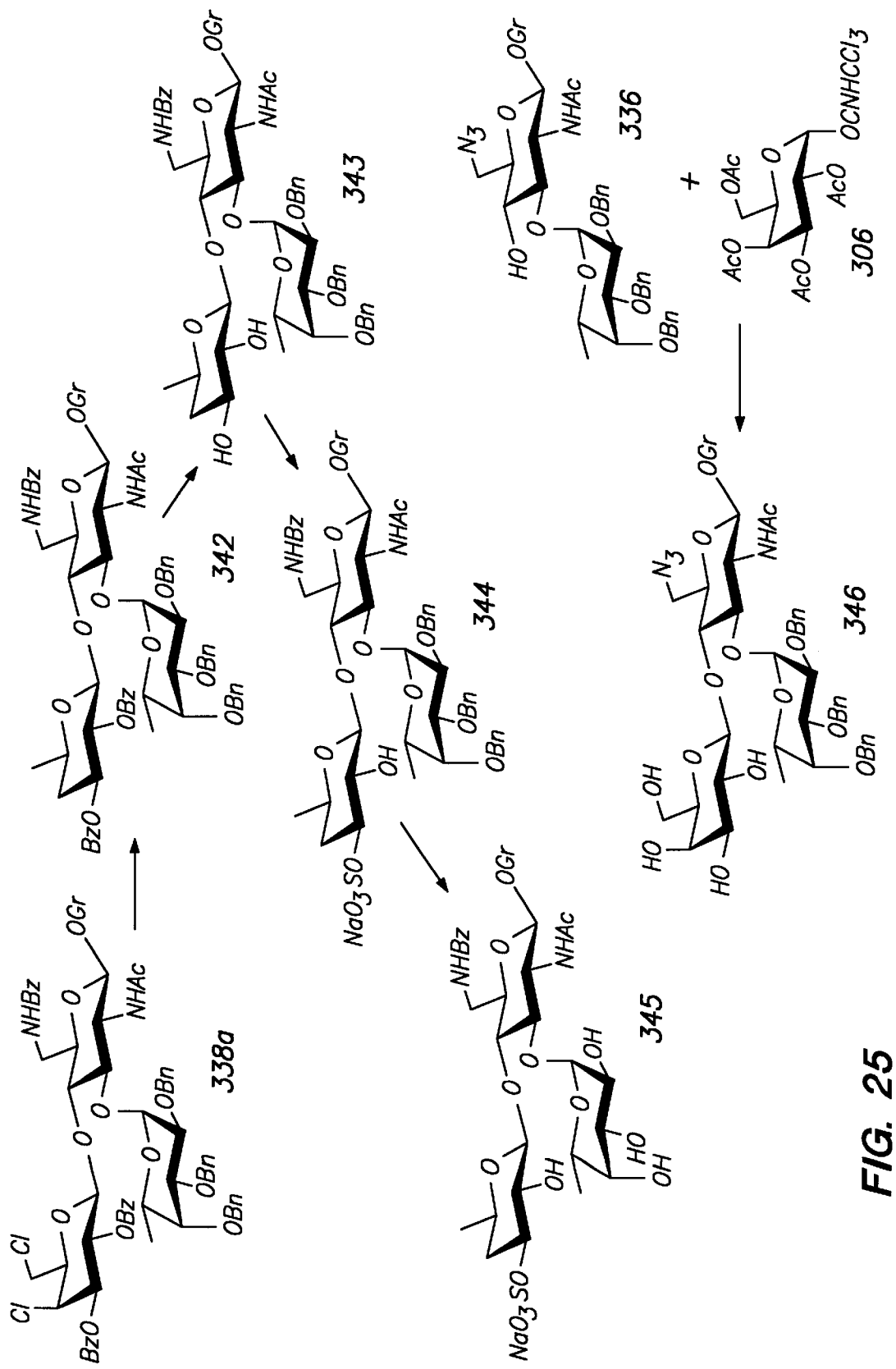

The synthesis of compound 345 is illustrated in FIG. 25.
Step A—Preparation of 8-methoxycarbonyloctyl-2-acetamido-3-O-(2,3,4-tri-O-benzyl-α-L-fucopyranosyl)-4O-[2,3-dibenzoyl-4,6-dideoxy-β-D-galactopyranosyl]-6-benzamido-2,6-dideoxy-β-D-glucopyranoside (compound 342)

Compound 338a (6.5 mg, 4.93 mmol) was dissolved in toluene (30.0 mL) and tributyltin hydride (2.76 mL) and AIBN (30.0 mg) were added thereto. The reaction solution was then heated to reflux (90° C.) for 5 hours by which time the reaction was complete. The solvent was evaporated and the residue was chromatographed on silica gel using hexane-ethyl acetate as the eluant (3:2, 1:1) to provide for compound 342 (4.8 mg, 78%).

Step B—Preparation of 8-methoxycarbonyloctyl-2-acetamido-3-O-(2,3,4-tri-O-benzyl-α-L-fucopyranosyl)-4-O-[4,6-dideoxy-β-D-galactopyranosyl]-6-benzamido-2,6-dideoxy-β-D-glucopyranoside (compound 343)

Compound 342 (396 mg, 0.32 mmol) was dissolved in methanol (10.0 mL) and sodium methoxide in methanol (5.0 mL, 0.5M) was added thereto. The reaction mixture was stirred for 4 hours at room temperature. After neutralization with Amberlite IR-120 (H⁺) resin, filtration and evaporation, the material was purified by chromatography on silica gel using dichloromethane-methanol (95:5) as eluent to provide for compound 343 (322 mg, 97.6%).

Step C—Preparation of 8-methoxycarbonyloctyl-2-acetamido-3-O-(2,3,4-tri-O-benzyl-α-L-fucopyranosyl)-4-O-[4,6-dideoxy-3-sulfo-β-D-galactopyranosyl]-6-benzamido-2,6-dideoxy-β-D-glucopyranoside sodium salt (compound 344)

Compound 343 (266 mg, 0.26 mmol) was dissolved in pyridine (5.0 mL) and SO₃-pyridine complex (183 mg, 1.15 mmol) was added thereto at 0° C. The reaction mixture was stirred for 0.5 hours at 0° C. and 4 hours at room temperature. After addition of methanol (2.0 mL), the reaction mixture was evaporated and the residue was purified by chromatography on silica gel using dichloromethane-methanol (95:5) as eluent to provide for compound 344 as the sodium salt (245 mg, 84% after sodium exchange resin).

Step D—Preparation of 8-methoxycarbonyloatyl-2-acetamido-3-O-(α-L-fucopyranosyl)-4-O-[4,6-dideoxy-3-sulfo-β-D-galactopyranosyl]-6-benzamido-2,6-dideoxy-β-D-glucopyranoside (compound 345)

A solution of compound 344 (315 mg, 0.28 mmol) in methanol (30.0 mL) containing 5% palladium on carbon (315 mg) as a catalyst was hydrogenated at room temperature for 1.5 hours as described above to provide for compound 345 (188 mg, 78%) after purification by chromatography on silica gel using dichloromethane-methanol-water-pyridine (80:20:2:0.1) as eluent and conversion into the sodium salt by passage through Dowex 50-X-8 (Na⁺) sodium exchange resin.

Example 41

Preparation of 8-methoxycarbonyloctyl-2-acetamido-3-O-(α-L-fucopyranosyl)-4-O-[3-O-sulfo-β-D-galactopyranosyl]-6-amino-2,6-dideoxy-β-D-glucopyranoside (compound 349)

Figure 26A:
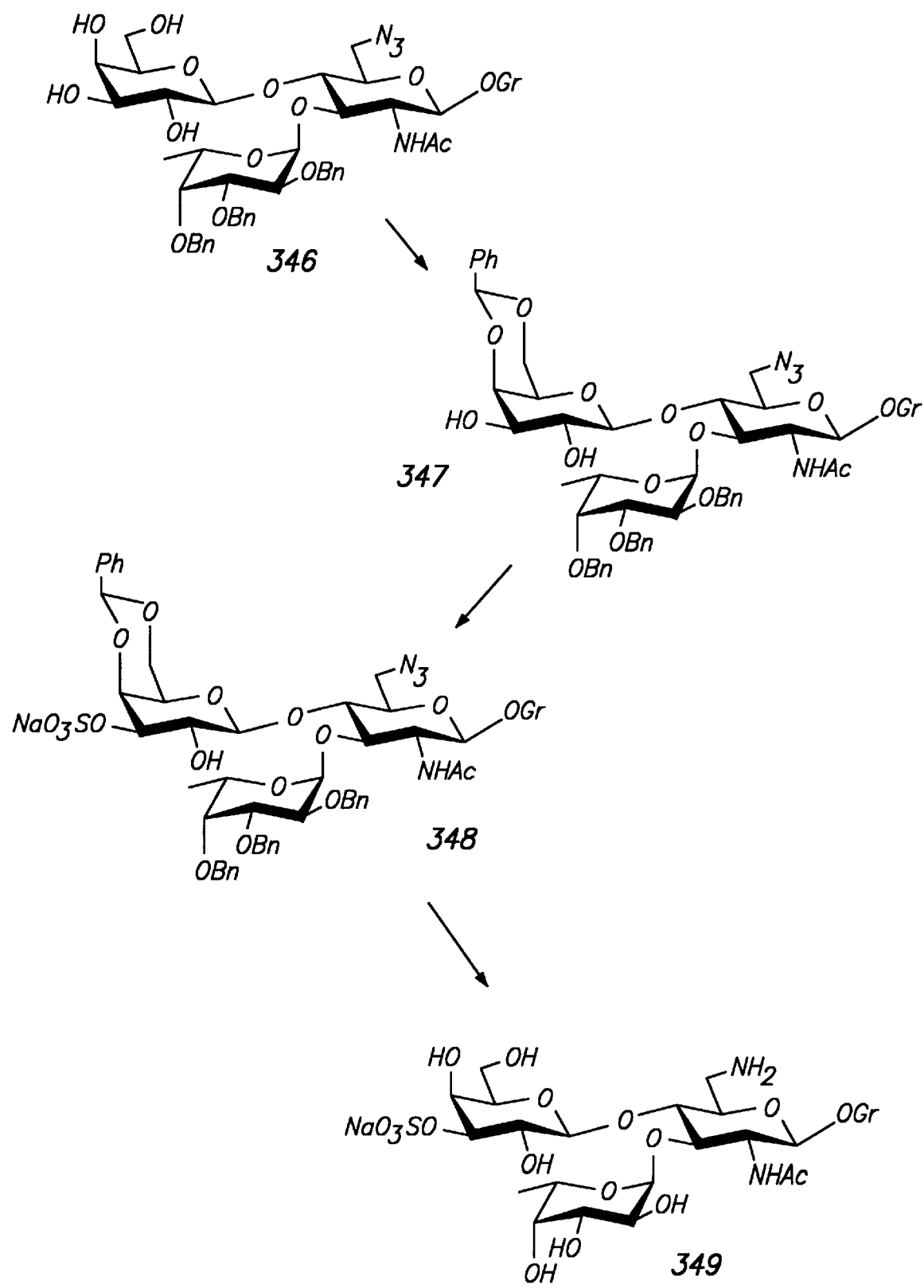
Figure 26B:
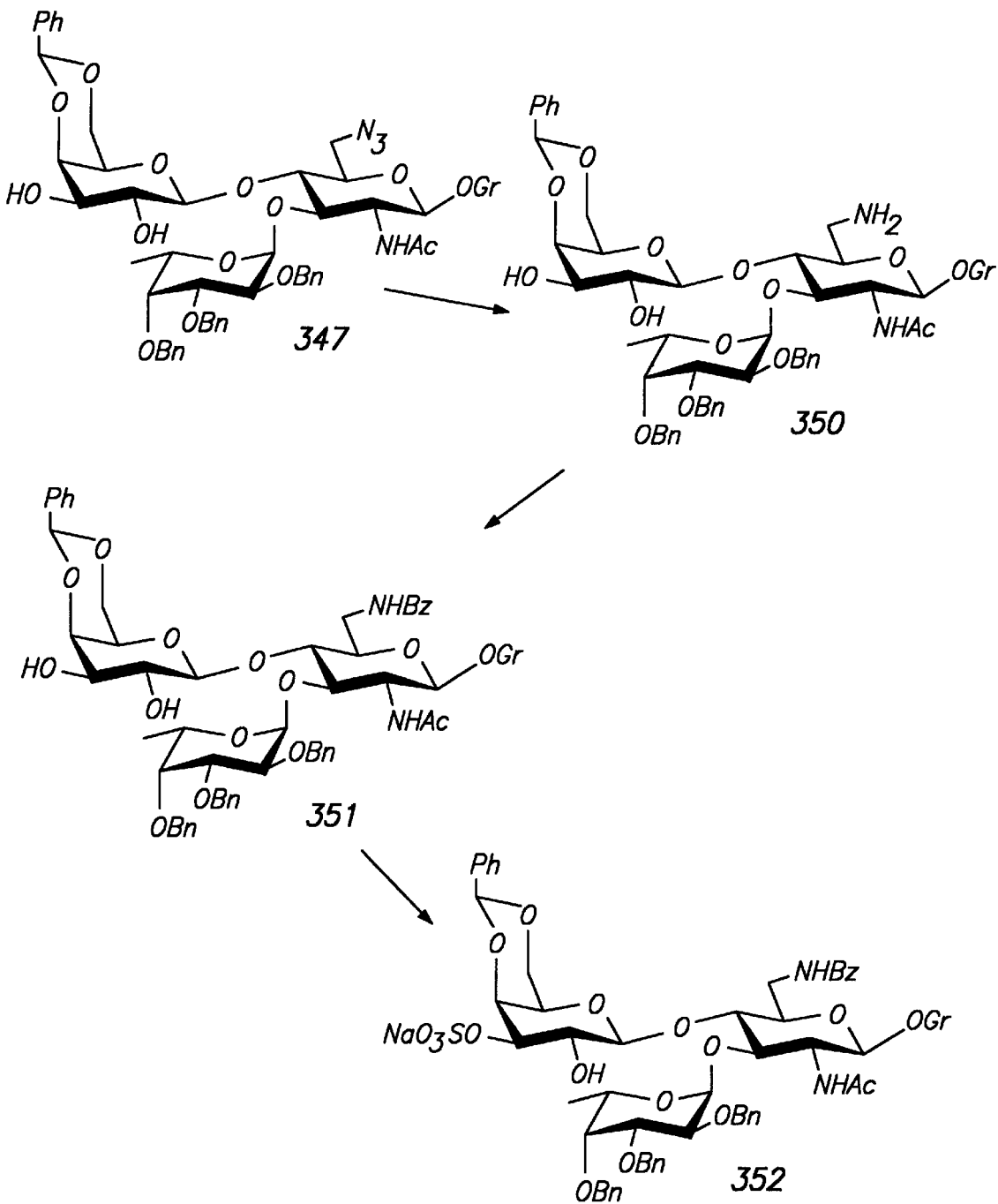

The synthesis of compound 349 is illustrated in FIGS. 25 and 26.
Step A—Preparation of 8-methoxycarbonyloctyl-2-acetamido-3-O-(2,3,4-tri-O-benzyl-α-L-fucopyranosyl)-4-O-(β-D-galactopyranosyl)-6-azido-2,6-dideoxy-β-D-glucopyranoside (compound 346)

A solution of compound 336 (600 mg, 0.72 mmol) and 2,3,4,6-tetraacetyl galactose-imidate, compound 306a, (709.47 mg, 1.44 mmol) in ether-dichloromethane (3:2) was cooled to −5° C. and BF3Et₂O solution (265 µL, 2.16 mmol) was added dropwise. The resulting reaction solution was stirred for 1.5 hours at this temperature. Then sodium hydrogen carbonate (1.6 g) was added and the resulting solution stirred for 10 minutes. A solution of sodium methoxide in methanol (3.0 mL, 1.0M) was then added and the system stirred. After 1 hour, an additional amount of 1M NaOMe/MeOH (2 mL) was added. The reaction mixture was then neutralized by addition of IR-120 (H⁺) resin (2.0 g) to adjust the pH to 6.0. The system was then filtered to remove the resin, the solvent evaporated, and the residue redissolved in ethyl acetate. The organic layer was washed with water (2×100 mL), dried over Na₂SO₄, filtered and evaporated to provide for compound 346 which was purified by chromatography on silica gel using dichloromethane-methanol (95:5) as eluent to provide for 392 mg (54.7%) of this compound.

Step B—Preparation of 8-methoxycarbonyloctyl 2-acetamido-3-O-(2,3,4-tri-O-benzyl-α-L-fucopyranosyl)-4-O-[4,6-O-benzylidene-β-D-galactopyranosyl]-6-azido-2,6-dideoxy-β-D-glucopyranoside (compound 347)

A solution of compound 346 (350 mg, 0.35 mmol) was dissolved in dry acetonitrile (5 mL). α,α-Dimethoxytoluene (79.3 µL, 0.53 mmol) and p-toluene sulfonic acid (10 mg) was added and the reaction mixture was stirred at room temperature for 5 hours. The mixture was then neutralized with triethylamine and the solvent evaporated. The residue was chromatographed on silica gel eluting with dichloromethane-methanol (98:2) as eluent to provide compound 347 (300 mg, 78.7%).

Step C—Preparation of 8-methoxycarbonyloctyl 2-acetamido-3-O-(2,3,4-tri-O-benzyl-α-L-fucopyranosyl)-4-O-[4,6-O-benzylidene-3-O-sulfo-β-D-galactopyranosyl]-6 azido-2,6-dideoxy-β-D-glucopyranoside sodium salt (compound 348).

To a solution of compound 347 (280 mg, 0.26 mmol) in pyridine (5 mL) at 0° C. was added $SO_3$-pyridine complex (61.6 mg, 0.39 mmol). The reaction mixture was allowed to warm to room temperature and additional $SO_3$-pyridine complex was added after 0.5 hours (0.5 eq) and 1 hour (0.5 eq). The reaction was terminated after 2 hours by adding methanol and the solvents were then evaporated. The residue was chromatographed on a silica gel column, eluting with dichloromethane-methanol-pyridine (95:5:0.1) as eluent, to provide for compound 348 (220 mg, 72%) after passage through Dowex-50-X-8 ($Na^+$) ion exchange resin.

Step D—Preparation of 8-methoxycarbonyloctyl-2-acetamido-3-O-(α-L-fucopyranosyl)-4-O-[3-O-sulfo-β-D-galactopyranosyl]-6-amino-2,6-dideoxy-β-D-glucopyranoside sodium salt (compound 349)

A solution of compound 348 (220 mg, 0.19 mmol) was hydrogenated in methanol (6 mL containing 1.5 eq. of HCl) using 5% palladium on carbon (220 mg) for 5 hours at atmospheric pressure. The solution was then filtered and the solvent evaporated. The residue was purified by chromatography on Iatrobeads using isopropanol-water-ammonia (7:1.5:0.5) an eluent to provide for compound 349 (120 mg, 80.7%) after conversion to its sodium salt by passage through Dowex-50-X-8 ($Na^+$) ion exchange resin.

Example 42

Preparation of 8-methoxycarbonyloctyl-2-acetamido-3-O-(α-L-fucopyranosyl)-4-O-[3-O-sulfo-β-D-galactopyranosyl]-6-benzamido-2,6-dideoxy-β-D-glucopyranoside (compound 353)

Figure 27:
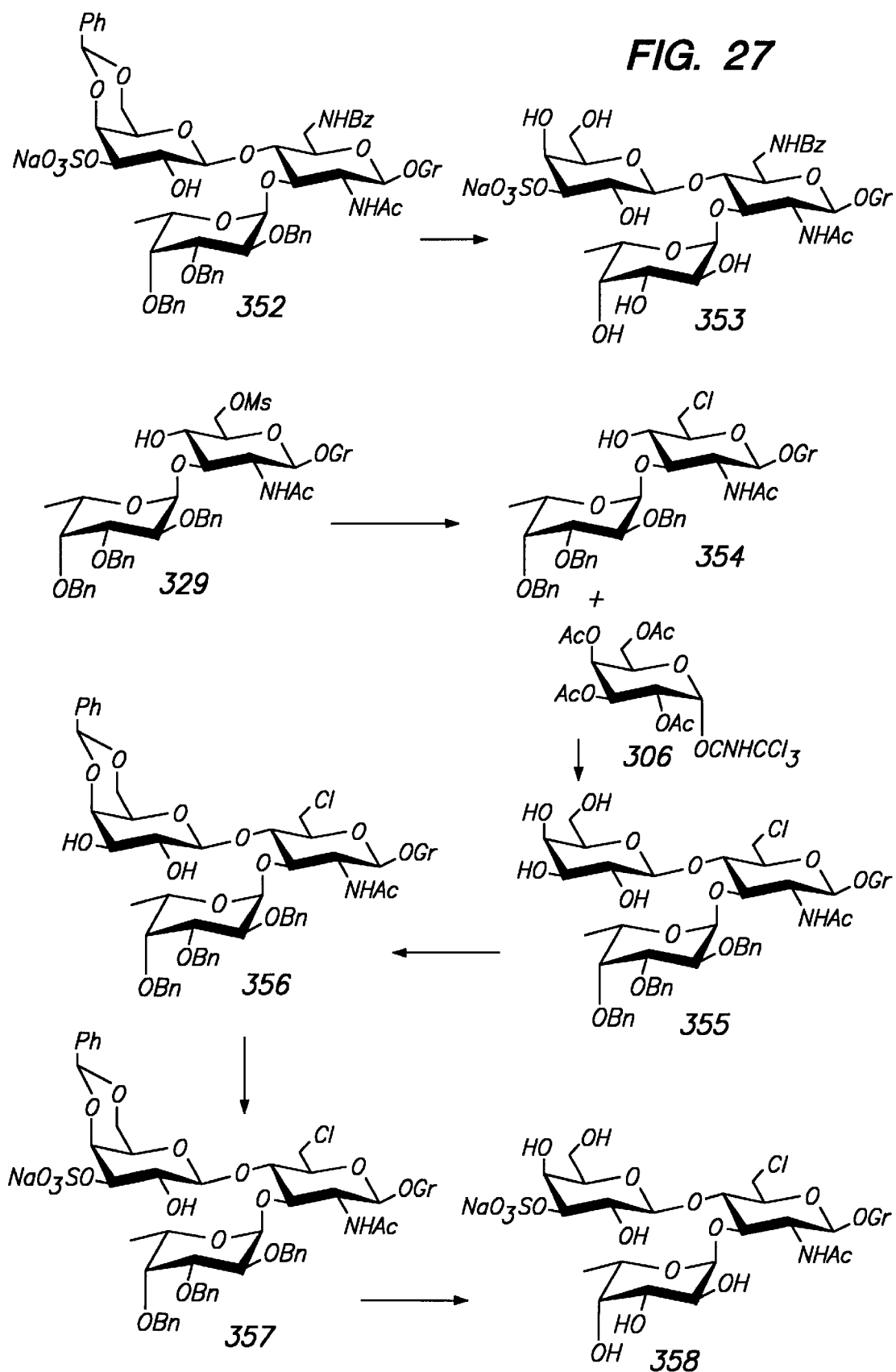
FIGS. 27–37 illustrate reaction schemes for the synthesis of compounds 301–423.

The synthesis of compound 353 is illustrated in FIGS. 26 and 27.

Step A—Preparation of 8-methoxycarbonyloctyl-2-acetamido-3-O-(2,3,4tri-O-benzyl-α-L-fucopyranosyl)-4-O-[4,6-O-benzylidene-β-D-galactopyranosyl]-6-benzamido-2,6-dideoxy-β-D-glucopyranoside (compound 351)

Compound 347 (250 mg, 0.23 mmol) was dissolved in a mixture of pyridine, triethylamine and water (2:0.5:0.05, 5 mL) and hydrogen sulfide was bubbled through the solution at 0° C. for 2 hours and then at room temperature for 15 hours. The solvent was evaporated and co-evaporated with toluene to provide a residue, compound 350, which was converted into its benzamido derivative by reacting it with benzoyl choride (250 L) in a mixture of methanol-saturated sodium hydrogen carbonate (3:1). The product was evaporated dissolved in dichloromethane (50 mL) washed with water (2×50 mL), dried over $Na_2SO_4$, filtered and evaporated to dryness. The residue was purified by chromatography on silica gel column using dichloromethane-methanol (98:2) as eluent, to provide for compound 351 (220 mg, 82%).

Step B—Preparation of 8-methoxycarbonyloctyl-2-acetamido-3-O-(2,3,4-tri-O-benzyl-α-L-fucopyranosyl)-4-O-[4,6-O-benzylidene-3-O-sulfo-β-D-galactopyranosyl]-6-benzamido-2,6-dideoxy-β-D-glucopyranoside (compound 352).

To a solution of compound 351 (220 mg, 0.20 mmol) in pyridine (5 mL) at 0° C. was added $SO_3$-pyridine complex (45.2 mg, 0.28 mmol). The reaction mixture was allowed to warm to room temperature and additional $SO_3$-pyridine complex (22.1 mg, 0.14 mmol) was added and stirring was continued for 5 hours at room temperature by which time all the starting material was completely converted into product. The reaction mixture was quenched with methanol (2 mL) and evaporated to dryness. The residue was purified by chromatography on silica gel using dichloromethane-methanol-pyridine (95:5:0.1) as eluant to provide for compound 352 (190 mg, 79.3%) as a sodium salt by passage through Dowex-50-X-8 ($Na^+$) resin.

Step C—Preparation of 8-methoxycarbonyloctyl-2-acetamido-3-O-(α-L-fucopyranosyl)-4-O-[3-O-sulfo-β-D-galactopyranosyl]-6-benzamido-2,6-dideoxy-β-D-glucopyranoside (compound 353)

Compound 352 (190 mg, 0.15 mmol) was hydrogenated in methanol (5 mL) using 5% palladium on carbon (200 mg) as described earlier to provide for compound 353 (110 mg, 80.8%) after sodium conversion to the sodium salt by passage through Dowex-50-X-8 ($Na^+$) resin.

Example 43

Preparation of 8-methoxycarbonyloctyl-2-acetamido-3-O-[α-L-fucopyranosyl]-4-O-[3-O-sulfo-β-D-galactopyranosyl]-6-chloro-2,6-dideoxy-β-D-glucopyranoside (compound 358)

The synthesis of compound 358 is illustrated in FIG. 27.

Step A—Preparation of 8-methoxycarbonyloctyl-2-acetamido-3-O-(2,3,4-tri-O-benzyl-α-L-fucopyranosyl)-6-chloro-2,6-dideoxy-β-D-glucopyranoside (compound 354)

Compound 329 (200 mg, 0.23 mmol) was dissolved in anhydrous acetonitrile (3 mL) and tetrabutylammonium chloride (150 mg, 0.54 mmol) was added. The reaction mixture was heated at 80° C. for 15 hours. The solvent was then evaporated and the residue dissolved in dichloromethane (50 mL). The organic layer was washed with a 6% solution of $NaHCO_3$ (2×50 mL) and water (2×50 mL), dried over $Na_2SO_4$ evaporated and the residue was purified by chromatography on silica gel using hexane-ethyl acetate (1:1) as the eluent to provide for compound 354 (150 mg, 80.4%).

Step B—Preparation of 8-methoxycarbonyloctyl-2-acetamido-3-O-(2,3,6-tri-O-benzyl-α-L-fucopyranosyl)-4-O-[β-D-galactopyranosyl]-6-chloro-2,6-dideoxy-β-D-glucopyranoside (compound 355)

Compound 354 (150 mg, 0.18 mmol) and imidate donor compound 306 (178.8 mg, 0.36 mmol), disclosed in Srivastava et al.[23], was dissolved in a mixture of ether-dichloromethane (3 mL, 3:2) and cooled to −10° C. $BF_3$-Et2O complex (144 μL, 0.54 mmol) was slowly added dropwise to the reaction mixture which was then stirred at −10° C. for 1 hour. Solid sodium bicarbonate (1.0 g) was then added to the mixture which was stirred for 10 minutes. A solution of sodium methoxide in methanol (2.0 mL, 1M) was then added and the system stirred for 1 hour at room temperature. The reaction mixture was then neutralized with IR-120 ($H^+$) resin, filtered, and the solvent evaporated. The residue was purified by chromatography on silica gel using dichloromethane-methanol (95:5) as eluent to provide compound 355 (98.5 mg, 54.9%).

Step C—Preparation of 8-methoxycarbonyloctyl-2-acetamido-3-O-(2,3,4-tri-O-benzyl-α-L-fucopyranosyl)-4-O-[4,6-O-benzylidene-β-D-galactopyranosyl]-6-chloro-2,6-dideoxy-β-D-glucopyranoside (compound 356)

A solution of compound 355 (98.5 mg, 0.1 mmol), α,α-dimethoxy-toluene (30 μL, 0.2 mmol) and p-toluene sulfonic acid (10 mg) in 8 mL acetonitrile was stirred at room temperature for 5 hours. The mixture was then neutralized with triethylamine and the solvent evaporated. The residue was chromatographed on silica gel using dichloromethane-methanol (98:2) as eluent to provide for compound 356 (90 mg, 84%).

Step D—Preparation of 8-methoxycarbonyloctyl-2-acetamido-3-O-[2,3,4-tri-O-benzyl-α-L-fucopyranosyl]-4-O-[4,6-O-benzylidene-3-O-sulfo-β-D-galactopyranosyl]-6-chloro-2,6-dideoxy-β-D-glucopyranoside (compound 357)

To a solution of compound 356 (90 mg, 0.084 mmol) in pyridine (2 mL) at 0° C. was added $SO_3$-pyridine complex (20 mg, 0.13 mmol) and the resulting reaction mixture was allowed to warm at room temperature. After stirring for 1 hour, tlc indicated that the starting material was not completely consumed so an additional amount of $SO_3$-pyridine complex (1 eq) was added and stirring was continued for 3 hours. The mixture was then quenched with methanol (2 mL) and evaporated to dryness. The residue was chromatographed on Iatrobeads, eluting with dichloromethane-methanol-pyridine (95:5:0.1), to provide for compound 357 (82.5 mg, 83.7%).

Step E—Preparation of 8-methoxycarbonyloctyl-2-acetamido-3-O-[α-L-fucopyranosyl]-4-O-[3-O-sulfo-β-D-galactopyranosyl]-6-chloro-2,6-dideoxy-β-D-glucopyranoside sodium salt (compound 358).

Compound 357 (82.5 mg, 0.07 mmol) was dissolved in methanol (5 mL) and hydrogenated with 5% palladium on carbon (50 mg) as described above to provide for compound 358 (45 mg, 78.4%) as its sodium salt.

Example 44

Preparation of 2-acetamido-3-O-[α-L-fucopyranosyl]-4-O-[4,6-dichloro-dideoxy-3-O-sulfo-β-D-galactopyranosyl]-2-deoxy-β-D-glucopyranosyl azide (compound 361)

Figure 28:
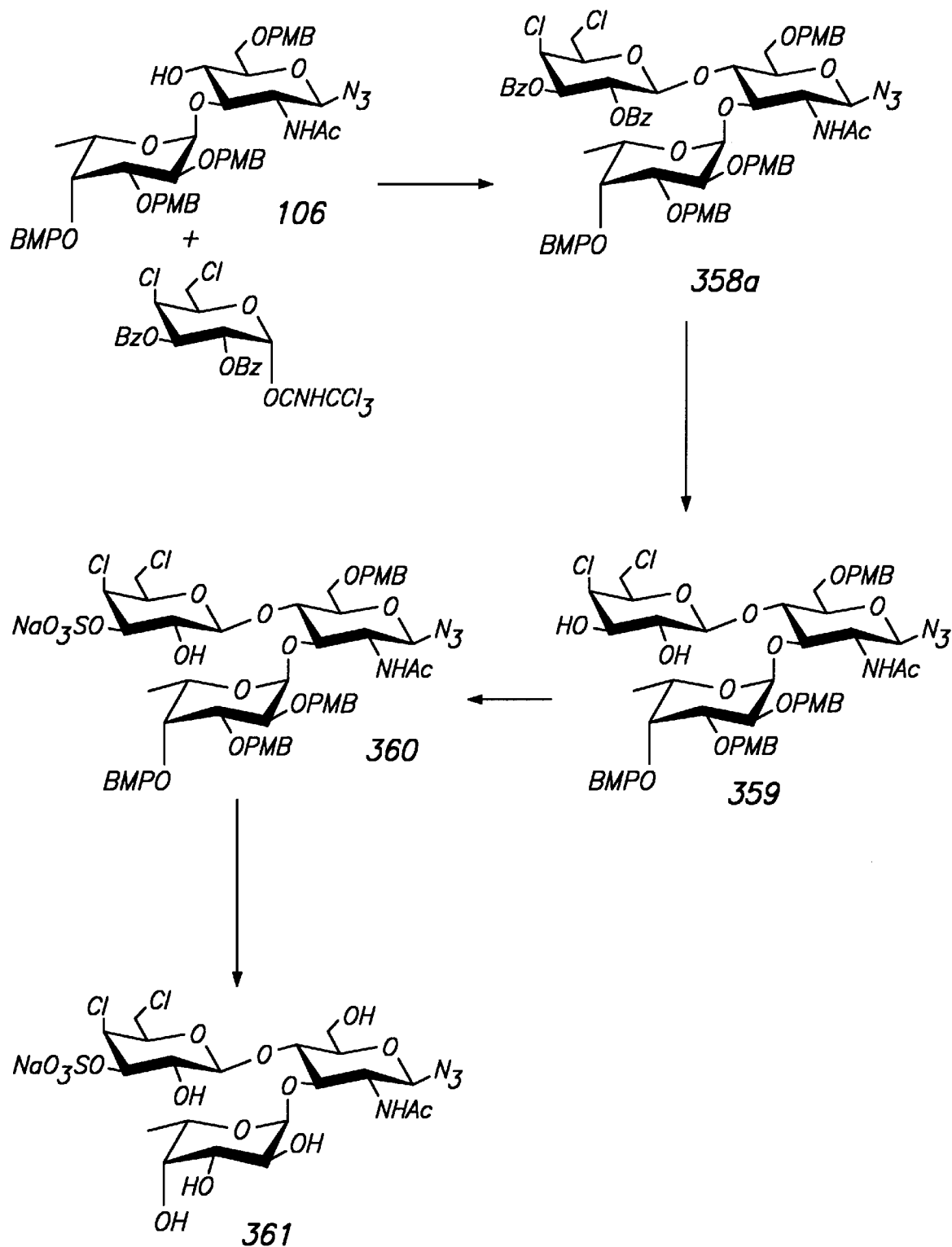

The synthesis of compound 361 is illustrated in FIG. 28.
Step A—Preparation of 2-acetamido-3-O-(2,3,4-tri-O-p-methoxybenzyl-α-L-fucopyranosyl)-4-O-[2,3-di-O-benzoyl-4,6-dichloro-dideoxy-β-D-galactopyranosyl]-6-O-p-methoxybenzyl-2-deoxy-β-D-glucopyranosyl azide (compound 358a)

2-Acetamido-2-deoxy-3-O-[2,3,4-tri-O-p-methoxybenzyl-α-L-fucopyranosyl]-6-O-p-methoxybenzyl-β-D-glucopyranosyl azide (compound 106 as described above) (2.95 g, 3.38 mmol) and 2,3-dibenzoyl-4,6-dichlorogalactose imidate donor (2.5 g, 4.39 mmol) was dissolved in dichloromethane (30 mL) and the reaction mixture was maintained at −20° C. to −10° C. Boron trifluoride etherate ($BF_3$-$Et_2O$) (0.52 mL, 1.25 eq) was added dropwise at this temperature and the resulting system was stirred for 3–5 hours. The reaction mixture was quenched by the addition of triethylamine. The solvent was evaporated and the residue was purified by chromatography on silica gel using hexane-ethyl acetate (55:45, 1:1) as eluent to provide for compound 358a (1.46 g, 34%).
Step B—Preparation of 2-acetamido-3-O-[2,3,4-tri-O-p-methoxybenzyl-α-L-fucopyranosyl)-4-O-[4,6-dichloro-dideoxy-β-D-galactopyranosyl]-6-O-p-methoxybenzyl-2-deoxy-β-D-glucopyranosyl azide (compound 359)

Compound 358a (493 mg, 0.39 mmol) was dissolved in methanol (10 mL) and sodium methoxide in methanol (0.4 mL, 0.5M) was added. The reaction mixture was stirred for 2 hours at room temperature. The reaction mixture was then neutralized with IR-120 ($H^+$) resin, filtered, and the solvent evaporated. The residue was purified by chromatography on silica gel using dichloromethane-methanol (97.5:2.5) as eluent to provide for compound 359 (3419 mg, 77%).
Step C—Preparation of 2-acetamido-3-O-[2,3,4-tri-O-p-methoxybenzyl]-4-O-[4,6-dichloro-dideoxy-3-O-sulfo-β-D-galactopyranosyl]-6-O-p-methoxybenzyl-2-deoxy-β-D-glucopyranosyl azide sodium salt (compound 360)

Compound 359 (468 mg, 0.44 mmol) was dissolved in pyridine (5 mL) and $SO_3$-pyridine complex (139 mg, 0.87 mmol) was added at 0° C. and the reaction system was allowed to warm to room temperature. An additional amount of $SO_3$-pyridine complex (69 mg, 1.0 eq) was added. The reaction mixture was then stirred at room temperature for 5 hours whereupon the reaction was quenched by addition of methanol (2 mL) and the solvent evaporated. The residue was purified by column chromatography using dichloromethane:methanol:pyridine (93:7:0.1) to provide for compound 360 as a sodium salt (380 mg, 74%) after sodium exchange column.

Step D—Preparation of 2-acetamido-3-O-[α-L-fucopyranosyl]-40-[4,6-dichloro-dideoxy-3-O-sulfo-β-D-galactopyranosyl]-2-deoxy-β-D-glucopyranosyl azide sodium salt (compound 361)

Compound 360 (335 mg, 0.29 mmol) was dissolved in a mixture of acetonitrile:water (9:1, 10 mL) and solid ceric ammonium nitrate (CAN) (895 mg, 1.63 mmol) was added to the reaction mixture. The reaction mixture was then stirred for 15 hours at 0° C. and then for 6.5 hours at room temperature. The solvent was evaporated after addition of pyridine (1.0 mL) and the residue was purified by chromatography on Iatrobeads using isopropanol:water:ammonia (90:7.5:2.5) as eluent to provide for compound 361 (129 mg) after purification using Bio-Gel-P-2 resin and conversion to sodium salt.

Example 45

Preparation of 2-acetamido-3-O-(α-L-fucopyranosyl)-4-O-[4,6-dideoxy-3-O-sulfo-β-D-galactopyranosyl]-2-deoxy-β-D-glucopyranosyl azide (compound 370)

Figure 29:
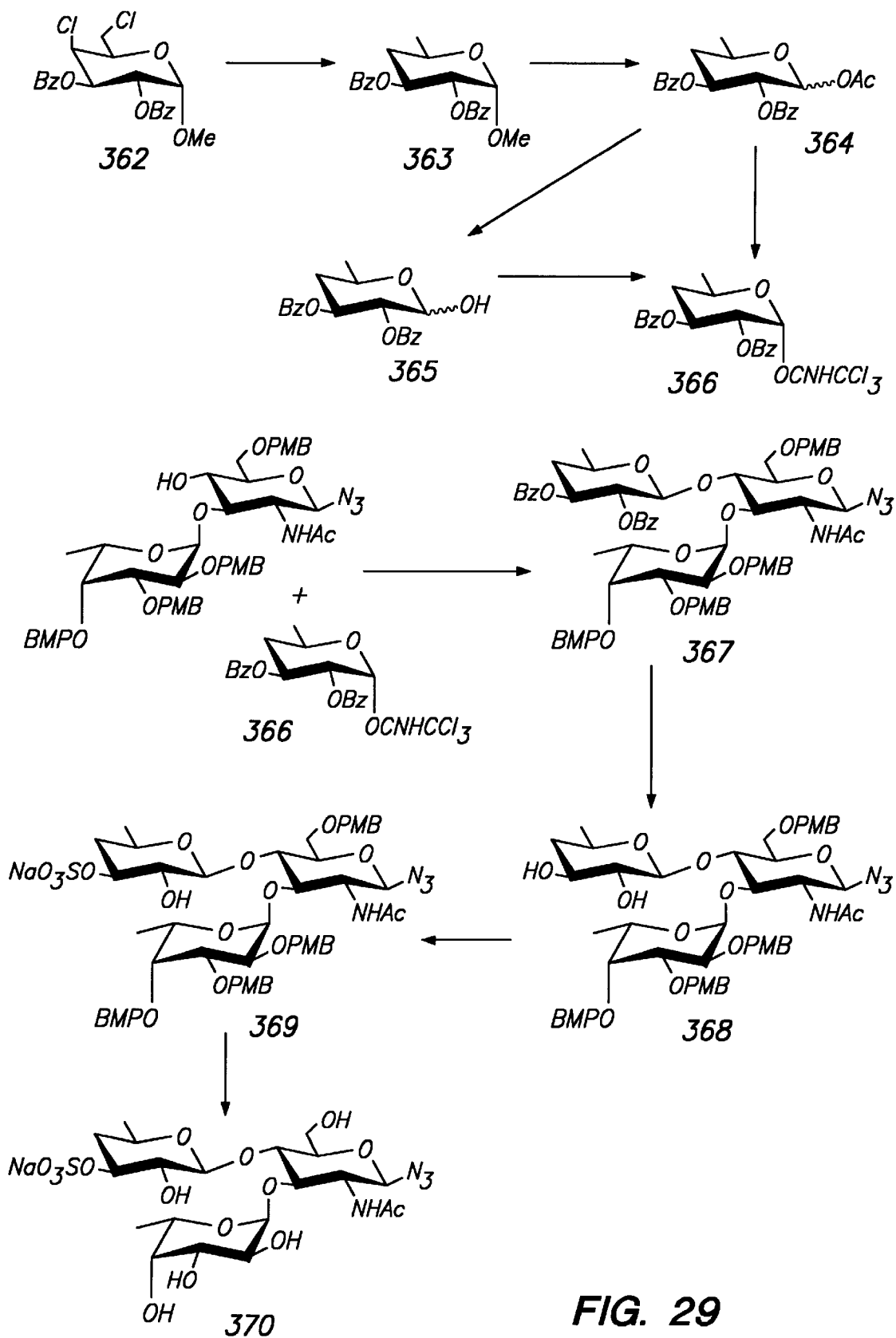

The synthesis of compound 362 is illustrated in FIG. 29.
Step A—Preparation of methyl-2,3-di-O-benzoyl-4,6-dideoxy-α-D-galactopyranosyl (compound 363)

Compound 362 (9.3 g, 21.2 mmol) was prepared from the known α-methyl-galactopyranosyl by reacting it with benzaldehyde dimethyl acetal and p-toluene sulfonic acid followed by benzoylation with benzoyl chloride in pyridine and removal of 4,6-O-benzylidene ring. Conversion of the 4,6-dihydroxy to the corresponding 4,6-dichloro-derivative was accomplished by reaction with sulfuryl chloride in pyridine.

The 4,6-dichloro derivative, compound 362, was converted to the corresponding 4,6-dideoxy derivative by reaction with tributyl tin hydride (100 mL, 37 mmol) and AIBN (100 mg) in toluene (400 mL) at 90° C. for 5 hours to provide for compound 363 (5.86 g, 74.7%) after purification by silica gel chromatography using hexane:ethyl acetate (9:1) as eluent.
Step B—Preparation of acetyl-2,3-di-O-benzoyl-4,6-dideoxy-galactopyranose (compound 364)

Compound 363 (4.5 g, 12.1 mmol) was reacted with a mixture of acetic anhydride:sulfuric acid (98.5:1.5) and stirred for 0.5 hours at room temperature. The reaction mixture was then quenched by addition of sodium bicarbonate. Dichloromethane (300 mL) was added and the organic layer was washed with 6% solution of sodium bicarbonate (2×300 mL) and water (2×300 mL), dried over Na$_2$SO$_4$, filtered and evaporated to obtain crude product 364 quantitatively which was used for the next reaction without further purification.

Step C—Preparation of 2,3-di-O-benzoyl-4,6-dideoxy-galactopyranose (compound 365)

Compound 364 from the previous reaction (~12.0 mmol) was dissolved in THF (40 mL) and benzylamine (2.0 mL, 18 mmol) was added. The reaction mixture was stirred for 15 hours at room temperature to provide for compound 365 (1.36 g).

Step D—Preparation of α-(2,3-di-O-benzoyl-4,6-dideoxy-D-glucopyranosyl)-trichloroacetimidate (compound 366)

Compound 365 (1.35 g, 3.8 mmol) was dissolved in dichloromethane (15 mL) and reacted with DBU (0.28 mL, 1.9 mmol) and trichloroacetonitrile (1.9 mL, 19 mmol) at 0° C. for 45 minutes to provide the desired product 366 (1.3 g, 68.5%) after purification by chromatography on silica gel using hexane:ethyl acetate (25:15) as eluent.

Step E—Preparation of 2-acetamido-3-O-(2,3,4-tri-O-p-methoxybenzyl-α-L-fucopyranosyl)-4-O-[2,3-di-O-benzoyl-4,6-dideoxy-β-D-galactopyranosyl]-6-O-p-methoxybenzyl-2-deoxy-β-D-glucopyranosyl azide (compound 367)

Compound 106 (1.2 g, 1.38 mmol) and compound 366 (1.00 g, 2.0 mmol) were dissolved in a mixture of ether and dichloromethane (1:1, 15.0 mL) and stirred at −20° C. for 0.5 hours. Boron trifluoride etherate (0.37 mL, 3.0 mmol) was added and the reaction mixture was stirred under nitrogen for 1 hour at −20° C. The reaction was quenched by the addition of triethylamine and the solvent evaporated. The residue was purified by chromatography on silica gel column using hexane:ethyl acetate (4:1) as eluent to provide the title compound 367 (1.20 g, 71.8%).

Step F—Preparation of 2-acetamido-3-O-(2,3,4-tri-O-p-methoxybenzyl-α-L-fucopyranosyl)-4-O-[4,6-di-deoxy-β-D-galactopyranosyl]-6-O-p-methoxybenzyl-2-deoxy-β-D-glucopyranosyl azide (compound 368)

Compound 367 (1.15 g, 0.95 mmol) was dissolved in methanol (10.0 mL) and deacylated by adding sodium methoxide in methanol (2 mL, 0.5M) and then stirring the reaction mixture for 15 hours at room temperature. After neutralization with Amberlite IR-120 (H$^+$) resin, filtration and evaporation, the product 368 was obtained quantitatively which was used without further purification.

Step G—Preparation of 2-acetamido-3-O-(2,3,4-tri-O-p-methoxybenzyl-α-L-fucopyranosyl)-4-O-[4,6-dideoxy-3-O-sulfo-β-D-galactopyranosyl]-6-O-p-methoxybenzyl-2-deoxy-β-D-glucopyranosyl azide (compound 369)

Compound 368 (900 mg, 0.9 mmol) was dissolved in pyridine (7 mL) and SO$_3$-pyridine complex (286 mg, 1.8 mmol) was added at 0° C. The reaction was allowed to warm to room temperature and, after stirring the mixture for 1 hour, an additional amount of SO$_3$-pyridine complex (143 mg, 0.9 mmol) was added and stirred for 2 hours at room temperature. The reaction mixture was quenched by the addition of methanol (5.0 mL), the solvent was evaporated and the residue purified by chromatography on silica gel using dichloromethane:methanol:pyridine (95:5:0.1) as eluent to provide for compound 369 (800 mg, 80.7% based on compound 368).

Step H—Preparation of 2-acetamido-3-O-(α-L-fucopyranosyl)-4-O-[4,6-dideoxy-3-O-sulfo-β-D-galactopyranosyl]-2-deoxy-β-D-glucopyranosyl azide sodium salt (compound 370).

Compound 369 (1.0 g, 0.90 mmol) was dissolved in acetonitrile:water (9:1, 50 mL) mixture and solid ceric ammonium nitrate (CAN) (2.83 g) was added at 0° C. and the reaction mixture was stirred for 3 hours at this temperature. Additional CAN (943 mg, 2 eq.) was added and stirring was continued for an additional 3.5 hours. After addition of pyridine (3.0 mL), the mixture was evaporated and purified by chromatography on silica gel using dichloromethane:methanol:water:pyridine (75:25:2.5:0.1) as eluent to provide for compound 370 (110 mg) as a sodium salt after sodium exchange column.

Example 46

Preparation of 2-benzamido-2-deoxy-3-O-(α-L-fucopyranosyl)-4-O-[3-O-sulfo-β-D-galactopyranosyl]-β-D-glucopyranosyl benzamide (compound 385)

Figure 30:
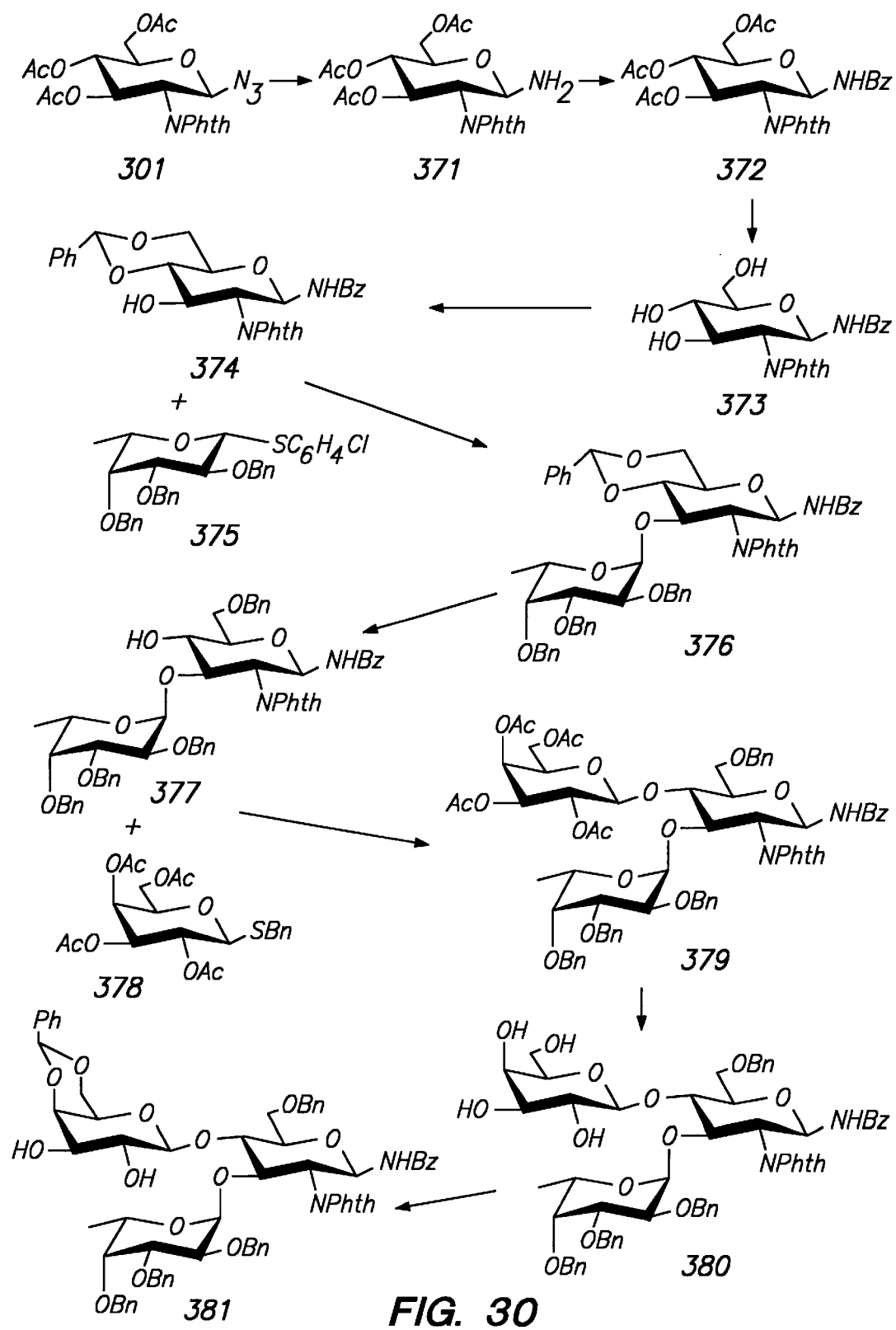
Figure 31:
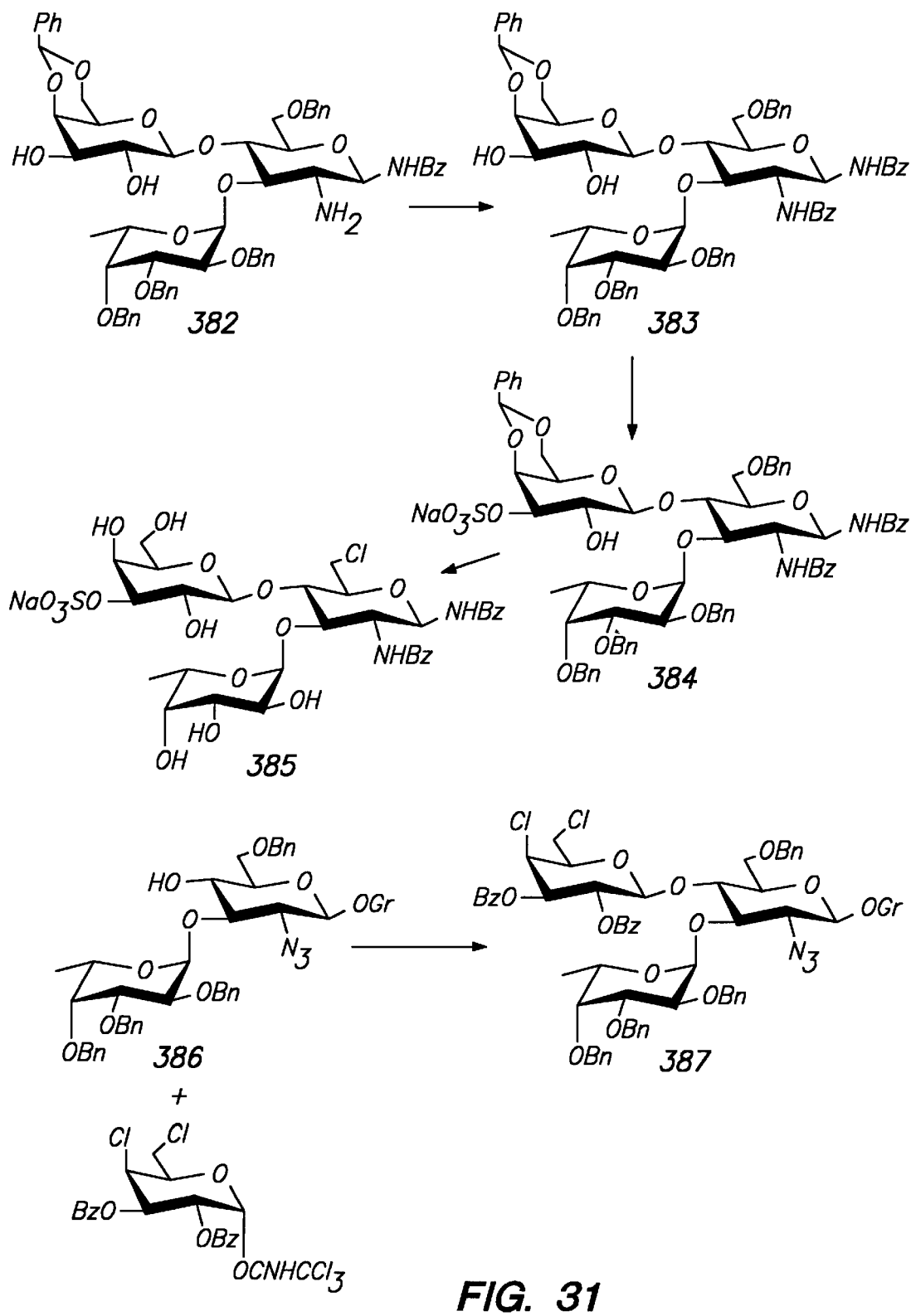

The synthesis of compound 385 is illustrated in FIGS. 30 and 31.

Step A—Preparation of 2-Deoxy-2-phthalimido-3,4,6-tri-O-acetyl-β-D-glucopyranosyl amine (compound 371)

Compound 301 (20 g, 43.4 mmol) was dissolved in methanol (100 mL) and was then hydrogenated with 5% palladium on carbon (10 g) for 3 hours. The catalyst was removed by filtration. The filtrate was evaporated and the residue was dried under vacuum to provide for compound 371 (18.2 g, 97%).

Step B—Preparation of 2-Deoxy-2-phthalimido-3,4,6-tri-O-acetyl-β-D-glucopyranosyl benzamide (compound 372)

A solution of compound 371 (18.2 g, 41.9 mmol) in dichloromethane (200 mL) and pyridine (5.2 mL) was cooled to 0° C. and benzoyl chloride (7.5 mL) was added. After 0.5 hours, methanol was added to quench excess benzoyl chloride. The reaction mixture was diluted with dichloromethane (500 mL) and washed successively with water (2×500 mL), 6% solution of sodium bicarbonate (2×500 mL), and water (2×500 mL), dried over sodium sulfate, filtered and the solvent evaporated. The product was crystallized by dissolving in hot ethyl acetate and cooling to room temperature to provide for compound 372 (17.3 g, 76.7%).

Step C—Preparation of 2-Deoxy-2-phthalimido-β-D-glucopyranosyl benzamide (compound 373)

Compound 372 (17.0 g, 31.6 mmol) was treated with 0.5N sodium methoxide in methanol (400 mL) at 0° C. while stirring the reaction mixture for 3 hours. The reaction solution was neutralized with Amberlite IR-120 (H$^+$) resin to maintain pH ~6. The resin was filtered and the solvent evaporated to provide for compound 373 (12.7 g, 97.6%).

Step D—Preparation of 4,6-O-Benzylidene-2-deoxy-2-phthalimido-β-D-glucopyranosyl benzamide (compound 374)

p-Toluene sulfonic acid (400 mg) was added to a solution of compound 373 (16.0 g, 38.8 mmol) in acetonitrile (300 mL) followed by addition of α,α-dimethoxytoluene (8.7 mL, 1.5 eq). The resulting reaction solution was stirred for 5 hours at room temperature and then the solution was neutralized with triethylamine and the solvent evaporated to provide for compound 374 quantitatively.

Step E—Preparation of 4,6-O-Benzylidene-2-deoxy-2-phthalimido-3-O-(2,3,4-tri-O-benzyl-α-L-fucopyranosyl)-α-D-glucopyranosyl benzamide (compound 376)

Copper (II) bromide (2.23 g, 5 eq.) and pulverized 4A molecular sieve (2.0 g) were added to a reaction flask. Dry dichloromethane (5 mL) was syringed into the flask followed by dry DMF (1.8 mL). Tetraethylammonium bromide (420 mg, 1 eq.) was added to the reaction flask and the greenish black mixture was stirred for 30 minutes. The acceptor 4,6-O-benzylidene-2-deoxy-2-phthalimido-β-D-glucosylbenzamide, compound 374 (1.0 g, 2.0 mmol), was added to the reaction mixture, followed by the p-chlorothiophenyl 2,3,4-tri-O-benzyl-α-L-fucopyranoside, compound 375 (1.68 mg, 3.0 mmol). The mixture was stirred for 5 hours at room temperature by which time all the starting material was completely converted into the product. The reaction mixture was diluted with dichloromethane (100 mL) and washed successively with saturated solution of EDTA (5×100 mL), 6% solution of sodium bicarbonate (5×100 mL) and water (5×100 mL) dried over $Na_2SO_4$, filtered, and the solvent evaporated to provide a crude residue which was crystallized with isopropyl alcohol to provide for compound 376 (1.5 g, 82%).

Step F—Preparation of 6-O-Benzyl-2-deoxy-2-phthalimido-3-O-(2,3,4-tri-O-benzyl-α-L-fucopyranosyl)-β-D-glucopyranosyl benzamide (compound 377)

Diethyl ether saturated with HCl was added to a mixture of compound 376 (8.4 g, 9.2 mmol), sodium cyanoborohydride (8.6 g, 15.0 eq), a few crystals of methyl orange and 3A molecular sieves (8.4 g) in dry THF (120 mL) at 0° C. until the color of the indicator turned red. Stirring was continued for 2 hours at 0° C. and then the reaction solution was neutralized with triethylamine. The reaction mixture was diluted with dichloromethane (150 mL), filtered and washed with 6% sodium bicarbonate (5×500 mL) and water (5×500 mL), dried over $Na_2SO_4$, filtered and the solvent evaporated. The residue was purified by chromatography on silica gel with hexane-ethyl acetate (2:1) as eluent to provide for compound 377 (7.0 g, 83%).

Step G—Preparation of 1-Benzamido-6-O-benzyl-2-deoxy-2-phthalimido-3-O-(2,3,4-tri-O-benzyl-α-L-fucopyranosyl)-4-O-[2,3,4,6-tetra-O-acetyl-β-D-galactopyranosyl]-β-D-glucopyranoside (compound 379).

A mixture of compound 377 (2.36 g, 2.60 mmol), phenyl 2,3,4,6-tetra-O-acetyl-β-D-thiogalactopyranoside, compound 378 (2.33 g, 5.2 mmol) and 4A molecular sieves (11.8 g) was stirred at −20° C. in dichloromethane-ether (1:1, 40 mL). NIS (N-iodosuccinimide) (1.73 g, 7.7 mmol) was added followed by triflic acid solution (0.24 mL). Stirring was continued for 2 hours at −20° C. and triethylamine was then added to quench the reaction. After evaporation of the solvent, the residue was purified by chromatography on silica gel column using hexane-ethyl acetate (1:1) as the eluent to provide compound 379 (2.1 g, 65.5%).

Step H—Preparation of 1-benzamido-6-O-benzyl-2-deoxy-2-phthalimido-3-O-(2,3,4-tri-O-benzyl-α-L-fucopyranosyl)-4-O-[β-D-galactopyranosyl]-β-D-glucopyranoside (compound 380).

Compound 379 (2.1 g, 1.68 mmol) was treated with 0.05M sodium methoxide in methanol (20 mL) at 0° C. for 4 hours. The reaction solution was then neutralized with Amberlite IR-120 ($H^+$) resin. The reaction solution was then filtered and the solvent evaporated to provide for compound 380 (1.5 g, 83%).

Step I—Preparation of 1-Benzamido-6-O-benzyl-2-deoxy-2-phthalimido-3-O-(2,3,4-tri-O-benzyl-α-L-fucopyranosyl)-4-O-[4,6-O-benzylidene-β-D-galactopyranosyl]-β-D-glucopyranoside (compound 381)

p-Toluene sulfonic acid (30 mg) was added to a solution of compound 380 (600 mg, 0.56 mmol) in acetonitrile (50 mL) followed by addition of benzaldehyde dimethylacetal (600 μL). After stirring for 2 hours at room temperature, the reaction mixture was neutralized with triethylamine and the solvent evaporated. The residue was purified by chromatography using hexane-ethyl acetate (1:1) an eluent to provide for compound 381 (535 mg, 82.4%).

Step J—Preparation of 1-Benzamido-6-O-benzyl-2-amino-2-deoxy-3-O-(2,3,4-tri-O-benzyl-α-L-fucopyranosyl)-4-O-[4,6-O-benzylidene-β-D-galactopyranosyl]-β-D-glucopyranoside (compound 382)

Compound 381 (535 mg, 0.46 mmol) was dissolved in methanol (5.0 mL) and a solution of hydrazine hydrate (1.75 mL, 70 eq) was added. The reaction mixture was refluxed for 9 hours at 75° C. followed by evaporation and co-evaporation with toluene (3×20 mL) to provide for compound 382 quantatively.

Step K—Preparation of 2-benzamido-6-O-benzyl-2-deoxy-3-O-(2,3,4-tri-O-benzyl-α-L-fucopyranosyl)-4-O-[4,6-O-benzylidene-β-D-galactopyranosyl]-β-D-glucopyranosyl benzamide (compound 383)

Compound 382 (450 mg, 0.43 mmol) was dissolved in methanol (10 mL) and then there was added thereto a saturated solution of sodium bicarbonate (20 mL) followed by benzoyl chloride (450 μL) at 0° C. The reaction solution was stirred for 0.5 hours by which time most of the starting material was converted to the product. The reaction solution was diluted with dichloromethane (150 mL) and washed with ice cold 6% solution of sodium bicarbonate (2×150 mL) and water (2×150 mL) dried over $Na_2SO_4$ filtered and the solvent evaporated. The residue was purified by chromatography on Iatrobeads using ethyl acetate as eluent to provide the product 383 (300 mg, 60.6%).

Step L—Preparation of 2-Benzamido-6-O-benzyl-2-deoxy-3-O-(2,3,4-tri-O-benzyl-α-L-fucopyranosyl)-4-O-[4,6-O-benzylidene-3-O-sulfo-β-D-galacto-pyranosyl]-β-D-glucopyranosyl benzamide (compound 384)

Sulfur trioxide-pyridine complex (62 mg, 0.39 mmol) was added to compound 383 (300 mg, 0.26 mmol) in pyridine (3 mL) at 0° C. The reaction mixture was allowed to warm to room temperature and more $SO_3$-pyridine complex was added (1.5 eq). Stirring was continued for 3 hours and methanol (5 mL) was then added. After evaporation of the solvent, the residue was purified by chromatography on silica gel Iatrobeads using dichloromethane-methanol-pyridine (9:1:0.1) as eluent to provide compound 384 (280 mg, 85.6%).

Step M—Preparation of 2-benzamido-2-deoxy-3-O-(α-L-fucopyranosyl)-4-O-[3-O-sulfo-β-D-galactopyranosyl]-β-D-glucopyranosyl benzamide sodium salt (compound 385)

Compound 384 (280 mg, 0.22 mmol) was hydrogenated in methanol (20 mL) using 5% palladium on carbon (1.5 g) as a catalyst as described above to provide for compound 385 (140 mg, 78%) as its sodium salt.

Example 47

Preparation of 8-methoxycarbonyloctyl-2-amino-3-O-(α-L-fucopyranosyl)-4-O-[4,6-dichloro-dideoxy-3-O-sulfo-β-D-galactopyranosyl]-2-deoxy-β-D-glucopyranoside (compound 390)

Figure 32:
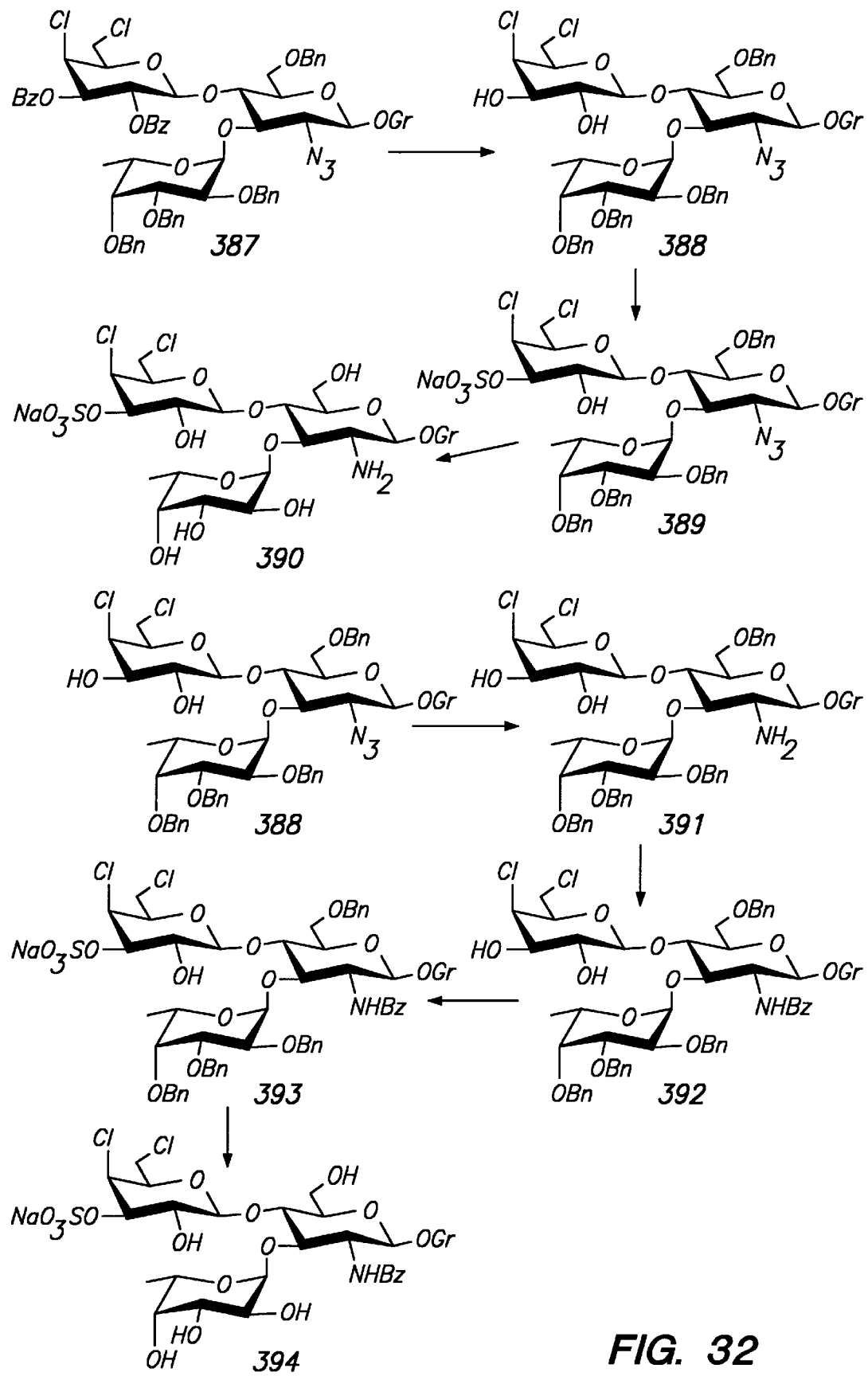

The synthesis of this compound is illustrated in FIG. 31 and 32.

Step A—Preparation of 8-methoxycarbonyloctyl-2-azido-3-O-(2,3,4tri-O-benzyl-α-L-fucopyranosyl)-40-[2,3-di-O-benzoyl-4,6-dichloro-dideoxy-β-D-galactopyranosyl)-6-O-benzyl-2-deoxy-β-D-glucopyranoside (compound 387).

Compound 386 (3.0 g, 3.40 mmol) and imidate donor (5.81 g, 10.2 mmol) were dissolved in a mixture of ether-dichloromethane (33 mL, 2:1) and stirred at −10° for 15 minutes. Boron trifluoride ethereate (2.3 mL) was added and the reaction mixture was stirred under nitrogen for 15 hours at 0° C. The reaction solution was diluted with dichloromethane (250 mL) and washed with cold saturated NaHCO$_3$ (2×250 mL) and cold water (2×250 mL), dried over Na$_2$SO$_4$, filtered and the solvent evaporated to dryness. The residue was purified by chromatography on Iatrobeads using dichloromethane-methanol (99:1) as the eluent to provide for compound 387 (3.5 g, 80%).

Step B—Preparation of 8-methoxycarbonyloctyl-2-azido-3-O-(2,3,4-tri-O-benzyl-α-L-fucopyranosyl)-4-O-[4,6-dichloro-dideoxy-β-D-galactopyranosyl]-6-O-benzyl-2-deoxy-β-D-glucopyranoside (compound 388)

Compound 387 (3.5 g, 2.71 mmol) was dissolved in methanol (100 mL) and a solution of sodium methoxide in methanol (10.0 mL, 0.5M) was added and the reaction mixture was stirred for 5 hours at room temperature. The reaction solution was neutralized with Amberlite IR-120 (H$^+$) resin, filtered and the solvent evaporated to provide for compound 388 (2.3 g, 79%).

Step C—Preparation of 8-methoxycarbonyloctyl-2-azido-3-O-(2,3,4-tri-O-benzyl-α-L-fucopyranosyl)-4-O-[4,6-dichloro-dideoxy-3-O-sulfo-β-D-galactopyranosyl]-6-O-benzyl-2-deoxy-β-D-glucopyranoside (compound 389)

Compound 388 (528 mg, 0.49 mmol) was dissolved in dry pyridine (3.0 mL) and SO$_3$-pyridine complex (117.78 mg, 0.74 mmol) was added at 0° C. and the reaction mixture was stirred for 0.5 hours at 0° C. and then for 9 hours at room temperature. An additional amount of SO$_3$-pyridine complex (117.78 mg, 0.74 mmol) was added followed by stirring the mixture for 0.5 hours at room temperature. Afterwards, methanol (5.0 mL) was added to the reaction solution and the solvent was evaporated and the residue purified by chromatography on Iatrobead using dichloromethane-methanol-pyridine (95:5:0.1) as eluent to provide for compound 389 (301 mg, 51%).

Step D—Preparation of 8-methoxycarbonyloctyl-2-amido-3-O-(α-L-fucopyranosyl)-4-O-[4,6-dichloro-dideoxy-3-O-sulfo-β-D-galactopyranosyl]-2-deoxy-β-D-glucopyranoside sodium salt (compound 390)

Compound 389 (301 mg, 0.25 mmol) was dissolved in methanol (16.0 mL) containing .01M HCl in methanol (2.2 mL) and hydrogenated with 5% palladium on carbon (500 mg) for 1 hour at atmospheric pressure to obtain the product 390 (150 mg, 76%) after purification on Iatrobeads using dichloromethane:methanol:water:pyridine (80:20:2:1) as eluent followed by conversion into sodium salt.

Example 48

Preparation of 8-methoxycarbonyloctyl-2-benzamido-3-O-(α-L-fucopyranosyl)-4-O-[4,6-dichloro-dideoxy-3-O-sulfo-β-D-galactopyranosyl]-2-deoxy-β-D-glucopyranoside (compound 394)

The synthesis of compound 394 is illustrated in FIG. 32. Step A—Preparation of 8-methoxycarbonyloctyl-2-amino-3-O-(2,3,4tri-O-benzyl-α-L-fucopyranosyl)-4-O-[4,6-dichloro-dideoxy-β-D-galactopyranosyl]-2-deoxy-β-D-glucopyranoside (compound 391).

Compound 388 (1.35 g, 1.25 mmol) was dissolved in a mixture of pyridine:water:triethylamine (6:1:0.2). A stream of hydrogen sulfide was bubbled through the solution at 0° C. for 0.5 hours and then at room temperature for 15 hours. The mixture was evaporated and co-evaporated with toluene and purified by chromatography on silica gel using ethyl acetate:hexane (4:1) as eluent to provide for compound 391 (800 mg, 61%).

Step B—Preparation of 8-methoxycarbonyloctyl-2-benzamido-3-O-(2,3,4-tri-O-benzyl-α-L-fucopyranosyl)-4-O-[4,6-dichloro-dideoxy-β-D-galactopyranosyl]-6-O-benzyl-2-deoxy-β-D-glucopyranoside (compound 392)

Compound 391 (800 mg, 0.76 mmol) was dissolved in methanol (10 mL) and a 6% solution of NaHCO$_3$ (10 mL) was added followed by addition of benzoyl chloride (500 μL) at 0° C. The reaction mixture was stirred for 0.5 hours at 0° C. by which time most of the starting material was converted to the product. The reaction solution was diluted with dichloromethane (150 mL) and washed with water (2×150 mL), dried over Na$_2$SO$_4$, filtered, evaporated and the residue was purified by chromatography on silica gel using ethyl acetate:hexane (4:1) as eluent to provide for compound 392 (690 mg, 79%).

Step C—Preparation of 8-methoxycarbonyloctyl-2-benzamido-3-O-(2,3,4-tri-O-benzyl-α-L-fucopyranosyl)-4-O-[4,6-dichloro-dideoxy-3-O-sulfo-β-D-galactopyranosyl]-6-O-benzyl-2-deoxy-β-D-glucopyranoside (compound 393)

Compound 392 (246 mg, 0.21 mmol) was dissolved in dry pyridine (3.0 mL) and SO$_3$-pyridine complex (50.9 mg, 0.32 mmol) was added thereto at 0° C. The reaction mixture was stirred at 0° C. for 0.5 hours then 1 hour at room temperature. An additional amount of SO$_3$-pyridine complex (50.9 mg, 0.35 mmol) was added followed by stirring for 2 hours at room temperature. The reaction mixture was evaporated after addition of methanol (2.0 mL) and the residue was purified by silica gel column chromatography using dichloromethane:methanol:pyridine (95:5:0.1) as eluent to provide for compound 393 (176 mg, 67%).

Step D—Preparation of 8-methoxycarbonyloctyl-2-benzamido-3-O-(α-L-fucopyranosyl)-4-O-[4,6-dichloro-dideoxy-3-O-sulfo-β-D-galactopyranosyl]-2-deoxy-β-D-glucopyranoside (compound 394)

Compound 393 (176 mg, 0.14 mmol) was hydrogenated in methanol (20 mL) using 5% palladium on carbon as the hydrogenation catalyst (352 mg) in the manner described above to provide for compound 394 (111.0 mg, 86%).

Example 49

Preparation of 8-methoxycarbonyloctyl-2-benzamido-3-O-(α-L-fucopyranosyl)-4-O-[4,6-dideoxy-3-O-sulfo-β-D-galactopyranosyl]-2-deoxy-β-D-glucopyranoside (compound 397)

Figure 33:
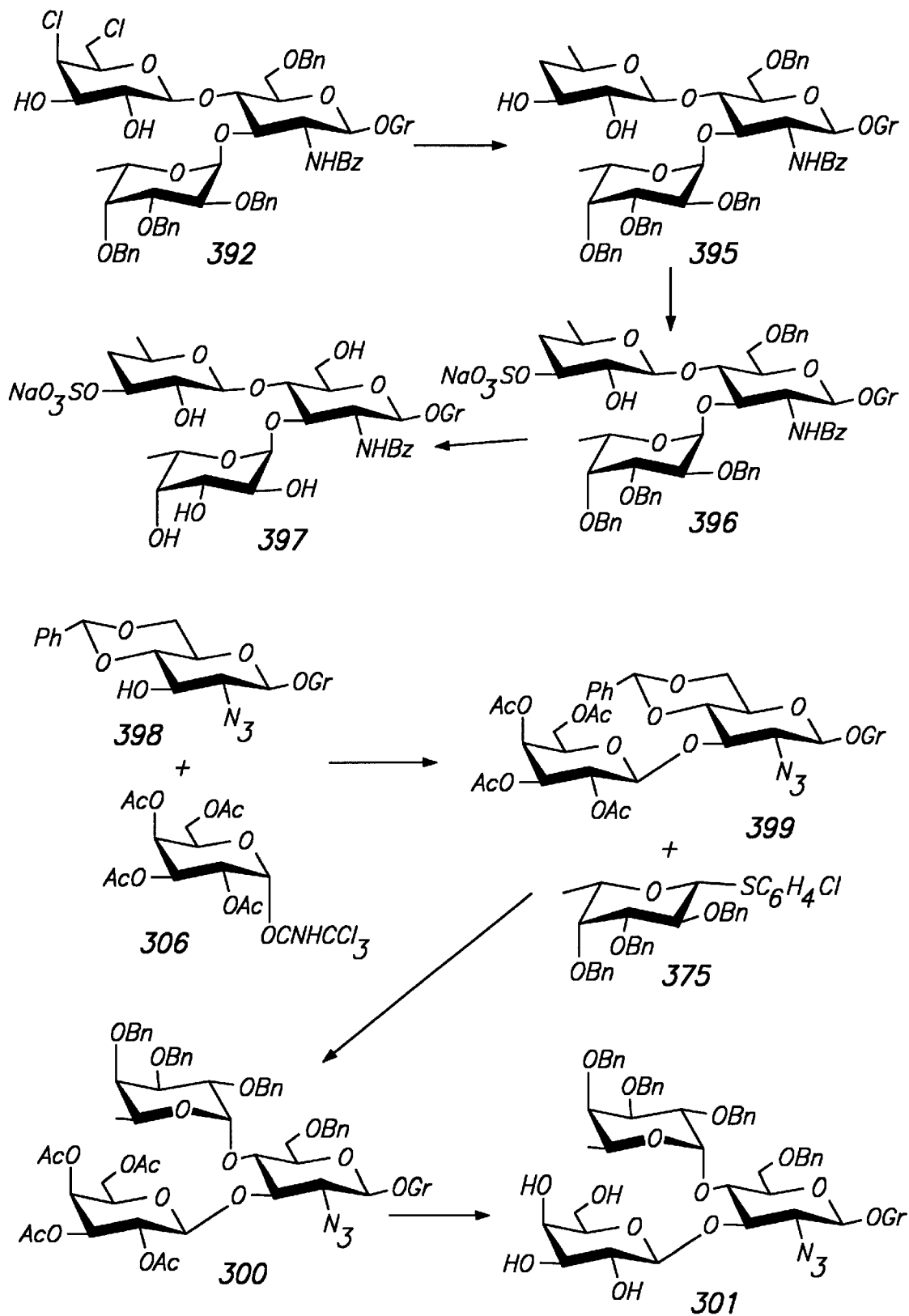

The synthesis of compound 397 is illustrated in FIG. 33. Step A—Preparation of 8-methoxycarbonyloctyl-2-benzamido-3-O-(2,3,4-tri-O-benzyl-α-L-fucopyranosyl)-4-O-[4,6-dideoxy-β-D-galactopyranosyl]-6-O-benzyl-2-deoxy-β-D-glucopyranoside (compound 395)

Tributyltin hydride (1.88 mL) and AIBN (20 mg) were added to a mixture of compound 392 (401 mg, 0.35 mmol) in dry toluene (20 mL) and the resulting solution was refluxed for 5 hours at 90° C. The solvent was evaporated and the residue purified by chromatography on Iatrobeads using hexane:ethyl acetate (1:1) as eluent to provide for compound 395 (340 mg, 89%).

Step B—Preparation of 8-methoxycarbonyloctyl-2-benzamido-3-O-(2,3,4-tri-O-benzyl-α-L-fucopyranosyl)-4-O-[4,6-dideoxy-3-O-sulfo-β-D-galactopyranosyl]-6-O-benzyl-2-deoxy-β-D-glucopyranoside (compound 396)

SO$_3$-pyridine complex (74.8 mg, 0.47 mmol) was added to a solution of compound 395 (340 mg, 0.33 mmol) in pyridine (3.0 mL) at 0° C. The reaction mixture was stirred for 15 minutes at this temperature and then for 1 hour at room temperature. An additional amount of SO$_3$-pyridine complex (74.8 mg) was added followed by stirring for 1 hour at room temperature. The solvent was evaporated. After addition of methanol (2.0 mL), the product was purified by chromatography on Iatrobeads using dichloromethane:methanol:pyridine as eluent (95:5:0.1) to provide for compound 396 (297 mg, 81%).

Step C—Preparation of 8-methoxycarbonyloctyl-2-benzamido-3-O-(αL-fucopyranosyl)-4-O-[4,6-dideoxy-3-O-sulfo-β-D-galactopyranosyl]-2-deoxy-β-D-glucopyranoside (compound 397)

Compound 396 (297 mg, 0.25 mmol) was dissolved in methanol (20 mL) and hydrogenated with 5% palladium on carbon (600 mg) for 0.5 hours at room temperature in the manner described above to provide for compound 397 (153.4 mg, 72%) as a sodium salt.

Example 50

Preparation of 8-methoxycarbonyloctyl-2-amino-4-O-(α-L-fucopyranosyl)-3-O-[3-O-sulfo-β-D-galactopyranosyl]-2-deoxy-β-D-glucopyranoside sodium salt (compound 404)

Figure 34:
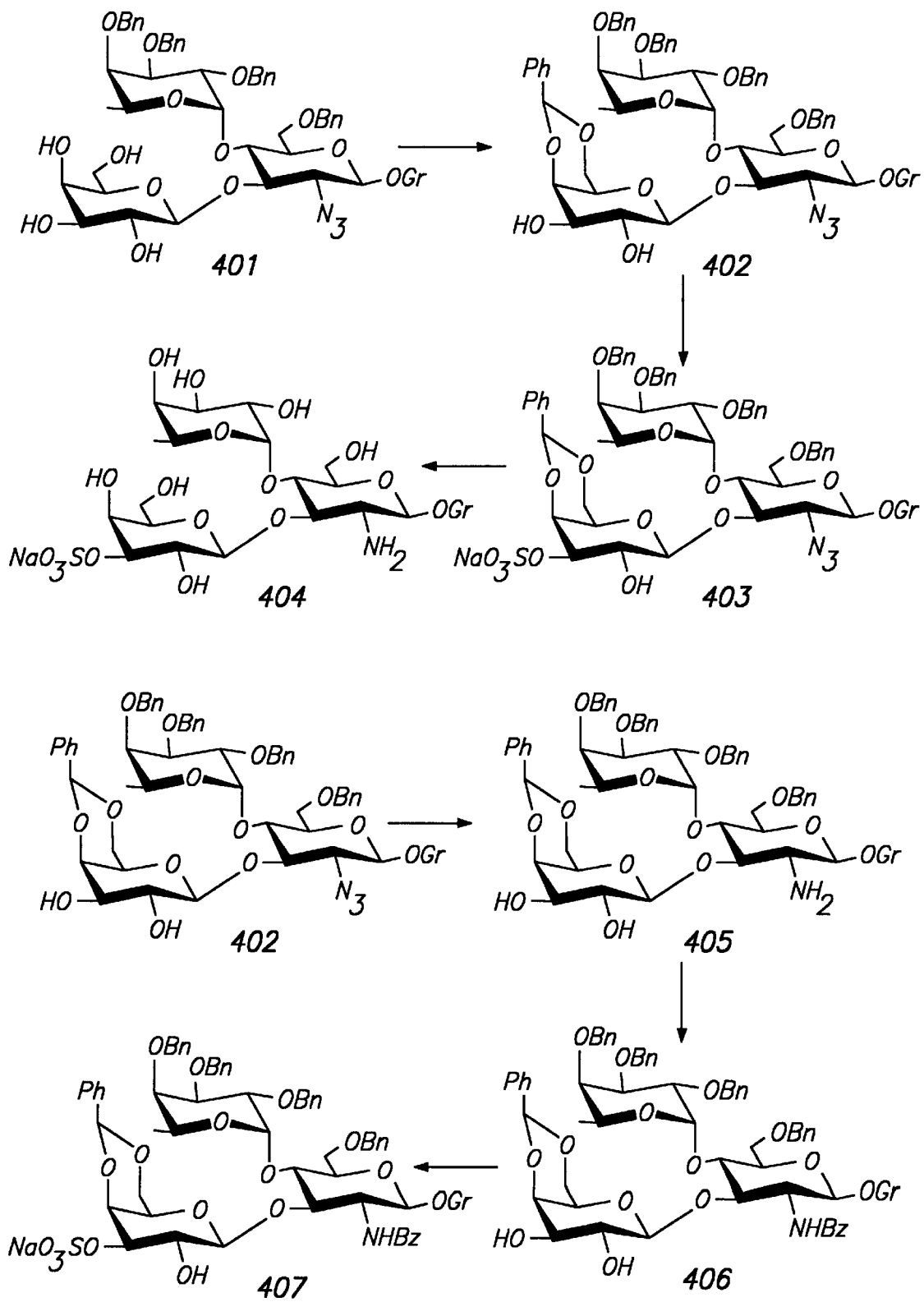

The synthesis of this compound is illustrated in FIGS. 33 and 34.

Step A—Preparation of azido-(2,3,4,6-tetra-O-acetyl-β-D-galactopyranosyl)-4,6-O-benzylidene-2-deoxy-β-D-glucopyranoside (compound 399).

Compound 398 (10.8 g, 23.3 mmol), compound 306 (14.9 g, 30.3 mmol) and molecular sieves were added to 1,2-dichloroethane (10.0 mL) and the resulting mixture stirred for 1 hour at room temperature. The mixture was then cooled to −18° C. and a solution of trimethylsilyltriflate (1.72 mL) in 1,2-dichloroethane (1.0 mL) was added and the resulting mixture stirred for 0.5 hours. Triethylamine was then added at −18° C. to quench the reaction and the reaction solution diluted with dichloromethane (50 mL) and filtered. The solvent was evaporated and the residue purified by chromatography on Iatrobeads using toluene-ethyl acetate (6:1) as eluent to provide for compound 399 (15.0 g, 81%).

Step B—Preparation of 8-methoxycarbonyloctyl-2-azido-3-O-(2,3,4,6tetra-O-acetyl-β-D-galactopyranosyl)-6-O-benzyl-2-deoxy-β-D-glucopyranoside (compound 399a)

To a mixture of compound 399 (9.36 g, 11.79 mmol) in diethyl ether saturated with HCl was added at 0° C. sodium cyanoborohydride (7.41 g, 117.9 mmol), a few crystals of methyl orange and 3A molecular sieves (9.36 g) in dry THF (300 mL) until the color of the indicator turned red. The stirring was continued for 3 hours and the reaction mixture was then neutralized with triethylamine and filtered. The filtrate was washed with water (2×500 mL), aqueous sodium bicarbonate (2×500 mL) and water (2×500 mL), dried over $Na_2SO_4$, filtered, evaporated. The residue was purified by chromatography on silica gel using hexane-ethyl acetate (2:1) as eluent to provide compound 399a (7.28 g, 78%).

Step C—Preparation of 8-methoxycarbonyloctyl-2-azido-4-O-(2,3,4-tri-O-benzyl-α-L-fucopyranosyl)-3-O-[2,3,4,6-tetra-O-acetyl-β-D-galactopyranosyl]-6-O-benzyl-2-deoxy-β-D-glucopyranoside (compound 400)

DMF (12.0 mL) and tetraethylammonium bromide (1.92 g, 9.15 mmol) were added to a suspension of copper bromide (18.40 g, 82.53 mmol) and 4A molecular sieves (14.56 g) in dichloromethane (30 mL). The reaction mixture was stirred at room temperature for 0.5 hours and then a solution of compound 399a (7.28 g, 9.15 mmol) in dichloromethane (10.0 mL) and thioglycoside 375 (25.67 g, 45.75 mmol) were added. The mixture was kept in the dark for 15 hours and the reaction solution was diluted with dichloromethane (250 mL). The molecular sieves were filtered and washed with dichloromethane (250 mL). The filtrate was washed successively with saturated EDTA solution (5×500 mL), 6% sodium bicarbonate solution (3×500 mL) and water (3×500 mL) dried over sodium sulfate, filtered, and the solvent evaporated. The residue was purified by chromatography on silica gel using hexane:ethyl acetate (3:1) as eluent to provide for compound 400 (9.15 g, 83%)

Step D—Preparation of 8-methoxycarbonyloctyl-2-azido-4-O-[2,3,4-tri-O-benzyl-α-L-fucopyranosyl]-3-O-[β-D-galactopyranosyl]-6-O-benzyl-2-deoxy-β-D-glucopyranoside (compound 401)

Compound 400 (9.1 g, 7.51 mmol) was dissolved in methanol (50 mL) and a solution of sodium methoxide in methanol (10.0 mL, 0.5M) was added thereto. The reaction mixture was stirred for 5 hours at room temperature and the reaction solution was then neutralized with Amberlite IR-120 ($H^+$) resin, filtered and the solvent evaporated to provide for compound 401 (7.5 g, 96%).

Step E—Preparation of 8-methoxycarbonyloctyl-2-azido-3-O-[4,6-O-benzylidene-β-D-galactopyranosyl]-4-O-[2,3,4-tri-O-benzyl-α-L-fucopyranosyl]-6-O-benzyl-2-deoxy-β-D-glucopyranose (compound 402)

p-Toluene sulfonic acid (310 mg) was added to a solution of compound 401 (7.2 g, 6.9 mmol) in acetonitrile (250 mL) followed by the addition of α,α-dimethoxytoluene (2.1 mL, 13.8 mmol). After stirring the reaction mixture for 5 hours at room temperature, it was neutralized with triethylamine and the solvent evaporated. The residue was purified by chromatography on silica gel using hexane-ethyl acetate (1:1) as eluent to provide for compound 402 (6.5 g, 83%).

Step F—Preparation of 8-methoxycarbonyloctyl-2-azido-3-O-[4,6-O-benzylidene-3-O-sulfo-β-D-galactopyranosyl]-4-O -(2,3,4-tri-O-benzyl-α-L-fucopyranosyl)-6-O-benzyl-2-deoxy-β-D-glucopyranoside (compound 403)

Sulfur trioxide-pyridine complex (127.33 mg, 0.80 mmol) was added to a solution of compound 402 (600 mg, 0.53 mmol) in pyridine (5.0 mL) at 0° C. and the reaction mixture was stirred for 1 hour at room temperature. An additional amount of $SO_3$-pyridine (1.5 eq) complex was added and the reaction mixture stirred for 3 hours at room temperature. After addition of methanol (2.0 mL), the solvent was evaporated and the residue was purified by chromatography on Iatrobeads using dichloromethane-methanol-pyridine (95:5:0.1) as eluent for compound 403 (420 mg, 64%).

Step G—Preparation of 8-methoxycarbonyloctyl-2-amino-3-O-[3-O-sulfo-β-D-galactopyranosyl]-4-O-(α-L-fucopyranosyl)-2-deoxy-β-D-glucopyranoside sodium salt (compound 404)

Compound 403 (350 mg, 0.28 mmol) and 5% palladium on carbon (700 mg) in methanol (20 mL) was hydrogenated as described above to provide for compound 404 (175 mg, 82%) after conversion to the sodium salt.

Example 51

Preparation of 8-methoxycarbonyloctyl-2-benzamido-3-O-[3-O-sulfo-β-D-galactopyranosyl]-4-O-(α-L-fucopyranosyl)-2-deoxy-β-D-glucopyranoside (compound 408)

Figure 35:
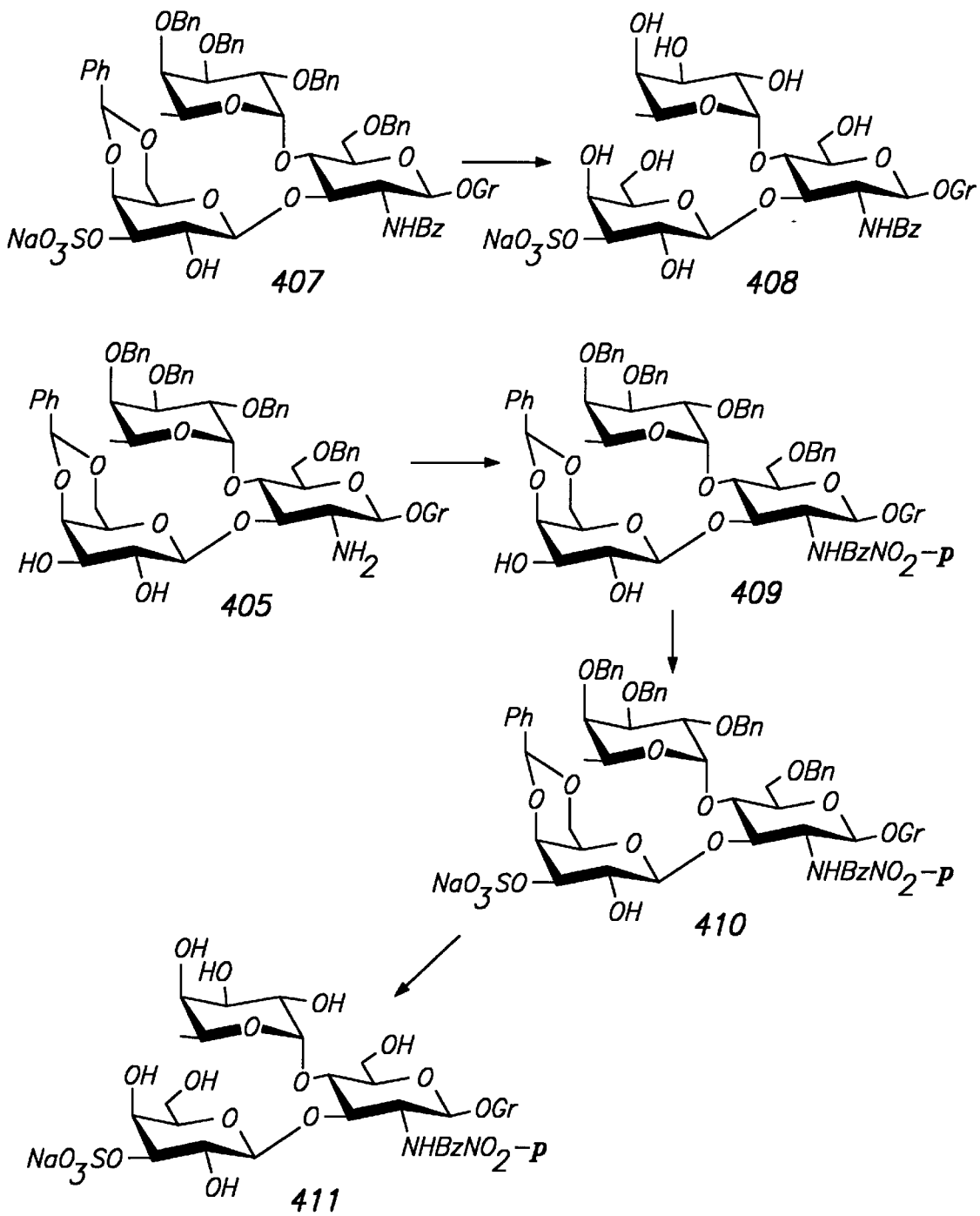

The synthesis of compound 408 is illustrated in FIGS. 34 and 35.

Step A—Preparation of 8-methoxycarbonyloctyl-2-amino-3-O-[4,6-O-benzylidene-β-D-galactopyranosyl]-4-O-(2,3,4-tri-O-benzyl-(αL-fucopyranosyl)-6-O-benzyl-2-deoxy-β-D-glucopyranoside (compound 405)

Compound 402 (750 mg, 0.66 mmol) was dissolved in a mixture of pyridine-water-triethylamine (4:1:0.1, 10 mL) at 0° C. and hydrogen sulfide gas was passed through over 1 hour at 0° C. and then 15 hours at room temperature. The reaction mixture was evaporated and co-evaporated with toluene to provide 2-amino-derivative, compound 405, quantitatively.

Step B—Preparation of 8-methoxycarbonyloctyl-2-benzamido-3-O-[4,6-O-benzylidene-β-D-galactopyranosyl]-4-O-(2,3,4-tri-O-benzyl-α-L-fucopyranosyl)-6-O-benzamido-2-deoxy-β-D-glucopyranoside (compound 406)

Compound 405 (450 mg, 0.41 mmol) was dissolved in methanol (5.0 mL) and a saturated sodium hydrogen carbonate solution (2.0 mL) was added at 0° C. followed by addition of benzoyl chloride (225 μL) and the reaction mixture was stirred for 1 hour at 0° C. and then for 3 hours at room temperature. The reaction solution was diluted with dichloromethane (100 mL), washed with water (2×100 mL), dried over $Na_2SO_4$, filtered and evaporated. The residue was purified by chromatography on Iatrobeads using ethyl acetate-hexane (2:1) as eluent to provide for compound 406 (400 mg, 80%).

Step C—Preparation of 8-methoxycarbonyloctyl-2-benzamido-3-O-[4,6-O-benzylidene-3-O-sulfo-β-D-galactopyranosyl]-4-O-(2,3,4-tri-O-benzyl-α-L-fucopyranosyl)-6-O-benzyl-2-deoxy-β-D-glucopyranoside sodium salt (compound 407)

Compound 406 (350 mg, 0.29 mmol) was dissolved in pyridine (3.0 mL) and $SO_3$-pyridine complex (70 mg, 0.44 mmol) was added as a solid at 0° C. The reaction mixture was stirred for 0.5 hours at 0° C. and 1 hour at room temperature. Further addition of $SO_3$-pyridine complex (1.0 eq) was made followed by stirring the mixture at room temperature for 3 hours. The solvent was evaporated after addition of methanol (2.0 mL) and purified by chromatography on Iatrobeads using dichloromethane-methanol-pyridine (95:5:0.1) as eluent to provide for compound 407 (285 mg, 76%) as a sodium salt by passage through Dowex-50-X-8 ($Na^+$) column.

Step D—Preparation of 8-methoxycarbonyloctyl-2-benzamido-3-O-[3-O-sulfo-β-D-galactopyranosyl]-4-O-(α-L-fucopyranosyl)-2-deoxy-β-D-glucopyranoside sodium salt (compound 408).

Compound 407 (250 mg, 0.19 mmol) was hydrogenated in methanol (10 mL) using 5% palladium on carbon (250 mg) for 5 hours at atmospheric pressure and room temperature in the manner described above to provide for compound 408 (155 mg, 95%) as a sodium salt.

Example 52

Preparation of 8-methoxycarbonyloctyl-2-p-nitrobenzamido-3-O-[3-O-sulfo-β-D-galactopyranosyl]-4-O-(α-L-fucopyranosyl)-2-deoxy-β-D-glucopyranoside (compound 411)

The synthesis of compound 411 is illustrated in FIG. 35.
Step A—Preparation of 8-methoxycarbonyloctyl-2-p-nitrobenzamido-3-O-[4,6-O-benzylidene-β-D-galactopyranosyl]-4-O-(2,3,4-tri-O-benzyl-α-L-fucopyranosyl)-6-O-benzyl-2-deoxy-β-D-glucopyranoside (409)

Compound 405 (500 mg, 0.45 mmol) was dissolved in dichloromethane (10.0 mL) and 4-nitrobenzoic acid (500 mg) and 1-(3-dimethylaminopropyl)-3-ethyl carbodiimide hydrochloride (500 mg) were added thereto. The reaction mixture was stirred for 1 hour at room temperature. The solvent was then evaporated and the residue purified by chromatography on Iatrobeads using hexane-ethyl acetate (1:1) as eluent to provide for compound 409 (314 mg, 56%).
Step B—Preparation of 8-methoxycarbonyloctyl-2-p-nitrobenzamido-3-O-[4,6-O-benzylidene-3-O-sulfo-β-D-galactopyranosyl]-4-O-(2,3,4tri-O-benzyl)-α-L-fucopyranosyl)-6-O-benzyl-2-deoxy-β-D-glucopyranoside (compound 410)

Compound 409 (314 mg, 0.25 mmol) was sulfated with $SO_3$-pyridine complex (118 mg) by dissolving in pyridine (3.0 mL) and stirring the reaction mixture at 0° C. for 0.5 hours and then for 2 hours at room temperature. The reaction was quenched by the addition of methanol and the solvent evaporated. The residue was purified by chromatography on Iatrobeads using dichloromethane-methanol-pyridine (95:5:0.5) as the eluent to provide for compound 410 (275 mg, 80%).
Step C—Preparation of 8-methoxycarbonyloctyl-2-p-nitrobenzamido-3-O-[3-O-sulfo-β-D-galactopyranosyl]-4-O-(α-L-fucopyranosyl)-2-deoxy-β-D-glucopyranoside sodium salt (compound 411)

Compound 410 (275 mg, 0.20 mmol) was hydrogenated in methanol (10 mL) using 5% palladium on carbon (275 mg) as described above to provide for compound 411 as a sodium salt (175 mg, 95%).

Example 53

Preparation of 8-methoxycarbonyloctyl-2-(fuc(c)-amido)-4-O-[3-O-sulfo-β-D-galactopyranosyl]-2-deoxy-β-D-glucopyranoside (compound 423)

Figure 36:
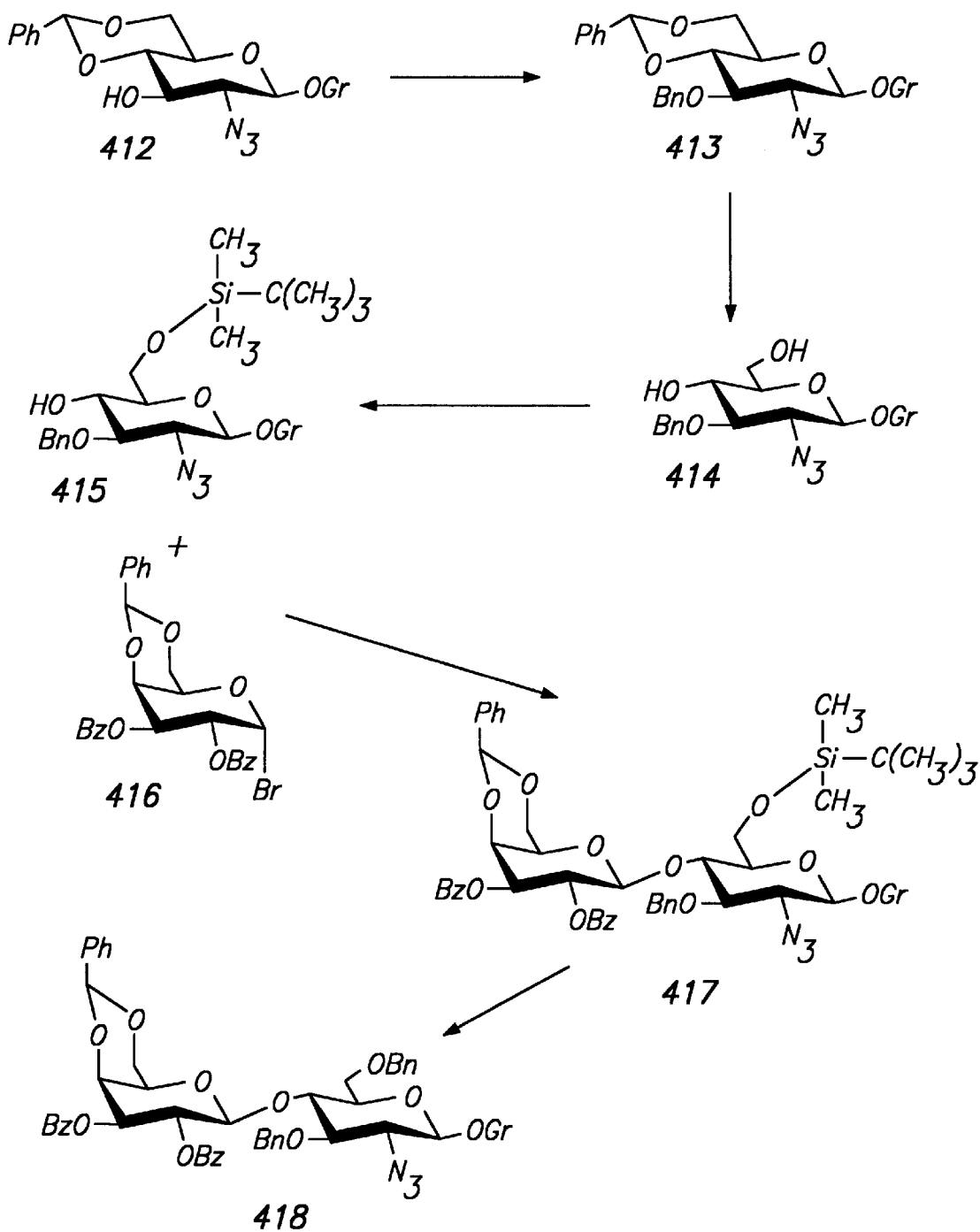
Figure 37:
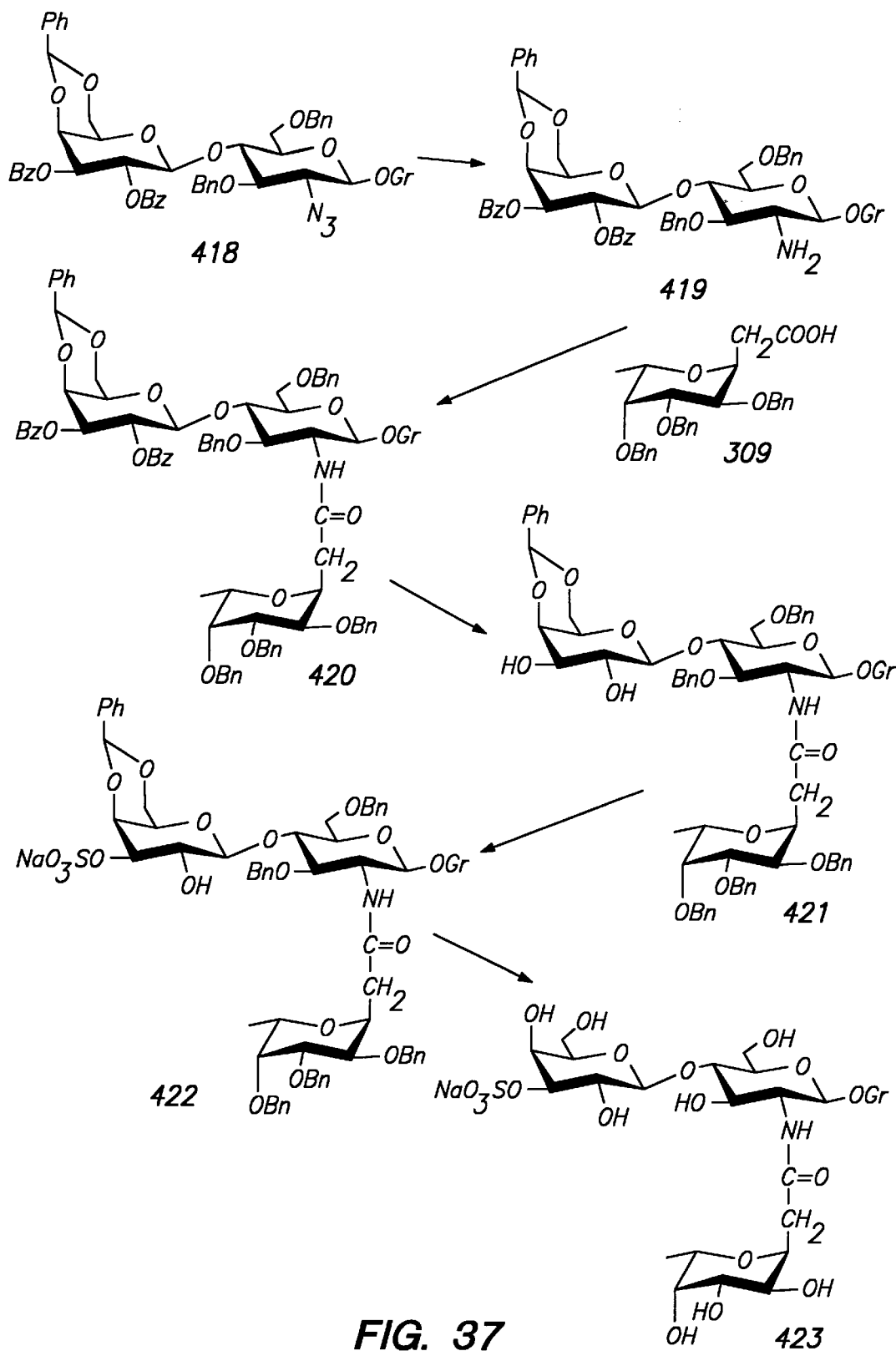

The synthesis of compound 423 is illustrated in FIGS. 36 and 37.
Step A—Preparation of 8-methoxycarbonyloctyl-2-azido-2-deoxy-3-O-benzyl-4,6-O-benzylidene-β-D-glucopyranoside (compound 413)

To a stirred solution of compound 412 (2.5 g, 5.39 mmol) in dry toluene (15.0 mL) were added benzyl bromide (1.28 mL, 10.78 mmol) and freshly prepared silver oxide (2.5 g), and the reaction mixture was then stirred for 15 hours. At this point, reaction was not complete and an additional amount of silver oxide (2.5 g) was added and the reaction stirred for 2 days. The reaction system was diluted with dichloromethane (100 mL) and the resulting solution was filtered through Celite and the residue was washed with dichloromethane. The solvent was evaporated and the residue purified by chromatography on silica gel using hexane-ethyl acetate (4:1) as eluent to provide for compound 413 (2.1 g, 70%).
Step B—Preparation of 8-methoxycarbonyloctyl-2-azido-2-deoxy-3-O-benzyl-β-D-glucopyranoside (compound 414)

Compound 413 (2.4 g, 4.33 mmol) was dissolved in 80% aqueous acetic acid (10.0 mL) and heated to 80° C. for 3 hours. The mixture was evaporated and diluted with dichloromethane (50 mL) and washed successively with saturated $NaHCO_3$ solution (2×5 mL), water (2×50 mL), dried over $Na_2SO_4$, filtered, and the solvent evaporated. The residue was purified by chromatography on silica gel using hexane-ethyl acetate (1:1) as eluent to provide for compound 414 (1.6 g, 79%).
Step C—Preparation of 8-methoxycarbonyloctyl-2-azido-2-deoxy-3-O-benzyl-6-O-tert-butyldimethylsilyl-β-D-glucopyranoside (compound 415)

Compound 414 (1.6 g, 3.44 mmol) was dissolved in dry DMF (5.0 mL) and imidazole (0.5 g, 2.2 eq) and tert-butyldimethyl silyl chloride (775 mg, 5.16 mmol) were added thereto. The reaction solution was stirred for 5 hours at room temperature and was then diluted with dichloromethane (50 mL) and washed successively with water (2×50 mL), 6% sodium bicarbonate (2×50 mL) and water (2×50 mL), dried over $Na_2SO_4$, filtered and evaporated to provide a residue which was purified by chromatography on silica gel using hexane-ethyl acetate (9:1) as eluent to provide for compound 415 (1.72 g, 86%).
Step D—Preparation of 8-methoxycarbonyloctyl-2-azido-3-O-benzyl-4-O-(4,6-O-benzylidene-2,3-di-O-benzoyl-β-D- galactopyranosyl)-6-O-tert-butyl-dimethyl-silyl-β-D-glucopyranoside (compound 417)

To a mixture of compound 415 (1.6 g, 2.7 mmol), galactosyl bromide 416 (3.72 g, 6.90 mmol) and molecular sieves (3.2 g) in nitromethane-toluene (1:1, 10 mL) at 0° C. was added dropwise a solution of 2,6-dimethylaminopyridine (843 mg, 6.90 mmol) and silver triflate (1.77 g, 6.90 mmol) in nitromethane-toluene (5.0 mL) and the resulting solution was allowed to room temperature after 1 hour. The reaction solution was then diluted with dichloromethane (50 mL) and washed with cold saturated solution of $NaHCO_3$ (2×50 mL), water (2×50 mL), dried over $Na_2SO_4$ filtered and the solvent co-evaporated to dryness. The residue was purified by chromatography on silica gel using hexane-ethyl acetate (9:1, 5:1) as eluent to provide product 417 (1.76 g, 62%).

Step E—Preparation of 8-methoxycarbonyloctyl-2-azido-2-deoxy-3,6-di-O-benzyl-4-O-(4,6-O-benzylidene-2,3-di-O-benzoyl)-β-D-glucopyranoside (compound 418)

Compound 417 (1.76 g, 1.70 mmol) was treated with 80% aqueous acetic acid for 8 hours at room temperature. Evaporated and co-evaporated with toluene and the residue was purified by chromatography on silica gel using hexane-ethyl acetate (4:1) as eluent to provide for compound (418a) which was benzylated with benzyl bromide and silver oxide in toluene as described earlier to provide compound 418 (1.0 g, 58%).

Step F—Preparation of 8-methoxycarbonyloctyl-2-amino-2-deoxy-3,6-di-O-benzyl-4-O-(4,6-O-benzylidene-2,3-di-O-benzoyl-β-D-galactopyranosyl)-β-D-glucopyranoside (compound 419)

Compound 418 (1.0 g, 0.99 mmol) was dissolved in a mixture of pyridine:water:triethylamine (4:1:0.1) and cooled to 0° C. Hydrogen sulfide gas was bubbled through the solution for 1 hour at 0° C. and the reaction was stirred at room temperature for 15 hours before evaporation and co-evaporation of the mixture with toluene. The yield of compound 419 at this stage was quantitative.

Step G—Preparation of 8-methoxycarbonyloctyl-2-(2,3,4tri-O-benzyl-fuc(c)-amido)-3,6-di-O-benzyl-4O-[4,6-O-benzylidene-2,3-di-O-benzyl]-β-D-galactopyranosyl-O-D-glucopyranoside (compound 420).

To a solution of compound 419 (850 mg, 0.86 mmol) in dry dichloromethane (20 mL) was added 2,3,4-tri-O-benzyl-α-L-fucopyrano-sylacetic acid (compound 309) (819.7 mg, 1.72 mmol) and EDC (850 mg). The reaction mixture was stirred for 15 hours at room temperature and diluted with dichloromethane (100 mL). The mixture was washed with aqueous sodium bicarbonate (2×100 mL) and water (2×100 mL), dried over $Na_2SO_4$, filtered and evaporated. The residue was then chromatographed on silica gel using hexane-ethyl acetate (2:1) as eluent to provide compound 420 (920 mg, 74%).

Step H—Preparation of 8-methoxycarbonyloctyl-2-(2,3, 4tri-O-benzyl-fuc(c)-amido)-3,6-di-O-benzyl-4O-[4,6-O-benzylidene-β-D-galactopyranosyl]-β-D-glucopyranoside (compound 421)

Compound 420 (920 mg, 0.64 mmol) was saponified in methanol (10 mL) using 0.5N sodium methoxide in methanol (5.0 mL). After neutralization with Amberlite IR-120 ($Na^+$) resin, filtration and evaporation of the solvent, the residue was purified by chromatography on silica gel using hexane-ethyl acetate (1:1) as eluent providing for compound 421 (750 mg, 95%).

Step I—Preparation of 8-methoxycarbonyloctyl-2-(2,3,4-tri-O-benzyl-fuc(c)-amido-3,6-di-O-benzyl-4-O-[4,6-O-benzylidene-3-O-sulfo-β-D-galactopyranosyl]-2-deoxy-β-D-glucopyranoside (compound 422)

$SO_3$-pyridine complex (146.43 mg, 0.92 mmol) was added to a solution of compound 421 (750 mg, 0.61 mmol) in pyridine (5 mL) at 0° C. and reaction was stirred for 0.5 hours at this temperature and 1 hour at room temperature. An additional amount of $SO_3$-pyridine complex (1.0 eq) was added and the reaction stirred for 3 hours at room temperature. Evaporated the mixture after addition of methanol and the residue was purified by chromatography on silica gel using dichloromethane-methanol-pyridine (95:5:0.1) as eluent providing compound 422 (620 mg, 75%).

Step J—Preparation of 8-methoxycarbonyloctyl-2-(fuc(c)-amido)-4-O-[3-O-sulfo-β-D-galacto-pyranosyl]-2-deoxy-β-D-glucopyranoside (compound 423)

Compound 422 (350 mg, 0.26 mmol) was dissolved in methanol (10 mL) and hydrogenated with 5% palladium on carbon (350 mg) as described earlier to provide for compound 423 (175 mg, 85%) as a sodium salt.

Example A

Inhibition of DTH Inflammatory Response

DTH inflammatory responses of representative oligosaccharide glycosides were measured using the mouse footpad swelling assay as described by Smith and Ziola[2]. Briefly, groups of Balb/c mice (about 19–20 grams each) were immunized with 100 μg of the OVA antigen (Albumin, Chicken Egg, Sigma, St. Louis, Mo.) containing 20 μg of the adjuvant (DDA—dimethyldioctadecyl-ammonium bromide, Eastman Kodak, Rochester, N.Y.) which also induces a strong inflammatory DTH response in PBS (phosphate buffer saline).

Seven days later, each group of mice was footpad-challenged with 20 μg of the OVA antigen (without adjuvant).

To assess the effect of the oligosaccharide glycoside on the inflammatory DTH response, mice received 10 μg or 100 μg of the oligosaccharide glycoside to be tested five hours after challenge. Control groups were left untreated or received 100 μL of phosphate-buffered saline (PBS). Any resulting inflammatory footpad swelling was measured with a Mitutoyo Engineering micrometer 24 hours after challenge. The amount of footpad swelling observed in mice treated with the oligosaccharide glycoside being tested was measured as a percentage reduction relative to the amount of swelling observed for the control. The results are set forth in Table I.

TABLE I

| | | % REDUCTION | | | |
|---|---|---|---|---|---|
| COMPOUND[1] | DOSE | Trial 1 | Trial 2 | Trial 3 | Average |
| A. | 100 μg | 15 | | | 15 |
| — | 100 μg | 25 | | | 25 |
| — | 100 μg | 46 | 47.9 | | 46.95 |
| — | 10 μg | 46 | | | 46 |
| — | 10 μg | 25.2 | | | 25.2 |
| — | 10 μg | 52.7 | 42.5 | 50 | 48.4 |
| B | 10 μg | 27.1 | | | 27.1 |
| — | 100 μg | 44.8 | 47 | 30.6 | 40.8 |
| C | 100 μg | 30.7 | | | 30.7 |
| C | 10 μg | 21.3 | | | 21.3 |
| — | 100 μg | 28.5 | | | 28.5 |
| D | 100 μg | 46.2 | | | 46.2 |

TABLE I-continued

| COMPOUND[1] | DOSE | % REDUCTION | | | |
|---|---|---|---|---|---|
| | | Trial 1 | Trial 2 | Trial 3 | Average |
| E | 100 μg | 45.7 | | | 45.7 |
| F | 10 μg | 44.2 | | | 44.2 |

[1]Compounds tested were:
Compound A = 8-Methoxycarbonyloctyl-2-p-nitrobenzamido-4-O-(β-D-galactopyranosyl)-2-deoxy-β-D-glucopyranose;
Compound B = 8-Methoxycarbonyloctyl-4-O-(4-O-phospho-β-D-galactopyranosyl)-β-D-glucopyranoside disodium salt;
Compound C = 8-Methoxycarbonyloctyl-2-acetamido-3-O-(α-L-fucopyranosyl)-4-O-[3,4,6-tri-O-sulfo-β-D-galactopyranosyl]-2-deoxy-β-D-glucopyranoside trisodium salt; and
Compound D = 8-Methoxycarbonyloctyl-2-acetamido-3-O-(2,3,4-tri-O-benzyl-α-L-fucopyranosyl)-4-O-[3-O-sulfo-2-O-(α-L-fucopyranosyl)-β-D-galactopyranosyl]-2-deoxy-β-D-glucopyranoside sodium salt.
Compound E = 8-Methoxycarbonyloctyl-4-O-(4-O-sulfo-D-galactopyranosyl)-D-glucopyranbside sodium salt;
Compound F = 8-Methoxycarbonyloctyl-2-acetamido-3-O-(3,6-diphospho-β)-galactopyranosyl)-2-deoxy-β-D-glucopyranoside tetrasodium salt;

The data in Table I demonstrate that the oligosaccharide glycosides represented by compounds A–F are effective in reducing antigen induced inflammation in a sensitized mammal.

While the present invention has been described with reference to what are considered to be the preferred examples, it is to be understood that the invention is not limited to the disclosed examples.

What is claimed is:

1. A compound of formula I and II below:

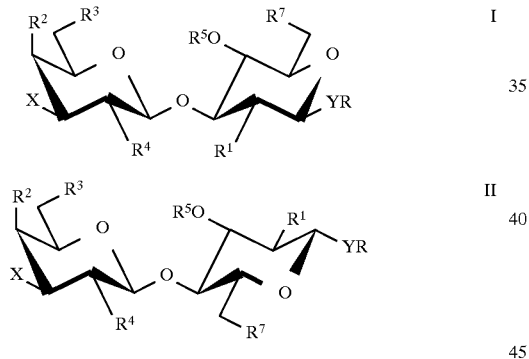

wherein:

Y is oxygen, sulfur or —NH—;

R is an aglycon of at least 1 carbon atom or Y and R are joined to form an azido or an amino group;

$R^1$ is selected from the group consisting of —OH, $NH_2$, —$N_3$, —NHC(O)$R^6$, and -fuc(C)amido, wherein $R^6$ is selected from the group consisting of
alkyl of from 1 to 6 carbon atoms,
cycloalkyl of from 3 to 8 carbon atoms,
aryl of from 6 to 14 carbon atoms,
alkaryl of from 7 to 20 carbon atoms,
heteroaryl of from 2 to 5 carbon atoms and from 1 to 3 hetero atoms selected from the group consisting of nitrogen, sulfur and oxygen,
substituted alkyl of from 1 to 6 carbon atoms having one to three substituents independently selected from the group consisting of halo, nitro, cyano, carboxyl, amino, alkylamine of from 1 to 6 carbon atoms, alkoxy of from 1 to 6 carbon atoms, thiol, hydroxyl, thioalkoxy of from 1 to 6 carbon atoms and —C(O)$R^7$ where $R^7$ is selected from the group consisting of hydrogen and alkyl of from 1 to 6 carbon atoms,
substituted aryl of from 6 to 14 carbon atoms having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)$R^6$ where $R^6$ is selected from the group consisting of hydrogen and alkyl of from 1 to 6 carbon atoms, and
substituted alkaryl having from 7 to 20 carbon atoms and having one to three substituents on the aryl moiety independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)$R^7$ where $R^7$ is selected from the group consisting of hydrogen and alkyl of from 1 to 6 carbon atoms,
substituted heteroaryl of from 2 to 5 carbon atoms and from 1 to 3 hetero atoms selected from the group consisting of nitrogen, sulfur and oxygen having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)$R^7$ where $R^7$ is selected from the group consisting of hydrogen and alkyl of from 1 to 6 carbon atoms;

$R^2$ is selected from the group consisting of hydrogen, halo, —OSO$_3$H and —OP(O)(OH)$_2$;

$R^3$ is selected from the group consisting of hydrogen, hydroxyl, halo, —OSO$_3$H and —OP(O)(OH)$_2$;

$R^4$ is selected from the group consisting of hydroxyl, halo and —O-L-fucosyl;

$R^5$ is selected from the group consisting of hydrogen, L-fucose and L-fucose substituted at the 2,3, and/or 4-positions with a substituent selected from the group consisting of halo, hydrogen, alkoxy, —OSO$_3$H and —OP(O)(OH)$_2$;

$R^7$ is selected from the group consisting of hydrogen, hydroxy, —OS(O)$_3$H, —OP(O)(OH)$_2$, halo, azido, —NH$_2$, —NHC(O)$R^6$, and -fuc(C)amido, wherein $R^6$ is selected from the group consisting of
alkyl of from 1 to 6 carbon atoms,
cycloalkyl of from 3 to 6 carbon atoms,
aryl of from 6 to 14 carbon atoms,
alkaryl of from 7 to 20 carbon atoms,
heteroaryl of from 1 to 8 carbon atoms and from 1 to 4 hetero atoms selected from the group consisting of nitrogen, sulfur and oxygen,
heterocyclic of from 1 to 8 carbon atoms and from 1 to 4 hetero atoms selected from nitrogen, sulfur or oxygen within the ring
substituted alkyl of from 1 to 6 carbon atoms having one to three substituents independently selected from the group consisting of halo, nitro, cyano, carboxyl, amino, alkylamine of from 1 to 6 carbon atoms, alkoxy of from 1 to 6 carbon atoms, thiol, hydroxyl, thioalkoxy of from 1 to 6 carbon atoms and —C(O)$R^7$ where $R^7$ is selected from the group consisting of hydrogen and alkyl of from 1 to 6 carbon atoms,
substituted aryl of from 6 to 14 carbon atoms having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)$R^7$ where $R^7$ is selected from the group consisting of hydrogen and alkyl of from 1 to 6 carbon atoms; and substituted alkaryl having from 7 to 20 carbon atoms and having one to three substituents on the aryl moiety independently selected from the group consisting of halo, nitro, cyano, carboxyl, amino, alkyl of from 1 to 6 carbon atoms and —C(O)R$^7$ where R$^7$ is selected from the grou consisting of hydrogen and alkyl of from 1 to 6 carbon atoms, substituted heteroaryl of from 2 to 5 carbon atoms and from 1 to 3 hetero atoms selected from the group consisting of nitrogen, sulfur, and oxygen having one to three substituents independently selected from the group consisting of halo, nitro, cyano, carboxyl, amino, alkyl, of from 1 to 6 carbon atoms, alkoxy of from 1 to 6 carbon atoms, thiol, hydroxyl, thioalkoxy of from 1 to 6 carbon atoms and —C(O)R$^7$ is selected from the group consisting of hydrogen and alkyl of from 1 to 6 carbon atoms;

and X is selected from the group consisting of hydroxyl, chloro, —OSO$_3$H or —OP(O)(OH)$_2$, and pharmaceutically acceptable salts thereof.

2. The compound of claim 1 wherein R is an aglycon of from 1 to 20 carbon atoms.

3. The compound of claim 1 wherein R$^1$ is fuc(C)amido or —NHC(O)R$^6$ where R$^6$ is alkyl containing 1 to 4 carbon atoms, cycloalkyl containing 5 or 6 carbon atoms, phenyl, substituted phenyl having one or two substituents independently selected from acetyl, nitro, or amino.

4. The compound of claim 1 wherein R$^2$ is selected from the group consisting of chloro and deoxy.

5. The compound of claim 1 wherein R$^3$ is selected from the group consisting of hydroxy, chloro and deoxy.

6. A compound of formula I and II below:

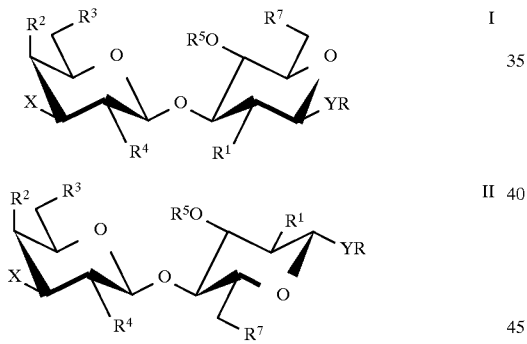

wherein:

Y is oxygen, sulfur or —NH—;

R is an aglycon of at least 1 carbon atom or Y and R are joined to form an azido or an amino group;

R$^1$ is selected from the group consisting of —NHC(O)R$^6$, and -fuc(C)amido, wherein R$^6$ is selected from the group consisting of cycloalkyl of from 3 to 8 carbon atoms, aryl of from 6 to 14 carbon atoms, alkaryl of from 7 to 20 carbon atoms, heteroaryl of from 2 to 5 carbon atoms and from 1 to 3 hetero atoms selected from the group consisting of nitrogen, sulfur and oxygen, substituted alkyl of from 1 to 6 carbon atoms having one to three substituents independently selected from the group consisting of halo, nitro, cyano, carboxyl, amino, alkylamine of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms, substituted aryl of from 6 to 14 carbon atoms having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^6$ where R$^6$ is selected from the group consisting of hydrogen and alkyl of from 1 to 6 carbon atoms, and substituted alkaryl having from 7 to 20 carbon atoms and having one to three substituents on the aryl moiety independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms, substituted heteroaryl of from 2 to 5 carbon atoms and from 1 to 3 hetero atoms selected from the group consisting of nitrogen, sulfur and oxygen having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms;

R$^2$ is selected from the group consisting of hydrogen, hydroxyl, halo, —OSO$_3$H and —OP(O)(OH)$_2$;

R$^3$ is selected from the group consisting of hydrogen, hydroxyl, halo, —OSO$_3$H and —OP(O)(OH)$_2$;

R$^4$ is selected from the group consisting of hydroxyl, halo and —O-L-fucosyl;

R$^5$ is selected from the group consisting of hydrogen, L-fucose and L-fucose substituted at the 2,3, and/or 4-positions with a substituent selected from the group consisting of halo, hydrogen, alkoxy, —OSO$_3$H and —OP(O)(OH)$_2$;

R$^7$ is selected from the group consisting of hydrogen, hydroxy, —OS(O)$_3$H, —OP(O)(OH)$_2$, halo, azido, —NH$_2$, —NHC(O)R$^6$, and -fuc(C)amido, wherein R$^6$ is selected from the group consisting of alkyl of from 1 to 6 carbon atoms, cycloalkyl of from 3 to 6 carbon atoms, aryl of from 6 to 14 carbon atoms, alkaryl of from 7 to 20 carbon atoms, heteroaryl of from 1 to 8 carbon atoms and from 1 to 4 hetero atoms selected from the group consisting of nitrogen, sulfur and oxygen, heterocyclic of from 1 to 8 carbon atoms and from 1 to 4 hetero atoms selected from nitrogen, sulfur or oxygen within the ring substituted alkyl of from 1 to 6 carbon atoms having one to three substituents independently selected from the group consisting of halo, nitro, cyano, carboxyl, amino, alkylamine of from 1 to 6 carbon atoms, alkoxy of from 1 to 6 carbon atoms, thiol, hydroxyl, thioalkoxy of from 1 to 6 carbon atoms and —C(O) R$^7$ where R$^7$ is selected from the group consisting of hydrogen and alkyl of from 1 to 6 carbon atoms, substituted aryl of from 6 to 14 carbon atoms having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms, and substituted alkaryl having from 7 to 20 carbon atoms and having one to three substituents on the aryl moiety independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms, substituted heteroaryl of from 2 to 5 carbon atoms and from 1 to 3 hetero atoms selected from the group consisting of nitrogen, sulfur and oxygen having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms;

and X is selected from the group consisting of hydroxyl, chloro, —OSO$_3$H or —OP(O)(OH)$_2$, and pharmaceutically acceptable salts thereof.

7. A compound of formula I and II below:

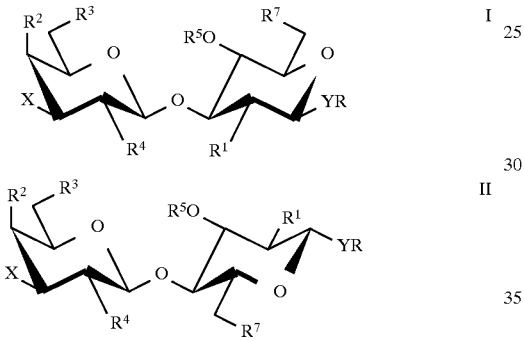

wherein:

Y is oxygen, sulfur or —NH—;

R is an aglycon of at least 1 carbon atom or Y and R are joined to form an azido or an amino group;

R$^1$ is selected from the group consisting of —OH, NH$_2$, —N$_3$, —NHC(O)R$^6$, and -fuc(C)amido, wherein R$^6$ is selected from the group consisting of alkyl of from 1 to 6 carbon atoms, cycloalkyl of from 3 to 8 carbon atoms, aryl of from 6 to 14 carbon atoms, alkaryl of from 7 to 20 carbon atoms, heteroaryl of from 2 to 5 carbon atoms and from 1 to 3 hetero atoms selected from the group consisting of nitrogen, sulfur and oxygen, substituted alkyl of from 1 to 6 carbon atoms having one to three substituents independently selected from the group consisting of halo, nitro, cyano, carboxyl, amino, alkylamine of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms, substituted aryl of from 6 to 14 carbon atoms having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^6$ where R$^6$ is selected from the group consisting of hydrogen and alkyl of from 1 to 6 carbon atoms, and substituted alkaryl having from 7 to 20 carbon atoms and having one to three substituents on the aryl moiety independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms, substituted heteroaryl of from 2 to 5 carbon atoms and from 1 to 3 hetero atoms selected from the group consisting of nitrogen, sulfur and oxygen having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms;

R$^2$ is selected from the group consisting of hydrogen, hydroxyl, halo, —OSO$_3$H and —OP(O)(OH)$_2$;

R$^3$ is selected from the group consisting of hydrogen, hydroxyl, halo, —OSO$_3$H and —OP(O)(OH)$_2$;

R$^4$ is —O-L-fucosyl;

R$^5$ is selected from the group consisting of hydrogen, L-fucose and L-fucose substituted at the 2,3, and/or 4-positions with a substituent selected from the group consisting of halo, hydrogen, alkoxy, —OSO$_3$H and —OP(O)(OH)$_2$;

R$^7$ is selected from the group consisting of hydrogen, hydroxy, —OS(O)$_3$H, —OP(O)(OH)$_2$, halo, azido, —NH$_2$, —NHC(O)R$^6$, and -fuc(C)amido, wherein R$^6$ is selected from the group consisting of alkyl of from 1 to 6 carbon atoms, cycloalkyl of from 3 to 6 carbon atoms, aryl of from 6 to 14 carbon atoms, alkaryl of from 7 to 20 carbon atoms, heteroaryl of from 1 to 8 carbon atoms and from 1 to 4 hetero atoms selected from the group consisting of nitrogen, sulfur and oxygen, heterocyclic of from 1 to 8 carbon atoms and from 1 to 4 hetero atoms selected from nitrogen, sulfur or oxygen within the ring substituted alkyl of from 1 to 6 carbon atoms having one to three substituents independently selected from the group consisting of halo, nitro, cyano, carboxyl, amino, alkylamine of from 1 to 6 carbon atoms, alkoxy of from 1 to 6 carbon atoms, thiol, hydroxyl, thioalkoxy of from 1 to 6 carbon atoms and —C(O) R$^7$ where R$^7$ is selected from the group consisting of hydrogen and alkyl of from 1 to 6 carbon atoms, substituted aryl of from 6 to 14 carbon atoms having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms, and substituted alkaryl having from 7 to 20 carbon atoms and having one to three substituents on the aryl moiety independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms, substituted heteroaryl of from 2 to 5 carbon atoms and from 1 to 3 hetero atoms selected from the group consisting of nitrogen, sulfur and oxygen having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms;

and X is selected from the group consisting of hydroxyl, chloro, —OSO$_3$H or —OP(O)(OH)$_2$, and pharmaceutically acceptable salts thereof.

8. A compound of formula I and II below:

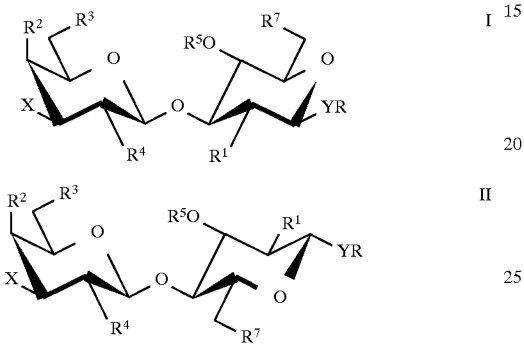

wherein:

Y is oxygen, sulfur or —NH—;

R is an aglycon of at least 1 carbon atom or Y and R are joined to form an azido or an amino group;

R$^1$ is selected from the group consisting of —OH, NH$_2$, —N$_3$, —NHC(O)R$^6$, and -fuc(C)amido, wherein R$^6$ is selected from the group consisting of
  alkyl of from 1 to 6 carbon atoms,
  cycloalkyl of from 3 to 8 carbon atoms,
  aryl of from 6 to 14 carbon atoms,
  alkaryl of from 7 to 20 carbon atoms,
  heteroaryl of from 2 to 5 carbon atoms and from 1 to 3 hetero atoms selected from the group consisting of nitrogen, sulfur and oxygen,
  substituted alkyl of from 1 to 6 carbon atoms having one to three substituents independently selected from the group consisting of halo, nitro, cyano, carboxyl, amino, alkylamine of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms,
  substituted aryl of from 6 to 14 carbon atoms having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^6$ where R$^6$ is selected from the group consisting of hydrogen and alkyl of from 1 to 6 carbon atoms, and
  substituted alkaryl having from 7 to 20 carbon atoms and having one to three substituents on the aryl moiety independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms,
  substituted heteroaryl of from 2 to 5 carbon atoms and from 1 to 3 hetero atoms selected from the group consisting of nitrogen, sulfur and oxygen having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms;

R$^2$ is selected from the group consisting of hydrogen, hydroxyl, halo, —OSO$_3$H and —OP(O)(OH)$_2$;

R$^3$ is selected from the group consisting of hydrogen, hydroxyl, halo, —OSO$_3$H and —OP(O)(OH)$_2$;

R$^4$ is selected from the group consisting of hydroxyl, halo and —O-L-fucosyl;

R$^5$ is selected from the group consisting of L-fucose and L-fucose substituted at the 2,3, and/or 4-positions with a substituent selected from the group consisting of halo, hydrogen, alkoxy, —OSO$_3$H and —OP(O)(OH)$_2$;

R$^7$ is selected from the group consisting of hydrogen, hydroxy, —OS(O)$_3$H, —OP(O)(OH)$_2$, halo, azido, —NH$_2$, —NHC(O)R$^6$, and -fuc(C)amido, wherein R$^6$ is selected from the group consisting of
  alkyl of from 1 to 6 carbon atoms,
  cycloalkyl of from 3 to 6 carbon atoms,
  aryl of from 6 to 14 carbon atoms,
  alkaryl of from 7 to 20 carbon atoms,
  heteroaryl of from 1 to 8 carbon atoms and from 1 to 4 hetero atoms selected from the group consisting of nitrogen, sulfur and oxygen,
  heterocyclic of from 1 to 8 carbon atoms and from 1 to 4 hetero atoms selected from nitrogen, sulfur or oxygen within the ring
  substituted alkyl of from 1 to 6 carbon atoms having one to three substituents independently selected from the group consisting of halo, nitro, cyano, carboxyl, amino, alkylamine of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms,
  substituted aryl of from 6 to 14 carbon atoms having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms, and
  substituted alkaryl having from 7 to 20 carbon atoms and having one to three substituents on the aryl moiety independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms,
  substituted heteroaryl of from 2 to 5 carbon atoms and from 1 to 3 hetero atoms selected from the group consisting of nitrogen, sulfur and oxygen having one to three substituents independently selected from the group consisting of halo, nitro, cyano, carboxyl, amino, alkyl of from 1 to 6 carbon atoms, alkoxy of from 1 to 6 carbon atoms, thiol, hydroxyl, thioalkoxy of from 1 to 6 carbon atoms and —C(O)R$^7$ where R$^7$ is selected from the group consisting of hydrogen and alkyl of from 1 to 6 carbon atoms;

and X is selected from the group consisting of hydroxyl, chloro, —OSO$_3$H or —OP(O)(OH)$_2$, and pharmaceutically acceptable salts thereof with the proviso that when R$^2$ is hydroxyl and R$^4$ is hydroxyl or fluoro, then R$^1$ is not hydroxyl, —N$_3$, —NH$_2$ or —NHC(O)R$^6$ where R$^6$ is alkyl of from 1 to 4 carbon atoms.

9. The compound according to claims 1, 6, 7 or 8 which is selected from the group consisting of:

8-methoxycarbonyloctyl-2-benzamido-3-O-(α-L-fucopyranosyl)-4-O-[3-O-sulfo-β-D-galactopyranosyl]-2-deoxy-β-D-glucopyranoside 8-methoxycarbonyloctyl-2-p-nitrobenzamido-3-O-(α-L-fucopyranosyl)-4-O-[3-O-sulfo-β-D-galactopyranosyl]-2-deoxy-β-D-glucopyranoside 8-methoxycarbonyloctyl-2-o-acetylbenzamido-3-O-(α-L-fucopyranosyl)-4-O-[3-O-sulfo-β-D-galactopyranosyl]-2-deoxy-β-D-glucopyranoside 8-methoxycarbonyloctyl-2-cyclohexamido-3-O-(α-L-fucopyranosyl)-4-O-[3-O-sulfo-β-D-galactopyranosyl]-2-deoxy-β-D-glucopyranoside 8-methoxycarbonyloctyl-2-fuc(C)amido-3-O-(α-L-fucopyranosyl)-4-O-[3-O-sulfo-β-D-galactopyranosyl]-2-deoxy-β-D-glucopyranoside 8-methoxycarbonyloctyl-2-p-nitrobenzamido-4-O-(β-D-galactopyranosyl)-2-deoxy-β-D-glucopyranoside 8-methoxycarbonyloctyl-4-O-(4-O-sulfo-β-D-galactopyranosyl)-β-D-glucopyranoside 8-methoxycarbonyloctyl-4-O-(4-O-phosphor-β-D-galactopyranosyl)-β-D-glucopyranoside 8-methoxycarbonyloctyl-2-acetamido-3-O-(α-L-fucopyranosyl)-4-O-[3,4,6-tri-O-sulfo-β-D-galactopyranosyl]-2-deoxy-β-D-glucopyranoside 8-methoxycarbonyloctyl-2-acetamido-3-O-(α-L-fucopyranosyl)-4-O-[3-O-sulfo-2-O-(α-L-fucopyranosyl)-β-D-galactopyranosyl]-2-deoxy-β-D-glucopyranoside 8-methoxycarbonyloctyl-2-acetamido-3-O-(α-L-fucopyranosyl)-4-O-[6-chloro-6-deoxy-3-O-sulfo-β-D-galactopyranosyl)]-2-deoxy-β-D-glucopyranoside 8-methoxycarbonyloctyl-2-acetamido-3-O-(α-L-fucopyranosyl)-4-O-[6-deoxy-3-O-sulfo-β-D-galactopyranosyl]-2-deoxy-β-D-glucopyranoside 8-methoxycarbonyloctyl-2-acetamido-3-O-(α-L-fucopyranosyl)-4-O-[4-chloro-4-deoxy-3-O-sulfo-β-D-galactopyranosyl]-2-deoxy-β-D-glucopyranoside 8-methoxycarbonyloctyl-2-acetamido-3-O-α-L-fucopyranosyl)-4-O-[4,6-dichloro-4,6-dideoxy-3-O-sulfo-β-D-galactopyranosyl]-2-deoxy-β-D-glucopyranoside 8-methoxycarbonyloctyl-2-acetamido-3-O-(α-L-fucopyranosyl)-4-O-[4,6-dideoxy-3-O-sulfo-β-D-galactopyranosyl]-2-deoxy-β-D-glucopyranoside 2-acetamido-2-deoxy-3-O-(α-L-fucopyranosyl)-4-O-[3-O-sulfo-β-D-galactopyranosyl]-β-D-glucopyranosyl azide 2-acetamido-2-deoxy-3-O-(α-L-fucopyranosyl)-4-O-[3-O-sulfo-β-D-galactopyranosyl]-β-D-glucopyranosyl amine 2-acetamido-2-deoxy-3-O-(α-L-fucopyranosyl)-4-O-[3-O-sulfo-β-D-galactopyranosyl]-β-D-glucopyranosyl benzamide 2-acetamido-2-deoxy-3-O-(α-L-fucopyranosyl)-4-O-[3-O-sulfo-β-D-galactopyranosyl]-β-D-glucopyranosyl p-nitrobenzamide 2-acetamido-2-deoxy-3-O-(α-L-fucopyranosyl)-4-O-[3-O-sulfo-β-D-galactopyranosyl]-β-D-glucopyranosyl butyramide 2-acetamido-2-deoxy-3-O-(α-L-fucopyranosyl)-4-O-[3-O-sulfo-β-D-galactopyranosyl]-β-D-glucopyranosyl acetamide 2-acetamido-2-deoxy-3-O-(α-L-fucopyranosyl)-4-O-[3-O-sulfo-β-D-galactopyranosyl]-β-D-glucopyranosyl stearamide 2-acetamido-2-deoxy-3-O-(α-L-fucopyranosyl)-4-O-[3-O-sulfo-β-D-galactopyranosyl]-β-D-glucopyranosyl L-serine 2-acetamido-2-deoxy-3-O-(4-deoxy-α-L-fucopyranosyl)-4-O-(3-O-sulfo-β-D-galactopyranosyl)-β-D-glucopyranoside 8-methoxycarbonyloctyl 2-acetamido-2-deoxy-3-O-(4-O-sulfo-α-L-fucopyranosyl)-4-O-(3-O-sulfo-β-D-galactopyranosyl)-β-D-glucopyranoside 8-methoxycarbonyloctyl 2-acetamido-2-deoxy-3-O-(3-O-sulfo-α-L-fucopyranosyl)-4-O-(3-O-sulfo-β-D-galactopyranosyl)-β-D-glucopyranoside 8-methoxycarbonyloctyl 2-acetamido-2-deoxy-3-O-(3-O-methyl-c-L-fucopyranosyl)-4-O-(3-O-sulfo-β-D-galactopyranosyl)-β-D-glucopyranoside phenylalanine amido-2-(fuc(C)-amido)-4-O-[3-O-sulfo-β-D-galactopyranosyl]-β-D-glucopyranoside 2-benzamido-2-deoxy-3-O-(4-deoxy-α-L-fucopyranosyl)-4-O-(3-O-sulfo-β-D-galactopyranosyl)-β-D-glucopyranosyl benzamide cyclohexylalanine amido-2-(fuc(C)-amido)-4-O-[3-O-sulfo-β-D-galactopyranosyl]-β-D-glucopyranoside tryptophanamido-2-fuc(C)-amido-4-O-(3-O-sulfo-β-D-galactopyranosyl)-β-D-glucopyranoside acetainido-2-(fuc(C)-amido-4-O-[3-O-sulfo-β-D-galactopyranosyl]-2-deoxy-β-D-glucopyranoside benzamido 2-(fuc(C)-amido)-4-O-[3-O-sulfo-β-D-galactopyranosyl])-2-deoxy-β-D-glucopyranoside 8-methoxycarbonyloctyl 2-acetamido-3-O-(α-L-fucopyranosyl)-4-O-[4,6-dichloro-dideoxy-3-O-sulfo-β-D-galactopyranosyl]-6-benzamido-2,6-dideoxy-β-D-glucopyranoside 8-methoxycarbonyloctyl-2-acetamido-3-O-(α-L-fucopyranosyl)-4-O-[4,6-dideoxy-3-O-sulfo-β-D-galactopyranosyl]-6-benzamido-2,6-dideoxy-β-D-glucopyranoside 8-methoxycarbonyloctyl-2-acetamido-3-O-(α-L-fucopyranosyl)-4-O-[3-O-sulfo-β-D-galactopyranosyl]-6-benzamido-2,6-dideoxy-β-D-glucopyranoside 8-methoxycarbonyloctyl-2-acetamido-3-O-(α-L-fucopyranosyl)-4-O-[3-O-sulfo-β-D-galactopyranosyl]-6-chloro-2,6-dideoxy-β-D-glucopyranoside 2-acetamido-3-O-(α-L-fucopyranosyl)-4-O-[4,6-dichloro-dideoxy-3-O-sulfo-β-D-galactopyranosyl]-2-deoxy-β-D-glucopyranosyl azide 2-acetamido-3-O-(α-L-fucopyranosyl)-4-O-[4,6-dideoxy-3-O-sulfo-β-D-galactopyranosyl]-2-deoxy-β-D-glucopyranosyl azide 2-benzamido-2-deoxy-3-O-(α-L-fucopyranosyl)-4-O-[3-O-sulfo-β-D-galactopyranosyl]-β-D-glucopyranoside benzamide 8-methoxycarbonyloctyl-2-amino-3-O-(α-L-
fucopyranosyl)-4-O-[4,6-dichloro-dideoxy-3-O-sulfo-
β-D-galactopyranosyl]-2-deoxy-β-D-glucopyranoside 8-methoxycarbonyloctyl-2-benzamido-3-O-(α-L-
fucopyranosyl)-4-O-[4,6-dichloro-dideoxy-3-O-sulfo-
β-D-galactopyranosyl]-2-deoxy-β-D-glucopyranoside 8-methoxycarbonyloctyl-2-benzamido-3-O-(α-L-
fucopyranosyl)-4-O-[4,6-dideoxy-3-O-sulfo-β-D-
galactopyranosyl]-2-deoxy-β-D-glucopyranoside 8-methoxycarbonyloctyl-2-benzamido-4-O-(α-L-
fucopyranosyl)-3-O-[3-O-sulfo-β-D-galactopyranosyl]
-2-deoxy-β-D-glucopyranoside 8-methoxycarbonyloctyl-2-p-nitrobenzamido-4-O-(α-L-
fucopyranosyl)-3-O-[3-O-sulfo-β-D-galactopyranosyl]
-2-deoxy-β-D-glucopyranoside 8-methoxycarbonyloctyl-2-(fuc(c)-amido)-4-O-[3-O-
sulfo-β-D-galactopyranosyl]-2-deoxy-β-D-
glucopyranoside and pharmaceutically acceptable salts thereof.

10. A pharmaceutical composition comprising a pharmaceutically acceptable inert carrier and an effective inflammation-reducing amount of an oligosaccharide glycoside of claim 1, 6, 7, or 8.

11. A method for reducing antigen-induced inflammation in a mammal which method comprises administering to said mammal an effective inflammation-reducing amount of an oligosaccharide glycoside of claim 1.

* * * * *